(12) United States Patent
Suzuki et al.

(10) Patent No.: US 6,329,389 B1
(45) Date of Patent: Dec. 11, 2001

(54) AMINE COMPOUNDS, THEIR PRODUCTION AND USE

(75) Inventors: Nobuhiro Suzuki, Tsukuba; Kaneyoshi Kato, Kawanishi; Shiro Takekawa, Tsukuba; Jun Terauchi, Ikeda; Satoshi Endo, Takatsuki, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/424,285

(22) PCT Filed: Apr. 8, 1999

(86) PCT No.: PCT/JP99/01871

§ 371 Date: Nov. 19, 1999

§ 102(e) Date: Nov. 19, 1999

(87) PCT Pub. No.: WO99/52875

PCT Pub. Date: Oct. 21, 1999

(30) Foreign Application Priority Data

Apr. 8, 1998 (JP) .................................................. 10-096422
Dec. 4, 1998 (JP) .................................................. 10-345328

(51) Int. Cl.$^7$ .................................................... A01N 43/42
(52) U.S. Cl. .......................... 514/307; 514/310; 514/311; 514/313; 546/153; 546/154; 546/155; 546/156; 546/157; 546/158; 546/165; 546/166; 546/168; 546/169; 546/170
(58) Field of Search ..................................... 546/153–158, 546/165, 166, 168–170; 514/307, 310, 311, 313

(56) References Cited

U.S. PATENT DOCUMENTS 5,719,141  2/1998  Rasetti et al. .

FOREIGN PATENT DOCUMENTS

| 0866059 A | 9/1998 | (EP) . |
| WO 97/03054 | 1/1997 | (WO) . |
| WO 97/12860 | 4/1997 | (WO) . |
| WO 98/44921 | 10/1998 | (WO) . |
| WO 98/47882 | 10/1998 | (WO) . |

OTHER PUBLICATIONS

Yang et al., "Synthesis and biological activities of potent peptidomimetics . . ." *Proc. Natl. Acad. Sci. USA*, vol. 95 No. 18 (Sep. 1, 1998) pp. 10836–10841.

V. Vecchietti et al., "(1S)–1–(Aminomethyl)–2–(arylacetyl) . . ." *J. Med. Chem.* 1991, 34, pp. 2624–2633.

C. Papageorgiou et al., "A non–peptide ligand for the somatostatin receptor . . ." *Bioorganic and Medical Chemistry Letters*, vol. 6, No. 3 (Feb. 6, 1996) pp. 267–272.

Primary Examiner—D. Margaret Seaman
(74) Attorney, Agent, or Firm—Philippe Y. Riesen; Mark Chao

(57) ABSTRACT

The present invention provides a compound of the formula:

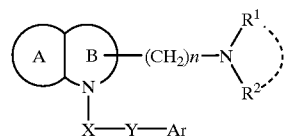

wherein Ar represents an aromatic group which may be substituted;

X represents methylene, S, SO, $SO_2$ or CO;

Y represents a spacer having a main chain of 2 to 5 atoms;

n represents an integer of 1 to 5;

i) $R^1$ and $R^2$ each represents a hydrogen atom or a lower alkyl which may be substituted, ii) $R^1$ and $R^2$ form, taken together with the adjacent nitrogen atom, a nitrogen-containing heterocyclic ring which may be substituted, or iii) $R^1$ or $R^2$ together with —$(CH_2)_n$—N= form, bonded to a component atom of Ring B, a spiro-ring which may be substituted;

Ring A represents an aromatic ring which may be substituted;

Ring B represents a 4- to 7-membered nitrogen-containing non-aromatic ring which may be further substituted by alkyl or acyl, with a proviso that X represents S, SO, $SO_2$ or CO when Ring A has as a substituent a group represented by the formula:

—$NHCOR^{11}$ where $R^{11}$ represents alkyl, alkoxyalkyl, alkylthioalkyl, cycloalkyl, cycloalkylalkyl, aryl, arylalkyl or a group represented by the formula:

—$NHR^{12}$ where $R^{12}$ represents alkyl, cycloalkyl, cycloalkylalkyl, aryl or arylalkyl, or a salt thereof; which has an excellent somatostatin receptor binding inhibition action.

28 Claims, No Drawings

AMINE COMPOUNDS, THEIR PRODUCTION AND USE

This application is a 371 of PCT/JP99/01871 filed Apr. 8, 1999.

TECHNICAL FIELD

The present invention relates to novel amine compounds, production thereof and a pharmaceutical composition comprising them. In further detail, the present invention relates to a compound which has a somatostatin receptor binding inhibition activity, and is useful for preventing and/or treating diseases associated with somatostatin.

BACKGROUND ART

Somatostatin was found to be a growth hormone inhibiting factor (somatotropin release inhibiting factor; SRIF) in 1973.

Somatostatin receptors were found to comprise five subtypes and named as SSTR1, SSTR2, SSTR3, SSTR4 and SSTR5 respectively (e.g., Endocrinology, vol. 136, pp.3695–3697, 1995; Trends in Pharmacological Sciences, pp.87–94, 1997; Life Science, Vol.57, pp.1249–1265, 1995).

Somatostatin is known to inhibit production and/or secretion of various hormones, growth factors, and physiologically active substances. As the hormones inhibited by somatostatin, mentioned are growth hormone (GH), thyroid-stimulating hormones (TSH), prolactin, insulin, and glucagon. Therefore, somatostatin has various functions in endocrine systems, exocrine systems and nerve systems, and drugs targeting somatostatin are being developed (e.g., Endocrinology, vol.136, p.3695–3697, 1995; Trends in Pharmacological Sciences, pp.87–94, vol.18, 1997).

Diseases caused by somatostatin include life-style related diseases such as diabetes; central nervous system diseases, immune system diseases, and hormone-dependent tumors. Trials to develop somatostatin itself or somatostatin analogues as a drug have been conducted. For instance, octreotide known as a somatostatin receptor agonist has been marketed as a drug for treating hormone-dependent tumors.

As a compound having a somatostatin receptor binding activity, especially a selective SSTRL antagonist activity, there is known a compound represented by the formula:

wherein X represents O or H, H; Y represents —CH$_2$—, —O—, —NH— or —S—; R$_1$ represents H or C$_{1-4}$ alkyl; R$_2$ represents H, benzyl, etc.; R$_3$ represents H, C$_{1-4}$ alkyl, etc.; R$_4$ represents hydrogen atom or halogen (WO97/03054).

As a compound which has a selective SSTR4 binding activity and is expected to have a glaucoma treating activity, there is known a compound represented by the formula:

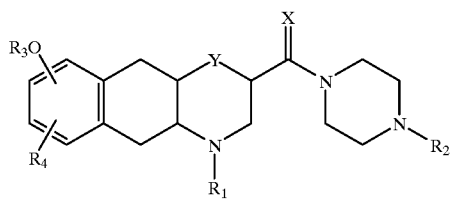

(J. Am. Chem. Soc., vol.120, pp.1368–1373, 1998; WO97/43728).

On the other hand, the following compounds are known as amine compounds.

1) J. Med. Chem., vol.34, pp.2624–2633, 1991 describes, as a compound having a weak analgesic activity, a compound represented by the following formula:

2) JP-A 8(1996)-176087 describes 3-(N,N-dimethylaminomethyl)-1,2,3,4-tetrahydroquinoline as a synthetic intermediate of a compound represented by the formula:

wherein R$_1$ represents arylamino such as

A represents a direct bond, methylene, ethylene, imino, oxy or thio; R$_9$ represents C$_{1-4}$ alkoxycarbonylamino-C$_{1-4}$ alkyl, etc,; R$_{10}$ represents hydrogen or C$_{1-4}$ alkyl; R$_{11}$ represents hydrogen or halogen; etc.; X represents carbonyl, etc.; R$_2$ and R$_3$ represent hydrogen, etc.; R$_5$ represents hydroxyl, etc.; R$_6$ represents hydrogen, etc.; R$_7$ represents hydrogen, etc.; R$_8$ represents aliphatic group, etc., which is described to be useful in the treatment of hypertension.

3) WO97/12860 describes, as a compound having an acyl-coenzyme A: cholesterol acyltransferase inhibiting activity and a lipid peroxidation inhibiting activity, a heterocyclic compound represented by the formula:

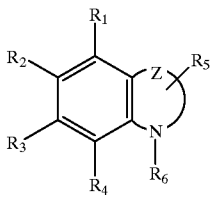

wherein at least one of $R_1$, $R_2$ and $R_5$ represents alkyl or alkenyl which is substituted by hydroxy, an acidic group, alkoxycarbonyl or —$NR_9R_{10}$ wherein $R_9$ and $R_{10}$ respectively represent hydrogen atom or lower alkyl, etc., and the remaining two groups independently represent hydrogen atom, lower alkyl or lower alkoxy; either of $R_2$ and $R_5$ represents a group represented by the formula: —$NHCOR_7$ wherein $R_7$ represents alkyl, etc., and the remaining groups represent hydrogen atom, lower alkyl or lower alkoxy; $R_6$ represents alkyl, alkenyl, alkoxyalkyl, alkylthioalkyl, cycloalkyl, cycloalkylalkyl or arylalkyl; Z represents nitrogen atom substituted by $R_6$, or a combined group forming 5-membered ring or 6-membered ring together with a carbon atom of benzene ring attached to the nitrogen atom and a carbon atom adjacent to the carbon atom, or a pharmaceutically acceptable salt thereof.

Conventional somatostatin and its analogues are all peptides. They are problematic in their oral absorbability, pharmacokinetics, etc. and are therefore unsatisfactory as medicines. It is desired to develop a compound which is different from conventional known compounds in its chemical structure, and which has a selective or nonselective affinity to somatostatin receptor subtypes, or an excellent somatostatin receptor binding inhibiting activity, and which has satisfactory properties as a medicine.

DISCLOSURE OF INVENTION

The present inventors have studied various compounds having a somatostatin receptor binding inhibiting activity, and, as a result, have succeeded in, for the first time, the production of a compound represented by the formula (I):

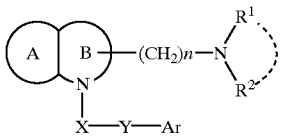

wherein Ar represents an aromatic group which may be substituted;
X represents methylene, S, SO, $SO_2$ or CO;
Y represents a spacer having a main chain of 2 to 5 atoms;
n represents an integer of 1 to 5;
i) $R^1$ and $R^2$ each represents a hydrogen atom or a lower alkyl which may be substituted,
ii) $R^1$ and $R^2$ form, taken together with the adjacent nitrogen atom, a nitrogen-containing heterocyclic ring which may be substituted, or
iii) $R^1$ or $R^2$ together with —$(CH_2)_n$—N= form, bonded to a component atom of Ring B, a spiro-ring which may be substituted;
Ring A represents an aromatic ring which may be substituted;
Ring B represents a 4- to 7-membered nitrogen-containing non-aromatic ring which may be further substituted by alkyl or acyl, with a proviso that X represents S, SO, $SO_2$ or CO when Ring A has as a substituent a group represented by the formula:

—$NHCOR^{11}$ where $R^{11}$ represents alkyl, alkoxyalkyl, alkylthioalkyl, cycloalkyl, cycloalkylalkyl, aryl, arylalkyl or a group represented by the formula:

—$NHR^{12}$ where $R^{12}$ represents alkyl, cycloalkyl, cycloalkylalkyl, aryl or arylalkyl, or a salt thereof [hereafter sometimes referred to as compound (I)], which is characterized by the chemical structure in that the nitrogen atom of Ring B in the skeletal structure represented by the formula:

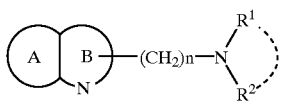

wherein symbols have the same meanings as above, is substituted by the group represented by the formula:

—X—Y—Ar where each symbol has the same meaning as above.

We have found for the first time that based on its specific chemical structure, compound (I) has an unexpectedly excellent somatostatin receptor binding inhibiting activity, etc., that a compound of the formula (I'):

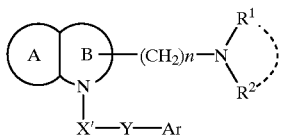

wherein X' represents methylene, S, SO, $SO_2$ or CO, other symbols have the same meanings as above, or a salt thereof [hereinafter sometimes referred to as compound (I')] also has an unexpectedly excellent somatostatin receptor binding inhibiting activity, and that these compounds have low toxicity and are therefore satisfactory as medicines. Compound (I) is within the scope of compound (I'). On the basis of these findings, the inventors have completed the present invention.

Specifically, the present invention relates to:
(1) compound (I),
(2) a compound of the above (1), wherein Ring B represents a 4- to 7-membered nitrogen-containing non-aromatic ring which may be substituted by alkyl;
(3) a compound of the above (1), wherein Ar represents an aromatic ring assembly group which may be substituted or a fused aromatic group which may be substituted;
(4) a compound of the above (1), wherein X represents CO;
(5) a compound of the above (1), wherein Y represents a $C_{2-5}$ alkylene which may be substituted;
(6) a compound of the above (5), wherein the substituent of the $C_{2-5}$ alkylene represented by Y is acylamino;
(7) a compound of the above (1), wherein n represents 1 or 2;
(8) a compound of the above (1), wherein $R^1$ and $R^2$ each represents a hydrogen atom or a lower alkyl which may be substituted;

(9) a compound of the above (1), wherein $R^1$ and $R^2$ form, taken together with the adjacent nitrogen atom, a nitrogen-containing heterocyclic ring which may be substituted;

(10) a compound of the above (9), wherein the nitrogen-containing heterocyclic ring is pyrrolidine, piperidine, piperazine or morpholine;

(11) a compound of the above (1), wherein Ring A is a benzene ring which may be substituted;

(12) a compound of the above (1), which is a compound of the formula:

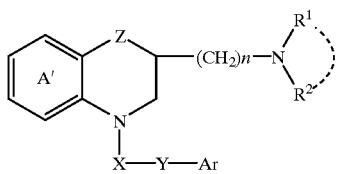

wherein Ring A' is a benzene ring which may be substituted;
Z represents methylene or imino which may be substituted;
the other symbols have the same meanings as in the above (1), or a salt thereof;

(13) a compound of the above (12), wherein Z is methylene;

(14) a compound of the above (1), wherein Ar represents
(i) phenyl; 2-, 4- or 5-thiazolyl; 2-, 4- or 5-oxazolyl; 2-, 3- or 4-pyridyl; or 1,2,4- or 1,3,4-oxadiazlolyl;
(ii) 2-, 3- or 4-biphenylyl; 3-(1-naphthyl)-1,2,4-oxadiazlol-5-yl; 3-(2-naphthyl)-1,2,4-oxadiazol-5-yl; 3-(2-benzofuranyl)-1,2,4-oxadiazol-5-yl; 3-phenyl-1,2,4-oxadiazol-5-yl; 3-(2-benzoxazolyl)-1,2,4-oxadiazol-5-yl; 3-(3-indolyl)-1,2,4-oxadiazol-5-yl; 3-(2-indolyl)-1,2,4-oxadiazol-5-yl; 4-phenylthiazol-2-yl; 4-(2-benzofuranyl) thiazol-2-yl; 4-phenyl-1,3-oxazol-5-yl; 5-phenyl-oxazol-2-yl; 4-(2-thienyl)phenyl; 4-(3-pyridyl)phenyl; 4-(2-naphthyl) phenyl; or 4,4'-terphenyl; or
(iii) 2-, 3- or 4-quinolyl; or 1-, 2- or 3-indolyl; each of which (i), (ii) and (iii) may be substituted by a group selected from the group consisting of halogen atom; $C_{1-3}$ alkylenedioxy; optionally halogenated $C_{1-6}$ alkyl; $C_{6-10}$ aryloxy-$C_{1-6}$ alkyl; $C_{1-6}$ alkyl-$C_{6-10}$ aryl-$C_{2-6}$ alkenyl; $C_{7-16}$ aralkyl optionally substituted by halogen atom or $C_{1-6}$ alkoxy; hydroxy; $C_{6-10}$ aryloxy optionally substituted by halogen atom or $C_{1-6}$ alkoxy; optionally halogenated $C_{1-6}$ alkyl-carbonyl; $C_{1-6}$ alkoxy-carbonyl; $C_{6-10}$ aryl-carbonyl and $C_{6-10}$ arylsulfonyl optionally substituted by $C_{1-6}$ alkyl;
X represents methylene, CO or $SO_2$;
Y represents
(a) $C_{2-5}$ alkylene which may be substituted by
① cyano,
② $C_{6-10}$ aryl,
③ a group represented by the formula:

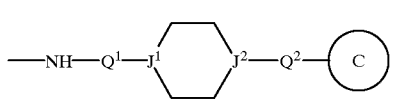

wherein $J^1$ and $J^2$ each represents CH, C(OH) or N; $Q^1$ and $Q^2$ each represents —$(CH_2)_p$— or —$(CH_2)_p$—CO—$(CH_2)_q$— where p and q each represents an integer of 0 to 3;

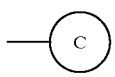

represents (i) a group represented by the formula:

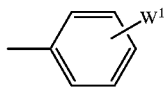

wherein $W^1$ represents halogen atom, cyano, optionally halogenated $C_{1-6}$ alkyl, optionally halogenated $C_{1-6}$ alkoxy, optionally halogenated $C_{1-6}$ alkyl-carbonyl, nitro or $C_{6-10}$ aryl;
(ii) pyridyl, or pyrimidinyl, or
(iii) a group represented by the formula:

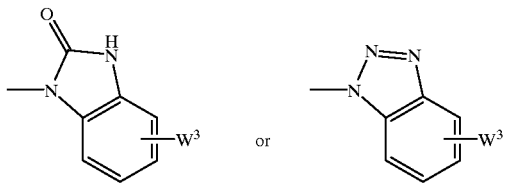

wherein $W^3$ represents hydrogen atom or optionally halogenated $C_{1-6}$ alkyl,
④ $C_{7-16}$ aralkyloxy-carboxamido,
⑤ amino,
⑥ C7-16 aralkyl-carboxamido,
⑦ $C_{1-6}$ alkoxy-carbonyl-piperazinyl-carboxamido, or
⑧ a group represented by the formula:

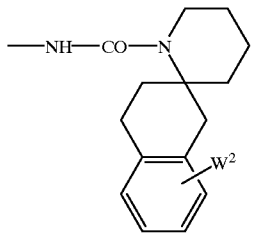

wherein $W^2$ represents optionally halogenated $C_{1-6}$ alkoxy;
(b) $C_{2-5}$ alkenylene,
(c) —$(CH)_m$—$Y^{1a}$— wherein m represents an integer of 1 to 4,
$Y^{1a}$ represents $ORNR^{8a}$ where $R^{8a}$ represents hydrogen atom or $C_{6-10}$ arylsulfonyl which may be substituted by $C_{1-6}$ alkyl, or
(d) —NH—$(CH_2)_r$— wherein r represents an integer of 1 to 4; n represents 1 or 2;
i) $R^1$ and $R^2$ each represents a hydrogen atom or $C_{1-6}$ alkyl which may be substituted by $C_{6-10}$ aryl,
ii) $R^1$ and $R^2$ form, taken together with the adjacent nitrogen atom, morpholine, piperidine, piperazine or pyrrolidine, each of which may be substituted by $C_{6-10}$ aryl, or
iii) $R^1$ together with —$(CH_2)_n$—$N(R^2)$— forms, bonded to a component atom of Ring B, a 6-membered spiro-ring represented by the formula:

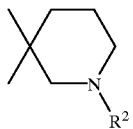

wherein R² represents C₁₋₆ alkyl;
Ring A represents benzene ring which may be substituted by C₁₋₆ alkoxy, C₆₋₁₀ aryl-C₇₋₁₆ aralkyloxy, halogen atom, or optionally halogenated C₁₋₆ alkyl-carboxamido; and
Ring B represents

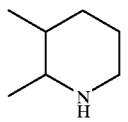 , 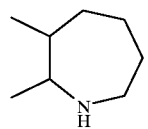 or

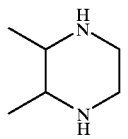

each of which may be substituted by C₁₋₆ alkyl, formyl or C₁₋₆ alkyl-carbonyl;

(15) a compound of the above (14), wherein Y represents
(a) C₂₋₅ alkylene which may be substituted by
① cyano,
② C₆₋₁₀ aryl,
③ C₇₋₁₆ aralkyloxy-carboxamido, or
④ amino,
(b) C₂₋₅ alkenylene,
(c) —(CH)$_m$—Y$^{1a}$— wherein m represents an integer of 1 to 4, Y$^{1a}$ represents O or NR$^{8a}$ where R$^{8a}$ represents hydrogen atom or C₆₋₁₀ arylsulfonyl which may be substituted by C₁₋₆ alkyl, or
(d) —NH—(CH₂)$_r$— wherein r represents an integer of 1 to 4;

(16) a compound of the above (14), wherein X represents CO;
Y represents
(a) C₂₋₅ alkylene which may be substituted by
① a group represented by the formula:

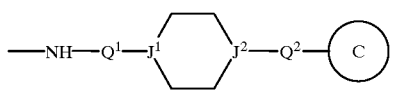

wherein J¹ and J² each represents CH, C(OH) or N; Q¹ and Q² each represents —(CH₂)$_p$— or —(CH₂)$_p$—CO—(CH₂)$_q$— where p and q each represents an integer of 0 to 3;

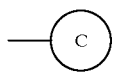

represents (i) a group represented by the formula:

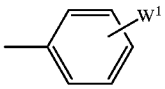

wherein W¹ represents halogen atom, cyano, optionally halogenated C₁₋₆ alkyl, optionally halogenated C₁₋₆ alkoxy, optionally halogenated C₁₋₆ alkyl-carbonyl, nitro, or C₆₋₁₀ aryl;
(ii) pyridyl, or pyrimidinyl, or
(iii) a group represented by the formula:

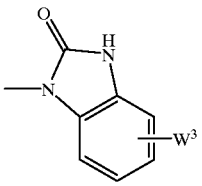 or 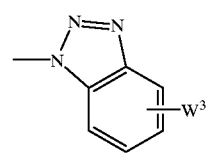

wherein W³ represents hydrogen atom or optionally halogenated C₁₋₆ alkyl,
② C₇₋₁₆ aralkyloxy-carboxamido,
③ amino,
④ C₇₋₁₆ aralkyl-carboxamido,
⑤ C₁₋₆ alkoxy-carbonyl-piperazinyl-carboxamido, or
⑥ a group represented by the formula:

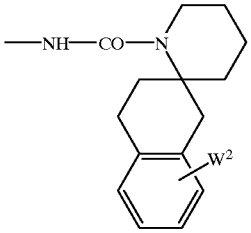

wherein W² represents optionally halogenated C₁₋₆ alkoxy;
(b) —(CH)$_m$—Y$^{1a}$— wherein m represents an integer of 1 to 4,
Y$^{1a}$ represents O or NR$^{8a}$ where R$^{8a}$ represents hydrogen atom or C₆₋₁₀ arylsulfonyl which may be substituted by C₁₋₆ alkyl, or
(c) —NH—(CH₂)$_r$— wherein r represents an integer of 1 to 4;
n represents 1;
i) R¹ and R² each represents a hydrogen atom or C₁₋₆ alkyl;
Ring A represents benzene ring; and
Ring B represents

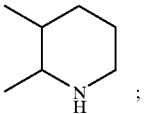 ;

(17) a compound of the above (16), wherein Ar is 3-indolyl;
(18) a compound of the above (1), which is 3-(R)-(N,N-Dimethylamino)methyl-1-[3-(indol-3-yl)-2-[(R)-(4-phenylpiperazin-1-yl)carbonylamino]propanoyl]-1,2,3,4-tetrahydroquinoline or a salt thereof,
3-(S)-(N,N-Dimethylamino)methyl-1-[3-(indol-3-yl)-2-[(R)-(4-phenylpiperazin-1-yl)carbonylamino]propanoyl]-1,2,3,4-tetrahydroquinoline or a salt thereof, 3-(R)-(N,N-Dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline or a salt thereof, 3-(S)-(N,N-Dimethylamino)methyl-1-(3-(indol-3-yl)-2-[(R)-4-(2-oxo-2,3-dihydro-1H-benzimidazol-1-yl)piperidinocarbonylamino]propanoyl]-1,2,3,4-tetrahydroquinoline or a salt thereof, 3-(R)-(N,N-Dimethylamino)methyl-1-[3-(indol-3-yl)-2-(R)-[4-(2-methyl)phenylpiperazin-1-yl]carbonylaminopropanoyl]-1,2,3,4-tetrahydroquinoline or a salt thereof, 3-(S)-(N,N-Dimethylamino)methyl-1-[3-(indol-3-yl)-2-(R)-[4-(2-methyl)phenylpiperazin-1-yl]carbonylaminopropanoyl]-1,2,3,4-tetrahydroquinoline or a salt thereof, 3-(R,S)-(N,N-Dimethylamino)methyl-1-[3-(indol-3-yl)-2-[(R)-1-benzoyl-4-piperidinocarbonylamino]propanoyl]-6-methoxy-1,2,3,4-tetrahydroquinoline or a salt thereof, 6-Chloro-3-(R,S)-(N,N-dimethylamino)methyl-1-[3-(indol-3-yl)-2-[(R)-(4-phenylpiperazin-1-yl)carbonylamino]propanoyl]-1,2,3,4-tetrahydroquinoline or a salt thereof, 6-Chloro-3-(R,S)-(N,N-dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline or a salt thereof, 1-Benzoyl-N-[(R)-2-]6-chloro-3-[(N,N-dimethylamino)methyl]-1,2,3,4-tetrahydroquinolin-1-yl]-1-[3-(indol-3-yl)propanoyl]-4-piperidinecarboxamide or a salt thereof, 1-[3-(4-Biphenylyl)propanoyl]-3-(R)-(N,N-dimethylamino)methyl-1,2,3,4-tetrahydroquinoline p-toluenesulfonate or a salt thereof, or 1-[3-(4-Biphenylyl)propanoyl]-3-(S)-(N,N-dimethylamino)methyl-1,2,3,4-tetrahydroquinoline or a salt thereof;

(19) a process for producing a compound of the above (1), which comprises;
reacting a compound of the formula:

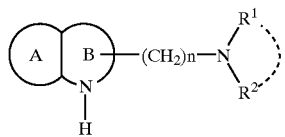

wherein each symbols has the same meanings as in claim 1, or a salt thereof, with a compound of the formula:

wherein L represents a leaving group, and the other symbols have the same meanings as in the above (1), or a salt thereof;

(20) a pharmaceutical composition which comprises a compound of the above (1);

(21) a pharmaceutical composition of the above (20) which is a somatostatin receptor binding inhibitor;

(22) a pharmaceutical composition of the above (21) which is a somatostatin receptor agonist;

(23) a pharmaceutical composition of the above (21) which is a somatostatin receptor antagonist;

(24) a prodrug of a compound of the above (1);

(25) a pharmaceutical composition which comprises a prodrug of the above (24);

(26) a somatostatin receptor binding inhibitor which comprises compound (I');

(27) an inhibitor of the above (26), which is for preventing or treating glaucoma, acromegaly, diabetes, diabetic complications, depression or tumor;

(28) an inhibitor of the above (26), which is an analgesic agent; etc.

The "hydrocarbon group" in the present specification means a group formed by removing one hydrogen atom from a hydrocarbon compound, as exemplified by acyclic or cyclic hydrocarbon group such as alkyl, alkenyl, alkynyl, cycloalkyl, aryl and aralkyl. Among them, the following $C_{1-19}$ acyclic or cyclic hydrocarbon groups are preferable:

a) $C_{1-6}$ alkyl (e.g., methyl, ethyl, propyl, isopropyl, butyl, isobutyl, sec-butyl, tert-butyl, pentyl, hexyl, etc.), b) $C_{2-6}$ alkenyl (e.g., vinyl, allyl, isopropenyl, 2-butenyl, etc.), c) $C_{2-6}$ alkynyl (e.g., ethynyl, propargyl, 2-butynyl, etc.), d) $C_{3-6}$ cycloalkyl (e.g., cyclopropyl, cyclobutyl, cyclopentyl, cyclohexyl, etc.), and $C_{3-6}$ cycloalkyl being optionally condensed with one benzene ring, e) $C_{6-14}$ aryl (e.g., phenyl, 1-naphthyl, 2-naphthyl, 2-indenyl, 2-anthryl, etc.), preferably phenyl, f) $C_{7-9}$ aralkyl (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc.), preferably benzyl.

The "optionally halogenated $C_{1-6}$ alkyl" in the present specification includes, for example, $C_{1-6}$ alkyl (e.g., methyl, ethyl, propyl, isopropyl, butyl, isobutyl, sec-butyl, tert-butyl, pentyl, hexyl, etc.) optionally having 1 to 5, preferably 1 to 3 halogen atoms (e.g., fluorine, chlorine, bromine, iodine, etc.). Thus, for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. can be mentioned.

The "optionally halogenated $C_{3-6}$ cycloalkyl" in the present specification includes, for example, $C_{3-6}$ cycloalkyl (e.g., cyclopropyl, cyclobutyl, cyclopentyl, cyclohexyl, etc.) optionally having 1 to 5, preferably 1 to 3 halogen atoms (e.g., fluorine, chlorine, bromine, iodine, etc.). Thus, for example, cyclopropyl, cyclobutyl, cyclopentyl, cyclohexyl, 4,4-dichlorocyclohexyl, 2,2,3,3-tetrafluorocyclopentyl, 4-chlorocyclohexyl, etc. can be mentioned.

The "optionally halogenated $C_{1-6}$ alkoxy" in the present specification includes, for example, $C_{1-6}$ alkoxy (e.g., methoxy, ethoxy, propoxy, butoxy, pentyloxy, etc.) optionally having 1 to 5, preferably 1 to 3 halogen atoms (e.g., fluorine, chlorine, bromine, iodine, etc.). Thus, for example, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc. can be mentioned.

The "optionally halogenated $C_{1-6}$ alkylthio" in the present specification includes, for example, $C_{1-6}$ alkylthio (e.g., methylthio, ethylthio, propylthio, isopropylthio, butylthio, sec-butylthio, tert-butylthlo, etc.) optionally having 1 to 5, preferably 1 to 3 halogen atoms (e.g., fluorine, chlorine, bromine, iodine, etc.). Thus, for example, methylthio, difluoromethylthio, trifluoromethylthio, ethylthio, propylthio, isopropylthio, butylthio, 4,4,4-trifluorobutylthio, pentylthio, hexylthio, etc. can be mentioned.

The "optionally halogenated $C_{1-6}$ alkyl-carbonyl" in the present specification includes, for example, $C_{1-6}$ alkyl-carbonyl (e.g., acetyl, propanoyl, butanoyl, pentanoyl, hexanoyl, etc.) optionally having 1 to 5, preferably 1 to 3 halogen atoms (e.g., fluorine, chlorine, bromine, iodine, etc.). Thus, for example, acetyl, monochloroacetyl, trifluoroacetyl, trichloroacetyl, propanoyl, butanoyl, pentanoyl, hexanoyl, etc. can be mentioned.

The "optionally halogenated $C_{1-6}$ alkylsulfonyl" in the present specification includes, for example, $C_{1-6}$ alkylsulfonyl (e.g., methylsulfonyl, ethylsulfonyl, propylsulfonyl, isopropylsulfonyl, butylsulfonyl, sec-butylsulfonyl, tert-butylsulfonyl, etc.) optionally having 1 to 5, preferably 1 to 3 halogen atoms (e.g., fluorine, chlorine, bromine, iodine, etc.). Thus, for example, methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl, etc. can be mentioned.

The "optionally halogenated $C_{1-6}$ alkyl-carboxamido" in the present specification includes, for example, $C_{1-6}$ alkyl-carboxamido (e.g., acetamide, etc.) optionally having 1 to 5, preferably 1 to 3 halogen atoms (e.g., fluorine, chlorine, bromine, iodine, etc.). Thus, for example, acetamido, trifluoroacetamido, propanamido, butanamido, etc. can be mentioned.

In the above-mentioned formulae, the "aromatic group" of the "aromatic group which may be substituted" for Ar includes, for example, a monocyclic aromatic group, an aromatic ring assembly group, a fused aromatic group, etc.

The "monocyclic aromatic group" includes, for example, a monovalent group which is derived by removing an optional hydrogen atom from benzene ring, or a 5- or 6-membered aromatic heterocyclic ring.

The "5- or 6-membered aromatic heterocyclic ring" includes, for example, 5- or 6-membered aromatic heterocyclic rings containing one or more (e.g., 1 to 3) hetero atoms selected from the group consisting of nitrogen, sulfur and oxygen atoms in addition to carbon atoms, etc. Concretely mentioned are thiophene, furan, pyrrole, imidazole, pyrazole, thiazole, oxazole, pyridine, pyrazine, pyrimidine, pyridazine, etc.

Concrete examples of the "monocyclic aromatic group" includes, phenyl; 2- or 3-thienyl; 2- or 3-furyl; 1-, 2- or 3-pyrrolyl; 2- or 4-imidazolyl; 3- or 4-pyrazolyl; 2-, 4- or 5-thiazolyl; 2-4- or 5-oxazolyl; 2-. 3- or 4-pyridyl; 2-pyrazinyl; 2-4- or 5-pyrimidinyl; 2-, 4- or 5-pyridazinyl; etc.

The "aromatic ring assembly group" includes, for example, a group derived by removing an optional hydrogen atom from aromatic ring assemblies in which two or more, preferably two or three aromatic rings are directly connected with each other by single bond(s) and the number of such direct ring junctions is one less than the number of the aromatic rings involved. The "aromatic ring" includes, for example, an aromatic hydrocarbon, an aromatic heterocyclic ring, etc.

The above-mentioned "aromatic hydrocarbon" includes, for example, a $C_{6-14}$ monocyclic or fused polycyclic (bi- or tri-cyclic) aromatic hydrocarbon (e.g., benzene, naphthalene, indene, anthracene, etc.).

The above-mentioned "aromatic heterocyclic ring" includes, for example, 5- to 14-membered, preferably 5- to 10-membered aromatic heterocyclic rings containing one or more (e.g., 1 to 4) hetero atoms selected from the group consisting of nitrogen, sulfur and oxygen atoms in addition to carbon atoms, etc. Concretely mentioned is an aromatic heterocyclic ring, such as thiophene, benzothiophene, benzofuran, benzimidazole, benzoxazole, benzothiazole, benzisothiazole, naphtho[2,3-b]thiophene, furan, phenoxathiin, pyrrole, imidazole, pyrazole, oxazole, isoxazole, 1,2,4-oxadiazole, 1,3,4-oxadiazole, 1,2,4-thiadiazole, 1,3,4-thiadiazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, furazan, phenoxazine, phthalimide, etc.; and a ring as formed through condensation of the above ring, preferably a monocyclic ring, with one or more, preferably one or two aromatic rings (e.g., benzene ring, etc.), etc.

The aromatic ring assemblies in which these rings are directly bonded to each other via a single bond includes, for example, one to be composed of two or three, preferably two aromatic rings selected from the group consisting of benzene ring, naphthalene ring and 5- to 10-membered (preferably 5- or 6-membered) aromatic heterocyclic ring. Preferred examples of the aromatic ring assemblies include one composed of two or three aromatic rings selected from the group consisting of benzene, naphthalene, pyridine, pyrimidine, thiophene, furan, thiazole, isothiazole, oxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole, and benzofuran. As specific examples of the aromatic ring assembly group, mentioned are 2-, 3- or 4-biphenylyl; 3-(1-naphthyl)-1,2,4-oxadiazol-5-yl; 3-(2-naphthyl)-1,2,4-oxadiazol-5-yl; 3-(2-benzofuranyl)-1,2,4-oxadiazol-5-yl; 3-phenyl-1,2,4-oxadiazol-5-yl; 3-(2-benzoxazolyl)-1,2,4-oxadiazol-5-yl; 3-(3-indolyl)-1,2,4-oxadiazol-5-yl; 3-(3-indolyl)-1,2,4-oxadiazol-5-yl; 4-phenylthiazol-2-yl; 4-(2-benzofuranyl)-thiazol-2-yl; 4-phenyl-1,3-oxazol-5-yl; 5-phenyl-isothiazol-4-yl; 5-phenyloxazol-2-yl; 4-(2-thienyl)phenyl; 4-(3-thienyl)phenyl; 3-(3-pyridyl)phenyl; 4-(3-pyridyl)phenyl; 6-phenyl-3-pyridyl; 5-phenyl-1,3,4-oxadiazol-2-yl; 4-(2-naphthyl)phenyl; 4-(2-benzofuranyl)phenyl; 4,4'-terphenyl; etc.

The "fused aromatic ring" includes, for example, a monovalent group derived by removing an optional hydrogen atom from a fused polycyclic (preferably bi- or tetra-cyclic, preferably bi- or tri-cyclic) aromatic ring. The "fused polycyclic aromatic ring" includes, for example, a fused polycyclic aromatic hydrocarbon, a fused polycyclic aromatic heterocyclic ring, etc.

The "fused polycyclic aromatic hydrocarbon" includes, for example, a $C_{9-14}$ fused polycyclic (bi- or tri-cyclic) aromatic hydrocarbon (e.g., naphthalene, indene, anthracene, etc.).

The "fused polycyclic aromatic heterocyclic ring" includes, for example, 9- to 14-membered, preferably 9- to 10-membered fused polycyclic aromatic heterocyclic rings containing one or more (e.g., 1 to 4) hetero atoms selected from the group consisting of. nitrogen, sulfur and oxygen atoms in addition to carbon atoms, etc. Concretely mentioned is an aromatic heterocyclic ring, such as benzofuran, benzimidazole, benzoxazole, benzothiazole, benzisothiazole, naphtho[2,3-b]thiophene, isoquinoline, quinoline, indole, quinoxaline, phenanthridine, phenothiazine, phenoxazine, phthalimide, and etc.

Specific examples of the "fused aromatic ring" includes, for example, 1-naphthyl, 2-naphthyl, 2-quinolyl, 3-quinolyl, 4-qunolyl, 2-benzofuranyl, 2-benzothiazolyl, 2-benzimidazolyl, 1-indolyl, 2-indolyl, 3-indolyl, etc.

Among the above groups, those preferred as the aromatic ring for Ar are
(i) monocyclic aromatic groups such as phenyl; 2-, 4- or 5-thiazolyl; 2-, 4- or 5-oxazolyl; 2-, 3- or 4-pyridyl; 1,2,4- or 1,3,4-oxadiazlolyl; and etc.;
(ii) aromatic ring assembly groups such as 2-, 3- or 4-biphenylyl; 3-(1-naphthyl)-1,2,4-oxadiazlol-5-yl; 3-(2-naphthyl)-1,2,4-oxadiazol-5-yl; 3-(2-benzofuranyl)-1,2,4- oxadiazol-5-yl; 3-phenyl-1,2,4-oxadiazol-5-yl; 3-(2-benzoxazolyl)-1,2,4-oxadiazol-5-yl; 3-(3-indolyl)-1,2,4-oxadiazol-5-yl; 3-(2-indolyl)-1,2,4-oxadiazol-5-yl; 4-phenylthiazol-2-yl; 4-(2-benzofuranyl)thiazol-2-yl; 4-phenyl-1,3-oxazol-5-yl; 5-phenyloxazol-2-yl; 4-(2-thienyl)phenyl; 4-(3-pyridyl)phenyl; 4-(2-naphthyl)phenyl; 4,4'-terphenyl; and etc.;

(iii) fused aromatic groups such as 2-, 3- or 4-quinolyl; 1-, 2- or 3-indolyl; etc.

The "substituent" for the "aromatic group which may be substituted" includes, for example, halogen atoms (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-6}$ alkyl, $C_{6-10}$ aryloxy-$C_{1-6}$ alkyl (e.g., phenoxymethyl, etc.), $C_{1-6}$ alkyl-$C_{6-10}$ aryl-$C_{2-6}$ alkenyl (e.g., methylphenylethenyl etc.), optionally halogenated $C_{3-6}$ cycloalkyl, $C_{7-16}$ aralkyl which may be substituted, optionally halogenated $C_{1-6}$ alkoxy, optionally halogenated $C_{1-6}$ alkylthio, hydroxy, $C_{6-10}$ aryloxy which may be substituted, $C_{6-10}$ aryl-$C_{7-16}$ aralkyloxy (e.g., phenylbenzyloxy etc.), amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), 5- to 7-membered saturated cyclic amino which may be substituted, acyl, acylamino, acyloxy. Among these groups, preferred are halogen atoms, $C_{1-3}$ alkylenedioxy, optionally halogenated $C_{1-6}$ alkyl, $C_{6-10}$ aryloxy-$C_{1-6}$ alkyl, $C_{1-6}$ alkyl-$C_{6-10}$ aryl-$C_{2-6}$ alkenyl, $C_{7-16}$ aralkyl which may be substituted, optionally halogenated $C_{1-6}$ alkoxy, hydroxy, $C_{6-10}$ aryloxy which may be substituted, acyl, acyloxy, etc.

The "aromatic group" may have 1 to 5, preferably 1 to 3 of the above substituents at substitutable positions on the aromatic group. When the number of the substituents is two or more, those substituents may be the same or different.

The "$C_{7-16}$ aralkyl" for the "$C_{7-16}$ aralkyl which may be substituted" includes, for example, benzyl, phenethyl, naphthylmethyl, etc.

The "$C_{6-10}$ aryloxyn for the "$C_{6-10}$ aryloxy which may be substituted" includes, for example, phenyloxy, naphthyloxy, etc.

The "substituent" for these "$C_{7-6}$ aralkyl which may be substituted" and "$C_{6-10}$ aryloxy which may be substituted" includes, for example, 1 to 5 substituents selected from the group consisting of halogen atoms (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), formyl, carboxy, carbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamido, $C_{1-6}$ alkoxy-carboxamido (e.g., methoxycarboxamido, ethoxycarboxamido, propoxycarboxamido, butoxycarboxamido, etc.), $C_{1-6}$ alkylsulfonylamIno (e.g., methylsulfonylamino, ethylsulfonylamino, etc.), $C_{1-6}$ alkyl-carbonyloxy (e.g., acetoxy, propanoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), etc.

The "5- to 7-membered saturated cyclic amino" for the above "5- to 7-membered saturated cyclic amino which may be substituted" includes, for example, morpholino, thiomorpholino, piperazin-1-yl, piperidino, pyrrolidin-1-yl, hexamethyleneimin-1-yl, etc.

The "substituent" for the "5- to 7-membered saturated cyclic amino which may be substituted" includes, for example, 1 to 3 substituents selected from the group consisting of $C_{1-6}$ alkyl, $C_{6-14}$ aryl which may be substituted, $C_{7-19}$ aralkyl which may be substituted, 5- to 10-membered aromatic heterocyclic group which may be substituted, $C_{6-14}$ aryl-carbonyl which may be substituted, optionally halogenated $C_{1-6}$ alkyl-carbonyl, optionally halogenated $C_{1-6}$ alkylsulfonyl, etc.

The "$C_{6-14}$ aryl" for the "$C_{6-14}$ aryl which may be substituted" includes, for example, phenyl, 1-naphthyl, 2-naphthyl, 2-indenyl, 2-anthryl, etc. Preferred is phenyl.

The "$C_{7-19}$ aralkyl" for the "$C_{7-19}$ aralkyl which may be substituted" includes, for example, benzyl, phenethyl, diphenylmethyl, triphenylmethyl, 1-naphthylmethyl, 2-naphthylmethyl, 2,2-diphenylmethyl, 3-phenylpropyl, 4-phenylbutyl, 5-phenylpentyl, etc. Preferred is benzyl.

The "5- to 10-membered aromatic heterocyclic group" for the above "5- to 10-membered aromatic heterocyclic group which may be substituted" includes, for example, 2-, 3- or 4-pyridyl; 1-, 2- or 3-indolyl; 2- or 3-thienyl; etc. Preferred are 2-, 3- or 4-pyridyl, etc.

The "$C_{6-10}$ aryl-carbonyl" for the "$C_{6-10}$ aryl-carbonyl which may be substituted" includes, for example, benzoyl, 1-naphthoyl, 2-naphthoyl, etc.

The "substituent" for these "$C_{6-14}$ aryl which may be substituted", "$C_{7-19}$ aralkyl which may be substituted", "5- to 10-membered aromatic heterocyclic group which may be substituted" and "$C_{6-10}$ aryl-carbonyl which may be substituted" includes, for example, 1 to 5 substituents selected from the group consisting of halogen atoms (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g., methylamino, ethylamino, propylamino, isopropylamino, butylamino, etc.), di-$C_{1-6}$ alkylamino (e.g., dimethylamino, diethylamino, dipropylamino, dibutylamino, ethylmethylamino, etc.), formyl, carboxy, carbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamido, $C_{1-6}$ alkoxy-carboxamido (e.g., methoxycarboxamido, ethoxycarboxamido, propoxycarboxamido, butoxycarboxamido, etc.), $C_{1-6}$ alkylsulfonylamino (e.g., methylsulfonylamino, ethylsulfonylamino, etc.), $C_{1-6}$ alkyl-carbonyloxy (e.g., acetoxy, propanoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), etc.

The "acyl" as the "substituent" for the "aromatic group which may be substituted", and the "acyl" in the "acylamino" and the "acyloxy" include, for example, an acyl represented by the formula:

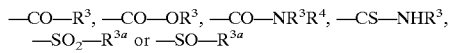

where $R^3$ is (i) hydrogen,
(ii) a hydrocarbon group which may be substituted, for example, a hydrocarbon group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered cyclic amino which may be substituted, formyl, carboxy, carbamoyl, optionally halogenated $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, optionally halogenated $C_{1-6}$ alkylsulfonyl, $C_{6-10}$ arylsulfonyl, formylamino, optionally halogenated $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or
(iii) a heterocyclic group which may be substituted, for example, a heterocyclic group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered cyclic amino which may be substituted, formyl, carboxy, carbamoyl, optionally halogenated $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, optionally halogenated $C_{1-6}$ alkylsulfonyl, $C_{6-10}$ arylsulfonyl, formylamino, optionally halogenated $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$_{1-6}$ alkyl-carbamoyloxy, $C_{6-10}$ aryl-carbamoyloxy, nicotinoyloxy and $C_{6-10}$ aryloxy;
$R^{3a}$ is (i) a hydrocarbon group which may be substituted, for example, a hydrocarbon group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$, cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, 5- to 7-membered cyclic amino which may be substituted, formyl, carboxy, carbamoyl, optionally halogenated $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, optionally halogenated $C_{1-6}$ alkylsulfonyl, $C_{6-10}$ arylsulfonyl, formylamino, optionally halogenated $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy, or
(ii) a heterocyclic group which may be substituted, for example, a heterocyclic group which may be substituted by 1 to 5 substituents selected from the group consisting of halogen atoms, $C_{1-3}$ alkylenedioxy, nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$Cl_{1-6}$ alkylamino, di-$C_{1-6}$ alkylamino, 5- to 7-membered cyclic amino which may be substituted, formyl, carboxy, carbamoyl, optionally halogenated $C_{1-6}$ alkyl-carbonyl, $C_{1-6}$ alkoxy-carbonyl, $C_{6-10}$ aryl-carbonyl, $C_{6-10}$ aryloxy-carbonyl, $C_{7-16}$ aralkyloxy-carbonyl, mono-$C_{1-6}$ alkyl-carbamoyl, di-$C_{1-6}$ alkyl-carbamoyl, $C_{6-10}$ aryl-carbamoyl, optionally halogenated $C_{1-6}$ alkylsulfonyl, $C_{6-10}$ arylsulfonyl, formylamino, optionally halogenated $C_{1-6}$ alkyl-carboxamido, $C_{6-10}$ aryl-carboxamido, $C_{1-6}$ alkoxy-carboxamido, $C_{1-6}$ alkylsulfonylamino, $C_{1-6}$ alkyl-carbonyloxy, $C_{6-10}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-10}$ aryl-carbamoyloxy, nicotinoyloxy and $C_{6-10}$ aryloxy;
$R^4$ represents hydrogen atom or $C_{1-6}$ alkyl, or
$R^3$ and $R^4$, taken together with the adjacent nitrogen atom, may form a nitrogen-containing heterocyclic ring.

The "5- to 7-membered cyclic amino which may be substituted" as the substituent for $R^3$ and $R^{3a}$ includes the same as those mentioned above for the substituent of the aromatic group for Ar.

The above-mentioned "heterocyclic group" includes, for example, a group derived by removing an optional hydrogen atom from 5- to 14-membered (monocyclic, di- or tri-cyclic) heterocyclic rings containing 1 to 4 of 1 or 2 kinds of hetero atoms selected from the group consisting of nitrogen, sulfur and oxygen atoms in addition to carbon atoms, etc. Preferred examples of the heterocyclic rings include (i) 5- to 14-membered, preferably 5- to 10-membered aromatic heterocyclic rings, (ii) 5- to 10-membered non-aromatic heterocyclic rings, and (iii) 7- to 10-membered bridged heterocyclic rings.

The above-mentioned "5- to 14-membered, preferably 5- to 10-membered aromatic heterocyclic rings" includes, for example, an aromatic heterocyclic ring, such as thiophene, benzothiophene, benzofuran, benzimidazole, benzoxazole, benzothiazole, benzisothiazole, naphtho[2,3-b]thiophene, furan, phenoxathuin, pyrrole, imidazole, pyrazole, oxazole, 1,2,4-oxadiazole, 1,3,4-oxadiazole, 1,2,4-thiadiazole, 1,3,4-thiadiazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc.; and a ring as formed through condensation of these rings, preferably monocyclic ring, with one or more, preferably one or two aromatic rings (e.g., benzene ring, etc.), etc.

The above-mentioned "5- to 10-membered non-aromatic heterocyclic rings" includes, for example, pyrrolidine, imidazoline, pyrazolidine, piperidine, piperazine, morpholine, thiomorpholine, etc.

The above-mentioned "7- to 10-membered bridged heterocyclic rings" includes, for example, quinuclidine, 7-azabicyclo[2.2.1]heptane, etc.

The "heterocyclic group" is preferably 5- to 10-membered (monocyclic or dicyclic) heterocyclic groups containing preferably 1 to 4 of 1 or 2 kinds of hetero atoms selected from the group consisting of nitrogen, sulfur and oxygen atoms in addition to carbon atoms, etc. Concretely mentioned are aromatic heterocyclic groups such as 2- or 3-thienyl; 2-, 3- or 4-pyridyl; 2- or 3-furyl; 2-, 3-, 4-, 5- or 8-quinolyl; 4-isoquinolyl; pyrazinyl; 2- or 4-pyrimidinyl; 3-pyrrolyl; 2-imidazolyl; 3-pyridazinyl: 3-isothiazolyl; 3-isooxazoyl; 1-indolyl; 2-indolyl; 2-isoindolyl; and etc.; non-aromatic heterocyclic groups such as 1-, 2- or 3-pyrrolidinyl; 2- or 4-imidazolinyl; 2-, 3- or 4-pyrazolidinyl; piperidino; 2-, 3- or 4-piperidyl; 1- or 2-piperazinyl; morpholino; etc.

Among these groups, 5- or 6-membered heterocyclic groups containing 1 to 3 hetero atoms selected from the group consisting of nitrogen, sulfur and oxygen atoms in addition to carbon atoms, etc. are more preferable. Concretely mentioned are 2-thienyl; 3 -thienyl; 2- pyridyl; 3-pyridyl; 4-pyridyl; 2-furyl; 3-furyl; pyrazinyl; 2-pyrimidinyl; 3-pyrrolyl; 3-pyridazinyl: 3-isothiazolyl; 3-isooxazoyl; 1-, 2- or 3-pyrrolidinyl; 2- or 4 -imidazolinyl; 2-, 3- or 4-pyrazolidinyl; piperidino; 2-, 3- or 4-piperidyl; 1- or 2-piperazinyl; morpholino; etc.

The "$C_{1-6}$ alkyl" for $R^4$ includes, for example, methyl, ethyl, propyl, isopropyl, butyl, isobutyl, sec-butyl, tert-butyl, pentyl, hexyl, etc.

The "nitrogen-containing heterocyclic ring" as formed by $R^3$ and $R^4$ together with the adjacent nitrogen atom includes, for example, 5- to 7-membered nitrogen-containing heterocyclic groups containing at least one nitrogen atom and optionally 1 to 3 hetero atoms selected from the group consisting of nitrogen, sulfur and oxygen atoms in addition to carbon atoms, etc. Concretely mentioned are piperidine, morpholine, thiomorpholine, piperazine, pyrrolidine, etc.

Preferred examples of the "acyl" as the "substituent" for the "aromatic group which may be substituted" for Ar include formyl, carboxy, carbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), $C_{6-10}$ aryl-carbonyl which may be substituted, $C_{6-10}$ aryloxy-carbonyl which maybe substituted, $C_{7-16}$ aralkyloxy-carbonyl which may be substituted, 5- or 6-membered heterocyclic-carbonyl which may be substituted, mono-$C_{1-6}$ alkyl-carbamoyl, di-$C_{1-6}$ alkyl-carbamoyl (e.g., dimethylcarbamoyl, diethylcarbamoyl, ethylmethylcarbamoyl, etc.), $C_{6-10}$ aryl-carbamoyl which may be substituted, 5- or 6-membered heterocyclic-carbamoyl which may be substituted, optionally halogenated $C_{1-6}$ alkylsulfonyl, $C_{6-10}$ arylsulfonyl which may be substituted, etc. Among these, preferred are optionally halogenated $C_{1-6}$ alkyl-carbonyl, $C_{1-6}$ alkoxy-carbonyl (e.g., ethoxycarbonyl, etc.), $C_{6-10}$ aryl-carbonyl which may be substituted, $C_{6-10}$ arylsulfonyl which may be substituted, etc.

The "$C_{6-10}$ aryl-carbonyl" for the above "$C_{6-10}$ aryl-carbonyl which may be substituted" includes, for example, benzoyl, 1-naphthoyl, 2-naphthoyl, etc.

The "$C_{6-10}$ aryloxy-carbonyl" for the above "$C_{6-10}$ aryloxy-carbonyl which may be substituted" includes, for example, phenoxycarbonyl, etc.

The "$C_{7-16}$ aralkyloxy-carbonyl" for the above "$C_{7-16}$ aralkyloxy-carbonyl which may be substituted" includes, for example, benzyloxycarbonyl, phenethyloxycabornyl, etc.

The "5- or 6-membered heterocyclic-carbonyl" for the above "5- or 6-membered heterocyclic-carbonyl which may be substituted" includes, for example, nicotinoyl, isonicotinoyl, 2-thenoyl, 3-thenoyl, 2-furoyl, 3-furoyl, morpholinocarbonyl, piperidinocarbonyl, pyrrolidin-1-ylcarbonyl, etc.

The "$C_{6-10}$ aryl-carbamoyl" for the above "$C_{6-10}$ aryl-carbamoyl which may be substituted" includes, for example, phenylcarbamoyl, 1-naphthylcarbamoyl, 2-naphthylcarbamoyl, etc.

The "5- or 6 -membered heterocyclic-carbamoyl" for the above "5- or 6-membered heterocyclic-carbamoyl which may be substituted" includes, for example, 2-pyridylcarbamoyl, 3-pyridylcarbamoyl, 4-pyridylcarbamoyl, 2-thienylcarbamoyl, 3-thienylcarbamoyl, etc.

The "C6-10 arylsulfonyl" for the above "$C_{6-10}$ arylsulfonyl which may be substituted" includes, for example, benzenesulfonyl, 1-naphthalenesulfonyl, 2-naphthalenesulfonyl, etc.

The "substituent" for these "$C_{6-10}$ aryl-carbonyl which may be substituted", "$C_{6-10}$ aryloxy-carbonyl which may be substituted", "$C_{7-16}$ aralkyloxy-carbonyl which may be substituted", "5- or 6-membered heterocyclic-carbonyl which may be substituted", "$C_{6-10}$ aryl-carbamoyl which may be substituted", "5- or 6-membered heterocyclic-carbamoyl which may be substituted" and "$C_{6-10}$ arylsulfonyl which may be substituted" includes, for example, 1 to 5, preferably 1 to 3 substituents selected from the group consisting of halogen atoms, $C_{1-3}$ alkylenedioxy, nitro, cyano, optionally halogenated $C_{1-6}$ alkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, formyl, carboxy, carbamoyl, optionally halogenated $C_{1-6}$ alkyl-carbonyl, $C_{1-6}$ alkoxy-carbonyl, mono-$C_{1-6}$ alkyl-carbamoyl, di-$C_{1-6}$ alkyl-carbamoyl, optionally halogenated $C_{1-6}$ alkylsulfonyl, formylamino, optionally halogenated $C_{1-6}$ alkyl- carboxamido, $C_{1-6}$ alkoxy-carboxamido, $C_{1-6}$ alkylsulfonylamino, $C_{1-6}$ alkyl-carbonyloxy, $C_{1-6}$ alkoxy-carbonyloxy, mono-$C_{1-6}$ alkyl-carbamoyloxy, di-$C_{1-6}$ alkyl-carbamoyloxy, and etc. Among these, preferred are halogen atoms, optionally halogenated $C_{1-6}$ alkyl, optionally halogenated $C_{1-6}$ alkoxy, etc.

The "acylamino" as the above-mentioned "substituent" for the "aromatic group which may be substituted" for Ar includes, for example, an amino substituted by 1 or 2 "acyl" described in detail in the foregoing referring to the "substituent" for the "aromatic group which may be substituted". Preferred is an acylamino of the formula:

wherein $R^5$ represents hydrogen or $C_{1-6}$ alkyl, $R^6$ has the same meanings as the above $R^3$, $R^{6a}$ has the same meanings as the above $R^{3a}$, $R^{6b}$ has the same meanings as the above $R^{3b}$.

The "$C_{1-6}$ alkyl" for $R^5$ and $R^{6b}$ includes the same as "$C_{1-6}$ alkyl" for $R^4$.

Preferred examples of the "acylamino" as the "substituent" for the "aromatic group which may be substituted" for Ar are formylamino, optionally halogenated $C_{1-6}$ alkyl-carboxamido, $C_{6-10}$ aryl-carboxamido which may be substituted (e.g., phenylcarboxamido, naphthylcarboxamido, etc.), $C_{1-6}$ alkoxy-carboxamido (e.g., methoxycarboxamido, ethoxycarboxamido, propoxycarboxamido, butoxycarboxamido, etc.), $C_{1-6}$ alkylsulfonylamino (e.g., methylsulfonylamino, ethylsulfonylamino, etc.), etc.

The "acyloxy" as the "substituent" for the "aromatic group which may be substituted" for Ar includes, for example, an oxy substituted by one "acyl" described in detail in the foregoing referring to the "substituent" for the "aromatic group which may be substituted". Preferred is an acyloxy of the formula:

wherein $R^7$ has the same meanings as the above $R^3$.

Preferred examples of the "acyloxy" as the "substituent" for the "aromatic group which may be substituted" for Ar are $C_{1-6}$ alkyl-carbonyloxy (e.g., acetoxy, propanoyloxy, etc.), $C_{6-10}$ aryl-carbonyloxy which may be substituted (e.g., benzoyloxy, 1-naphthoyloxy, 2-naphthoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.), $C_{6-10}$ aryl-carbamoyloxy which may be substituted (e.g., phenylcarbamoyloxy, naphthylcarbamoyloxy, etc.), nicotinoyloxy, etc.

The "substituent" and "its preferred examples" for the above "$C_{6-10}$ aryl-carboxamido which may be substituted", "$C_{6-10}$ aryl-carbonyloxy which may be substituted" and "$C_{6-10}$ aryl-carbamoyloxy which may be substituted", include the same as those described in the above "$C_{6-10}$ aryl-carbonyl which may be substituted" as the substituent of the aromatic group for Ar.

Among the above-mentioned substituents, preferred examples of the substituent of the aromatic group for Ar are halogen atoms (e.g., fluorine, chlorine, bromine, etc.); $C_{1-3}$ alkylenedioxy (e.g., methylenedioxy, etc.); optionally halogenated $C_{1-6}$ alkyl (e.g., methyl, etc.); $C_{6-10}$ aryloxy-$C_{1-6}$ alkyl (e.g., phenoxymethyl, etc.); $C_{1-6}$ alkyl-$C_{6-10}$ aryl-$C_{2-6}$ alkenyl (e.g., methylphenylethenyl, etc.); $C_{7-16}$ aralkyl (e.g., benzyl, etc.) which may be substituted by halogen atoms (e.g., chlorine, etc.) or $C_{1-6}$ alkoxy (e.g., methoxy, etc.); optionally halogenated $C_{1-6}$ alkoxy (e.g., methoxy, etc.); hydroxy; $C_{6-10}$ aryloxy (e.g., phenoxy, etc.) which may be substituted by halogen atoms (e.g., chlorine, etc.) or $C_{1-6}$ alkoxy (e.g., methoxy, etc.); optionally halogenated $C_{1-6}$ alkyl-carbonyl (e.g., acetyl, etc.); $C_{1-6}$ alkoxy-carbonyl (e.g., ethoxycarbonyl, etc.); $C_{6-10}$ aryl-carbonyl; $C_{6-10}$ arylsulfonyl (e.g., phenylsulfonyl, etc.) which may be substituted by $C_{1-6}$ alkyl (e.g., isopropyl, etc.).

The "spacer having a main chain of 2 to 5 atoms" for Y means a space between X and Ar in which 2 to 5 atoms of a main chain are combined in a straight-chain form. In the present specification, the "number of atoms" is counted so that the number of atoms between X and Ar is minimum.

The "spacer having a main chain of 2 to 5 atoms" includes, for example, divalent groups having a main chain of 2 to 5 atoms, and selected from the group consisting of $C_{1-5}$ alkylene which may be substituted; $C_{2-5}$ alkenylene which maybe substituted; $C_{2-5}$ alkynylene which may be substituted; —O—; —S—; —SO—; —SO$_2$—; and a group represented by the formula: —NR$^8$— where R$^8$ represents hydrogen, a hydrocarbon group which may be substituted or acyl.

These "divalent groups" may form Y by the combination of 1 to 3 of them, and each group may be the same or different when two or more of these divalent groups are combined.

The "$C_{1-5}$ alkylene" for the "$C_{1-5}$ alkylene which may be substituted" includes, for example, —CH$_2$—, —(CH$_2$)$_2$—, —(CH$_2$)$_3$—, —(CH$_2$)$_4$—, —(CH$_2$)$_5$—, etc.

The "$C_{2-5}$ alkenylene" for the "$C_{2-5}$ alkenylene which may be substituted" includes, for example, —CH═CH—, —CH$_2$—CH═CH—, —CH$_2$—CH═CH—CH$_2$—, —CH$_2$—CH$_2$—CH═CH—, —CH═CH—CH═CH—, —CH═CH— CH$_2$—CH$_2$—CH$_2$—, etc.

The "$C_{2-5}$ alkynylene" for the "$C_{2-5}$ alkynylene which may be substituted" includes, for example, —C≡C—, —CH$_2$—C≡C—, —CH$_2$—C≡C—CH$_2$—CH$_2$—, etc.

The "substituent" for these "$C_{1-5}$ alkylene which may be substituted", "$C_{2-5}$ alkenylene which may be substituted" and "$C_{2-5}$ alkynylene which may be substituted"; and the "substituent" for the "hydrocarbon group which may be substituted" for R$^8$ includes, for example, 1 to 5, preferably 1 to 3 substituents selected from the group consisting of halogen atoms (e.g., fluorine, chlorine, bromine, etc.); $C_{1-3}$ alkylenedioxy (e.g., methylenedioxy, etc.); nitro; cyano; optionally halogenated $C_{1-6}$ alkyl; optionally halogenated $C_{3-6}$ cycloalkyl; $C_{6-10}$ aryl which may be substituted; 5- to 10-membered aromatic heterocyclic group which may be substituted; optionally halogenated $C_{1-6}$ alkoxy; optionally halogenated $C_{1-6}$ alkylthio; hydroxy; amino; mono-$C_{1-6}$ alkylamino (e.g., methylamino, ethylamino, propylamino, isopropylamino, butylamino, etc.); di-$C_{1-6}$ alkylamino (e.g., dimethylamino, diethylamino, dipropylamino, dibutylamino, ethylmethylamino, etc.); formyl; carboxy; carbamoyl; optionally halogenated $C_{1-6}$ alkyl-carbonyl; $C_{1-6}$ alkoxy-carbonyl (e.g., methoxycarbonyl, ethoxycarbonyl, propoxycarbonyl, tert-butoxycarbonyl, etc.); $C_{6-10}$ aryl-carbonyl which may be substituted; $C_{6-10}$ aryloxy-carbonyl which may be substituted; $C_{7-16}$ aralkyloxy-carbonyl which may be substituted; 5- or 6-membered heterocyclic-carbonyl (e.g., nicotinoyl, isonicotinoyl, 2-thenoyl, 3-thenoyl, 2-furoyl, 3-furoyl, morpholinocarbonyl, piperidinocarbonyl, pyrrolidin-1-ylcarbonyl, etc.); mono-$C_{1-6}$ alkyl-carbamoyl (e.g., methylcarbamoyl, ethylcarbamoyl, etc.); di-$C_{1-6}$ alkyl-carbamoyl (e.g., dimethylcarbamoyl, diethylcarbamoyl, ethylmethylcarbamoyl, etc.); $C_{6-10}$ aryl-carbamoyl which may be substituted; 5- or 6-membered heterocyclic-carbamoyl (e.g., 2-pyridylcarbamoyl, 3-pyridylcarbamoyl, 4-pyridylcarbamoyl, 2-thienylcarbamoyl, 3-thienylcarbamoyl, etc.); optionally halogenated $C_{1-6}$ alkylsulfonyl (e.g., methylsulfonyl, ethylsulfonyl, etc.); $C_{6-10}$ arylsulfonyl which may be substituted; formylamino; acylamino; $C_{1-6}$ alkyl-carbonyloxy (e.g., acetoxy, propanoyloxy, etc.); $C_{6-10}$ aryl-carbonyloxy which may be substituted; $C_{1-6}$ alkoxy-carbonyloxy (e.g., methoxycarbonyloxy, ethoxycarbonyloxy, propoxycarbonyloxy, butoxycarbonyloxy, etc.); mono-$C_{1-6}$ alkyl-carbamoyloxy (e.g., methylcarbamoyloxy, ethylcarbamoyloxy, etc.); di-$C_{1-6}$ alkyl-carbamoyloxy (e.g., dimethylcarbamoyloxy, diethylcarbamoyloxy, etc.); $C_{6-10}$ aryl-carbamoyloxy which may be substituted; and nicotinoyloxy which may be substituted; etc. When the number of the substituent is 2 or more, these substituents may be the same or different.

The "$C_{6-10}$ aryl" for the above "$C_{6-10}$ aryl which may be substituted" includes, for example, phenyl, 1-naphthyl, 2-naphthyl, etc. The "5- to 10-membered aromatic heterocyclic group" for the above "5- to 10-membered aromatic heterocyclic group which may be substituted" includes, for example, 2-, 3- or 4-pyridyl; 1-, 2- or 3-indolyl; 2- or 3-thienyl; etc.

The "$C_{6-10}$ aryl-carbonyl" for the above "$C_{6-10}$ aryl-carbonyl which may be substituted" includes, for example, benzoyl, 1-naphthoyl, 2-naphthoyl, etc.

The "$C_{6-10}$ aryloxy-carbonyl" for the above "$C_{6-10}$ aryloxy-carbonyl which may be substituted" includes, for example, phenoxycarbonyl, etc.

The "C$_{7-16}$ aralkyloxy-carbonyl" for the above "C$_{7-16}$ aralkyloxy-carbonyl which may be substituted" includes, for example, benzyloxycarbonyl, phenethyloxycabornyl, etc.

The "C$_{6-10}$ aryl-carbamoyl" for the above "C$_{6-10}$ aryl-carbamoyl which may be substituted" includes, for example, phenylcarbamoyl, 1-naphthylcarbamoyl, 2-naphthylcarbamoyl, etc.

The "C$_{6-10}$ arylsulfonyl" for the above "C$_{6-10}$ arylsulfonyl which may be substituted" includes, for example, benzenesulfonyl, 1-naphthalenesulfonyl, 2-naphthalenesulfonyl, etc.

The "C$_{6-10}$ aryl-carbonyloxy" for the above "C$_{6-10}$ aryl-carbonyloxy which may be substituted" includes, for example, benzoyloxy, 1-naphthoyloxy, 2-naphthoyloxy, etc.

The "C$_{6-10}$ aryl-carbamoyloxy" for the above "C$_{6-10}$ aryl-carbamoyloxy which may be substituted" includes, for example, phenylcarbamoyloxy, naphthylcarbamoyloxy, etc.

The "substituent" for these "C$_{6-10}$ aryl which may be substituted", "5- to 10-membered aromatic heterocyclic group which may be substituted", "C$_{6-10}$ aryl-carbonyl which may be substituted", "C$_{6-10}$ aryloxy-carbonyl which may be substituted", "C$_{7-16}$ aralkyloxy-carbonyl which may be substituted", "C$_{6-10}$ aryl-carbamoyl which may be substituted", "C$_{6-10}$ arylsulfonyl which may be substituted", "C$_{6-10}$ aryl-carbonyloxy which may be substituted", "C$_{6-10}$ aryl-carbamoyloxy which may be substituted"; and "nicotinoyloxy which may be substituted" includes, for example, 1 to 5 substituents selected from the group consisting of halogen atoms (e.g., fluorine, chlorine, bromine, iodine, etc.); C$_{1-3}$ alkylenedioxy (e.g., methylenedioxy, ethylenedioxy, etc.); nitro; cyano; optionally halogenated C$_{1-6}$ alkyl; optionally halogenated C$_{3-6}$ cycloalkyl; optionally halogenated C$_{1-6}$ alkoxy; optionally halogenated C$_{1-6}$ alkylthio; hydroxy; amino; mono-C$_{1-6}$ alkylamino (e.g., methylamino, ethylamino, propylamino, isopropylamino, butylamino, etc.); di-C$_{1-6}$ alkylamino (e.g., dimethylamino, diethylamino, dipropylamino, dibutylamino, ethylmethylamino, etc.); formyl; carboxy; carbamoyl: optionally halogenated C$_{1-6}$ alkyl-carbonyl; C$_{1-6}$ alkoxy-carbonyl (e.g., methoxycarbonyl, ethoxycarbonyl, propoxycarbonyl, tert-butoxycarbonyl, etc.); mono-C$_{1-6}$ alkyl-carbamoyl (e.g., methylcarbamoyl, ethylcarbamoyl, etc.); di-C$_{1-6}$ alkyl-carbamoyl (e.g., dimethylcarbamoyl, diethylcarbamoyl, ethylmethylcarbamoyl, etc.); optionally halogenated C$_{1-6}$ alkylsulfonyl; formylamino; optionally halogenated C$_{1-6}$ alkyl-carboxamido; C$_{1-6}$ alkoxy-carboxamido (e.g., methoxycarboxamido, ethoxycarboxamido, propoxycarboxamido, butoxycarboxamido, etc.); C$_{1-6}$ alkylsulfonylamino (e.g., methylsulfonylamino, ethylsulfonylamino, etc.); C$_{1-6}$ alkyl-carbonyloxy (e.g., acetoxy, propanoyloxy, etc.); C$_{1-6}$ alkoxy-carbonyloxy (e.g., methoxycarbonyloxy, ethoxycarbonyloxy, propoxycarbonyloxy, butoxycarbonyloxy, etc.); mono-C$_{1-6}$ alkyl-carbamoyloxy (e.g., methylcarbamoyloxy, ethylcarbamoyloxy, etc.); di-C$_{1-6}$ alkyl-carbamoyloxy (e.g., dimethylcarbamoyloxy, diethylcarbamoyloxy, etc.); etc.

The "acyl" for R$^8$ includes the same as the above-mentioned "acyl" as the "substituent" for the "aromatic group which may be substituted" for Ar.

The "acylamino" as the "substituent" for "C$_{1-5}$ alkylene which may be substituted", "C$_{2-5}$ alkenylene which may be substituted" and "C$_{2-5}$ alkynylene which may be substituted" as the spacer for Y; and the "acylamino" as the "substituent" for the "hydrocarbon group which may be substituted" for R$^8$ includes, the same as the above-mentioned "macylamino" as the "substituent" for the "aromatic group which may be substituted" for Ar. Concrete examples of the acylamino include formylamino; optionally halogenated C$_{1-6}$ alkyl-carboxamido; C$_{6-10}$ aryl-carboxamido which may be substituted (e.g., phenylcarboxamido, naphthylcarboxamido, etc.); C$_{7-15}$ aralkyl-carboxamido (e.g., phenylethylcarboxamido, etc.); C$_{7-16}$ aralkyloxy-carboxamido which may be substituted (e.g., benzyloxycarboxamido, fluorenylmethyloxycarboxamido, etc.); C$_{1-6}$ alkoxy-carboxamido (e.g., methoxycarboxamido, ethoxycarboxamido, propoxycarboxamido, butoxycarboxamido. etc.); C$_{1-6}$ alkylsulfonylamino (e.g., methylsulfonylamino, ethylsulfonylamino, etc.); spiro [naphthalene-2,2'-piperidin]-1'-yl-carboxamido which may be substituted by C$_{1-6}$ alkoxy (e.g., methoxy, etc.); a group represented by the formula:

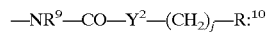

wherein R$^9$ represents hydrogen or C$_{1-6}$ alkyl, Y$^2$ represents a bond, O or imino which may be substituted by C$_{1-6}$ alkyl, j represents an integer of 0 to 5, R$^{10}$ represents a group derived by removing one hydrogen atom from a 5- to 7-membered saturated nitrogen-containing cycloalkane; etc.

The "substituent" for the "C$_{6-10}$ aryl-carboxamido which may be substituted" and "C$_{7-16}$ aralkyloxy-carboxamido which may be substituted" includes the same as those for the above-mentioned "C$_{6-10}$ aryl which may be substituted".

The "group derived by removing one hydrogen atom from a 5- to 7-membered saturated nitrogen-containing cycloalkane, which may be substituted" includes, for example, piperidino, piperazin-1-yl, pyrrolidin-1-yl, piperidin-4-yl, hexamethylenimin-1-yl, etc.

The "substituent" for the "group derived by removing one hydrogen atom from a 5- to 7-membered saturated nitrogen-containing cycloalkane" includes, for example, 1 to 3 substituents selected from the group consisting of hydroxy, C$_{1-6}$ alkyl, C$_{6-14}$ aryl which may be substituted, C$_{7-19}$ aralkyl which may be substituted, 5- to 10-membered aromatic heterocyclic group which may be substituted, C$_{6-10}$ aryl-carbonyl which may be substituted, optionally halogenated C$_{1-6}$ alkyl-carbonyl, optionally halogenated C$_{1-6}$ alkylsulfonyl, C$_{1-6}$ alkoxy-carbonyl, etc.

The "C$_{6-14}$ aryl" for the "C$_{6-14}$ aryl which may be substituted" includes, for example, phenyl, 1-naphthyl, 2-naphthyl, 2-indenyl, 2-anthryl, etc.

The "C$_{7-19}$ aralkyl" for the "C$_{7-19}$ aralkyl which may be substituted" includes, for example, benzyl, phenethyl, diphenylmethyl, triphenylmethyl, 1-naphthylmethyl, 2-naphthylmethyl, 2,2-diphenylethyl, 3-pheniylpropyl, 4-phenylbutyl, 5-phenylpentyl, etc. Preferred are benzyl, etc.

The "5- to 10-membered aromatic heterocyclic group" for the "5- to 10-membered aromatic heterocyclic group which may be substituted" includes, for example, 2-, 3- or 4-pyridyl; 1-, 2- or 3-indolyl; 2- or 3-thienyl; 2-, 4- or 5-pyrimidinyl; 2-oxo-2,3-dihydro-1H-benzimidazol-1-yl; benzotriazol-1-yl; etc. Preferred are 2-, 3- or 4-pyridyl; 2-, 4- or 5-pyrimidinyl; 2-oxo-2,3-dihydro-1H-benzimidazol-1-yl; benzotriazol-1-yl; etc.

The "C$_{6-10}$ aryl-carbonyl" for the "C$_{6-10}$ aryl-carbonyl which may be substituted" includes, for example, benzoyl, 1-naphthoyl, 2-naphthoyl, etc.

The "substituent" for these "C$_{6-14}$ aryl which may be substituted", "C$_{7-19}$ aralkyl which may be substituted", "5- to 10-membered aromatic heterocyclic group which may be substituted" and "C$_{6-10}$ aryl-carbonyl which may be substituted" includes, for example, 1 to 5 substituents selected from the group consisting of halogen atoms (e.g., fluorine, chlorine, bromine, iodine, etc.); $C_{1-3}$ alkylenedioxy (e.g., methylenedioxy, ethylenedioxy, etc.); nitro; cyano; optionally halogenated $C_{1-6}$ alkyl; optionally halogenated $C_{3-6}$ cycloalkyl; optionally halogenated $C_{1-6}$ alkoxy; optionally halogenated $C_{1-6}$ alkylthio; hydroxy; amino; mono-$C_{1-6}$ alkylamino (e.g., methylamino, ethylamino, propylamino, isopropylamino, butylamino, etc.); di-$C_{1-6}$alkylamino (e.g., dimethylamino, diethylamino, dipropylamino, dibutylamino, ethylmethylamino, etc.); formyl; carboxy; carbamoyl; optionally halogenated $C_{1-6}$, alkyl-carbonyl; $C_{1-6}$ alkoxy-carbonyl (e.g., methoxycarbonyl, ethoxycarbonyl, propoxycarbonyl, tert-butoxycarbonyl, etc.); mono-$C_{1-6}$ alkyl-carbamoyl (e.g., methylcarbamoyl, ethylcarbamoyl, etc.); di-$C_{1-6}$ alkyl-carbamoyl (e.g., dimethylcarbamoyl, diethylcarbamoyl, ethylmethylcarbamoyl, etc.); optionally halogenated $C_{1-6}$ alkylsulfonyl; formylamino; optionally halogenated $C_{1-6}$ alkyl-carboxamido; $C_{1-6}$ alkoxy-carboxamido (e.g., methoxycarboxamido, ethoxycarboxamido, propoxycarboxamido, butoxycarboxamido, etc.); $C_{1-6}$ alkyl-sulfonylamino (e.g., methylsulfonylamino, ethylsulfonylamino, etc.); $C_{1-6}$ alkyl-carbonyloxy (e.g., acetoxy, propanoyloxy, etc.); $C_{1-6}$ alkoxy-carbonyloxy (e.g., methoxycarbonyloxy, ethoxycarbonyloxy, propoxycarbonyloxy, butoxycarbonyloxy, etc.); mono-$C_{1-6}$ alkyl-carbamoyloxy (e.g., methylcarbamoyloxy, ethylcarbamoyloxy, etc.); di-$C_{1-6}$ alkyl-carbamoyloxy (e.g., dimethylcarbamoyloxy, diethylcarbamoyloxy, etc.); etc.

Concrete examples of the "spacer having a main chain of 2 to 5 atoms" for Y include, for example, $C_{2-5}$ alkylene which may be substituted; $C_{2-5}$ alkenylene which may be substituted; $C_{2-5}$ alkynylene which may be substituted; divalent groups represented by the formula:

—CH$_2$—Y$^1$—, —(CH$_2$)$_2$—Y$^1$—, —(CH$_2$)$_3$—Y$^1$—, —(CH$_2$)$_4$—Y$^1$—, —Y$^1$

—CH$_2$—, —Y$^1$—(CH$_2$)$_2$—, —Y$^1$—(CH$_2$)$_3$—, —Y$^1$—(CH$_2$)$_4$—, —Y$^1$—CH$_2$—Y$^1$—, —Y$^1$

—(CH$_2$)$_2$—Y$^1$—, —Y$^1$—(CH$_2$)$_3$—Y$^1$—, —CH$_2$—Y$^1$—CH$_2$—, —(CH$_2$)$_2$—Y$^1$—CH$_2$—,

—(CH$_2$)$_3$—Y$^1$—CH$_2$—, —CH$_2$—Y$^1$—(CH$_2$)$_2$—, or —CH$_2$—Y$^1$—(CH$_2$)$_3$— wherein Y$^1$ represents O, S, SO, SO$_2$ or NR$^8$ where R$^8$ has the same meanings as above; etc. When two of Y$^1$ exist in the same formula, they may be the same or different.

The "$C_{2-5}$ alkylene" for the "$C_{2-5}$ alkylene which may be substituted" includes, for example, —(CH$_2$)$_2$—, —(CH$_2$)$_3$—, —(CH$_2$)$_4$—, —(CH$_2$)$_5$—, etc.

The "substituent" for the "$C_{2-5}$ alkylene which may be substituted" includes, for example, the same "substituent" for the above "$C_{1-5}$ alkylene which may be substituted".

Preferred examples of Y includes, for example,
(a) $C_{2-5}$ alkylene which may be substituted by
① cyano,
② $C_{6-10}$ aryl (e.g., phenyl, etc.),
③ a group represented by the formula:

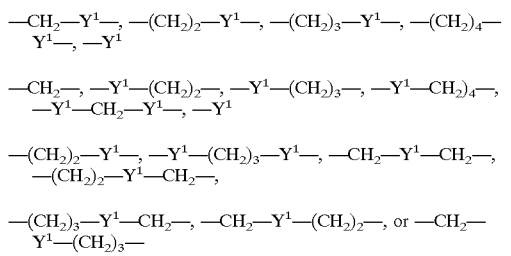

wherein J$^1$ and J$^2$ each represents CH, C(OH) or N; Q$^1$ and Q$^2$ each represents —(CH$_2$)$_p$— or —(CH$_2$)$_p$—CO—(CH$_2$)$_q$— where p and q each represents an integer of 0 to 3;

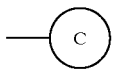

represents (i) a group represented by the formula:

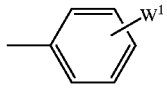

wherein W$^1$ represents halogen atom, cyano, optionally halogenated $C_{1-6}$ alkyl, optionally halogenated $C_{1-6}$ alkoxy, optionally halogenated $C_{1-6}$ alkyl-carbonyl, nitro, or $C_{6-10}$ aryl;
(ii) 5- or 6-membered nitrogen-containing heterocyclic group which maybe substituted (e.g., pyridyl, pyrimidinyl, etc.), or
(iii) a group represented by the formula:

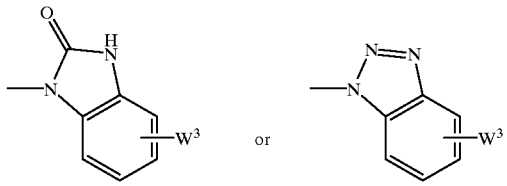

wherein W$^3$ represents hydrogen atom or optionally halogenated $C_{1-6}$ alkyl,
④ $C_{7-16}$ aralkyloxy-carboxamido which may be substituted (e.g., fluorenylmethyloxycarboxamido, etc.),
⑤ amino,
⑥ $C_{7-16}$ aralkyl-carboxamido,
⑦ $C_{1-6}$ alkoxy-carbonyl-piperazinyl-carboxamido, or
⑧ a group represented by the formula:

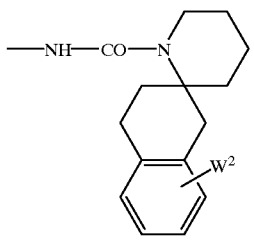

wherein W$^2$ represents optionally halogenated $C_{1-6}$ alkoxy;
(b) $C_{2-5}$ alkenylene (especially —CH=CH—, etc.),
(c) —(CH)$_m$—Y$^1$— wherein m represents an integer of 1 to 4, Y$^1$ has the same meanings as above, or
(d) —Y$^1$—(CH$_2$)$_r$— wherein r represents an integer of 1 to 4, Y$^1$ has the same meanings as above.

Among the above definitions, p and q are preferably 0 or 1, especially preferably 0.

As —(CH$_2$)$_p$—CO—(CH$_2$)$_q$—, —CO— is especially preferable.

W$^1$ is preferably 1 or 2 substituents selected from the group consisting of halogen atoms (e.g., fluorine, chlorine, etc.), $C_{1-6}$ alkoxy (e.g., methoxy, etc.), etc.

The 5- or 6-membered nitrogen-containing heterocyclic group which may be substituted is preferably pyridyl or pyrimidinyl each of which may be substituted by optionally halogenated $C_{1-6}$ alkyl (e.g., methyl, trifluoromethyl, etc.) or nitro.

$W^2$ is preferably 1 or 2 of $C_{1-6}$ alkoxy (e.g., methoxy, etc.), etc.

The definitions m and r are preferably 1 or 2.

$Y^1$ is preferably O or $NR^8$. $Y^1$ is more preferably $Y^{1a}$ wherein $Y^{1a}$ represents O or $NR^{8a}$ where $R^{8a}$ represents hydrogen atom or $C_{6-10}$ arylsulfonyl (e.g., phenylsulfonyl, etc.) which may be substituted by $C_{1-6}$ alkyl (e.g., methyl, etc.). $Y^1$ is especially preferably O or NH.

The "lower alkyl" for the "lower alkyl which may be substituted" for $R^1$ and $R^2$ includes, for example, $C_{1-6}$ alkyl (e.g., methyl, ethyl, propyl, isopropyl, butyl, isobutyl, sec-butyl, tert-butyl, pentyl, hexyl, etc.). Preferred are methyl, ethyl and propyl.

The "substituent" for the "lower alkyl which may be substituted" for $R^1$ and $R^2$ includes, for example, 1 to 5, preferably 1 to 3 substituents selected from the "substituent" for the above "hydrocarbon group which may be substituted" for $R^8$. These substituents may be the same or different. Among these, preferred is $C_{6-10}$ aryl such as phenyl, etc.

The "nitrogen-containing heterocyclic ring" for the "nitrogen-containing heterocyclic ring which may be substituted" as formed by $R^1$ and $R^2$ together with the adjacent nitrogen atom includes, for example, 3- to 8-membered nitrogen-containing heterocyclic groups containing at least one nitrogen atom and optionally 1 to 3 hetero atoms selected from the group consisting of nitrogen, sulfur and oxygen atoms in addition to carbon atoms. Concretely mentioned are aziridine, azetidine, morpholine, thiomorpholine, piperidine, piperazine, pyrrolidine, hexamethyleneimine, heptamethyleneimine, hexahydropyrimidine, 1,4-diazepane, and unsaturated cyclic amines thereof (e.g., 1,2,5,6-tetrahydropyridine, etc.), etc. Among these, preferred are morpholine, piperidine, piperazine, pyrrolidine, etc.

The "substituent" for the "nitrogen-containing heterocyclic ring which may be substituted" as formed by $R^1$ and $R^2$ together with the adjacent nitrogen atom includes, for example, 1 to 3 substituents selected from the same substituent for the above "5- to 7-membered saturated cyclic amino which may be substituted". Among these, preferred is $C_{6-10}$ aryl such as phenyl, etc.

The "spiro-ring" for the "spiro-ring which may be substituted" as formed by $R^1$ or $R^2$ together with —$(CH_2)_n$—N= bonded to a component atom of Ring B includes, for example, 5- to 7-membered spiro-ring containing at least one nitrogen atom and optionally 1 to 3 hetero atoms selected from the group consisting of nitrogen, sulfur and oxygen atoms in addition to carbon atoms. Preferred is a 6-membered spiro-ring. Examples of the bone structure formed by combination of $R^1$ and a component atom of Ring B include that represented by the formulae:

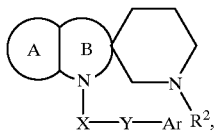

wherein the symbols have the same meanings as above.

The "substituent" for the "spiro-ring which may be substituted" includes, for example, 1 to 3 substituents selected from the group consisting of oxo, $C_{1-6}$ alkyl (e.g., methyl, ethyl, propyl, isopropyl, butyl, isobutyl, sec-butyl, tert-butyl, pentyl, hexyl, etc.), etc.

The "aromatic ring" for the "aromatic ring which may be substituted" for Ring A includes, for example, an aromatic hydrocarbon, an aromatic heterocyclic ring, etc.

The "aromatic hydrocarbon" includes, for example, a $C_{6-14}$ monocyclic or fused polycyclic (bi- or tri-cyclic) aromatic hydrocarbon (e.g., benzene, naphthalene, indene, anthracene, etc.). Among these, preferred are benzene and naphthalene. More preferred is benzene.

The "aromatic heterocyclic ring" includes, for example, 5- to 14-membered, preferably 5- to 10-membered aromatic heterocyclic rings containing one or more (e.g., 1 to 4) hetero atoms selected from the group consisting of nitrogen, sulfur and oxygen atoms in addition to carbon atoms, etc. Concretely mentioned is an aromatic heterocyclic ring, such as thiophene, benzothiophene, benzofuran, benzimidazole, benzoxazole, benzothiazole, benzisothiazole, naphtho[2,3-b]thiophene, furan, phenoxathin, pyrrole, imidazole, pyrazole, oxazole, isoxazole, 1,2,4-oxadiazole, 1,3,4-oxadiazole, 1,2,4-thiadiazole, 1,3,4-thiadiazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, phthalimide, etc.; and a ring as formed through condensation of the above ring, preferably monocyclic ring, with one or more, preferably one or two aromatic rings (e.g., benzene ring, etc.), etc. Among these, preferred are thiophene, furan, pyrrole, pyridine, pyrimidine, pyridazine, etc.

Among the above rings, Ring A is preferably benzene ring.

The "substituent" for the "aromatic ring which may be substituted" for Ring A is the same both in its kind and number as the "substituent" for the above "aromatic group which may be substituted" for Ar. Among these, preferred are $C_{1-6}$ alkoxy (e.g., methoxy, etc.), $C_{6-10}$ aryl-$C_{7-16}$ aralkyloxy (e.g., biphenylmethyloxy, etc.), halogen atoms (e.g., chlorine, etc.), optionally halogenated $C_{1-6}$ alkyl-carboxamido (e.g., acetamide, etc.), etc.

The "4- to 7-membered nitrogen-containing non-aromatic ring" for the "4- to 7-membered nitrogen-containing non-aromatic ring which may be further substituted by alkyl or acyl" for Ring B includes, for example, 4- to 7-membered non-aromatic rings containing at least one nitrogen atom and optionally 1 to 3 hetero atoms selected from the group consisting of nitrogen, sulfur and oxygen atoms in addition to carbon atoms, etc. Concrete examples include 4- to 7-membered non-aromatic rings represented by the formulae:

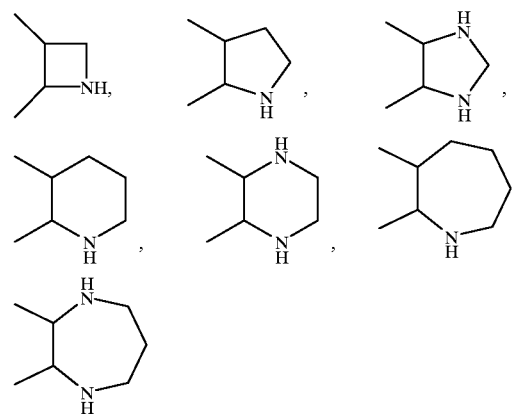

Among these, 6- or 7-membered non-aromatic rings are preferable.

The "alkyl" for the "4- to 7-membered nitrogen-containing non-aromatic ring which may be further substituted by alkyl or acyl" includes preferably 1 to 3 of $C_{1-6}$ alkyl (e.g., methyl, ethyl, propyl, isopropyl, butyl, isobutyl, sec-butyl, tert-butyl, pentyl, hexyl, etc.), etc. Especially preferred is $C_{1-3}$ alkyl such as methyl, ethyl, etc.

The "acyl" for the "4- to 7-membered nitrogen-containing non-aromatic ring which may be further substituted by alkyl or acyl" includes the same as the "acyl" as the substituent for the aromatic group for the above Ar. Preferred are the above-mentioned formyl, carboxy, carbamoyl, optionally halogenated $C_{1-6}$ alkyl-carbonyl (e.g., acetyl, etc.), $C_{1-6}$ alkoxy-carbonyl (e.g., methoxycarbonyl, ethoxycarbonyl, propoxycarbonyl, tert-butoxycarbonyl, etc.), $C_{6-10}$ aryl-carbonyl which may be substituted, $C_{6-10}$ aryloxy-carbonyl which may be substituted, $C_{7-16}$ aralkyloxy-carbonyl which may be substituted, 5- or 6-membered heterocyclic-carbonyl which may be substituted, mono-$C_{1-6}$ alkyl-carbamoyl, di-$C_{1-6}$ alkyl-carbamoyl (e.g., dimethylcarbamoyl, diethylcarbamoyl, ethylmethylcarbamoyl, etc.), $C_{6-10}$ aryl-carbamoyl which may be substituted, 5- or 6-membered heterocyclic-carbamoyl which may be substituted, optionally halogenated $C_{1-6}$ alkylsulfonyl, $C_{6-10}$ arylsulfonyl which may be substituted, etc. Among these, optionally halogenated $C_{1-6}$ alkyl-carbonyl, $C_{1-6}$ alkoxy-carbonyl (e.g., ethoxycarbonyl, etc.), $C_{6-10}$ aryl-carbonyl which may be substituted, $C_{6-10}$ arylsulfonyl which may be substituted, etc. are preferable. Especially preferred are formyl, $C_{1-6}$ alkyl-carbonyl (e.g., acetyl, etc.), etc.

Concrete examples of the fused ring represented by the formula:

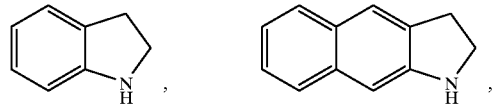 include

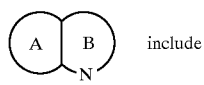

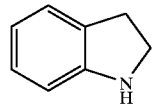

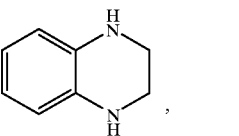

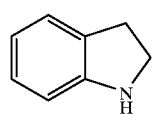

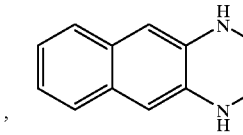

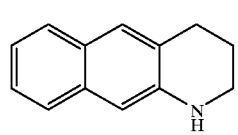

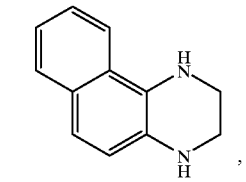

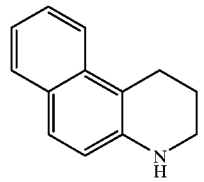

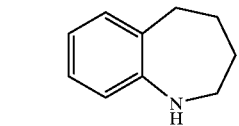

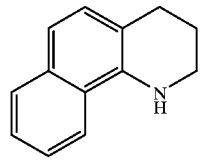

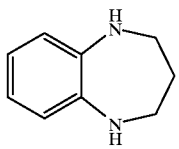

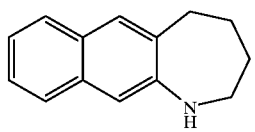

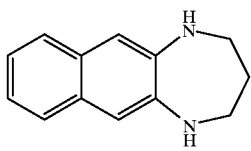

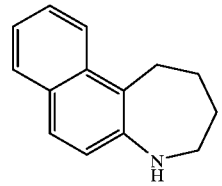

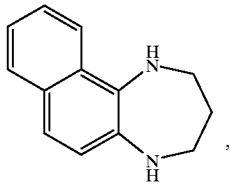

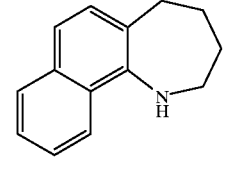

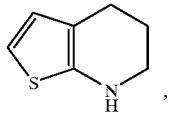

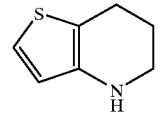

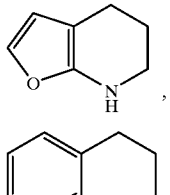

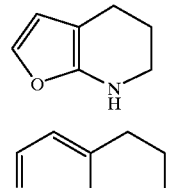

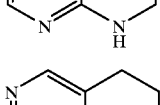

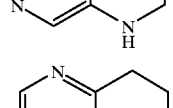

ect. Among these, preferred are

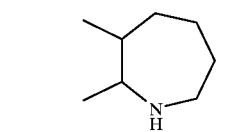

  or

  , etc.

Ar is preferably an aromatic ring assembly group which may be substituted or a fused aromatic group which may be substituted.

X is preferably methylene, CO or $SO_2$. Among these, methylene or CO is preferable. Especially, CO is preferable.

Y is preferably a $C_{2-5}$ alkylene which may be substituted.

The symbol n is preferably 1 or 2.

$R^1$ and $R^2$, preferably (i) each represents a hydrogen atom or a lower alkyl which may be substituted, or (ii) form, taken together with the adjacent nitrogen atom, a nitrogen-containing heterocyclic ring which may be substituted.

Ring A is preferably a benzene ring which may be substituted, more preferably a benzene ring which may be substituted by a group selected from the group consisting of $C_{1-6}$ alkoxy (e.g., methoxy, etc.), $C_{6-10}$ aryl-$C_{7-16}$ aralkyloxy (e.g., biphenylmethyloxy, etc.), halogen atoms (e.g., chlorine, etc.), optionally halogenated $C_{1-6}$ alkyl-carboxamido (e.g., acetamide, etc.), etc.

Ring B is preferably

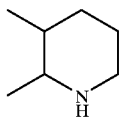

Preferred examples of the compound (I) include (1) compound (I-I) represented by the formula:

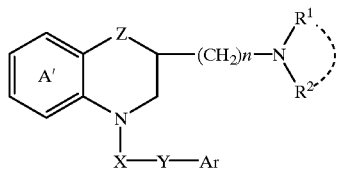

wherein Ring A' is a benzene ring which may be substituted; Z represents methylene or imino which may be substituted; the other symbols have the same meanings as above;
(2) compound (I-II) represented by the formula:

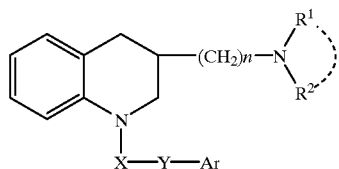

wherein the symbols have the same meanings as above;
(3) compound (I-III) represented by the formula:

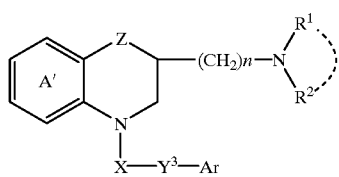

wherein $Y^3$ represents $C_{1-5}$ alkylene or $C_{2-5}$ alkenylene, the other symbols have the same meanings as above;
(4) compound (I-IV) represented by the formula:

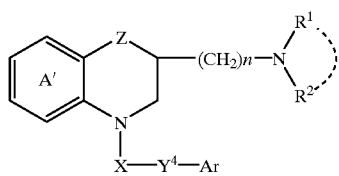

wherein $Y^4$ represents $C_{1-5}$ alkylene or $C_{2-5}$ alkenylene, each of which may be substituted by acylamino, the other symbols have the same meanings as above; etc.

The "substituent" for the benzene ring for Ring A' includes the same as the substituent for the aromatic ring for Ring A. Concrete examples of the substituent include, for example, 1 to 5 substituents selected from the group consisting of halogen atoms (e.g., fluorine, chlorine, bromine, iodine, etc.); $C_{1-3}$ alkylenedioxy (e.g., methylenedioxy, ethylenedioxy, etc.); nitro; cyano; optionally halogenated $C_{1-6}$ alkyl; optionally halogenated $C_{3-6}$ cycloalkyl; optionally halogenated $C_{1-6}$ alkoxy; optionally halogenated $C_{1-6}$ alkylthio; hydroxy; amino; mono-$C_{1-6}$ alkylamino (e.g., methylamino, ethylamino, propylamino, isopropylamino, butylamino, etc.); di-$C_{1-6}$ alkylamino (e.g., dimethylamino, diethylamino, dipropylamino, dibutylamino, ethylmethylamino, etc.); formyl; carboxy; carbamoyl; optionally halogenated $C_{1-6}$ alkyl-carbonyl; $C_{1-6}$ alkoxy-carbonyl (e.g., methoxycarbonyl, ethoxycarbonyl, propoxycarbonyl, tert-butoxycarbonyl, etc.); mono-$C_{1-6}$ alkyl-carbamoyl (e.g., methylcarbamoyl, ethylcarbamoyl, etc.); di-$C_{1-6}$ alkyl-carbamoyl (e.g., dimethylcarbamoyl, diethylcarbamoyl, ethylmethylcarbamoyl, etc.); optionally halogenated $C_{1-6}$ alkylsulfonyl; formylamino; optionally halogenated $C_{1-6}$ alkyl-carboxamido (e.g., acetamide, etc.); $C_{1-6}$ alkoxy-carboxamido (e.g., methoxycarboxamido, ethoxyqarboxamido, propoxycarboxamido, butoxycarboxamido, etc.); $C_{1-6}$ alkylsulfonylamino (e.g., methylsulfonylamino, ethylsulfonylamino, etc.); $C_{1-6}$ alkyl-carbonyloxy (e.g., acetoxy, propanoyloxy, etc.); $C_{1-6}$ alkoxy-carbonyloxy (e.g., methoxycarbonyloxy, ethoxycarbonyloxy, propoxycarbonyloxy, butoxycarbonyloxy, etc.); mono-$C_{1-6}$ alkyl-carbamoyloxy (e.g., methylcarbamoyloxy, ethylcarbamoyloxy, etc.); di-$C_{1-6}$ alkyl-carbamoyloxy (e.g., dimethylcarbamoyloxy, diethylcarbamoyloxy, etc.); and etc. Among these, preferred are $C_{1-6}$ alkoxy (e.g., methoxy, etc.), $C_{6-10}$ aryl-$C_{7-16}$ aralkyloxy (e.g., biphenylmethyloxy, etc.), halogen atoms (e.g., chlorine, etc.), optionally halogenated $C_{1-6}$ alkyl-carboxamido (e.g., acetamido, etc.), etc.

The substituent for the "imino which may be substituted" for Z includes, for example, optionally halogenated $C_{1-6}$ alkyl; optionally halogenated $C_{3-6}$ cycloalkyl; $C_{7-16}$ aralkyl which may be substituted; $C_{6-14}$ aryl which may be substituted; formyl; carboxy; carbamoyl; optionally halogenated $C_{1-6}$ alkyl-carbonyl; $C_{1-6}$ alkoxy-carbonyl (e.g., methoxycarbonyl, ethoxycarbonyl, propoxycarbonyl, tert-butoxycarbonyl, etc.); $C_{7-16}$ aralkyloxy-carbonyl which may be substituted; mono-$C_{1-6}$ alkyl-carbamoyl (e.g., methylcarbamoyl, ethylcarbamoyl, etc.); di-$C_{1-6}$ alkyl-carbamoyl (e.g., dimethylcarbamoyl, diethylcarbamoyl, ethylmethylcarbamoyl, etc.); optionally halogenated $C_{1-6}$ alkylsulfonyl; $C_{6-14}$ arylsulfonyl which may be substituted; 5- or 6-membered heterocyclic-carbonyl which may be substituted; etc. Among these, preferred are formyl, optionally halogenated $C_{1-6}$ alkyl (e.g., methyl, ethyl, etc.), etc.

The preferred groups for the other symbols are the same as those mentioned above. Especially, preferred is the compound in which Ar is 1-, 2- or 3-indolyl, or aromatic ring assembly group; X is CO; Y is ethylene which is unsubstituted or substituted by acylamino; $R^1$ and $R^2$ are each $C_{1-3}$ alkyl, or form, taken together with the adjacent nitrogen atom, pyrrolidine.

The $C_{1-5}$ alkylene and $C_{2-5}$ alkenylene for $Y^3$ and $Y^4$ include the same $C_{1-5}$ alkylene and $C_{2-5}$ alkenylene as the spacer for the above Y.

The acylamino which the $C_{1-5}$ alkylene and $C_{2-5}$ alkenylene for $Y^4$ may have includes the same described as the substituent for the $C_{1-5}$ alkylene and $C_{2-5}$ alkenylene as the spacer for the above Y.

Preferred examples of the compound (I) include the followings:

(1) Compound (I-V)

A compound wherein Ar represents (i) phenyl, (ii) 3-pyridyl, (iii) 1,2,4-oxadiazol-5-yl; (iv) 3-quinolyl, (v) 3-indolyl, (vi) 4-biphenylyl, (vii) 4-(2-naphthyl)phenyl, (viii) 4,4'-terphenyl, (ix) 4-(3-pyridyl)phenyl, (x) 4-(2-thienyl)phenyl, (xi) 3-(2-naphthyl)-1,2,4-oxadiazol-5-yl, (xii) 3-(1-naphthyl)-1,2,4-oxadiazlol-5-yl, (xiii) 3-(3-indolyl)-1,2,4-oxadiazol-5-yl, (xiv) 3-(2-benzoxazolyl)-1,2,4 -oxadiazol-5-yl, (xv) 3-(2-benzofuranyl)-1,2,4-oxadiazol-5-yl, (xvi) 4-phenylthiazol-2-yl, (xvii) 3-(2-benzofuranyl)thiazol-2-yl, or (xviii) 5-phenyl-oxazol-2-yl; each of which may be substituted by 1 to 3 substituents selected from the group consisting of halogen atom; $C_{1-3}$ alkylenedioxy; $C_{1-6}$ alkyl; $C_{6-10}$ aryloxy-$C_{1-6}$ alkyl; $C_{1-6}$ alkyl-$C_{6-10}$ aryl-$C_{2-6}$ alkenyl; $C_{7-16}$ aralkyl (preferably benzyl) which may be substituted by halogen atom or $C_{1-6}$ alkoxy; $C_{1-6}$ alkoxy; hydroxy; $C_{6-10}$ aryloxy optionally substituted by halogen atom or $C_{1-6}$ alkoxy; $C_{1-6}$ alkyl-carbonyl; and $C_{1-6}$ alkoxy-carbonyl;

X represents methylene or CO;

Y represents (i) $C_{2-5}$ alkylene which may be substituted by 1 or 2 substituents selected from the group consisting of cyano, acylamino and phenyl, (ii) $C_{2-3}$ alkenylene, (iii) —CH$_2$—O—, or (iv) a divalent group represented by the formula:

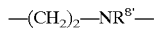

where $R^{8'}$ represents hydrogen atom or $C_{1-3}$ alkyl-phenylsulfonyl;

n is 1 or 2;

i) $R^1$ and $R^2$ each represents a hydrogen atom or $C_{1-6}$ alkyl which may be substituted by $C_{6-10}$ aryl (e.g., phenyl, etc.), ii) $R^1$ and $R^2$ form, taken together with the adjacent nitrogen atom, morpholine, piperidine, piperazine or pyrrolidine, each of which may be substituted by $C_{6-10}$ aryl (e.g., phenyl, etc.), or iii) $R^1$ forms, bonded to a component atom of Ring B, a 6-membered spiro-ring represented by the formula:

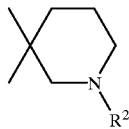

wherein $R^2$ represents hydrogen atom;

Ring A represents benzene ring which may be substituted by $C_{1-3}$ alkoxy or phenylbenzyloxy; and Ring B represents

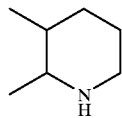 or 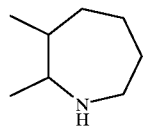

(2) Compound (I-VI)

A compound wherein Ar represents (i) monocyclic aromatic groups such as phenyl; 2-, 4- or 5-thiazolyl; 2-, 4- or 5-oxazolyl; 2-, 3- or 4-pyridyl; and etc.;

(ii) aromatic ring assembly groups such as 2-, 3- or 4-biphenylyl; 3-(1-naphthyl)-1,2,4-oxadiazlol-5-yl; 3-(2-naphthyl)-1,2,4-oxadiazol-5-yl; 3-(2-benzofuranyl)-1,2,4-oxadiazol-5-yl; 3-phenyl-1,2,4-oxadiazol-5-yl; 3-(2-benzoxazolyl)-1,2,4-oxadiazol-2-yl; 3-(3-indolyl)-1,2,4-oxadiazol-2-yl; 3-(2-indolyl)-1,2,4-oxadiazol-2-yl; 4-phenylthiazol-2-yl; 4-(2-benzofuranyl)thiazol-2-yl; 4-phenyl-1,3-oxazol-5-yl; 4-(2-thienyl)phenyl; 4-(3-pyridyl)phenyl; 4-(2-naphthyl)phenyl; 4,4'-terphenyl; and etc.; or (iii) fused aromatic groups such as 2-, 3- or 4-quinolyl; 1-, 2- or 3-indolyl; and etc.; each of which may be substituted by substituents selected from the group consisting of halogen atoms (e.g., fluorine, chlorine, bromine, etc.); $C_{1-3}$ alkylenedioxy (e.g., methylenedioxy, etc.); optionally halogenated $C_{1-6}$ alkyl (e.g., methyl, etc.); $C_{6-10}$ aryloxy-$C_{1-6}$ alkyl (e.g., phenoxymethyl, etc.); $C_{1-6}$ alkyl-$C_{6-10}$ aryl-$C_{2-6}$ alkenyl (e.g., methylphenylethenyl, etc.); $C_{7-16}$ aralkyl (preferably benzyl) which may be substituted by halogen atom (e.g., chlorine, etc.) or $C_{1-6}$ alkoxy (e.g., methoxy, etc.); optionally halogenated $C_{1-6}$ alkoxy (e.g., methoxy, etc.); hydroxy; $C_{6-10}$ aryloxy (e.g., phenoxy, etc.) which may be substituted by halogen atom (e.g., chlorine, etc.) or $C_{1-6}$ alkoxy (e.g., methoxy, etc.); optionally halogenated $C_{1-6}$ alkylcarbonyl (e.g., acetyl, etc.); $C_{1-6}$ alkoxy-carbonyl(e.g., ethoxycarbonyl, etc.); $C_{6-10}$ aryl-carbonyl; $C_{6-10}$ arylsulfonyl (e.g., phenylsulfonyl, etc.) which may be substituted by $C_{1-6}$ alkyl (e.g., isopropyl, etc.); etc.;

X represents methylene, CO or SO$_2$;

Y represents a divalent group represented by (a) $C_{2-5}$ alkylene which may be substituted by ① cyano, ② $C_{6-10}$ aryl (e.g., phenyl, etc.), ③ a group represented by the formula:

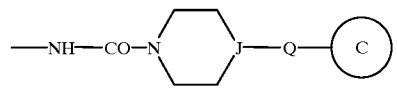

wherein J represents CH, C(OH) or N; Q represents —(CH$_2$)$_p$— or —(CH$_2$)$_p$—CO—(CH$_2$)$_q$— where p and q each represents an integer of 0 to 3; the formula:

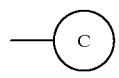

represents (i) a group represented by the formula:

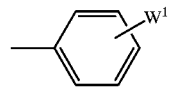

wherein $W^1$ represents halogen atom, cyano, optionally halogenated $C_{1-6}$ alkyl, optionally halogenated $C_{1-6}$ alkoxy, optionally halogenated $C_{1-6}$ alkyl-carbonyl, or nitro;

(ii) 5- or 6-membered nitrogen-containing heterocyclic group which may be substituted (e.g., pyridyl, piperidyl, etc.) or (iii) a group represented by the formula:

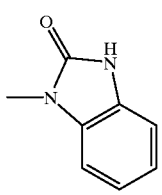 or 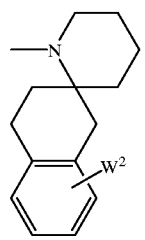

wherein $W^2$ represents $C_{1-6}$ alkoxy, or
④ $C_{7-15}$ aralkyloxycarboxamido which may be substituted (e.g., fluorenylmethyloxycarboxamido, etc.),
(b) $C_{2-5}$ alkenylene (especially, —CH=CH—, etc.),
(c) —(CH)$_m$—Y$^1$— wherein m represents an integer of 1 to 4, $Y^1$ has the same meanings as above, or
(d) —Y$^1$—(CH$_2$)$_r$— wherein r represents an integer of 1 to 4, $Y^1$ has the same meanings as above;
n represents 1 or 2;
i) $R^1$ and $R^2$ each represents a hydrogen atom or $C_{1-6}$ alkyl which may be substituted by $C_{6-10}$ aryl (e.g., phenyl, etc.),
ii) $R^1$ and $R^2$ form, taken together with the adjacent nitrogen atom, morpholine, piperidine, piperazine or pyrrolidine, each of which may be substituted by $C_{6-10}$ aryl (e.g., phenyl, etc.), or
iii) $R^1$ forms, bonded to a component atom of Ring B, a 6-membered spiro-ring represented by the formula:

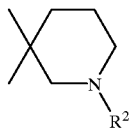

wherein $R^2$ represents hydrogen atom;
Ring A represents benzene ring which may be substituted by $C_{1-6}$ alkoxy (e.g., methoxy, etc.) or $C_{6-10}$ aryl-$C_{7-15}$ aralkyloxy (e.g., phenylbenzyloxy, etc.); and
Ring B represents

each of which may be substituted by $C_{1-6}$ alkyl or formyl.

The above compound (I-VI) has an excellent SSTR4 agonistic activity, and is useful especially as an SSTR4 agonist.

(3) Compound (I-VII)
A compound among the above compound (I-VI), wherein Y represents
(a) $C_{2-5}$ alkylene which may be substituted by
① a group represented by the formula:

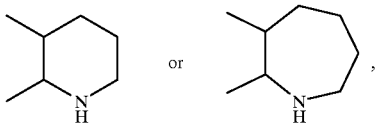

wherein J represents CH, C(OH) or N; Q represents —(CH$_2$)$_p$— or —(CH$_2$)$_p$—CO—(CH$_2$)$_q$— where p and q each represents an integer of 0 to 3; the formula:

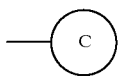

represents (i) a group represented by the formula:

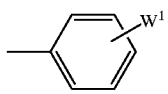

wherein $W^1$ represents halogen atom, cyano, optionally halogenated $C_{1-6}$ alkyl, optionally halogenated $C_{1-6}$ alkoxy, optionally halogenated $C_{1-6}$ alkyl-carbonyl, or nitro;
(ii) 5- or 6-membered nitrogen-containing heterocyclic group which may be substituted (e.g., pyridyl, piperidyl, etc.) or
(iii) a group represented by the formula:

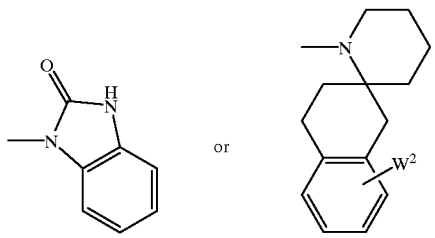

wherein $W^2$ represents $C_{1-6}$ alkoxy, or
② $C_{7-15}$ aralkyloxycarboxamido which may be substituted (e.g., fluorenylmethyloxycarboxamido, etc.),
(b) —(CH)$_m$—Y$^1$— wherein m represents an integer of 1 to 4, $Y^1$ has the same meanings as above., or
(c) —Y$^1$—(CH$_2$)$_r$— wherein r represents an integer of 1 to 4, $Y^1$ has the same meanings as above.

Among the above, the compound in which
Ar represents 1-, 2- or 3-indolyl;
X represents CO;
n represents 1;
$R^1$ and $R^2$ each represents a hydrogen atom or $C_{1-6}$ alkyl;
Ring A represents benzene ring; and
Ring B represents

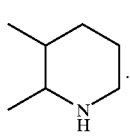

The above compound (I-VII) has an excellent SSTR2 binding inhibiting activity and is useful especially as an SSTR2 agonist/antagonist.

(4) Compound (I-VIII)
(i) 3-[(N,N-Dimethylamino)methyl]-1-[3-[3-(1-naphthyl)-1,2,4-oxadiazol-5-yl]propanoyl]-1,2,3,4-tetrahydroquinoline or a salt thereof.
(ii) 1-[3-(4-Biphenylyl)propanoyl]-3-[(N,N-dimethylamino)methyl]-1,2,3,4-tetrahydroquinoline or a salt thereof.
(iii) 1-[3-[3-(2-Benzofuranyl)-1,2,4-oxadiazol-5-yl]propanoyl]-3-(pyrrolidin-1-yl)methyl-1,2,3,4-tetrahydroquinoline or a salt thereof.
(iv) 1-[3-(4-Biphenylyl)propanoyl]-3-(pyrrolidin-1-yl) methyl-1,2,3,4-tetrahydroquinoline or a salt thereof.
(v) 4-[3-(4-Biphenylyl)propanoyl]-2-(pyrrolidin-1-yl) methyl-1,2,3,4-tetrahydroquinoxaline or a salt (especially oxalate) thereof.

(vi) 4-[3-(4-Biphenylyl)propanoyl]-2-(N,N-dimethylamino)methyl-1-formyl-1,2,3,4-tetrahydroquinoxaline or a salt thereof.
(vii) 3-(R,S)-(N,N-Dimethylamino)methyl-1-[3 -(indol-3-yl)-2- [ (R)-(4-phenylpiperadzin-1-yl)carbonylamino] propanoyl]-1,2,3,4-tetrahydroquinoline or a salt thereof.
(viii) 3-(R,S)-(N,N-Dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline or a salt thereof.
(ix) 1-[2-(R)-[4-(2-chlorophenyl)piperazin-1-yl]carbonylamino-3-(R,S)-(N,N-dimethylamino)methyl-3-(indol-3-yl)propanoyl]-1,2,3,4-tetrahydroquinoline or a salt thereof.
(x) 3-(R,S)-(N,N-Dimethylamino)methyl-1-[3-(indol-3-yl)-2-(R)-[4-(2-methoxy)phenyl)piperazin-1-yl]carbonylaminopropanoyl]-1,2,3,4-tetrahydroquinoline or a salt thereof.
(xi) 1-[2-(R)-[[4-(4-chlorophenyl)-4-hydroxypiperidino]carbonyl]]amino-3-(indol-3-yl)propanoyl]-3-(R,S)-(N,N-dimethylamino)methyl-1,2,3,4-tetrahydroquinoline or a salt thereof.

Among these compounds, compounds (i) to (vi) have an excellent SSTR4 agonistic activity, and are useful especially as an SSTR4 agonist. Compounds (vii) to (xi) have an excellent SSTR2 binding inhibiting activity and are useful especially as an SSTR2 agonist/antagonist.

(5) Compound (I-IX)
(xii) 3-(R)-(N,N-Dimethylamino)methyl-1-[3-(indol-3-yl)-2-[(R)-(4-phenylpiperazin-1-yl)carbonylamino]propanoyl]-1,2,3,4-tetrahydroquinoline or a salt thereof.
(xiii) 3-(S)-(N,N-Dimethylamino)methyl-1-[3-(indol-3-yl)-2-[(R)-(4-phenylpiperazin-1-yl)carbonylamino]propanoyl]-1,2,3,4-tetrahydroquinoline or a salt thereof.
(xiv) 3-(R)-(N,N-Dimethylamino)methyl-1-[3-(indol-3-yl)-2-[(R)-4-(2-oxo-2,3-dihydro-1H-benzimidazol-1 -yl)piperidinocarbonylamino]propanoyl]-1,2,3,4-tetrahydroquinoline or a salt thereof.
(xv) 3-(S)-(N,N-Dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline or a salt thereof.
(xvi) 3-(R)-(N,N-Dimethylamino)methyl-1-[3-(indol-3-yl)-2-(R)-[4-(2-methyl)phenylpiperazin-1-yl]carbonylaminopropanoyl]-1,2,3,4-tetrahydroquinoline or a salt thereof.
(xvii) 3-(S)-(N,N-Dimethylamino)methyl-1-[3-(indol-3-yl)-2-(R)-[4-(2-methyl)phenylpiperazin-1-yl]carbonylaminopropanoyl]-1,2,3,4-tetrahydroquinoline or a salt thereof.
(xviii) 3-(R,S)-(N,N-Dimethylamino)methyl-1-[3-(indol-3-yl)-2-[(R)-1-benzoyl-4-piperidinocarbonylamino]propanoyl]-6-methoxy-1,2,3,4-tetrahydroquinoline or a salt thereof.
(xix) 6-Chloro-3-(R,S)-(N,N-dimethylamino)methyl-1-[3-(indol-3-yl)-2-[(R)-(4-phenylpiperazin-1-yl)carbonylamino]propanoyl]-1,2,3,4-tetrahydroquinoline or a salt thereof.
(xx) 6-Chloro-3-(R,S)-(N,N-dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline or a salt thereof.
(xxi) 1-Benzoyl-N-[(R)-2-[6-chloro-3-[(N,N-dimethylamino)methyl]-1,2,3,4-tetrahydroquinolin-1-yl]-1-[3- (indol-3-yl)propanoyl]-4-piperidinecarboxamide or a salt thereof.
(xxii) 1-[3-(4-Biphenylyl)propanoyl]-3-(R)-(N,N-dimethylamino)methyl-1,2,3,4-tetrahydroquinoline or a salt thereof.
(xxiii) 1-[3-(4-Biphenylyl)propanoyl]-3-(S)-(N,N-dimethylamino)methyl-1,2,3,4-tetrahydroquinoline or a salt thereof.

Among these compounds, compounds (xii) to (xxi) have an excellent SSTR2 binding inhibiting activity and are useful especially as an SSTR2 agonist/antagonist. Compounds (xxii) and (xxiii) have an excellent SSTR4 agonistic activity, and are useful especially as an SSTR4 agonist.

As the salts of compound (I) and compound (I'), for example, inorganic salts, ammonium salts, salts with organic bases, salts with inorganic acids, salts with organic acids and salts with basic or acidic amino acids can be mentioned. Preferable examples of inorganic salts include alkali metal salts such as sodium salt and potassium salt; alkaline earth metal salts such as calcium salts, magnesium salts and barium salts; aluminum salts, etc. Preferred salts with organic bases are exemplified by salts with trimethylamine, triethylamine, pyridine, picoline, ethanolamine, diethanolamine, triethanolamine, dicyclohexylamine, N,N'-dibenzylethylenediamine, etc. Preferred salts with inorganic acids are exemplified by salts with hydrochloric acid, hydrobromic acid, nitric acid, sulfuric acid, phosphoric acid, etc. Preferred salts with organic acids are exemplified by salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferred salts with basic amino acids are exemplified by salts with arginine, lysine, ornithine, etc. Preferred salts with acidic amino acids are exemplified by salts with aspartic acid, glutamic acid, etc.

Among these, pharmaceutically acceptable salts are preferable. Preferable examples include, for example, when compound (I) or (I') has an acidic functional group, inorganic salts such as alkali metal salts (e.g., sodium salt, potassium salt, etc.), alkaline earth metal salts (e.g., calcium salt, magnesium salt, barium salt, etc.) and ammonium salts; and when compound (I) or (I') has a basic functional group, inorganic salts such as hydrochloride, sulfate, phosphate and hydrobromide, or, organic salts such as acetate, maleate, fumarate, succinate, methanesulfonate, p-toluenesulfonate, citrate and tartrate.

The prodrug of the compound (I) means a compound which is converted into compound (I) under the physiological condition or with a reaction due to an enzyme, a gastric acid, etc. in the living body, that is, a compound which is converted into compound (I) with oxidation, reduction, hydrolysis, etc. enzymatically; a compound which is converted into compound (I) with gastric acid, etc.; etc.

Examples of the prodrug of the compound (I) include a compound wherein an amino group of the compound (I) is substituted with acyl, alkyl, phosphoric acid, etc. (e.g. a compound wherein an amino group of the compound (I) is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein a hydroxy group of the compound (I) is substituted with acyl, alkyl, phosphoric acid, boric acid, etc. (e.g. a compound wherein a hydroxy group of the compound (I) is substituted with acetyl, palmitoyl, propanoyl, pivaloyl, succinyl, fumaryl, alanyl, dimethylaminomethylcarbonyl, etc.); a compound wherein a carboxyl group of the compound (I) is modified with ester, amide, etc. (e.g. a compound wherein a carboxyl group of the compound (I) is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These prodrugs can be produced by per se known methods from the compound (I).

The prodrug of the compound (I) may be a compound which is converted into the compound (I) under the physiological conditions as described in "Pharmaceutical Research and Development", Vol.7 (Drug Design), pages 163–198 published in 1990 by Hirokawa Publishing Co. (Tokyo, Japan).

Process for producing compound (I) is mentioned below.

Compound (I) can be produced by per se known means, for example, by the methods exemplified by the following schemes, etc. Compound (I') can be produced in accordance with the production of compound (I).

Compounds described in the following schemes include their salts. For their salts, for example, referred to are the same as the salts of compound (I).

"Room temperature" is normally meant to indicate a temperature falling between 0° C. and 30° C.

The symbols in chemical structural formulae in the schemes have the same meanings as above unless otherwise specifically described.

Scheme 1

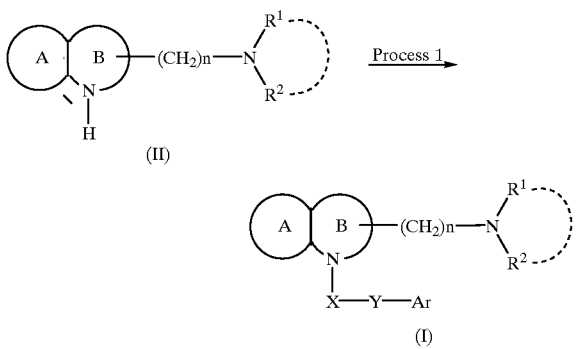

Process 1

Compound (II) is subjected to acylation or alkylation to obtain compound (I).

(1) Acylation

When X is SO, SO$_2$ or CO, compound (II) is subjected to acylation to obtain compound (I).

The "acylation" may be conducted in any per se known methods, for example, those described in Organic Functional Group Preparations, 2nd Ed., Academic Press Inc., 1989.

Concretely mentioned are methods in which (i) compound (II) is reacted with a compound of the formula:

$$L^1—X—Y—Ar$$

wherein $L^1$ represents a leaving group, the other symbols have the same meanings above, or a salt thereof, (hereafter simply referred to as Process A); or (ii) compound (II) is reacted with a compound of the formula:

$$HO—X—Y—Ar$$

wherein the symbols have the same meanings above, or a salt thereof, in the presence of a dehydrating and condensing agent, (hereafter simply referred to as Process B).

The "leaving group" for $L^1$ includes, for example, (1) halogen atoms (e.g., chlorine, bromine, iodine, etc.), (2) $C_{1-6}$ alkyl-carbonyloxy (e.g., acetoxy, propionyloxy, butyryloxy, valeryloxy, pivaloyoxy, etc.), (3) $C_{1-6}$ alkoxy-carbonyloxy (e.g., methoxycarbonyloxy, ethoxycarbonyloxy, isopropoxycarbonyloxy, tert-butoxycarbonyloxy, etc.), (4) $C_{6-10}$ aryloxy (e.g., phenoxy, pentachlorophenyloxy, pentafluorophenyloxy, p-nitrophenyloxy, etc.) which may be substituted by 1 to 5 substituents selected from the group consisting of halogen atoms, nitro, optionally halogenated $C_{1-6}$ alkyl and optionally halogenated $C_{1-6}$ alkoxy, (5) (benzotriazol-1-yl)oxy, (6) succinimidoxy, etc. Among these, preferred are halogen atoms, $C_{1-6}$ alkoxy-carbonyloxy, etc.

(i) Process A

Compound (II) is reacted with 1 to 1.5 equivalents of a compound of the formula:

$$L^1—X—Y—Ar$$

wherein the symbols have the same meanings above in the presence of a solvent.

The reaction temperature falls between about −20° C. and 100° C., preferably between room temperature and 80° C. The reaction time falls between 0.5 hours and 1 week.

The solvent is not limited as long as it is inert to the reaction (hereafter simply referred to as an inert solvent). For example, mentioned are ethers, halogenated hydrocarbons, aromatic solvents, nitriles, amides, ketones, sulfoxides, esters, water, etc., which may be used either singly or as a mixture of two or more species. Among these, preferred are tetrahydrofuran (THF), acetonitrile, N,N-dimethylformamide (DMF), acetone, pyridine, ethyl acetate, water, etc.

In the present reaction, a base is used if necessary. The amount of the base used is about 1 to 5 equivalents of compound (II).

The "base" includes, for example;

(1) strong bases such as alkali metal or alkaline earth metal hydrides (e.g., lithium hydride, sodium hydride, potassium hydride, calcium hydride, etc.), alkali metal or alkaline earth metal amides (e.g., lithium amide, sodium amide, lithium dulsopropylamide, lithium dicyclohexylamide, lithium hexamethyldisilazide, sodium hexamethyldisilazide, potassium hexamethyldisilazide, etc.), alkali metal or alkaline earth metal lower-alkoxides (e.g., sodium methoxide, sodium ethoxide, potassium tert-butoxide, etc.), etc.;

(2) inorganic bases such as alkali metal or alkaline earth metal hydroxides (e.g., sodium hydroxide, potassium hydroxide, lithium hydroxide, barium hydroxide, etc.), alkali metal or alkaline earth metal carbonates (e.g., sodium carbonate, potassium carbonate, cesium carbonate, etc.), alkali metal or alkaline earth metal hydrogencarbonates (e.g., sodium hydrogencarbonate, potassium hydrogencarbonate, etc.), etc.;

(3) organic bases such as amines e.g., triethylamine, diisopropylethylamine, N-methylmorpholine, dimethylaminopyridine, DBU (1,8-diazabicyclo[5.4.0]-7-undec-7-ene), DBN (1,5-diazabicyclo[4.3.0]non-5-ene), etc., basic heterocyclic compounds, e.g., pyridine, imidazole, 2,6-lutidine, etc. Among these, preferred are potassium carbonate, sodium hydrogencarbonate, triethylamine, N-methylmorpholine, pyridine, etc.

The compound of the formula:

$$L^1—X—Y—Ar$$

wherein symbols have the same meanings above, may be obtained from a compound of the formula:

$$HO—X—Y—Ar$$

wherein symbols have the same meanings above, by a per se known method. L¹ is preferably halogen.

The compound of the formula:

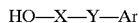
HO—X—Y—Ar wherein symbols have the same meanings above can be obtained easily, and further, may be produced easily by a per se known method. For example, (3-aryl-1,2,4-oxadiazol-5-yl)acetic acid, 3-(3-aryl-1,2,4-oxadiazol-5-yl)propionic acid, 4-(3-aryl-1,2,4-oxadiazol-5-yl)butyric acid, and their analogues can be produced according to the methods described in Journal of Heterocyclic Chemistry, Vol. 21, pp. 1193–1195 (1984); and 3-(4-aryl-oxazol-5-yl)propionic acid and its analogues can be produced according to the methods described in JP-A-59(1984)-190979.

(ii) Process B

Compound (II); about one equivalent to 5 equivalents of a compound of the formula:

HO—X—Y—Ar wherein the symbols have the same meanings above, or a salt thereof; about one equivalent to 2 equivalents of a dehydrating/condensing agent are reacted in an inert solvent under room temperature for about 10 to 24 hours.

The dehydrating/condensing agent includes, for example, dicylocarbodiimide (DCC), 1-ethyl-3-(3-dimethylaminopropyl)carbodiimide hydrochloride (WSC), etc. Among these, WSC is preferable.

The inert solvent include, for example, nitriles (preferably acetonitrile), amides (preferably DMF), halogenated hydrocarbons (preferably dichloromethane), ethers (preferably THF), etc., which may be used either singly or as a mixture of two or more species.

In the present reaction, about one equivalent to 1.5 equivalents of 1-hydroxybenzotriazole (HOBt) and /or about one equivalent to 5 equivalents of a base (e.g., triethylamine, etc.) may be added if necessary.

(2) Alkylation

When X is methylene or S, compound (II) is subjected to alkylation to obtain compound (I).

The "alkylation" may be conducted in any per se known methods, for example, those described in Organic Functional Group Preparations, 2nd Ed., Academic Press Inc., 1989.

Concretely mentioned is a method in which compound (II) is reacted with a compound of the formula:

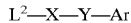
L²—X—Y—Ar wherein represents a leaving group, the symbols have the same meanings above, or a salt thereof.

The "leaving group" for L² includes, for example, halogen atoms (e.g., chlorine, bromine, iodine, etc.), optionally halogenated $C_{1-6}$ alkylsulfonyloxy (e.g., methanesulfonyloxy, ethanesulfonyloxy, trifluoromethanesulfonyloxy, etc.), $C_{6-10}$ arylsulfonyloxy which may be substituted, etc. The "substituent" for the "$C_{6-10}$ arylsulfonyloxy which may be substituted" includes, for example, 1 to 3 substituents selected from the group consisting of halogen atoms, and optionally halogenated $C_{1-6}$ alkyl or $C_{1-6}$ alkoxy. Specific examples of the "$C_{6-10}$ arylsulfonyloxy which may be substituted" are benzenesulfonyloxy, p-toluenesulfonyloxy, 1-naphthalenesulfonyloxy, 2-naphthalenesulfonyloxy, etc.

Compound (II) is reacted with about 1 to 5 equivalents (preferably 1 to 2 equivalents) of a compound of the formula:

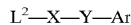
L²—X—Y—Ar wherein L²-represents a leaving group, the symbols have the same meanings above, in an inert solvent in the co-existence of a base.

The amount of the base used is normally about 1 to 5 equivalents of compound (II).

The "base" includes the above-mentioned "strong bases", "inorganic bases", "organic bases", and etc. Preferable base includes potassium carbonate, sodium hydride, sodium hydroxide, etc.

The reaction temperature falls between about −20° C. and 100° C., preferably between room temperature and 80° C. The reaction time falls between 0.5 hours and 1 day.

The inert solvent includes, for example, alcohols, ethers, halogenated hydrocarbons, aromatic solvents, nitrites, amides, ketones, sulfoxides, water, etc., which may be used either singly or as a mixture of two or more species. Among these, preferred are acetonitrile, N,N-dimethylformamide (DMF), acetone, ethanol, pyridine, water, etc.

In the thus obtained compound (I), intermolecular functional groups can be converted into the desired functional groups by combination of per se known chemical reactions. Examples of the chemical reactions include oxidation, reduction, alkylation, hydrolysis, amination, esterification, aryl-coupling reaction, deprotection, etc.

For example, compound (Ia) obtained by the method of scheme 1, and having CO for X in compound (I), may be subjected to reduction to obtain compound (Ib) having methylene for X.

The reduction may be conducted using any per se known methods, for example, those described in Organic Functional Group Preparations, 2nd Ed., Academic Press Inc., 1989.

Concretely mentioned is a method in which compound (Ia) is reacted with about 1 equivalent to 20 equivalents (preferably about 1 equivalent to 6 equivalents) of a metal hydride in an inert solvent.

The "metal hydride" includes, for example, aluminum hydride, lithium aluminum hydride, sodium borohydride, lithium borohydride, sodium cyanoborohydride, lithium cyanoborohydride, borane complexes (e.g., borane-THF complex, catechol-borane, etc.), dibutyl aluminum hydride, as well as mixtures of these metal hydrides and Lewis acids (e.g., aluminum chloride, titanium tetrachloride, cobalt chloride, etc.) or phosphorus oxychloride, etc. Preferred metal hydrides are lithium aluminum hydride, aluminum hydride, borane-THF complex, etc.

The inert solvent includes, for example, ethers.

The reaction temperature varies, depending on the metal hydride used, but normally falls between −70° C. and 100° C. Where lithium aluminum hydride is used, the reaction temperature may be between room temperature and 80° C. Where borane complex is used, the reaction temperature may be between room temperature and 100° C., preferably between room temperature and 60° C.

The reaction time falls between 0.1 hours and 48 hours.

Where a halogen atom (e.g., bromine, iodine, etc.) exists on the intermolecular aromatic ring of compound (I), this halogen atom can be substituted by an aromatic group by an aryl-coupling reaction.

The "aromatic group which may be substituted" includes the same as the above "aromatic group which may be substituted". Preferred are phenyl, 1-naphthyl, 2-naphthyl, 2-biphenylyl, 3-biphenylyl, 4-biphenylyl, 2-thienyl, 3-thienyl, 2-pyridyl, 3-pyridyl, 4-pyridyl, etc., each of which may be substituted by 1 to 3 substituents selected from the group consisting of nitro, halogen atoms, cyano, formyl, optionally halogenated $C_{1-6}$ alkyl, optionally halogenated $C_{1-6}$ alkoxy, mono-$C_{1-6}$ alkylamino, di-$C_{1-6}$ alkylamino and $C_{1-6}$ alkylcarboxamido.

The aryl-coupling reaction can be conducted by any per se known methods, for example, according to the methods described in Acta. Chemica Scandinavia, 221–230 (1993), etc.

Concretely, compound (I) having a halogen atom on its intermolecular aromatic ring (simply referred to as compound (Ic)), an aromatic metal compound which may be substituted and a base are reacted in an inert solvent in the presence of a transition metal catalyst.

The "aromatic metal compound" for the "aromatic metal compound which may be substituted" includes, for example, aryl-boric acid derivatives, aryl di-$C_{1-6}$ alkylboranes, aryl-zinc derivatives, aromatic heterocyclic-boric acid derivatives, aromatic heterocyclic di-$C_{1-6}$ alkylboranes, aromatic heterocyclic-zinc derivatives, etc. The "substituent" for the "aromatic metal compound which may be substituted" includes, for example, 1 to 5 substituents selected from the group consisting of halogen atoms (e.g., fluorine, chlorine, bromine, iodine, etc.); $C_{1-3}$ alkylenedioxy (e.g., methylenedioxy, ethylenedioxy, etc.); nitro; cyano; optionally halogenated $C_{1-6}$ alkyl; optionally halogenated $C_{3-6}$ cycloalkyl; optionally halogenated $C_{1-6}$ alkoxy; optionally halogenated $C_{1-6}$ alkylthio; hydroxy; amino; mono-$C_{1-6}$ alkylamino (e.g., methylamino, ethylamino, propylamino, isopropylamino, butylamino, etc.); di-$C_{1-6}$ alkylamino (e.g., dimethylamino, diethylamino, dipropylamino, dibutylamino, ethylmethylamino, etc.); formyl; carboxy; carbamoyl; optionally halogenated $C_{1-6}$ alkyl-carbonyl; $C_{1-6}$ alkoxy-carbonyl (e.g., methoxycarbonyl, ethoxycarbonyl, propoxycarbonyl, tert-butoxycarbonyl, etc.); mono-$C_{1-6}$ alkyl-carbamoyl (e.g., methylcarbamoyl, ethylcarbamoyl, etc.); di-$C_{1-6}$ alkyl-carbamoyl (e.g., dimethylcarbamoyl, diethylcarbamoyl, ethylmethylcarbamoyl, etc.); optionally halogenated $C_{1-6}$ alkylsulfonyl; formylamino; optionally halogenated $C_{1-6}$ alkyl-carboxamido (e.g., acetamido, etc.); $C_{1-6}$ alkoxy-carboxamide (e.g., methoxycarboxamido, ethoxycarboxamido, propoxycarboxamido, butoxycarboxamido, etc.); $C_{1-6}$ alkylsulfonylamino (e.g., methylsulfonylamino, ethylsulfonylamino, etc.); $C_{1-6}$ alkyl-carbonyloxy (e.g., acetoxy, propanoyloxy, etc.); $C_{1-6}$ alkoxy-carbonyloxy (e.g., methoxycarbonyloxy, ethoxycarbonyloxy, propoxycarbonyloxy, butoxycarbonyloxy, etc.); mono-$C_{1-6}$ alkyl-carbamoyloxy (e.g., methylcarbamoyloxy, ethylcarbamoyloxy, etc.); di-$C_{1-6}$ alkyl-carbamoyloxy (e.g., dimethylcarbamoyloxy, diethylcarbamoyloxy, etc.); etc.

The amount of the "aromatic metal compound which may be substituted" used is about 1 equivalent to 2 equivalents of the compound (Ic).

The "base" includes, for example, sodium carbonate, sodium hydrogencarbonate, etc.

The "transition metal catalyst" includes, for example, palladium catalysts, nickel catalysts, etc. The "palladium catalysts" include, for example, tetrakis (triphenylphosphine)palladium(0), palladium acetate, bis (triphenylphosphine)palladium(II) chloride, palladium-carbon, etc. The "nickel catalysts" include, for example, tetrakis (triphenylphosphine)nickel(0), etc.

The amount of the "transition metal catalyst" used is about 0.01 equivalents to 1 equivalent of the compound (Ic).

The reaction temperature falls between room temperature and 150° C., preferably about 80° C. and 150° C. The reaction time falls between about 1 hour and 48 hours.

The inert solvent includes, for example, water, alcohols, aromatic solvents, etc., which maybe used either singly or as a mixture of two or more species. Preferably, water, ethanol, toluene, or the like is used either singly or as a mixture of two or more species.

Compound (II) can be produced by any per se known methods or analogous methods thereto. For example, 3-(N, N-dimethylamino)methyl-1,2,3,4-tetrahydroquinoline is a known compound described in JP-A-8(1996)-176087.

Compound (IIa) having, as a fused ring formed by Ring A and Ring B, for example, indoline, 1,2,3,4-tetrahydroquinoline or 2,3,4,5-tetrahydro-1H-1-benzazepine, may be obtained according to the method described in the following scheme 2.

Scheme 2

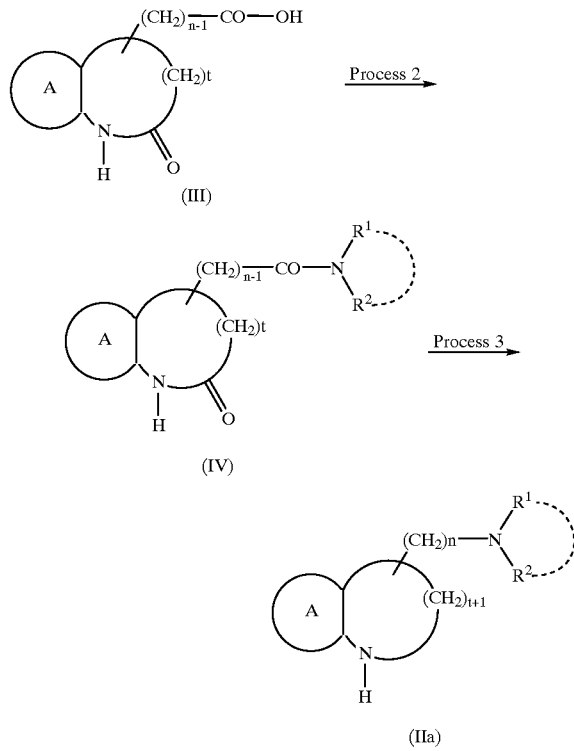

In the above formulae, t represents an integer of 1 to 3.

Process 2

Compound (III) is subjected to per se known amidation to obtain compound (IV).

Compound (III) can be obtained easily, and further, may be produced easily by a per se known method. For example, 2-oxo-1,2,3,4-tetrahydroquinolin-3-acetic acid, 2-oxo-2,3,4,5-tetrahydro-1H-1-benzazepine-4-carboxylic acid and its analogues can be produced according to the methods described in Journal of American Chemical Society (J. Am. Chem. Soc.), vol.77, pp.5932–5933, (1995); 2-oxo-1,2,3,4-tetrahydroquinolin-3-carboxylic acid and its analogues can be produced according to the methods described in JP-A-7 (1995)-126267.

As amidation, employed is amidation generally used in peptide chemicals, etc. Concretely, it is conducted in the similar manner as acylation described in the above process 1.

Process 3

Compound (IV) is subjected to reduction to obtain compound (IIa).

Reduction can be conducted in the similar manner as in the above reaction to obtain compound (Ib) from compound (Ia).

Concretely, mentioned is a method in which compound (IV) is reacted with about 1 equivalent to 10 equivalents (preferably about 1 equivalent to 6 equivalents) of a metal hydride in an inert solvent.

The "metal hydride" includes, for example, aluminum hydride, lithium aluminum hydride, sodium borohydride, lithium borohydride, sodium borohydride cyanide, lithium borohydride cyanide, borane complexes (e.g., borane-THF complex, catechol-borane, etc.), dibutyl aluminum hydride, as well as mixtures of these metal hydrides and Lewis acids (e.g., aluminum chloride, titanium tetrachloride, cobalt chloride, etc.) or phosphorus oxychloride, etc. Preferred metal hydrides are borane complexes, lithium aluminum hydride, aluminum hydride, etc.

The reaction temperature varies, depending on the metal hydride used, but normally falls between −70° C. and 100° C. Where lithium aluminum hydride is used, the reaction temperature may be between room temperature and 80° C. Where borane complex is used, the reaction temperature may be between room temperature and 100° C., preferably between room temperature and 60° C.

The reaction time falls between 0.1 hours and 48 hours.

The inert solvent includes, for example, ethers.

In the production of compound (I), compounds having CO or $SO_2$ as X can also be produced by combination of acylation and a carbon-carbon binding reaction.

The strong base includes, for example, alkali metal or alkaline earth metal hydrides (e.g., lithium hydride, sodium hydride, potassium hydride, calcium hydride, etc.), alkali metal or alkaline earth metal amides (e.g., lithium amide, sodium amide, lithium diisopropylamide, lithium dicyclohexylamide, lithium hexamethyldisilazide, sodium hexamethyldisilazide, potassium hexamethyldisilazide, etc.), alkali metal or alkaline earth metal lower-alkides (e.g., sodium methoxide, sodium ethoxide, potassium tert-butoxide, etc.), etc. Among these, alkali metal amides are preferable.

The inert solvent includes, for example, ethers, amides, halogenated hydrocarbons, which may be used either singly or as a mixture of them.

The reaction temperature may be between −70° C. and room temperature, preferably −20° C. and room temperature. The reaction time falls between about 0.1 hours and 1 day, preferably about 1 to 5 hours.

Where the spacer Y has acylamino as its substituent, such compound can be produced by the method described in the following scheme 4.

Scheme 3

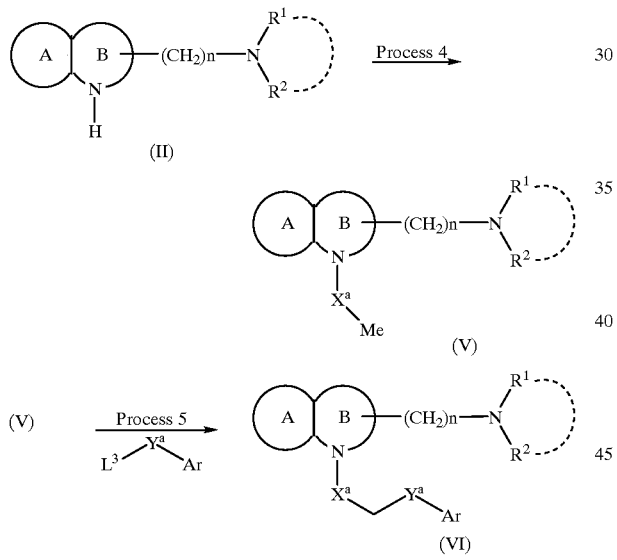

In the above formulae, $X^a$ represents CO or $SO_2$, $Y^a$ represents $C_{1-4}$ alkylene, $C_{2-4}$ alkenylene or $C_{2-4}$ alkynylene, $L^3$ represents the same leaving group as the above $L^2_1$, other symbols have the same meanings as above.

Process 4

Compound (II) is subjected to acylation described in Process 1 to obtain compound (V). The acylating agent includes acetyl chloride, acetic acid anhydride methanesulfonyl chloride, etc. The reaction conditions are the same as in Process 1.

Process 5

Compound (V) obtained in Process 4 is subjected to a carbon-carbon binding reaction. The carbon-carbon binding reaction includes a method using a strong base, etc. Normally, compound (V) is reacted with 1 to 2 equivalents of a strong base, and then with 1 to 3 equivalents, preferably 1 to 1.5 equivalents of $L^3$—$Y^a$—Ar.

Scheme 4

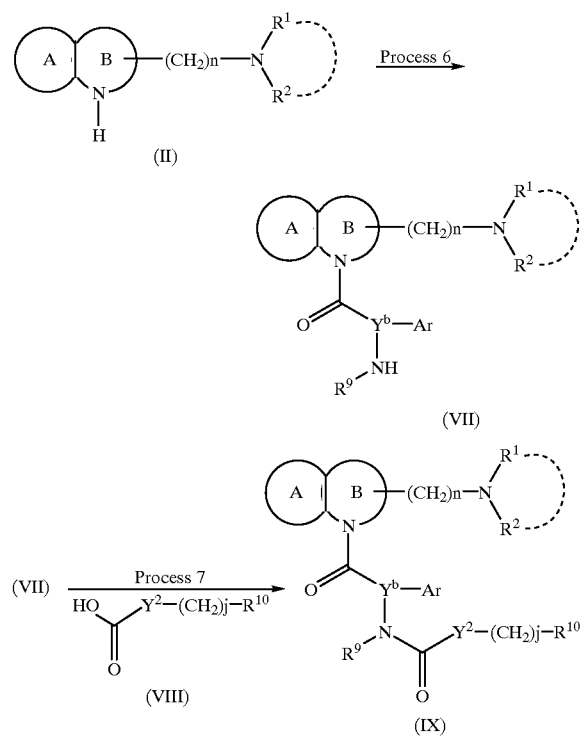

Scheme 5

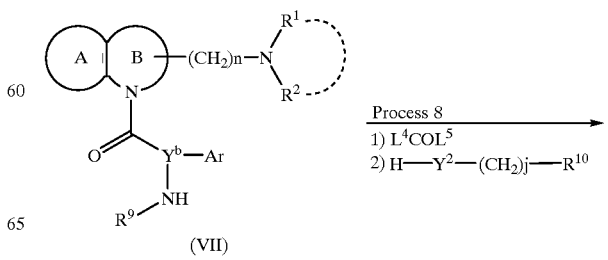

-continued

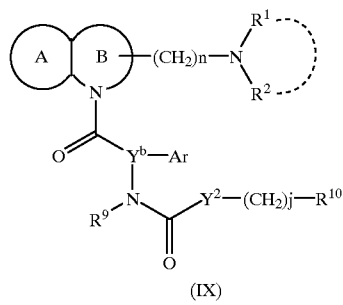

(IX)

In the above formulae, $Y^b$ represents a spacer without acylamino, $L^4$ and $L^5$ represent a leaving group, the other symbols have the same meanings as above.

Process 6

Compound (II) is subjected to condensation with natural or synthetic amino acids whose amino is protected with a protective group, then to deprotection to obtain compound (VII).

The condensation is the same as the reaction usually employed in peptide chemistry. Concretely, it is conducted in the similar manner as in the above "acylation". Especially, the method described in "Process A" is preferable.

The amino-protecting group includes that generally employed in peptide chemistry. Concretely, mentioned are $C_{7-14}$ aralkyloxy-carbonyl, trityl, phthaloyl, etc.

The deprotection is conducted according to per se known methods.

Process 7

Compound (VII) is reacted with compound (VIII) in the same manner as in the above acylation.

The above "natural or synthetic amino acids whose amino is protected with a protective group" and compound (VIII) are on the market, or they can be produced in a short process by known techniques using starting materials which can be obtained easily.

Conversion of compound (VII) into compound (IX) can be conducted by the method described in Scheme 5.

Process 8

Compound (VII) is reacted with 1 to 2 equivalents of $L^4COL^5$ in an inert solvent at room temperature for about 0.5 to 5 hours, then with 1 to 2 equivalents of $HY^2(CH_2)_j-R^{10}$ or a salt thereof (in the formulae, symbols have the same meanings as above) in an inert solvent at room temperature for about 0.5 to 24 hours. In this reaction, about 1 to 5 equivalents of a base (e.g., N-ethyldiisopropylamine, etc.) may be added according to necessity.

The leaving group for $L^4$ and $L^5$ is preferably, for example, succinimido.

The inert solvent includes, for example, nitriles (preferably acetonitrile), ethers (preferably THF), halogenated hydrocarbons (preferably dichloromethane), which may be used either singly or as a mixture of two or more species.

The above "alcohols" includes, for example, methanol, ethanol, isopropanol, tert-butanol, etc.

The above "ethers" includes, for example, diethyl ether, tetrahydrofuran (THF), 1,4-dioxane, 1,2-dimethoxyethane, etc.

The above "halogenated hydrocarbons" includes, for example, dichloromethane, chloroform, 1,2-dichloroethane, carbon tetrachloride, etc.

The above "aromatic solvents" includes, for example, benzene, toluene, xylene, pyridine, etc.

The above "hydrocarbons" includes, for example, hexane, pentane, cyclohexane, etc.

The above "amides" includes, for example, N,N'-dimethylformamide (DMF), N,N'-dimethylacetamide, N-methylpyrrolidone, etc.

The above "ketones" includes, for example, acetone, methyl ethyl ketone, etc.

The above "sulfoxides" includes, for example, dimethylsulfoxide (DMSO), etc.

The above "nitriles" includes, for example, acetonitrile, propionitrile, etc.

The above "esters" includes, for example, ethyl acetate, etc.

In the above-mentioned reactions where the starting compounds are substituted by any of amino, carboxy, hydroxy or carbonyl, those groups may be protected by ordinary protective groups which are generally used in peptide chemistry. The protective groups may be removed after the reaction to give the desired compounds.

The amino-protecting group includes, for example, formyl, $C_{1-6}$ alkyl-carbonyl (e.g., acetyl, propionyl, etc.), $C_{1-6}$ alkyloxy-carbonyl (e.g., methoxycarbonyl, ethoxycarbonyl, tert-butoxycarbonyl, etc.), benzoyl, $C_{7-10}$ aralkyl-carbonyl (e.g., benzylcarbonyl, etc.), $C_{7-14}$ aralkyloxy-carbonyl (e.g., benzyloxycarbonyl, 9-fluorenylmethoxycarbonyl, etc.), trityl, phthaloyl, N,N-dimethylaminomethylene, silyl (e.g., trimethylsilyl, triethylsilyl, dimethylphenylsilyl, tert-butyl-dimethylsilyl, tert-butyl-diethylsilyl, etc.), $C_{2-6}$ alkenyl (e.g., 1-allyl, etc.), etc. These groups may be substituted by 1 to 3 substituents of halogen atoms (e.g., fluoro, chloro, bromo, iodo, etc.), $C_{1-6}$ alkoxy (e.g., methoxy, ethoxy, propoxy, etc.) or nitro, etc.

The carboxy-protecting group includes, for example, $C_{1-6}$ alkyl (e.g., methyl, ethyl, propyl, isopropyl, butyl, tert-butyl, etc.), $C_{7-11}$ aralkyl (e.g., benzyl, etc.), phenyl, trityl, silyl (e.g., trimethylsilyl, triethylsilyl, dimethylphenylsilyl, tert-butyl-dimethylsilyl, tert-butyl-diethylsilyl, etc.), $C_{2-6}$ alkenyl (e.g., 1-allyl, etc.), etc. These groups may be substituted by 1 to 3 substituents of halogen atoms (e.g., fluorine, chlorine, bromine, iodine, etc.), $C_{1-6}$ alkoxy (e.g., methoxy, ethoxy, propoxy, etc.) or nitro, etc.

The hydroxy-protecting group includes, for example, $C_{1-6}$ alkyl (e.g., methyl, ethyl, propyl, isopropyl, butyl, tert-butyl, etc.), phenyl, trityl, $C_{7-10}$ aralkyl (e.g., benzyl, etc.), formyl, $C_{1-6}$ alkyl-carbonyl (e.g., acetyl, propionyl, etc.), benzoyl, $C_{7-10}$ aralkyl-carbonyl (e.g., benzylcarbonyl, etc.), 2-tetrahydropyranyl, 2-tetrahydrofuranyl, silyl (e.g., trimethylsilyl, triethylsilyl, dimethylphenylsilyl, tert-butyl-dimethylsilyl, tert-butyl-diethylsilyl, etc.), $C_{2-6}$ alkenyl (e.g., 1-allyl, etc.), etc. These groups may be substituted by 1 to 3 substituents of halogen atoms (e.g., fluorine, chlorine, bromine, iodine, etc.), $C_{1-6}$ alkyl (e.g., methyl, ethyl, propyl, etc.), $C_{1-6}$ alkoxy (e.g., methoxy, ethoxy, propoxy, etc.) or nitro, etc.

The carbonyl-protecting group includes, for example, cyclic acetals (e.g., 1,3-dioxane, etc.), acyclic acetals (e.g., di-$C_{1-6}$ alkylacetals, etc.), etc.

Those protective groups may be removed by any per se known methods, for example, the methods described in Protective Groups in Organic Synthesis, published by John Wiley and Sons, 1980, etc. For example, the method of removing these protective groups, includes the methods using acids, bases, ultraviolet ray, hydrazine, phenylhydrazine, sodium N-methyldithiocarbamate, tetrabutylammonium fluoride, palladium acetate, trialkylsilyl-halide (e.g., trimethylsilyliodide, trimethylsilylbromide, etc.), etc.; and reduction, etc.

Compound (I) can be isolated and purified by any known procedures, for example, through solvent extraction, PH adjustment, redistribution, crystallization, recrystallization, chromatography, etc. The starting compounds for compound (I) and their salts can also be isolated and purified according to the same known procedures as above, but without any isolation procedure, they may be used in the next step while they are in reaction mixtures.

Compound (I) may also be in the form of hydrates or non-hydrates thereof.

Where compound (I) includes optical isomers, stereoisomers, regio isomers and rotational isomers, those are within the scope of compound (I), and can be isolated as their single compound through per se known synthesis or separation. For example, where optical isomers of compound (I) exist, those resolved from their mixtures through optical resolution are within the scope of compound (I).

The optical isomers can be produced in any per se known methods. Concretely, optically active synthetic intermediates or mixtures of racemate of the final product are subjected to ordinary optical resolution to give the corresponding optical isomers.

For the optical resolution, employable are any per se known methods, such as a fractional recrystallization method, a chiral column method, a diastereomer method, etc.

1) Fractional Recrystallization

The method which comprises allowing a racemate to react with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) to give a salt, which is then isolated through fractional recrystallization, followed by, when desired, subjecting the isolated compound to neutralization to obtain free optical isomers.

2) Chiral Column Method

The method of separating a racemate or a salt thereof, which comprises utilizing a column for fractionating optical isomers (chiral column). In the case of liquid column chromatography, for example, a mixture of optical isomers is applied to a chiral column, such as ENANTIO-OVM (manufactured by Tosoh Corp.), CHIRAL SERIES (manufactured by Daicel Co.), etc., which is then eluted with water, various buffers (e.g., phosphate buffer) and organic solvents (e.g., ethanol, methanol, isopropanol, acetonitrile, trifluoroacetic acid, diethylamine, etc.), singly or as a suitable mixture of them, to isolate the individual optical isomers. In the case of gas chromatography, for example, a chiral column such as CP-Chirasil-DeX CB (manufactured by GL Science Co.), etc. is used for isolation.

3) Diastereomer Method

A racemic mixture is chemically reacted with an optically-active reagent to give a mixture of diastereomer, which is subjected to ordinary separation means (e.g., fractional recrystallization, chromatography, etc.) to give single compounds. The thus-isolated single compounds are then chemically processed, for example, through hydrolysis to thereby remove the optically-active reagent site from the compounds to obtain optical isomers. For example, where compound (I) has a hydroxy group or a primary or secondary amino group in the molecule, it is condensed with an optically-active organic acid (e.g., MPTA [α-methoxy-α-(trifluoromethyl)phenyl-acetic acid], (−)-menthoxyacetic acid, etc.) or the like to give the corresponding ester-type or amide-type diastereomer. On the other hand, where compound (I) has a carboxylic acid group, it is condensed with an optically-active amine or alcohol reagent to give the corresponding amide-type or ester-type diastereomer. The thus-isolated diastereomer is then subjected to acidic or basic hydrolysis, through which it is converted into the optical isomer of the original compound.

Compounds (I) and (I') have an excellent somatostatin receptor binding inhibition activity (namely, somatostatin receptor agonistic and antagonistic activities). Among compound (I), compound (I-I) represented by the formula:

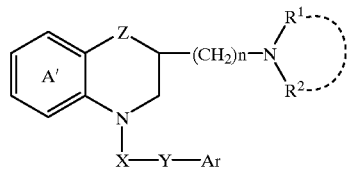

wherein symbols have the same meanings as above, or a salt thereof; especially, compound (I-II) represented by the formula:

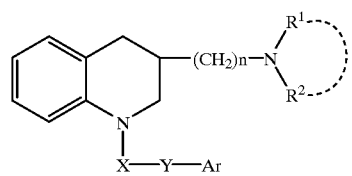

wherein symbols have the same meanings as above, or a salt thereof; has an excellent somatostatin receptor agonistic activity/antagonistic activity.

Among compound (I), especially compound (I-III) represented by the formula:

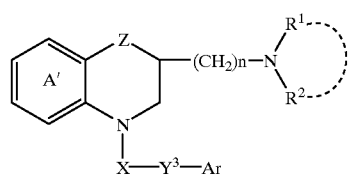

wherein symbols have the same meanings as above, or a salt thereof has an excellent SSTR4 agonistic activity.

Compound (I-IV) represented by the formula:

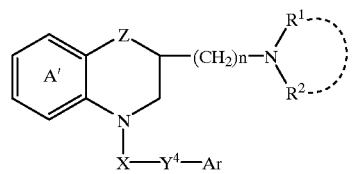

wherein symbols have the same meanings as above, or a salt thereof has an excellent SSTR2 and SSTR3 receptor affinity.

Compounds (I) and (I') function through various intracellular signal transduction systems with which somatostatin is associated. The "intracellular signal transduction systems" include, for example, that involves adenylate cyclase, $K^+$ channels, $Ca^{2+}$ channels, protein phosphatase, phospholipase C/inositol trisphosphate production systems, MAP kinase, $Na^+/H^+$ exchanger, phospholipase A2, a transcription factor such as NF-κB. The compound (I) modulates a direct or indirect cell proliferation inhibitory action or apoptosis both of which are associated with somatostatin.

Further, compounds (I) and (I') are low in their toxicity, and enhance or inhibit production or secretion of a variety of hormones, growth factors and physiologically active substances by effecting somatostatin receptors in mammals (e.g., human, cattle, horse, dog, cat, monkey, mouse and rat, especially, human).

The "hormones" include, for example, growth hormone (GH), growth hormone-releasing hormones (GHRH), thyroid stimulating hormone(TSH), prolactin, insulin, glucagon, etc. The "growth factors" include, for example, insulin-like growth factor-i (IGF-1) and vascular endothelial cell growth factor (VEGF). The "physiologically active substances" include, for example, vasoactive intestinal polypeptide (VIP), gastrin, glucagon-like peptide-1, amylin, substance-P, CCK(cholecystokinin), amylase, interleukins such as interleukin-1 (IL-1) and etc., cytokines such as TNF-$\alpha$ and etc., cardiotropin, etc.

Therefore, compounds (I) and (I') are safe, and useful in modulating diseases associated with disorders of the above intracellular signal transduction systems (e.g., diseases associated with excess enhancement or inhibition, etc.); disorders of regulation of cell proliferation; diseases associated with disorders of production or secretion of a variety of hormones, growth factors, physiologically active substances and etc.; growth; immune, gastroenteric or metabolic functions, etc.

Compounds (I) and (I') are useful (1) for drugs for treatment of tumors such as acromegaly, TSH-producing tumors, nonsecretory (afunctional) hypophysial tumors, ectopic ACTH (adrenocorticotrophic hormone)-producing tumors, medullar thyroid carcinoma, VIP-producing tumors, glucagon-producing tumors, gastrin-producing tumors, insulinoma and carotinoid tumor, (2) for drugs for treatment of insulin-dependent and non-insulin dependent diabetes mellitus or a variety of diseases associated with them, namely diabetic complications such as diabetic retinopathy, diabetic nephropathy, diabetic neuropathy, Doan syndrome and orthostatic hypotension, (3) for drugs for improvement of hyperinsulinemia or for treatment of obesity caused by inhibition of appetite, and overeating, (4) for drugs for treatment of acute pancreatitis, chronic pancreatitis, pancreal/intestinal fistula, hemorrhagic ulcer, peptic ulcer, gastritis, hyperchylia, regurgitant esophagitis, (5) for drugs for improvement of various symptoms associated with the *Helicobacter pylori* infection, for example, inhibitors of gastrin hypersecretion, (6) for drugs for inhibition of amylase secretion associated with endoscopic cholangiopancreatography, and drugs for prognostic treatment of surgical operation of pancreas, (7) for drugs for treatment of diarrhea due to intestinal malabsorption, promotion of secretion or dyskinesia of the digestive tracts (for example, short bowel syndrome), diarrhea due to the drugs for cancer chemotherapy, diarrhea due to congenital small intestine atrophy, diarrhea due to neuroendocrine tumors such as VIP-producing tumors, diarrhea due to AIDS, diarrhea due to graft versus host reaction associated with bone marrow transplantation, diarrhea due to diabetes mellitus, diarrhea due to celiac plexus blocking, diarrhea due to systemic sclerosis and diarrhea due to eosinophilia, (8) for drugs for treatment of dumping syndrome, irritable colitis, Crohn disease and inflammatory bowel disease, (9) for drugs for treatment of tumors or cancers (e.g., thyroid cancer, large bowel cancer, breast cancer, prostatic cancer, small cell lung cancer, non-small cell cancer, pancreatic cancer, stomach cancer, cholangiocarcinoma, hepatic cancer, vesical cancer, ovarian cancer, melanoma, osteosarcoma, chondrosarcoma, malignant pheochromocytoma, neuro-blastoma, brain tumors, thymoma, renal cancers), leukemia (e.g., leukemia of basophilic leukemia, chronic lymphocytic leukemia, chronic myeloid leukemia, Hodgkin disease, and non-Hodgkin lymphoma) (drugs for treatment of these cancers can be used for monotherapy or concomitant therapy with other anticancer drugs such as Tamoxifen, LHRH agonists, LHRH antagonists, interferon-$\alpha$, $\beta$ and $\gamma$, interleukin-2 and etc,), (10) for drugs for prevention and treatment of hypertrophic cardiomyopathy, arteriosclerosis, valvular disease, myocardiac infarction (especially, myocardiac infarction post percutaneous transluminal coronary arterioplasty) and reangioplasty, (11) for drugs for treatment of hemorrhage of esophageal varicosis, cirrhosis and peripheral blood vessel disorders, (12) for drugs for treatment of diseases associated with general or local inflammation, for example, polyarteritis, rheumatoid arthritis, psoriasis, sunburn, eczema and allergy (e.g., asthma, atopic dermatitis and allergic rhinitis) because they inhibit or modulate the secretion of physiologically active substances acting on the immune system (e.g., Substance P, tachykinin and cytokines), (13) for drugs for treatment of dementia (e.g., Alzheimer disease, Alzheimer-type senile dementia, vascular/multi-infarct dementia), schizophrenia, epilepsy, depression, generalized anxiety disorder, sleep disorder, and multiple sclerosis, because they give influence on the production and secretion of nerve regulators, (14) for drugs for treatment of oculopathy (e.g., glaucoma, etc.), (15) for drugs for prevention and treatment of acute bacterial meningitis, acute virus encephalitis, adult respiratory distress syndrome, bacterial pneumonia, severe systemic mycotic infection, tuberculosis, spinal damage, bone fracture, hepatic failure, pneumonia, alcoholic hepatitis, virus A hepatitis, virus B hepatitis, virus C hepatitis, AIDS infection, human papilloma virus infection, influenza infection, metastasis of cancer, multiple myeloma, osteomalacia, osteoporosis, bone Paget disease, nephritis, renal failure, sepsis, septic shock, hypercalcemia, C: hypercholesterolemia, hypertriglyceridemia, hyperlipemia, systemic lupus erythematosus, transient ischemic attach and alcoholic hepatitis, (16) for cure of organ transplantation, burns, trauma, and alopecia, (17) as analgesics for chronic or acute pain (e.g., postoperative pain, inflammatory pain, dental pain, bone disease (e.g., arthritis, rheumatism, osteoporosis etc.) derived pain), (18) for imaging of tumors having somatostatin receptors after administering radioactive substance (e.g., $^{123}$I, $^{125}$I, $^{111}$In, etc.) to compound (I) or (I') either directly or via a suitable spacer, and (19) for targeting tumors with somatostatin receptors using compound (I) or (I') conjugated with anti-cancer drugs directly or using a suitable spacer.

Somatostatin is associated with secretion of growth hormone (especially in the case of SSTR2), therefore, compound (I) or (I'), when it is used directly or for the purpose of promoting secretion of growth hormone, can provide the same effect and use as growth hormone itself.

Thus, compounds having a SSTR2 antagonistic activity or a salt thereof among compound (I-VII) can be used for prevention or treatment of diseases or symptoms caused by insufficiency of growth hormone or IGF-1.

The "prevention or treatment of diseases or symptoms caused by insufficiency of growth hormone or IGF-1" includes, for example, treatment of insulin-dependent and non-insulin dependent diabetes mellitus or a variety of diseases associated with them, namely diabetic complications such as diabetic retinopathy, diabetic nephropathy, diabetic neuropathy, Doan syndrome and orthostatic hypotension; prevention of adverse effects caused by disassimilation of glucocorticoid; prevention or treatment of osteoporosis; stimulation of immune system (e.g., promotion of increase in hemocytes such as lymphocyte; strengthening of an antimicrobial activity or an antiviral activity); promotion of cure of burns and trauma; acceleration in the treatment of bone fracture; treatment of acute or chronic renal diseases; treatment or improvement of diseases or symptoms (short stature, delayed growth) associated with insufficiency of growth hormone in adults or infants; treatment of obesity; promotion of recovery after surgical operations; improvement of delayed growth associated with Prader-Willi syndrome and Turner's syndrome; treatment of delayed intrauterine growth and skeletogenous disorders; treatment of peripheral neuropathy; treatment of Noonan's syndrome, schizophrenia and depression; treatment or prevention of neurodegenerative diseases such as Alzheimer's disease and Parkinson's disease; treatment of pulmonary insufficiency and ventilation dependence; treatment of malabsorption syndrome; improvement of cachexia or protein loss caused by cancer or AIDS; promotion of weight increase and proteopexis in patients in the case of TPN (total parenteral nutrition); treatment of hyperinsulinemia; promotion of induction of ovulation; improvement of menopausal disorders; improvement of senile constitution. Further, the compound of the present invention is useful in mammals such as domestic animals for promotion of growth; increase in milk production; strengthening of an antimicrobial and antiviral activity by stimulation of immune system; stimulation in growth of wool in sheeps. In use for the above purposes, for example, in the treatment of osteoporosis, other drugs for treatment of osteoporosis (e.g., bisphosphonates, vitamin D preparations, calcitonin preparations, PTH preparations, Osten, etc.) can be used concomitantly. In the treatment of diabetes mellitus or diseases associated with them, other antidiabetic agents (e.g., thiazolidinediones such as Troglitazone, pioglitazone, Rosiglitazone, and etc.; glucagon antagonists; glucose absorption inhibitors such as acarbose, and etc) can be used concomitantly. Further, r other hormones promoting growth hormone secretion (e.g., GHRH), GH or IGF-1 can be used concomitantly. In improvement of menopausal disorders, a hormone supplemental therapy (e.g., therapy by estrogen preparations, Raloxifene, Tamoxifen) can be used concomitantly. In the case in which stimulation of immune system is intended, cytokines or cytokine activity enhancing agents can be used concomitantly.

Compounds (I) and (I') can be formulated into pharmaceutical compositions by any per se known methods. Compounds (I) and (I'), as they are or as a pharmaceutical composition prepared by optionally admixing with suitable amounts of any pharmaceutically acceptable carriers, can be safely administered either orally or non-orally (for example, topically, rectally, intravenously, etc.). The pharmaceutical composition includes, for example, tablets (including sugar-coated tablets, film-coated tablets), powders, granules, capsules (including soft capsules), liquids, injections, suppositories, sustained release preparations, etc.

In the pharmaceutical composition of the present invention, the contents of compound (I) or (I') is 0.1 to 100% by weight of the total weight of the composition. The dose of the composition varies depending on the subject to which the composition is administered, the administration route employed, the disorder of the subject, etc. For example, for the peroral composition for treating glaucoma, its dose may be about 0.1 to 500 mg, preferably about 1 to 100 mg, more preferably 5 to 100 mg, per adult (weighing about 60 kg), in terms of the active ingredient [compound (I) or (I')], and this may be administered once or several times a day.

Any ordinary organic and inorganic carrier substances that are generally used in formulating medicines are usable as the carriers for formulating the pharmaceutical composition of the present invention. For example, employable are ordinary excipients, lubricants, binders,. disintegrators, etc. for formulating solid preparations; and solvents, solubilizers, suspending agents, isotonizing agents, buffers, soothing agents, etc. for formulating liquid preparations. If desired, further employable are other additives such as preservatives, antioxidants, colorants, sweeteners, adsorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, etc.

The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

The preservatives include, for example, parahydroxybenzoates, chlorobutanol, benzyl alcohol, phenethyl alcohol, dehydroacetic acid, sorbic acid, etc.

The antioxidants include, for example, sulfites, ascorbic acid, etc.

BEST MODE FOR CARRYING OUT THE INVENTION

The present invention will be explained in more detail by the following Reference Examples, Examples, Formulation Example and Experimental Examples. These are mere examples and are not intended to restrict the present invention, and may be modified within the range of not deviating the scope of this invention.

"Room temperature" in the following Reference Examples and Examples means a temperature of 0° C. to 30° C. For drying an organic solution, anhydrous magnesium sulfate or anhydrous sodium sulfate was employed. Unless otherwise specifically indicated, "%" means percent by weight.

The IR absorption spectra were measured in a diffused reflection method using a Fourier transform infrared spectrophotometer.

The meanings of the abbreviations used in the present specification are as follows:

s: singlet
d: doublet
ddd: double double doublet
t: triplet,
q: quartet
m: multiplet
br: broad
J: coupling constant
Hz: Hertz
CDCl$_3$: deuterated chloroform
DMSO-d$_6$: deuterated dimethylsulfoxide
THF: tetrahydrofuran
DMF: N,N-dimethylformamide
DMSO: dimethylsulfoxide
WSC: 1-ethyl-3-(3-dimethylaminopropyl)carbodiimide hydrochloride
$^1$H-NMR: proton nuclear magnetic resonance spectrum (generally measured as the free form of each sample in CDCl$_3$)
IR: infrared absorption spectrum
Me: methyl
Et: Ethyl
HOBt: 1-hydroxy-1H-benzotriazol
LDA: lithium isopropylamide
IPE: duisopropyl ether Reference Example 1-1

(2-Formylphenyl)oxyacetonitrile

Bromoacetonitrile (7 g) was added to an acetone solution (500 ml) of salycylaldehyde (36.3 g). To the reaction mixture was added potassium carbonate (82.1 g), which was stirred at room temperature overnight. Water was added to the reaction mixture, which was concentrated. The residue was extracted with ethyl acetate. The organic layer was washed with water and a saturated aqueous sodium chloride solution, then dried and concentrated. The residue was recrystallized from ethyl acetate-IPE to obtain the entitled compound (38.7 g).

m.p. 70–71° C.

Reference Example 1-2

(2-Formyl-5-methoxyphenyl)oxyacetonitrile

The mixture of 2-hydroxy-4-methoxybenzaldehyde (9.50 g), potassium carbonate (17.3 g), bromoacetonitrile (11.2 g) and acetonitrile (100 ml) was stirred at room temperature for 12 hours. Water was added to the reaction mixture, which was extracted with ethyl acetate. The organic layer was washed with water and a saturated aqueous sodium chloride solution, then dried and concentrated. The residue was purified by alumina column chromatography (eluent: ethyl acetate), and then recrystallized from ethyl acetate-hexane to obtain the entitled compound (10.7 g).

m.p. 96–101° C.

Reference Example 2

Benzofuran-2-carbonitrile

Potassium carbonate (65.2 g) was added to a DMF solution (500 ml) of (2-formylphenyl)oxyacetonitrile (38 g), which was stirred at 60° C. for 2.5 hours. Water was added to the reaction mixture, which was extracted with diethyl ether. The organic layer was washed with water and a saturated aqueous sodium chloride solution, then dried and concentrated. The residue was purified by silica gel column chromatography (eluent: hexane/ethyl acetate=10/1) to obtain the entitled compound (14.5 g).

m.p. 30–33° C. (Solvent for recrystallization hexane).

Reference Example 3

6-Methoxybenzofuran-2-carbonitrile

Potassium carbonate (15.1 g) and molecular sieves 4A (3 g) were added to a DMF solution (100 ml) of (2-formyl-5-methoxyphenyl)oxyacetonitrile (10.4 g), which was stirred at 100° C. for 10 hours. Water was added to the reaction mixture, which was extracted with ethyl acetate. The organic layer was washed with water and a saturated aqueous sodium chloride solution, then dried and concentrated. The residue was purified by silica gel column chromatography (ethyl acetate) to obtain the entitled compound (4.65 g).

Amorphous powder.

$^1$H-NMR δ: 3.88(3H,s),6.92–7.06(1H,m),7.01(1H,s),7.83(1H,s),7.46–7.58(1H,m).

Reference Example 4

N-Hydroxy-benzofuran-2-carboxyimidamide

An aqueous solution (50 ml) of hydroxylamine hydrochloride (35 g) was added to an ethanol solution (100 ml) of benzofuran-2-carbonitrile (14.4 g). To the reaction mixture was added potassium carbonate (26.7 g), which was heated under reflux overnight. The reaction mixture was poured into water (400 ml), which was ice-cooled, and then crystals were collected by filtration. The crystals were washed with ice-cooled ethanol, then dried to obtain the entitled compound (14.7 g).

m.p. 200–201° C.

Compounds of the following Reference Example 5 to 8 were synthesized by the similar manner as in Reference Example 4.

Reference Example 5

N-Hydroxy-naphthalene-2-carboxyimidamide m.p. 115–116° C.

Reference Example 6

N-Hydroxy-naphthalene-1-carboxyimidamide m.p. 62–63° C.

Reference Example 7

N-Hydroxy-(4-methoxyphenyl)ethaneimidamide m.p. 97–98° C.

Reference Example 8

N-Hydroxy-6-methoxy-1-benzofuran-2-carboxyimidamide m.p. 151–153° C.

Reference Example 9

3-[3-(4-Methoxyphenyl)methyl-1,2,4-oxadiazol-5-yl]propanoic acid

3-Methoxycarbonylpropionyl chloride (4.5 g) was added dropwise to a mixed solution of N-hydroxy-2-(4- methoxyphenyl)ethaneimidamide (3 g) in acetonitrile (20 ml) and pyridine (5 ml) under ice-cooling. The reaction mixture was stirred at room temperature for 3 hours, which was diluted with ethyl acetate. The reaction mixture was washed twice with 2N hydrochloric acid and water, then dried and concentrated. The obtained residue was dissolved in pyridine (20 ml) and stirred under heating at 100° C. for 18 hours. The reaction mixture was concentrated, and the residue was purified by silica gel column chromatography (eluent: hexane/ethyl acetate=1/1) to obtain methyl 3-[3-(4-methoxyphenyl)methyl-1,2,4-oxadiazol-5-yl]propionate (2.5 g).

Methyl 3-[3-(4-methoxyphenyl)methyl-1,2,4-oxadiazol-5-yl]propionate (2.4 g) was dissolved in a mixed solvent of ethanol (20 ml) and water (10 ml). Sodium hydroxide (3 g) was added to the reaction mixture, which was stirred at room temperature for one hour. The reaction mixture was concentrated. 2N hydrochloric acid was added to the residue to become acidic, which was extracted with ethyl acetate. The extract was washed with water, then dried and concentrated. The residue was recrystallized from ethyl acetate-hexane to obtain the entitled compound.

m.p. 82–83° C.

Reference Example 10

3-[3-(2-Benzofuranyl)-1,2,4-oxadiazol-5-yl] propionic acid (1) Methyl 3-[3-(2-benzofuranyl)-1,2,4-oxadiazol-5-yl]propionate Ethyl acetate (200 ml), potassium carbonate (60 g) and water (270 ml) were added to a THF solution (70 ml) of N-hydroxy-benzofuran-2-carboxyimidamide(10.0g). To the reaction mixture was added a THF solution (70 ml) of 3-methoxycarbonylpropionyl chloride (7.35 ml), which was stirred for one hour, and the reaction mixture was extracted with ethyl acetate. The organic layer was washed with water and a saturated aqueous sodium chloride solution, then dried and concentrated. A pyridine solution (100 ml) of the residue (15.0 g) was stirred at 100° C. overnight. The reaction mixture was concentrated, and the residue was extracted with ethyl acetate. The organic layer was washed subsequently with 1N hydrochloric acid, 10% aqueous potassium carbonate solution and a saturated aqueous sodium chloride solution, and then dried and concentrated. The residue was purified by silica gel column chromatography (eluent: hexane/ethyl acetate=1/1) to obtain methyl 3-[3-(2-benzofuranyl)-1,2,4-oxadiazol-5-yl]propionate (13.2 g).

m.p. 112–113° C. (Solvent for recrystallization: ethyl acetate/hexane)

(2) 3-[3-(2-Benzofuranyl)-1,2,4-oxadiazol-5-yl] propionic acid

Methanol (180 ml) was added to a THF solution (180 ml) of methyl 3-]3-(2-benzofuranyl)-1,2,4-oxadiazol-5-yl] propionate (10.0 g). 1N sodium hydroxide (72 ml) was added dropwise to the reaction mixture under ice-cooling. The reaction mixture was stirred at room temperature for 2 hours, and then concentrated. 1N hydrochloric acid (107 ml) was added to the residue, and the precipitated crystals were collected by filtration. The crystals were washed with water and IPE, and dried to obtain the entitled compound (8.0 g).

m.p. 154–155° C. (Solvent for recrystallization: methanol/water)

Compounds of the following Reference Example 11 to 17 were synthesized by the similar manner as in Reference Example 10.

Reference Example 11

4-[3-(2-Benzofuranyl)-1,2,4-oxadiazol-5-yl]butyric acid m.p. 137–139° C.

Reference Example 12

2-[3-(2-Benzofuranyl)-1,2,4-oxadiazol-5-yl]acetic acid m.p. 132–133° C.

Reference Example 13

3-[3-(2-Naphthyl)-1,2,4-oxadiazol-5-yl]propionic acid m.p. 157–158° C.

Reference Example 14

3-[3-(1-Naphthyl)-1,2,4-oxadiazol-5-yl]propionic acid m.p. 117–118° C.

Reference Example 15

3-[3-(Phenoxymethyl)-1,2,4-oxadiazol-5-yl] propionic acid m.p. 80–81° C.

Reference Example 16

3-[3-((E)-2-(4-methylphenylethenyl)]-1,2,4 -oxadiazol-5-yl]propionic acid m.p. 139–140° C.

Reference Example 17

3-[3-(6-Methoxybenzofuran-2-yl)-1,2,4-oxadiazol-5-yl]propionic acid m.p. 140–142° C.

Reference Example 18

2-Acetylbenzofuran

Bromoacetone (25 g) was added to an acetone solution (500 ml) of salycylaldehyde (20.3 g). To the reaction mixture was added potassium carbonate (45.9 g) at room temperature and the stirring was continued overnight. Water was added to the reaction mixture, which was concentrated. The residue was extracted with ethyl acetate. The organic layer was washed with water and a saturated aqueous sodium chloride solution, then dried and concentrated. The residue was recrystallized from ethyl acetate-IPE to obtain the entitled compound (10 g).

m.p. 64–65° C.

Reference Example 19

2-Bromoacetylbenzofuran

Pyridinium bromide perbromide (20 g) was added to a THF solution (200 ml) of 2-acetylbenzofuran (8.35 g). The reaction mixture was stirred at room temperature for 20 minutes. The precipitated crystals were collected by filtration, and the filtrate was concentrated. The residue was purified by silica gel column chromatography (eluent: hexane/ethyl acetate=4/1) to obtain the entitled compound (6.5 g).

m.p. 79–80° C.

Reference Example 20

Methyl 4-amino-4-thioxobutyrate

Lawesson's reagent (2.6 g) was added to a toluene (10 ml) solution of methyl succinamate (1.7 g). The reaction mixture was heated under reflux for 4 hours, cooled, and then concentrated. The residue was purified by silica gel column chromatography (eluent: hexane/ethyl acetate=1/1) to obtain the entitled compound (400 mg) as an oily substance.

$^1$H-NMR δ: 2.8–3.0(4H,m),3.70(3H,s),7.6–8.2(2H,br).

Reference Example 21

3-[4-(2-Benzofuranyl)thiazol-2-yl]propionic acid (1) Ethyl 3-[4-(2-benzofuranyl)thiazol-2-yl]propionate 2-(Bromoacetyl)benzofuran (650 ml) was added to an ethanol (12 ml) solution of methyl 4-amino-4-thioxobutyrate (400 mg), which was heated under reflux overnight. After cooling, water was added to the reaction mixture, which was extracted with ethyl acetate. The organic layer was dried, concentrated, and then purified by silica gel column chromatography (eluent: hexane/ethyl acetate=4/1). The obtained crystals were washed with hexane to obtain ethyl 3-[4-(2-benzofuranyl)thiazol-2-yl]propionate (460 mg).

m.p. 65–66° C. (Solvent for recrystallization: hexane/ethyl acetate)

(2) 3-[4-(2-Benzofuranyl)thiazol-2-yl]propionic acid

1N Sodium hydroxide (3 ml) was added dropwise to a methanol solution (3 ml) of ethyl 3-[4-(2-benzofuranyl)thiazol-2-yl]propionate (460 mg) under ice-cooling. The reaction mixture was stirred at room temperature overnight, to which was added 10% aqueous potassium carbonate solution (10 ml), and the mixture was washed with ethyl acetate. The aqueous layer was made acidic (pH 3) by adding 1N hydrochloric acid and extracted with ethyl acetate. The organic layer was dried and concentrated to obtain the entitled compound (306 mg).

m.p. 203–205° C. (Solvent for recrystallization: methanol/water).

Reference Example 22

3-(4-Phenylthiazol-2-yl)propionic acid

The titled compound was synthesized from phenacyl bromide by the similar manner as in Reference Example 21.

m.p. 72–73° C. (Solvent for recrystallization: hexane/IPE).

Reference Example 23

3-(4-Bromophenyl)propionic acid

Sodium hydride (60% dispersion in oil; 4 g) was added portionwise to an ethanol (100 ml) solution of diethyl malonate (16 g) under ice-cooling. The reaction mixture was stirred at room temperature for 10 minutes, to which was added dropwise a THF (50 ml) solution of p-bromobenzylbromide (12 g) at room temperature. The reaction mixture was stirred at room temperature for 2 hours, and concentrated. Acetic acid (200 ml) and 6N hydrochloric acid (100 ml) were added to the residue. The reaction mixture was stirred under heating at 90° C. for 18 hours, and concentrated. Water was added to the residue, which was extracted with ethyl acetate. The organic layer was washed with water, then dried and concentrated. The residue was purified by silica gel column chromatography (eluent: ethyl acetate/hexane=1/1), which was recrystallized from IPE to obtain the entitled compound (1.2 g).

m.p. 136–137° C.

Reference Example 24

(4-Biphenylyloxy)acetic acid

Sodium hydride (60% dispersion in oil; 0.8 g) was added portionwise to a DMF (10 ml) solution of 4-hydroxybiphenyl (1.7 g) under ice-cooling. The reaction mixture was stirred at room temperature for 30 minutes, to which was added bromoacetic acid (1.4 g). The reaction mixture was further stirred at room temperature for 18 hours, which was poured into water. 2N hydrochloric acid was added to the mixture to adjust the pH to 4, which was extracted with ethyl acetate. The organic layer was washed with water, then dried and concentrated. The residue was purified by silica gel column chromatography (eluent: ethyl acetate/hexane=1/1), and the crude crystals were recrystallized from IPE to obtain the entitled compound (1.5 g).

m.p. 184–185° C.

Reference Example 25

(E)-3-[4-(4-methoxyphenyl)oxyphenyl]propenoic acid (1) 4-[(4-Methoxyphenyl)oxy]benzenecarbonitrile Sodium hydride (60% dispersion in oil; 0.8 g) was added to a DMF (20 ml) solution of 4-methoxyphenol (2.4 g). The reaction mixture was stirred at room temperature for 5 minutes, to which was added 4-fluorobenzenecarbonitrile (2.4 g). The reaction mixture was stirred at room temperature for 4 hours, which was further stirred at 50° C. for one hour. The reaction mixture was poured into water, which was extracted with toluene. The organic layer was washed with water, then dried and concentrated. The residue was purified by silica gel column chromatography (eluent: hexane/ethyl acetate=1/1), and then recrystallized from toluene-hexane to obtain 4-[(4-methoxyphenyl)oxy]benzenecarbonitrile (2.0 g).

m.p. 102–103° C.

(2) 4-[(4-Methoxyphenyl)oxy]benzenecarboaldehyde

A toluene (50 ml) solution of 4-[(4-methoxyphenyl)oxy]benzenecarbonitrile (1.8 g) was cooled to −70° C. Diisobutylaluminum hydride (1M toluene solution; 12 ml) was added dropwise to the reaction mixture. The reaction mixture was stirred at −70° C. for one hour, and poured into 2N hydrochloric acid (50 ml). The reaction mixture was further stirred under heating at 50° C. for 2 hours, and the organic layer was separated. The organic layer was washed with water, dried, and then concentrated. The residue was purified by silica gel column chromatography (eluent: hexane/ethyl acetate-1/1), and then recrystallized from hexane-ethyl acetate to obtain 4-[(4-methoxyphenyl)oxy]benzenecarboaldehyde (1.6 g).

m.p. 58–59° C.

(3) (E)-3-[4-(4-methoxyphenyl)oxyphenyl]propenoic acid

Sodium hydride (60% dispersion in oil; 0.36 g) was added to an ethanol (30 ml) solution of ethyl diethylphosphonoacetate (1.4 g) at room temperature. The reaction mixture was stirred at room temperature for 10 minutes, to which was added 4-[(4-methoxyphenyl)oxy]benzenecarboaldehyde (1.2 g). The reaction mixture was stirred at room temperature for 2 hours, which was further stirred at 50° C. for 30 minutes. The reaction mixture was cooled, to which were added water (20 ml) and sodium hydroxide (0.5 g). The reaction mixture was stirred at room temperature for 2 hours, and concentrated. 2N Hydrochloric acid was added to the residue to become acidic, which was extracted with ethyl acetate. The organic layer was washed with water, then dried and concentrated. The residue was recrystallized from ethyl acetate-hexane to obtain the entitled compound (1.2 g).

m.p. 165–167° C.

Reference Example 26

Methyl 4-hydroxyimino-1,2,3,4-tetrahydro-2-naphthalenecarboxylate

Thionyl chloride (5 drops) was added to a methanol (50 ml) solution of 4-oxo-1,2,3,4-tetrahydro-2-naphthalenecarboxylic acid (2.0 g), which was stirred at room temperature for 2 hours. The reaction mixture was poured into water, which was extracted with ethyl acetate. The organic layer was washed with a saturated aqueous sodium bicarbonate solution, then dried and concentrated. To a methanol (15 ml) solution of the residue was added an aqueous (6 ml) solution of hydroxylamine hydrochloride (850 mg) and sodium acetate (1.0 g), which was heated under reflux for 12 hours. The reaction mixture was poured into water and extracted with ethyl acetate. The organic layer was washed with a saturated aqueous sodium bicarbonate solution, then dried and concentrated. The residue was purified by silica gel column chromatography (eluent: hexane/ethyl acetate=3/1) to obtain the entitled compound (1.62 g).

$^1$H-NMR δ: 2.62–3.15(4H,m),3,34–3.48(1H,m),3.74(3H, s), 7.14–7.36(3H, m), 7.90(1H, d).

Reference Example 27

Methyl 2-oxo-2,3,4,5-tetrahydro-1H-1-benzazepine-4-carboxylate

Polyphosphoric acid (20 g) was added to methyl 4-hydroxyimino-1,2,3,4-tetrahydro-2-naphthalenecarboxylate (1.6 g), which was stirred at 110° C. for 30 minutes. The reaction mixture was ice-cooled, was added with ice, and then extracted with ethyl acetate. The organic layer was washed with water and a saturated aqueous sodium chloride solution, then dried and concentrated. The residue was purified by silica gel column chromatography (eluent: hexane/ethyl acetate=1/1) to obtain the entitled compound (1.15 g).

m.p. 114–115° C. (Solvent for recrystallization: hexane/ethyl acetate).

Reference Example 28

2-Oxo-1,2,3,4-tetrahydro-3-quinolineacetic acid

A concentrated hydrochloric acid (12 ml) solution of methyl 2-oxo-2,3,4,5-tetrahydro-1H-1-benzazepine-4-carbonate (960 mg) was heated under reflux for 30 minutes. The reaction mixture was poured into water, to which was added 1N aqueous sodium hydroxide solution to adjust the pH to 4. The mixture was extracted with a mixed solvent of ethyl acetate-THF (1:1). The organic layer was washed with a saturated aqueous sodium chloride solution, then dried and concentrated to obtain the entitled compound (820 mg).

m.p. 145–146° C. (Solvent for recrystallization: THF/hexane).

Reference Example 29

8-Methoxy-2-oxo-2,3,4,5-tetrahydro-1H-1-benzazepine-4-carboxylic acid 1N sodium hydroxide (38 ml) was added dropwise to a methanol (40 ml) solution of methyl 8-methoxy-2-oxo-2,3,4,5-tetrahydro-1H-1-benzazepine-4-carbonate (4.8 g) under ice-cooling. The reaction mixture was stirred at room temperature overnight, to which was added dropwise 1N aqueous hydrochloric acid solution (42 ml). The mixture was extracted with a mixed solvent of ethyl acetate-THF (1:1). The organic layer was washed with water and a saturated aqueous sodium chloride solution, then dried and concentrated. The obtained crystals were washed with IPE to obtain the entitled compound (3.27 g).

m.p. 210–212° C. (Solvent for recrystallization: THF/IPE).

Reference Example 30

N,N-Dimethyl-2-oxo-1,2,3,4-tetrahydro-3-quinolineacetoamide

To the mixed solution of 2-oxo-1,2,3,4-tetrahydro-3-quinolineacetic acid (810 mg) in THF (10 ml) and acetonitrile (10 ml), WSC (1.15 g), HOBt (610 mg), dimethylamine hydrochloride (650 mg) and triethylamine (1.67 ml) were added subsequently, which was stirred at room temperature overnight. Water was added to the reaction mixture, which was extracted with a mixed solvent of ethyl acetate-THF (1:1). The organic layer was washed subsequently with 0.1N aqueous hydrochloric acid solution, a saturated aqueous sodium bicarbonate solution, and a saturated aqueous sodium chloride solution, then dried and concentrated to obtain the entitled compound (620 mg).

m.p. 172–173° C. (Solvent for recrystallization: ethyl acetate/IPE).

Compound of the following Reference Example 31 was synthesized by the similar manner as in Reference Example 30.

Reference Example 31

N,N-Dimethyl-8-methoxy-2-oxo-2,3,4,5-tetrahydro-1H-1-benzazepine-4-carboxamide m.p. 172–173° C. (Solvent for recrystallization: ethyl acetate/IPE)

Reference Example 32

3-[2-(N,N-Dimethylamino)ethyl]-1,2,3,4-tetrahydroquinoline

Borane-THF complex (1M; 15 ml) was added to N,N-dimethyl-2-oxo-1,2,3,4-tetrahydro-3-quinolineacetoamide (590 mg), which was heated under reflux for 3.5 hours. 6N hydrochloric acid (10 ml) was added to the reaction mixture, which was heated under reflux overnight. 6N sodium hydroxide was added to the reaction mixture to adjust pH to 7 and extracted with ethyl acetate. The organic layer was washed with a saturated aqueous sodium bicarbonate solution and a saturated aqueous sodium chloride solution, then dried and concentrated. The residue was purified by alumina column chromatography (eluent: hexane/ethyl acetate=1/1) to obtain the entitled compound (390 mg) as an oily substance.

$^1$H-NMR δ: 1.45–1.58(2H, m), 2.24(6H, s), 2.30–2.56 (3H, m), 2.75–2.90(1H, m), 2.90–3.04(1H, m), 3.26–3.40 (1H, m), 3.54–3.74(1H, m), 6.47(1H, d), 6.54–6.66(1H, m), 6.90–7.04(2H, m).

Compound of the following Reference Example 33 was synthesized by the similar manner as in Reference Example 32.

Reference Example 33

4-(N,N-Dimethylaminomethyl)-8-methoxy-2,3,4,5-tetrahydro-1H-benzazepine oxalate m.p. 187–188° C. (Solvent for recrystallization: methanol/IPE).

Reference Example 34

Dimethyl 2-[(2-nitrophenyl)methylidene]malonate

A methanol (300 ml) solution of o-nitrobenzaldehyde (103.1 g), dimethylmalonate (90.1 g), acetic acid (1.2 ml) and piperidine (12 ml) was heated under reflux for 25 hours. The reaction mixture was concentrated. Water was added to the mixture, which was extracted with ethylacetate. The organic layer was washed with 1N hydrochloric acid, water, a saturated aqueous sodium hydrogencarbonate solution and a saturated aqueous sodium chloride solution, then dried and concentrated. The obtained crude crystals were washed with IPE to give the entitled compound (59.79 g). The mother liquor was further purified by silica gel column chromatography (eluent: ethyl acetate/hexane=1/2). The obtained crude crystals were recrystallized from ethyl acetate-hexane to give the entitled compound (34.13 g).

m.p. 67–70° C.

Reference Example 35

Methyl 2-oxo-1,2,3,4-tetrahydro-3-quinolinecarboxylate

Sodium borohydride (1.10 g) was added to the mixed solution of dimethyl 2-[(2-nitrophenyl)methylidene] malonate (15.2 g) in ethyl acetate (50 ml) and methanol (200 ml) at 0° C. The reaction mixture was stirred at 0° C. for 20 minutes. Water was added to the mixture, which was extracted with ethyl acetate. The organic layer was washed with a saturated aqueous sodium chloride solution, then dried and concentrated. 5% Palladium-carbon (6.26 g) was added to the mixed solution of the residue in THF (100 ml) and methanol (100 ml), and catalytic hydrogenation was conducted at room temperature under atmospheric pressure for 3 days. The catalyst was removed by filtration, and the filtrate was concentrated. The obtained crude crystals were washed with a mixed solution of ethyl acetate/hexane=1/4 to give the entitled compound (9.487 g).

m.p. 165–168° C.

Reference Example 36

2-Oxo-1,2,3,4-tetrahydro-3-quinolinecarboxylic acid

1N Aqueous sodium hydroxide solution (80 ml) was added dropwise to the mixed solution of methyl 2-oxo-1,2, 3,4-tetrahydro-3-quinolinecarboxylate (8.322 g) in THF (80 ml) and methanol (80 ml) at 0° C. The reaction mixture was stirred at room temperature for 4 hours. 1N Hydrochloric acid (90 ml) was added dropwise to the reaction mixture at 0° C., which was then extracted with ethyl acetate. The organic layer was washed with a saturated aqueous sodium chloride solution, then dried and concentrated to obtain crude crystals of the entitled compound (7.032 g). The obtained crude crystals were put to use in the following reaction without purification.

$^1$H-NMR(DMSO-d$_6$) δ: 3.11(2H, d), 3.47(1H, t), 6.90 (1H, dd), 7.09–7.24(2H, m).

Reference Example 37

N,N-Dimethyl-2-oxo-1,2,3,4-tetrahydro-3-quinolinecarboxamide

2-Oxo-1,2,3,4-tetrahydro-3-quinolinecarboxylic acid (8.56 g), dimethylamine hydrochloride (4.60 g), HOBt (7.18 g), WSC (11.1 g) and triethylamine (20 ml) were added to acetonitrile (400ml). The reaction mixture was stirred at room temperature for 43 hours. 10% aqueous citric acid solution was added to the reaction mixture, which was extracted with ethyl acetate. The organic layer was washed with water, a saturated aqueous sodium hydrogencarbonate solution and a saturated aqueous sodium chloride solution, then dried and concentrated. The obtained crude crystals were washed with IPE to give the entitled compound (9.486 g).

m.p. 224–226° C.

Compounds of the following Reference Examples 38 to 43 were synthesized by the similar manner as in Reference Example 37.

Reference Example 38

N,N-Diethyl-2-oxo-1,2,3,4-tetrahydro-3-quinolinecarboxamide m.p. 155–158° C. (washed with IPE).

Reference Example 39

4-Phenyl-1-[(1,2,3,4-tetrahydro-2-oxoquinolin-3-yl) carbonyl]piperazine m.p. 225–228° C. (Solvent for recrystallization: THF/IPE).

Reference Example 40

2-Oxo-3-(pyrrolidin-1-yl)carbonyl-1,2,3,4-tetrahydroquinoline m.p. 225–228° C. (decomposed) (washed with IPE).

Reference Example 41

2-Oxo-3-piperidinocarbonyl-1,2,3,4-tetrahydroquinoline m.p. 179–183° C. (washed with IPE).

Reference Example 42

2-Oxo-3-morpholinocarbonyl-1,2,3,4-tetrahydroquinoline m.p. 204–209° C. (washed with IPE).

Reference Example 43

N-Benzyl-N-methyl-2-oxo-1,2,3,4-tetrahydro-3-quinolinecarboxamide m.p. 176–179° C. (washed with IPE).

Reference Example 44

3-(N,N-Dimethylamino)methyl-1,2,3,4-tetrahydroquinoline

N,N-Dimethyl-2-oxo-1,2,3,4-tetrahydro-3-quinolinecarboxamide (9.486 g) was added to 1M Borane-THF complex (200 ml). The reaction mixture was heated under reflux for 45 minutes, and left standing for cooling. The reaction mixture was ice-cooled, to which were added water (20 ml) and 6N hydrochloric acid (50 ml). The mixture was stirred at room temperature for 15 hours, and concentrated. A methanol solution (200 ml) of the residue was heated under reflux for 6 hours, and concentrated. 3N aqueous sodium hydroxide solution was added to the residue to become basic, which was extracted with ethyl acetate. The residue was purified by alumina column chromatography (eluent: ethyl acetate/hexane=1/10). The obtained crude crystals were washed with hexane to give the entitled compound (5.569 g)

m.p. 85–89° C.

Compounds of the following Reference Examples 45 to 50 were synthesized by the similar manner as in Reference Example 44.

Reference Example 45

3-(N,N-Diethylamino)methyl-1,2,3,4-tetrahydroquinoline $^1$H-NMR δ: 1.00(6H, t), 2.01–2.23(1H, m), 2.26–2.62 (7H, m), 2.74–3.02(2H, m), 3.36–3.47(1H, m), 6.48(1H, d), 6.59(1H, t), 6.91–7.01(2H, m).

Reference Example 46

3-(4-Phenylpiperazin-1-yl)methyl-1,2,3,4-tetrahydroquinoline m.p. 127–132° C. (Solvent for recrystallization: ethyl acetate/hexane).

Reference Example 47

3-(Pyrrolidin-1-yl)methyl-1,2,3,4-tetrahydroquinoline m.p. 84–87° C. (Solvent for recrystallization: ethyl acetate/hexane).

Reference Example 48

3-Piperidinomethyl-1,2,3,4-tetrahydroquinoline m.p. 65–68° C. (Solvent for recrystallization: ethyl acetate/hexane).

Reference Example 49

3-Morpholinomethyl-1,2,3,4-tetrahydroquinoline m.p. 61–65° C. (Solvent for recrystallization: ethyl acetate/hexane).

Reference Example 50

3-(N-Benzyl-N-methylamino)methyl-1,2,3,4-tetrahydroquinoline $^1$H-NMR δ: 2.15–2.52(4H, m), 2.22(3H, s), 2.78–3.00 (2H, m), 3.39–3.50(1H, m), 3.50(2H, dd), 6.46(1H, d), 6.60(1H, t), 6.91–7.00(2H, m), 7.18–7.56(5H, m).

Reference Example 51

Ethyl 3-(2-nitrobenzyl)-2-oxo-3-piperidinecarboxylate

Sodium hydride (60% dispersion in oil, 2.45 g) was added to ethanol (100 ml), to which was added 3-carboethoxy-2-piperidone (10.0 g). The reaction mixture was stirred for 15 minutes, to which was added 2-nitrobenzyl bromide (13.2 g) at room temperature. The reaction mixture was stirred at 60° C. for 3 hours. Water was added to the reaction mixture, which was concentrated. The residue was diluted with water and extracted with ethyl acetate. The organic layer was washed with water and a saturated aqueous sodium chloride solution, then dried and concentrated. The obtained crude crystals were recrystallized from ethyl acetate-hexane to give the entitled compound (14.6 g).

m.p. 137–139° C.

Reference Example 52

Ethyl 3-(2-nitrobenzyl)-2-oxo-1-propyl-3-piperidinecarboxylate

Sodium hydride (60% dispersion in oil, 1.59 g) was added to a DMF solution (100 ml) of ethyl 3-(2-nitrobenzyl)-2-oxo-3-piperidinecarboxylate (11.0 g) and propyl iodide (5.79 ml) under ice-cooling. The reaction mixture was stirred at room temperature for 30 minutes. The reaction mixture was diluted with water and extracted with a mixture of ethyl acetate and diethyl ether. The residue was purified by silica gel column chromatography (eluent: ethyl acetate/hexane=1/4 to 1/2) to obtain the entitled compound (10.6 g).

Oily substance.

$^1$H-NMR δ: 0.87(3H, t), 1.26(3H, t), 1.35–2.23(6H, m), 2.98–3.55(4H, m), 3.68(1H, d), 3.83(1H,d), 4.03–4.35(2H, m), 7.28–7.63(3H, m), 7.77–7.88(1H, m).

Reference Example 53

2,2'-Dioxo-1-propyl-1',2',3',4'-tetrahydrospiro [piperidin-3,3'-quinoline]

10% Palladium-carbon (0.2 g) was added to an ethanol solution (20 ml) of ethyl 3-(2-nitrobenzyl)-2-oxo-1-propyl-3-piperidinecarboxylate (1.00 g), and catalytic hydrogenation was conducted at room temperature under one atmospheric pressure for 6 hours. The catalyst was removed by filtration and the filtrate was concentrated. The residue was dissolved in toluene (20 ml), which was heated under reflux for 12 hours. The reaction mixture was concentrated, and the obtained crude crystals were recrystallized from ethyl acetate-hexane to give the entitled compound (0.55 g).

m.p. 151–154° C.

Reference Example 54

1-Propyl-1',2',3',4'-tetrahydrospiro[piperidin-3,3'-quinoline]

In the similar manner as in

Reference Example 44, the entitled compound (1.204 g) was synthesized from 2,2'-dioxo-1-propyl-1',2',3',4'-tetrahydrospiro[piperidin-3,3'-quinoline] (1.369 g).

m.p. 85–88° C. (washed with hexane).

Reference Example 55

Dimethyl (4-methoxy-2-nitrophenyl) methylidenemalonate

A methanol (125 ml) solution of 4-methoxy-2-nitrobenzaldehyde (21.3 g, described in Org. Synth., volume V, p-139, 1973), dimethyl malonate (16.5 g), piperidine (2.5 ml) and acetic acid (0.25 ml) was heated under reflux for 24 hours. The reaction mixture was concentrated, to which was added 1N hydrochloride, and the mixture was extracted with ethyl acetate. The organic layer was washed with 10% aqueous potassium carbonate solution and a saturated aqueous sodium chloride solution, then dried and concentrated. The residue was purified by silica gel column chromatography (eluent: ethyl acetate/hexane=1/2) to obtain the entitled compound (25 g).

$^1$H-NMR δ: 3.67(3H, s), 3.88(3H, s), 3.92(3H, s), 7.16 (1H, dd), 7.36(1H, d), 7.70(1H, d), 8.14(1H, s).

Reference Example 56

Dimethyl (4-methoxy-2-nitrobenzyl)malonate

Sodium borohydride (3.36 g) was added to a methanol (200 ml) solution of dimethyl (4-methoxy-2-nitrophenyl)methylidenemalonate (25 g) under ice-cooling. The reaction mixture was stirred at room temperature for one hour and then neutralized by adding dropwise 1N aqueous hydrochloric acid solution. The reaction mixture was concentrated and extracted with ethyl acetate. The organic layer was washed with water, a saturated aqueous potassium bicarbonate solution and a saturated aqueous sodium chloride solution, then dried and concentrated. The residue was purified by silica gel column chromatography (eluent: ethyl acetate/hexane=1/4) to obtain the entitled compound (19 g).

$^1$H-NMR δ: 3.44(2H, d), 3.71(6H, s), 3.86(3H, s), 3.80–4.00(1H, m), 7.08(1H, dd), 7.28(1H, d), 7.52(1H, d).

Reference Example 57

7-Methoxy-2-oxo-1,2,3,4-tetrahydro-3-quinolinecarboxylic acid

10% Palladium- carbon (2.0 g) was added to an ethanol (200 ml) solution of dimethyl (4-methoxy-2-nitrobenzyl)malonate (19 g), and catalytic hydrogenation was conducted at room temperature under an atmospheric pressure for 24 hours. The reaction mixture was further stirred at 80° C. for 24 hours. The catalyst was removed by filtration, and the filtrate was concentrated. The residue was dissolved in a mixed solvent of THF (250 ml) and methanol (250 ml), to which was added dropwise 1N aqueous sodium hydroxide solution (126 ml) under ice-cooling. The reaction mixture was stirred at room temperature for 72 hours and concentrated. 1N Hydrochloric acid was added to the residue to make acidic, and the precipitated crystals were collected by filtration. The obtained crude crystals were washed with acetone to give the entitled compound (11.7 g).

m.p. 145–146° C. (decomposed).

Reference Example 58

7-Methoxy-N,N-dimethyl-2-oxo-1,2,3,4-tetrahydro-3-quinolinecarboxamide

WSC (6.5 g) was added to an acetonitrile solution of 7-methoxy-2-oxo-1,2,3,4-tetrahydro-3-quinolinecarboxylic acid (3.74 g), dimethylamine hydrochloride (3.44 g), HOBt (2.85 g) and triethylamine (8.5 g). The reaction mixture was stirred at room temperature for 24 hours and concentrated. The residue was diluted with ethyl acetrate. The organic layer was washed with 1N aqueous hydrochloric acid solution, 10% aqueous potassium carbonate solution, and a saturated aqueous sodium chloride solution, then dried and concentrated. The obtained crude crystals were recrystallized from ethyl acetate-hexane to give the entitled compound (1.63 g).

m.p. 209–210° C.

Reference Example 59

3-(N,N-Dimethylamino)methyl-7-methoxy-1,2,3,4-tetrahydroquinoline dihydrochloride 1M Borane-THF complex (60 ml) was added to a THF (100 ml) solution of 7-methoxy-N,N-dimethyl-2-oxo-1,2,3,4-tetrahydro-3-quinolinecarboxamide(1.63 g). The reaction mixture was heated under reflux for 24 hours. The reaction mixture was concentrated and 6N hydrochloric acid (30 ml) was added to the residue, which was heated under reflux for 4 hours. 6N Aqueous sodium hydroxide solution was added the reaction mixture to make basic, which was extracted with ethyl acetate. The organic layer was washed with 10% aqueous potassium carbonate solution and a saturated aqueous sodium chloride solution, then dried and concentrated. The residue was processed into its dihydrochloride, which was recrystallized from methanol-IPE to obtain the entitled compound (1.27 g).

m.p. 150–151° C.

Reference Example 60

3-(N,N-Dimethylamino)methyl-1,2,3,4-tetrahydro-7-quinolinol

48% Hydrobromic acid solution (10 ml) of 3-(N,N-dimethylamino)methyl-7-methoxy-1,2,3,4-tetrahydroquinoline dihydrochloride (1.0 g) was heated under reflux for 4 hours. The reaction mixture was poured into 10% aqueous potassium carbonate solution and extracted with ethyl acetate. The organic layer was dried, and then concentrated. The obtained crude crystals were recrystallized from ethyl acetate-hexane to give the entitled compound (0.81 g).

Dihydrochloride salt of the entitled compound showed m.p. of 151–152° C. (Solvent for recrystallization: methanol/IPE).

Reference Example 61

7-(4-Bipenylyl)methoxy-3-(N,N-dimethylamino)methyl-1,2,3,4-tetrahydroquinoline hydrochloride Diethylazodicarboxylic acid (348 mg) was added dropwise to a THF solution (20 ml) of 3-(dimethylamino)methyl-1,2,3,4-tetrahydro-7-quinolinol (344 mg), 4-biphenylylmethanol (368 mg), and triphenylphosphine (525 mg). The reaction mixture was stirred at room temperature for one hour, which was poured into 1N hydrochloric acid and washed with ethyl acetate. The aqueous layer was neutralized with 1N aqueous sodium hydroxide solution, to which was added a saturated aqueous sodium bicarbonate solution and the mixture was extracted with ethyl acetate. The organic layer was washed with a saturated aqueous sodium chloride solution, then dried and concentrated. The residue was purified by alumina column chromatography (eluent: ethyl acetate/hexane=1/4), converted into its hydrochloride, and then recrystallized from ethanol-IPE to give the entitled compound (214 mg).

m.p. 183–184° C.

Reference Example 62

3-[1-(2,4-Dichlorobenzyl)indol-3-yl]propionic acid

Sodium hydride (60% dispersion in oil, 0.38 g) was added to the mixed solution of ethyl 3-(indol-3-yl)propionate (1.8 g) in DMF (20 ml) and THF (20 ml) under ice-cooling. The reaction mixture was stirred at room temperature for 10 minutes, to which were added 2,4-dichlorobenzyl bromide (1.8 g) and sodium iodide (0.3 g). The reaction mixture was stirred at room temperature for 3 hours and then poured into water, and the mixture was extracted with IPE. The organic layer was washed with water, then dried and concentrated. The residue was dissolved in ethanol (30 ml), which was stirred at 50° C. for 2 hours in the presence of water (10 ml) and sodium hydroxide (1 g). The reaction mixture was concentrated, made acidic, and then extracted with ethyl acetate. The organic layer was washed with water, then dried and concentrated. The residue was recrystallized from ethyl acetate-IPE to obtain the entitled compound (2.4 g).

m.p. 134–136° C.

Reference Example 63

3-(N,N-Dimethylamino)methyl-1-[2-(6-methoxy-1,2,3,4-tetrahydronaphthalen-2-yl)acetyl]-1,2,3,4-tetrahydroquinoline oxalate The entitled compound was synthesized by the similar manner as in Example 1 hereafter.

Eluent: hexane/ethyl acetate =3/1 to 2/1 m.p. 83–85° C. (Solvent for recrystallization: THF/diethyl ether).

Reference Example 64

3-(N,N-Dimethylamino)methyl-1-[3-(3-indolyl)acetyl]-1,2,3,4-tetrahydroquinoline hydrochloride The entitled compound was synthesized by the similar manner as in Example 1 hereafter.

Eluent: hexane/ethyl acetate =2/1 m.p. 231–237° C. (Decomposed, Solvent for recrystallization: methanol/IPE).

Reference Example 65

2-(4-Bipenylyl)ethylthiocyanate

Bromine (1.5 ml) was added dropwise to an acetonitrile (60 ml) solution of triphenylphosphine (5 g). After stirring for 5 minutes, an acetonitrile solution (30 ml) of 2-(4-biphenylyl)ethanol (5 g) was added to the reaction mixture. The reaction mixture was stirred at room temperature for one hour and concentrated. Diethyl ether was added to the residue. The supernatant was collected, then dried and concentrated. The residue was purified by silica gel column chromatography (eluent: IPE) to obtain 2-(4-bipenylyl) ethylbromide(6 g). 2-(4-Bipenylyl)ethyl bromide (6 g) was dissolved in methanol (100 ml), which was stirred at 70° C. for 48 hours together with potassium thiocyanate (4.0 g). The reaction mixture was concentrated, and the residue was extracted with ethyl acetate. The organic layer was washed with water, then dried and concentrated. The residue was recrystallized from ethyl acetate-hexane to obtain the entitled compound (4.1 g).

m.p. 91–92° C.

Reference Example 66

Ethyl 3,4-dihydro-3-oxo-2-quinoxalinecarboxylate

Diethyl ketomalonate (8 g) was added to an ethanol (100 ml) solution of 1,2-phenylenediamine (5 g). The reaction mixture was stirred at 50° C. for 14 hours. The precipitated crystals were filtrated, which was washed with IPE to obtain the entitled compound (8.2 g).

m.p. 169–170° C.

Reference Example 67

Ethyl 4-benzyl-3,4-dihydro-3-oxo-2-quinoxalinecarboxylate

Sodium hydride (60% dispersion in oil; 0.8 g) was added to a DMF (20 ml) solution of ethyl 3,4-dihydro-3-oxo-2-quinoxalinecarboxylate (4.4 g) under ice-cooling. The reaction mixture was stirred for 10 minutes, to which was added benzyl bromide (2.4 g). The reaction mixture was stirred at room temperature for 3 hours, poured into water, and the mixture was extracted with ethyl acetate. The organic layer was washed with water, then dried and concentrated. The residue was recrystallized from ethyl acetate-hexane to obtain the entitled compound (3.6 g).

m.p. 102–103° C.

Reference Example 68

4-Benzyl-3,4-dihydro-3-oxo-2-quinoxalinecarboxylic acid

Water (15 ml) and sodium hydroxide (1.3 g) were added to a methanol (30 ml) solution of ethyl 4-benzyl-3,4-dihydro-3-oxo-2-quinoxalinecarboxylate (3.5 g). The reaction mixture was stirred at room temperature for 2 hours and concentrated. 2N Hydrochloric acid was added to the residue to adjust the pH to 4, which was extracted with ethyl acetate. The organic layer was washed with water, then dried and concentrated. The residue was recrystallized from ethyl acetate-hexane to obtain the entitled compound (2.9 g).

m.p. 149–150° C.

Reference Example 69

1-Benzyl-3-(pyrrolidin-1-ylcarbonyl)-2(1H)-quinoxaline

Pyrrolidine (0.5 ml) and triethylamine (1 ml) were added to a THF (100 ml) solution of 4-benzyl-3,4-dihydro-3-oxo-2-quinoxalinecarboxylic acid (2 g), WSC (1.4 g) and HOBt (1 g). The reaction mixture was stirred at room temperature for 18 hours and concentrated. The residue was dissolved in ethyl acetate, which was washed with water, and then concentrated. The residue was purified by silica gel column chromatography (eluent: ethyl acetate) to obtain the entitled compound (2.2 g).

m.p. 136–137° C.

Reference Example 70

1-Benzyl-3-(pyrrolidin-1-ylcarbonyl)-3,4-dihydro-2(1H)-quinoxaline

Triethyl silane (4 ml) was added to a trifluoroacetic acid (30 ml) solution of 1-benzyl-3-(pyrrolidin-1-ylcarbonyl)-2(1H)-quinoxaline (2 g). The reaction mixture was stirred at room temperature for 4 hours and concentrated. The residue was recrystallized from ethyl acetate to obtain the entitled compound (1.5 g).

m.p. 162–163° C.

Reference Example 71

4-Benzyl-N,N-dimethyl-3,4-dihydro-3-oxo-2-quinoxalinecarboxamide

Dimethylamine hydrochloride (0.57 g), WSC (1.33 g) and HOBt (0.86 g) were added to a mixed solution of 4-benzyl- 3,4-dihydro-3-oxo-2-quinoxalinecarboxylic acid (1.5 g) in THF (30 ml) and acetonitrile (30 ml), to which was added dropwise triethylamine (2.3 ml) under ice-cooling. The reaction mixture was stirred at room temperature for 15 hours. The precipitated insoluble substances were removed by filtration and the filtrate was concentrated. Water was added to the precipitate, which was extracted with ethyl acetate. The ethyl acetate layer was washed with 1N hydrochloric acid, water, a saturated aqueous sodium hydrogencarbonate solution, and a saturated aqueous sodium chloride solution, then dried and concentrated. The residue was recrystallized from ethyl acetate-hexane to obtain the entitled compound (1.47 g).

m.p. 154–155° C.

Reference Example 72

4-Benzyl-1,2,3,4-tetrahydro-N,N-dimethyl-3-oxo-2-quinoxalinecarboxamide

4-Benzyl-N,N-dimethyl-3,4-dihydro-3-oxo-2-quinoxalinecarboxamide (1.47 g) was added and dissolved in ice-cooled trifluoroacetic acid (45 ml), to which was further added triethyl silane (4.6 ml). The reaction mixture was stirred at room temperature for 3 hours, then concentrated. The residue was dissolved in ethyl acetate and washed with 10% aqueous potassium carbonate solution, water and a saturated aqueous sodium chloride solution, then dried and concentrated. The obtained crystals were washed with IPE to obtain the entitled compound (1.33 g).

m.p. 152–154° C.

Reference Example 73

3-(N,N-Dimethylamino)methyl-1-methylsulfonyl-1,2,3,4-tetrahydroquinoline

Methanesulfonyl chloride (0.6 g) was added to a THF (20 ml) solution of 3-(N,N-dimethylamino)methyl-1,2,3,4-tetrahydroquinoline (Reference Example 44; 1 g) under ice-cooling. The reaction mixture was stirred at room temperature for 10 minutes, to which was added triethylamine (2 ml), and the mixture was further stirred at room temperature for 3 hours. The reaction mixture was diluted with a saturated aqueous potassium bicarbonate solution and extracted with ethyl acetate. The organic layer was washed with water, then dried and concentrated. The residue was purified by alumina column chromatography (eluent: ethyl acetate) and recrystallized from IPE to obtain the entitled compound (1 g).

m.p. 69–70° C.

Reference Example 74

1-(Methylsulfonyl)-3-(pyrrolidin-1-yl)methyl-1,2,3,4-tetrahydroquinoline

Methanesulfonyl chloride (0.65 ml) was added dropwise to an acetonitrile (20 ml) solution of 3-(pyrrolidin-1-yl) methyl-1, 2,3, 4-tetrahydroquinoline (Reference Example 47; 1.5 g) and triethylamine (2.9 ml) under ice-cooling. The reaction mixture was stirred at the same temperature for one hour, to which was added water and the mixture was extracted with ethyl acetate. The ethyl acetate layer was washed with a saturated aqueous sodium chloride solution, then dried and concentrated. The residue was purified by alumina column chromatography (eluent: hexane to hexane/ethylacetate=7/1). The crystals were washed with IPE to obtain the entitled compound (1.20 g)

m.p. 72–73° C. .

Reference Example 75

2-(N,N-Dimethylamino)methyl-1-ethyl-1,2,3,4-tetrahydroquinoxaline trihydrochloride Borane-dimethylsulfide complex (10M THF solution; 4 ml) was added to a THF (10 ml) solution of 4-benzyl-1,2,3,4-tetrahydro-N,N-dimethyl-3-oxo-2-quinoxalinecarboxamide (2 g) at room temperature. The reaction mixture was stirred at room temperature for 18 hours, then concentrated. Methanol was added to the residue. 6N Hydrochloric acid (10 ml) was added to the reaction mixture, which was stirred at 60° C. for 6 hours. The reaction mixture was concentrated, and the residue was neutralized with 2N aqueous sodium hydroxide solution, which was extracted with ethyl acetate. The organic layer was washed with water, dried, then concentrated. The residue was dissolved in pyridine (6 ml) and acetic acid anhydride (1 ml), which was left standing at room temperature for 18 hours, then concentrated. The residue was azeotropically co-distilled twice with toluene and then dissolved in THF (10 ml). Borane-dimethylsulfide complex (10M THF solution; 4 ml) was added to the reaction mixture, which was stirred at room temperature for 18 hours and concentrated. Methanol was added to the residue. 6N Hydrochloric acid (10 ml) was added to the reaction mixture, which was stirred at 60° C. for 6 hours. The reaction mixture was concentrated. The residue was neutralized with 2N aqueous sodium hydroxide solution and extracted with ethyl acetate. The residue was dissolved in ethanol, and converted into its hydrochloride by the addition of an excess amount of 4N hydrochloric acid-ethyl acetate, and concentrated. The residue was recrystallized from ethanol-ether to obtain the entitled compound (0.3 g).

m.p. 130–135° C.

Reference Example 76

Diethyl 2-(5-methoxy-2-nitrobenzylidene)malonate

The entitled compound was synthesized by the similar manner as in Reference Example 55.

$^1$H-NMR (CDCl$_3$) δ: 1.09(3H, t), 1.36(3H, t), 3.88(3H, s), 4.11(2H, q), 4.35(2H, q), 6.88(1H, d), 6.98(1H, dd), 8.22 (1H, s), 8.24(1H, d).

Reference Example 77

Diethyl 2-(5-methoxy-2-nitrobenzyl)malonate

The entitled compound was synthesized by the similar manner as in Reference Example 56.

$^1$H-NMR(CDCl$_3$) δ: 1.22(6H, t), 3.54(2H, d), 3.87(3H, s), 3.89(1H, t), 4.17(4H, q), 6.80–6.92(2H, m), 8.08–8.20(1H, m).

Reference Example 78

Ethyl 6-methoxy-2-oxo-1,2,3,4-tetrahydro-3-quinolinecarboxylate

The entitled compound was synthesized by the similar manner as in Reference Example 35.

m.p. 158–165° C. (Solvent for recrystallization: ethyl acetate/hexane).

Reference Example 79

6-Methoxy-2-oxo-1,2,3,4-tetrahydro-3-quinolinecarboxylic acid

The entitled compound was synthesized by the similar manner as in Reference Example 36 m.p. 141–142° C. (Decomposed)(Solvent for washing: IPE). .

Reference Example 80

N,N-Dimethyl-6-methoxy-2-oxo-1,2,3,4-tetrahydro-3-quinolinecarboxamide

The entitled compound was synthesized by the similar manner as in Reference Example 30.

m.p. 248–250° C. (Solvent for washing: ethanol/IPE).

Reference Example 81

N,N-Dibenzyl-2-oxo-1,2,3,4-tetrahydro-3-quinolinecarboxamide

The entitled compound was synthesized by the similar manner as in Reference Example 30.

m.p. 207–208° C. (Solvent for recrystallization: IPE).

Reference Example 82

3-(R,S)-(N,N-Dibenzylamino)methyl-1,2,3,4-tetrahydroquinoline

The entitled compound was synthesized by the similar manner as in Reference Example 32.

$^1$H-NMR(CDCl$_3$) δ: 2.13–2.43(4H, m), 2.89–2.74(2H, m), 3.36–3.48(1H, m), 3.46(2H, d), 3.67(2H, d), 6.34–6.43 (1H, m), 6.57(1H, ddd), 6.86–7.00(2H, m), 7.25–7.43(10, m).

Reference Example 83

3-(N,N-Dibenzylamino)methyl-6-methoxy-1,2,3,4-tetrahydroqulnoline

The entitled compound was synthesized by the similar manner as in Reference Example 32.

$^1$H-NMR(CDCl$_3$) δ: 2.02–2.56(4H, m), 2.24(6H, s), 2.76–3.02(2H, m), 3.30–3.42(1H, m), 3.72(3H, s), 6.42–6.50(1H, m), 6.54–6.66(2H, m).

Reference Example 84

Diethyl 2[(5-chloro-2-nitrophenyl)methyl-idene)malonate

Potassium hydrogen carbonate (8.12 g) was added to an acetic acid anhydride (18 ml) solution of 5-chloro-2-nitrobenzaldehyde (9.99 g) and diethyl malonate (8.64 g), which was stirred at 110° C. for 2 hours. The reaction mixture was added to iced-water and extracted with ethyl acetate. The organic layer was washed with water and a saturated aqueous sodium chloride solution, then dried and concentrated. The residue was purified by silica gel column chromatography (eluent: ethyl acetate/hexane=1/10) to obtain the entitled compound (15.10 g). $^1$H-NMR δ: 1.10 (3H, t), 1.36(3H, t), 4.15(2H, q), 4.44(2H, q), 7.42(1H, d), 7.52(1H, dd), 8.11(1H, s), 8.18(1H, d).

Reference Example 85

Ethyl 6-chloro-2-oxo-1,2,3,4-tetrahydro-3-quinolinecarboxylate

Sodium borohydride (1.92 g) was added to an ethanol (100 ml) solution of diethyl 21(5-chloro-2-nitrophenyl) methylidene)malonate (15.10 g) at 0° C. The reaction mixture was stirred at 0° C. for 20 minutes, to which was added water, and the mixture was extracted with ethyl acetate. The organic layer was washed with a saturated aqueous sodium chloride solution, then dried and concentrated. Iron (9.90 g) was added to an acetic acid (150 ml) solution of the residue, which was heated under reflux for 30 minutes. The insoluble substances were removed by filtration, and the filtrate was concentrated. Water was added to the residue, which was extracted with ethyl acetate. The organic layer was washed with water and a saturated aqueous sodium chloride solution, then dried and concentrated. The obtained crude crystals were washed with IPE to give the entitled compound (7.278 g).

m.p. 173–175° C.

Reference Example 86

6-Chloro-2-oxo-1,2,3,4-tetrahydro-3-quinolinecarboxylic acid

1N Aqueous sodium hydroxide solution (30 ml) was added dropwise to a mixed solution of ethyl 6-chloro-2-oxo-1,2,3,4-tetrahydro-3-quinolinecarboxylate (7.278 g) in THF (90 ml) and methanol (60 ml) at 0° C. The reaction mixture was stirred at room temperature for 18 hours. 1N Hydrochloric acid (30 ml) was added dropwise to the reaction mixture at 0° C., which was extracted with ethyl acetate. The organic layer was washed with a saturated aqueous sodium chloride solution, then dried and concentrated. The obtained crude crystals were washed with diethyl ether to obtain the entitled compound (6.06 g).

m.p. 134–137° C. (Decomposed).

Reference Example 87

6-Chloro-N,N-dimethyl-2-oxo-1,2,3,4-tetrahydro-3-quinolinecarboxamide

6-Chloro-2-oxo-1,2,3,4-tetrahydro-3-quinolinecarboxylic acid (3.00 g), dimethylamine hydrochloride (1.332 g), HOBt (2.042 g), WSC (3.093 g) and triethylamine (4.5 ml) were added to acetonitrile (150 ml). The reaction mixture was stirred at room temperature for 18 hours. 10% Aqueous citric acid solution was added to the reaction mixture. The precipitated pellets were collected by filtration and washed with water and IPE to obtain the entitled compound (1.276 g).

m.p. 302–305° C.

Reference Example 88

6-Chloro-3-(N,N-dimethylamino)methyl-1,2,3,4-tetrahydroquinoline

1M Borane/THF complex (33 ml) was added to a THF (300 ml) suspension of 6-chloro-N,N-dimethyl-2-oxo-1,2,3, 4-tetrahydro-3-quinolinecarboxamide (2.135 g). The reaction mixture was heated under reflux for 6 hours, and left standing for cooling. The reaction mixture was ice-cooled, to which was added water (5 ml) and 6N hydrochloric acid (30 ml). The mixture was stirred at room temperature for 15 hours, then concentrated. 3N aqueous sodium hydroxide solution was added to the residue to make basic, which was extracted with ethyl acetate. The organic layer was washed with water and a saturated aqueous sodium chloride solution, then dried and concentrated. The residue was purified by alumina column chromatography (eluent: ethyl acetate/hexane=1/4). The obtained crude crystals were washed with hexane to obtain the entitled compound (1.432 g).

m.p. 94–96° C.

Reference Example 89

Diethyl 2-[(4-chloro-2-nitrophenyl)methylidene malonate

Potassium hydrogencarbonate (16.57 g) was added to an acetic acid anhydride (36 ml) solution of 4-chloro-2-nitrobenzaldehyde (20.35 g) and diethylmalonate (17.60 g), which was stirred at 110° C. for 4 hours. The reaction mixture was added to iced-water, which was extracted with ethyl acetate. The organic layer was washed with water and a saturated aqueous sodium chloride solution, and then dried and concentrated. The residue was purified by silica gel column chromatography (eluent: ethyl acetate/hexane=1/4) to obtain the entitled compound (34.92 g).

$^1$H-NMR δ: 1.10(3H, t), 1.36(3H, t), 4.12(2H, q), 4.35 (2H, q), 7.40(1H, d), 7.62(1H, dd), 8.09(1H, s), 8.21(1H, d).

Reference Example 90

Ethyl 7-chloro-2-oxo-1,2,3,4-tetrahydro-3-quinolinecarboxylate

Sodium borohydride (2.082 g) was added to an ethanol (200 ml) solution of diethyl 2-[(4-chloro-2-nitrophenyl) methylidene]malonate(34.92 g). The reaction mixture was stirred at 0° C. for one hour, to which was added water, and the mixture was extracted with ethyl acetate. The organic layer was washed with a saturated aqueous sodium chloride solution, then dried and concentrated. Iron (26.70 g) was added to an aqueous acetic acid (300 ml) solution of the residue, which was heated under reflux. The reaction mixture was left standing for cooling, and ethyl acetate (300 ml) was added to the reaction mixture. The precipitated insoluble substances were removed by filtration and the filtrate was concentrated. The organic layer was washed with water and a saturated aqueous sodium chloride solution and then dried and concentrated. The obtained crude crystals were washed with IPE to give the entitled compound (14.50 g).

m.p. 183–185° C.

Reference Example 91

7-Chloro-2-oxo-1,2,3,4-tetrahydro-3-quinolinecarboxylic acid

IN Aqueous sodium hydroxide solution (60 ml) was added dropwise to a mixed solution of ethyl 7-chloro-2-oxo-1,2,3,4-tetrahydro-3-quinolinecarboxylate (14.39 g) in THF (180 ml) and methanol (120 ml) at 0° C. The reaction mixture was stirred at room temperature for 24 hours. 1N Hydrochloric acid (70 ml) was added dropwise to the reaction mixture at 0° C., which was extracted with ethyl acetate. The organic layer was washed with a saturated aqueous sodium chloride solution, then dried and concentrated. The obtained crude crystals were washed with IPE to obtain the entitled compound (12.15 g).

m.p. 187–189° C.

Reference Example 92

7-Chloro-N,N-dimethyl-2-oxo-1,2,3,4-tetrahydro-3-quinollnecarboxamide

7-Chloro-2-oxo-1,2,3,4-tetrahydro-3-quinolinecarboxylic acid (11.282 g), dimethylamine hydrochloride (4.936 g), HOBt (7.694 g), WSC (10.63 g), and triethylamine (17 ml) were added to a mixed solution of acetonitrile (100 ml) and THF (100 ml). The reaction mixture was stirred at room temperature for 18 hours. Water was added to the reaction mixture. The precipitated pellets were collected by filtration, washed with water, and diethyl ether to obtain the entitled compound (9.529 g).

m.p. 281–2830° C.

Reference Example 93

7-Chloro-3-(N,N-dimethylamino)methyl-1,2,3,4-tetrahydroquinoline

1M Borane/THF complex (80 ml) was added to a THF (180 ml) suspension of 7-chloro-N,N-dimethyl-2-oxo-1,2,3, 4-tetrahydro-3-quinolinecarboxamide (5.055 g). The reaction mixture was heated under ref lux and left standing for cooling. The reaction mixture was ice-cooled, to which was added water (5 ml) and 6N hydrochloric acid (50 ml). The mixture was stirred at room temperature for one hour, then concentrated. A methanol solution (100 ml) of the residue was heated under reflux for 75 minutes and then concentrated. 3N Aqueous sodium hydroxide solution was added to the residue to make basic, which was extracted with ethyl acetate. The residue was purified by alumina column chromatography (eluent: ethyl acetate/hexane=1/4). The obtained crude crystals were washed with hexane to give the entitled compound (3.991 g).

m.p. 107–110° C.

Reference Example 94

(S)-(+)-3-(N,N-Dimethylamino)methyl-1,2,3,4-tetrahydroquinoline 3-(N,N-Dimethylamino)methyl-1,2,3,4-tetrahydroquinoline (4.2 g) and (−)-4-(2,4-dichlorophenyl)-5,5-dimethyl-2-hydroxy-1,3,2-dioxaphospholinane 2-oxide ((−)-2,4-Cl$_2$-CPA; 6.87 g) were dissolved in THF (80 ml) and ethanol (16 ml), which was stirred at room temperature overnight. The precipitated white crystals were filtrated and dried to obtain (−) -2,4-Cl$_2$-CPA salt (3.92 g) of (+)-3-(N,N -dimethylamino)methyl-1,2,3,4-tetrahydroquinoline. According to the results of HPLC analysis, the optical purity was 94% de. In the same manner, substantially the same operation using 1.0 g (5.3 mol) of 3-(N,N -dimethylamino) methyl-1,2,3,4-tetrahydroquinoline was conducted to obtain a salt of 92% de (0.91 g). The above salt (4.83 g) was recrystallized from isopropylalcohol (60 ml) and ethanol (45 ml) to obtain a salt of 98% de (4.11 g). This salt was stirred in water (35 ml) and 4N sodium hydroxide solution (4.5 ml) at room temperature for 6 hours, which was filtrated, washed with water, and dried to obtain the entitled compound (1.41 g). The absolute structure was determined by X ray crystal analysis of the above salt.

Optical purity: 99% ee.

m.p. 114° C.

Specific rotary power: $[\alpha]_D^{26}$=+60.19° (c=0.5; methanol).

Reference Example 95

(R)-(−)-3-(N,N-Dimethylamino)methyl-1,2,3,4-tetrahydroquinoline 3-(N,N-Dimethylamino)methyl-1,2,3,4-tetrahydroquinoline (10.3 g) was dissolved in THF (100 ml). To the mixture was added a mixed solution of (+)-4-(2,4- dichlorophenyl)-5,5-dimethyl-2-hydroxy-1,3,2-dioxaphospholinane 2-oxide ((+)-2,4-Cl$_2$-CPA; 16.8 g) in THF (100 ml) and ethanol (40 ml), while stirring under heating at 50° C. The reaction mixture was cooled to the room temperature and then stirred for 3 days. The precipitated white crystals were filtered and dried to obtain (+)-2,4-Cl$_2$-CPA salt (9.31 g) of (+)-3-(N,N-dimethylamino)methyl-1,2,3,4-tetrahydroquinoline. According to the results of HPLC analysis, the optical purity was 92% de.

The above salt (9.31 g) was recrystallized from isopropylalcohol/ethanol (55/45) to obtain a salt of 97% de (7.25 g). The crystal was stirred in water (60 ml), 4N sodium hydroxide solution (7 ml) and ether (30 ml) at room temperature for one hour. The ether layer was combined and the aqueous layer was extracted with 30 ml of ethyl acetate. The organic layers were combined, which was washed with water, then dried and concentrated. The residue was washed with hexane to obtain 2.3 g of white needle crystals.

Optical purity: >99% ee.

m.p. 113–114° C.

Specific rotary power: $[\alpha]_D^{27.4}=-61.2°$ (c=0.5; methanol).

Reference Example 96

3-(N-Benzyloxycarbonylamino)methyl-1,2,3,4-tetrahydroquinoline

10% Palladium-carbon (150 mg) and concentrated hydrochloric acid (2 ml) were added to a methanol (30 ml) solution of 3-(R,S)-(N,N-dibenzylamino)methyl-1,2,3,4-tetrahydroquinoline (1.5 g), and catalytic hydrogenation was conducted at room temperature under a hydrogen pressure of 4 atmospheric pressure for 2 hours. The catalyst was removed by filtration and the filtrate was concentrated. 10% aqueous potassium carbonate solution was added to the residue, which was extracted with ethyl acetate. The organic layer was washed with a saturated aqueous sodium chloride solution, then dried and concentrated. To a methanol (15 ml) solution of the residue was added 10% palladium-carbon (150 mg) and then an aqueous solution (3 ml) of ammonium formate (300 mg), which was heated under reflux for 2 hours. The catalyst was removed by filtration and the residue was concentrated. The residue was dissolved in THF, then dried, and concentrated. Triethylamine (0.9 ml) was added to a THF (14 ml) solution of the residue, to which was added dropwise benzyl chloroformate (0.5 ml) under ice-cooling. The reaction mixture was stirred at the same temperature for one hour. Water was added to the reaction mixture, which was extracted with ethyl acetate. The ethyl acetate layer was washed with a saturated aqueous sodium chloride solution, then dried, and concentrated. The residue was purified by silica gel column chromatography (eluent: ethyl acetate). The precipitated crystals were washed with hexane to obtain the entitled compound (825 mg).

m.p. 115–116° C.

Reference Example 97

1-[3(4-Biphenylyl)methyl-3-(N -benzyloxycarbonylamino)methyl-1,2,3,4-tetrahydroquinoline Oxalyl chloride (0.088 ml) was added dropwise to a THF (3 ml) solution of 3-(4-biphenylyl)propionic acid (183 mg) under ice-cooling. The reaction mixture was stirred at room temperature for one hour and then concentrated. The residue was dissolved in THF (2 ml), which was added dropwise to a THF (3 ml) solution of 3-(N -benzyloxycarbonylamino)methyl-1,2,3,4-tetrahydroquinoline (200 mg) and triethylamine (0.14 ml) under ice-cooling. The reaction mixture was stirred at the same temperature for one hour. Water was added to the mixture, which was extracted with ethyl acetate. The organic layer was washed with a saturated aqueous sodium chloride solution, then dried and concentrated. The residue was purified by silica gel column chromatography (eluent: ethyl acetate/hexane=1/1) to obtain the entitled compound (310 mg).

$^1$H-NMR(CDCl$_3$) δ: 2.11–2.35(2H, m), 2.69–3.07(6H, m), 3.09–3.29(1H, m), 3.49–3.65(1H, m), 3.78–3.88(1H, Br), 5.05–5.22(1H, m), 5.09(2H, s), 7.00–7.60(18H, m).

Reference Example 98

Diethyl 2-(2,4-dinitrobenzylidene)malonate

The mixture of 2,4-dinitrobenzaldehyde (25 g), diethylmalonate (20.3 g), potassium hydrogencarbonate (19.1 g), and acetic anhydride (50 ml) was stirred at 110° C. under nitrogen atmosphere for one hour. The reaction mixture was cooled, diluted with water, and extracted with ethyl acetate. The organic layer was washed with water and a saturated aqueous sodium chloride solution and then dried and concentrated. The residue was purified by alumina column chromatography (eluent: hexane/ethyl acetate=4: 1) to obtain the entitled compound (24 g).

$^1$H-NMR (CDCl$_3$) δ: 1.11(3H, t), 1.37(3H, t), 4.12(2H, q), 4.37(2H, q), 7.67(1H, d), 8.15(1H, s), 8.49(1H, dd), 9.05 (1H, d).

Reference Example 99

Diethyl 2-(2,4-dinitrobenzyl) malonate

To a ethanol (460 ml) solution of diethyl 2-(2,4-dinitrobenzylidene)malonate (23 g) was added sodium borohydride (1.65 g) while the temperature was kept under –10° C. and the mixture was stirred under ice-cooling for 30 minutes. The reaction mixture was made acidic by adding 10% aqueous solution and concentrated. The residue was diluted with 1N hydrochloric acid and extracted with ethyl acetate. The organic layer was washed with a saturated aqueous sodium chloride solution, dried and concentrated. The residue was purified by alumina column chromatography (eluent: hexane/ethyl acetate=4:1) to obtain the entitled compound (13.9 g).

$^1$H-NMR(CDCl$_3$) δ: 1.24(6H, t), 3.61(2H, d),3.86(1H, dd), 4.04–4.36(4H, q), 7.70(1H, d), 8.38(1H, dd), 8.86(1H, d).

Reference Example 100

Ethyl 7-amino-2-oxo-1,2,3,4-tetrahydro-3-quinolinecarboxylate

To a mixed solution diethyl 2-(2,4-dinitrobenzyl) malonate (13 g) in a mixed solution of ethanol (130 ml) and THF (130 ml) was added 10% palladium-Carbon (700 mg). The reaction mixture was stirred under 4 to 5 atmospheric pressure of hydrogen at room temperature for 4 hours. The catalyst was removed by filtration and the filtrate was concentrated. The residue was diluted with ethanol (130 ml) and the mixture was heated under ref lux for 12 hours and concentrated. The precipitated crystals were washed with IPE to obtain the entitled compound (7.4 g). The compound recrystallized from ethanol/IPE showed the following m.p.

m.p.: 182–184° C.

Reference example 101

Ethyl 7-benzyloxycarbonylamino-2-oxo-1,2,3,4-tetrahydro-3-quinolinecarboxylate

To a suspension of ethyl 7-amino-2-oxo-1,2,3,4-tetrahydro-3-quinolinecarboxylate (2.0 g) in THF(40 ml) was added aqueous sodium carbonate (4.5 g in 40 ml) and cooled, to which benzylchloroformate (1.8 ml) was added dropwise. The reaction mixture was diluted with water and extracted with ethyl acetate. The organic layer was washed with a saturated aqueous sodium chloride solution, dried, and concentrated. The precipitated crystals were washed with hexane to obtain the entitled compound (3.07 g).

m.p.: 187–189° C.

Reference example 102

7-Benzyloxycarbonylamino-2-oxo-1,2,3,4-tetrahydro-3-quinolinecarboxylic acid

To a solution of ethyl 7-benzyloxycarbonylamino-2-oxo-1,2,3,4-tetrahydro-3-quinolinecarboxylate (7.8 g) in a mixed solvent of THF (80 ml) and methanol (80 ml) was added 1N aqueous sodium hydroxide (32 ml) under 10° C. The reaction mixture was stirred at room temperature for 4 hours, to which was added 1N hydrochloric acid (35 ml) under 1° C. The reaction mixture was diluted with a saturated aqueous sodium chloride solution and extracted with ethyl acetate. The organic layer was washed with a saturated aqueous sodium chloride solution, dried, and concentrated to obtain the entitled compound (7.20 g).

$^1$H-NMR(CDCl$_3$) δ: 2.88–3.20(2H, m), 3.34–3.52(1H, m), 5.07(2H, s), 6.78–7.60(9H, m), 9.28(1H, brs).

Reference example 103

N,N-Dimethyl-7-benzyloxycarbonylamino-2-oxo-1,2,3,4-tetrahydro-3-quinolinecarboxamide

To a solution of 7-benzyloxycarbonylamino-2-oxo-1,2,3,4-tetrahydro-3-quinolinecarboxylic acid (7.0 g) in acetonitrile (80 ml) and THF (80 ml) were added dimethylamine hydrochloride (2.52 g), WSC(5.92 g), HOBt (3.15 g), and triethylamine (18 ml) subsequently at room temperature. The reaction mixture was stirred at room temperature for 10 hours, diluted with water, and extracted with combined solvent of ethyl acetate and THF. The organic layer was washed with 1N hydrochloric acid, water, saturated aqueous sodium hydrogencarbonate, water, saturated aqueous sodium chloride subsequently, dried, and concentrated. The precipitated crystals were washed with IPE to obtain the entitled compound (5.88 g).

m.p.: 218–228° C. (decomposed).

Reference example 104

N,N-Dimethyl-7-amino-2-oxo-1,2,3,4-tetrahydro-3-quinolinecarboxamide

To a suspension of N,N-dimethyl-7-benzyloxycarbonylamino-2-oxo-1,2,3,4-tetrahydro-3-quinolinecarboxamide (820 mg) in methanol (8 ml) and THF (8 ml) was added 10% palladium-carbon (100 mg). The reaction mixture was stirred under one atmospheric pressure of hydrogen at room temperature for 4 hours. The catalyst was removed by filtration and the filtrate was concentrated. The precipitated crystals were washed with combined solution of IPE and THF to obtain the entitled compound (480 mg).

m.p.: 219 to 223° C.

Reference example 105

7-Amino-3-(N,N-dimethylamino)methyl-1,2,3,4-tetrahydroquinoline

To a suspension of N,N-dimethyl-7-amino-2-oxo-1,2,3,4-tetrahydro-3-quinolinecarboxamide (450 mg) in THF (15 ml) was added Borane-THF complex (1M, 12 ml) under ice-cooling. The reaction mixture was heated under reflux for one hour. The reaction mixture was diluted with water (2 ml) under ice-cooling and concentrated. The residue was dissolved in methanol (12 ml), which was heated under reflux with 6N hydrochloric acid (4 ml) for 3 hours. After cooling, the reaction mixture was made basic and extracted with combined solution of THF and ethyl acetate. The organic layer was dried and concentrated. The residue was purified by alumina column chromatography (eluent: ethyl acetate to ethyl acetate/methanol=20:1) to obtain the entitled compound (380 mg).

$^1$H-NMR(CDCl$_3$) δ: 2.00–2.46(4H, m), 2.25(6H, s), 2.66–2.84(1H, m), 2.95(1H, dd), 3.20–3.60(4H, m), 5.86 (1H, d), 6.01(1H, dd), 6.75(1H, d).

Reference Example 106

7-Acetylamino-3-(N,N-dimethylamino)methyl-1,2,3,4-tetrahydroquinoline

To a solution of 7-amino-3-(N,N-dimethylamino)methyl-1,2,3,4-tetrahydroquinoline (300 mg) in pyridine (3 ml) was added a solution of acetic anhydride (150 mg) in THF (1 ml) and stirring was continued for 30 minutes. The reaction mixture was purified by alumina column chromatography (eluent; ethyl acetate to ethyl acetate/methanol=20:1) and the resulting crystals were washed with IPE to obtain the entitled compound (275 mg).

m.p.: 118–123° C.

EXAMPLE 1

3-(N,N-Dimethylamino)methyl-1-[3-[3-(1-naphthyl)-1,2,4-oxadiazol-5-yl]propanoyl]-1,2,3,4-tetrahydroquinoline p-toluenesulfonate

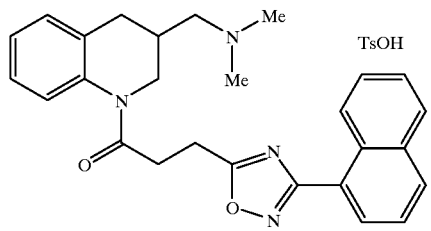

To a THF (10 ml) solution of 3-[3-(1-naphthyl)-1,2,4-oxadiazol-5-yl]propionic acid (compound of Reference Example 14, 381.4 mg) were added dropwise DMF (2 drops) and then oxalyl chloride (0.22 ml) at 0° C. The reaction mixture was stirred at room temperature for one hour, then concentrated. The residue was dissolved in acetonitrile (10 ml), which was added dropwise to an acetonitrile (10 ml) solution of 3-(N,N-dimethylamino)methyl-1,2,3,4-tetrahydroquinoline (190.3 mg) and triethylamine (0.21 ml) at 0° C. The reaction mixture was stirred at room temperature for one hour. 5% Aqueous sodium hydrogencarbonate solution was added to the reaction mixture, which was extracted with ethyl acetate. The organic layer was washed with a saturated aqueous sodium chloride solution, then dried and concentrated. The residue was purified by alumina column chromatography (eluent: hexane/ethyl acetate=3/1), which was converted into its p-toluenesulfonate. The mixture was recrystallized from THF/diethyl ether to give the entitled compound (578.3 mg).

m.p. 159–161° C.

Compounds of the following Examples 2 to 68 were synthesized by the similar manner as in Example 1 using the eluent described in the respective Example.

EXAMPLE 2

3-(N,N-Dimethylamino)methyl-1-[3-(4-methoxyphenyl)propanoyl]-1,2,3,4-tetrahydroquinoline p-toluenesulfonate

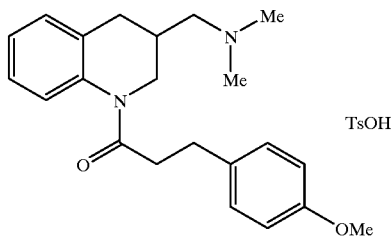

Eluent: hexane/ethyl acetate=4/1 m.p. 122–123° C. (Solvent for recrystallization: ethyl acetate/diethyl ether).

EXAMPLE 3

3-(N,N-Dimethylamino)methyl-1-(3-phenylpropanoly)-1,2,3,4-tetrahydroquinoline p-toluenesulfonate

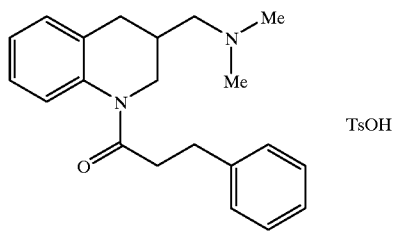

Eluent: hexane/ethyl acetate=3/1 m.p. 180–181° C. (Solvent for recrystallization: THF/diethyl ether).

EXAMPLE 4

3-(N,N-Dimethylamino)methyl-1-[3-(3-methoxyphenyl)propanoyl]-1,2,3,4-tetrahydroquinoline p-toluenesulfonate

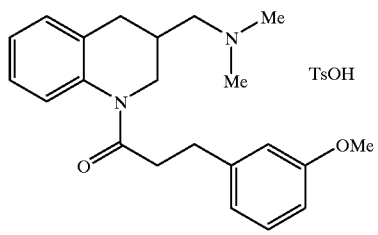

Eluent: hexane/ethyl acetate=3/1 m.p. 128–129° C. (Solvent for recrystallization: THF/diethyl ether).

EXAMPLE 5

3-(N,N-Dimethylamino)methyl-1-[3-(2-methoxyphenyl)propanoyl]-1,2,3,4-tetrahydroquinoline p-toluenesulfonate

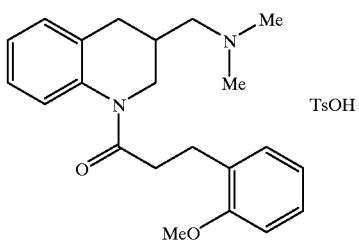

Eluent: hexane/ethyl acetate=3/1 m.p. 140–140.5° C. (Solvent for recrystallization: THF/diethyl ether)

EXAMPLE 6

1-[3-(3,4-Dimethoxyphenyl)propanoyl]-3-(N,N-dimethylamino)methyl-1,2,3,4-tetrahydroquinoline p-toluenesulfonate

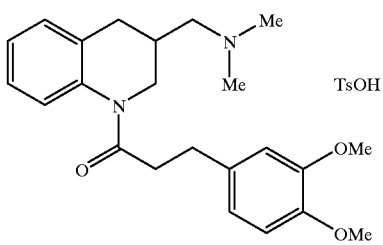

Eluent: hexane/ethyl acetate=2/3 m.p. 138–139° C. (Solvent for recrystallization: THF/diethyl ether)

EXAMPLE 7

3-(N,N-Dimethylamino)methyl-1-[3-(3,4-methylenedioxyphenyl)propanoyl]-1,2,3,4-tetrahydroquinoline p-toluenesulfonate

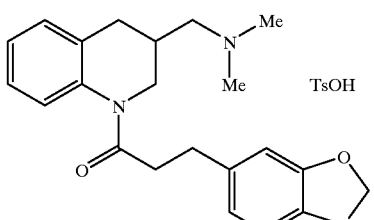

Eluent: hexane/ethyl acetate=3/1 m.p. 143–144° C. (Solvent for recrystallization: THF/diethyl ether)

EXAMPLE 8

3-(N,N-Dimethylamino)methyl-1-[3-(3,4,5-trimethoxyphenyl)propanoyl]-1,2,3,4-tetrahydroquinoline hydrochloride

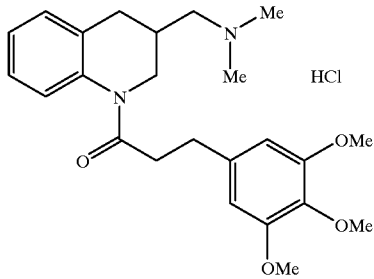

Eluent: hexane/ethyl acetate=1/1

Amorphous powder $^1$H-NMR δ: 2.05–2.3(4H, m), 2.20(6H, s), 2.65–3.0(5H, m), 3.22–3.33(1H, m), 3.78(6H, s), 3.81(3H, s), 3.95–4.05 (1H, m), 6.33(2H, br), 7.05–7.22(4H, m).

IR(KBr): 1647, 1590, 1508, 1493, 1460, 1422, 1399, 1240, 1127, 1005, 766 cm$^{-1}$.

EXAMPLE 9

3-(N,N-Dimethylamino)methyl-1-(3,3-diphenylpropanoyl)-1,2,3,4-tetrahydroquinoline oxalate

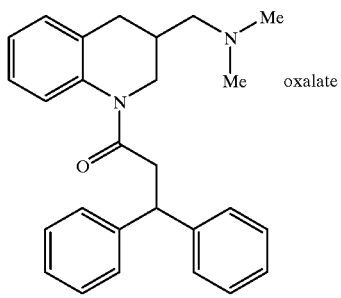

Eluent: hexane/ethyl acetate=3/1 m.p. 81–82° C. (Solvent for recrystallization: THF/diethyl ether)

EXAMPLE 10

3-(N,N-Dimethylamino)methyl-1-[3-(4-methylphenyl)propanoyl]-1,2,3,4-tetrahydroquinoline p-toluenesulfonate

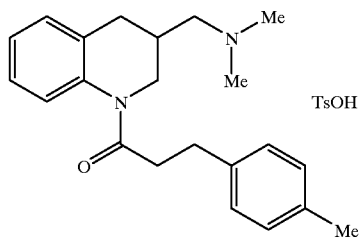

Eluent: hexane/ethyl acetate=2/1 m.p. 159–160° C. (Solvent for recrystallization: THF/diethyl ether)

EXAMPLE 11

3-(N,N-Dimethylamino)methyl-1-[3-(4-hydroxyphenyl)propanoyl]-1,2,3,4-tetrahydroquinoline hydrochloride

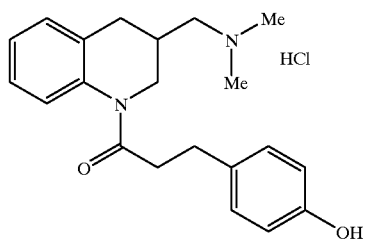

Eluent: hexane/ethyl acetate/(methanol)=3/2/(1%)

1Amorphous powder.

$^1$H-NMR δ: 2.22(6H, s), 2.0–2.4(4H, m), 2.7–3.0(5H, m), 3.22–3.32(1H, m), 3.96–4.05(1H, m), 6.69(2H, d), 6.85–7.05(6H, m).

IR(KBr): 1732, 1638, 1613, 1514, 1493, 1458, 1439, 1406, 1227, 1173, 833, 762 cm$^{-1}$.

EXAMPLE 12

3-(N,N-Dimethylamino)methyl-1-[3-(2-methylphenyl)propanoyl]-1,2,3,4-tetrahydroquinoline p-toluenesulfonate

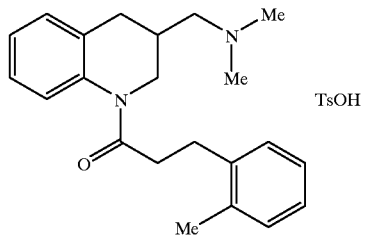

Eluent: hexane/ethyl acetate=5/1 m.p. 188–190° C. (Solvent for recrystallization: THF/diethyl ether)

EXAMPLE 13

1-[3-(4-Benzolyphenyl)propanoyl]-3-(N,N-dimethylamino)methyl-1,2,3,4-tetrahydroquinoline p-toluenesulfonate

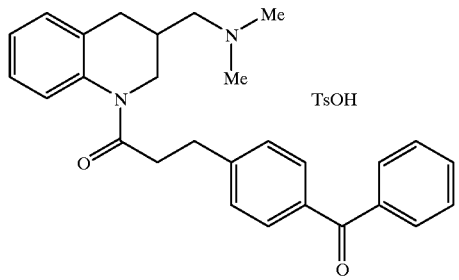

Eluent: hexane/ethyl acetate=3/1 m.p. 145–150° C. (Solvent for recrystallization: THF/diethyl ether)

EXAMPLE 14

1-[3-(4-Acetoxy-3-methoxyphenyl)propanoyl]-3-(N,N-dimethylamino)methyl-1,2,3,4-tetrahydroquinoline p-toluenesulfonate

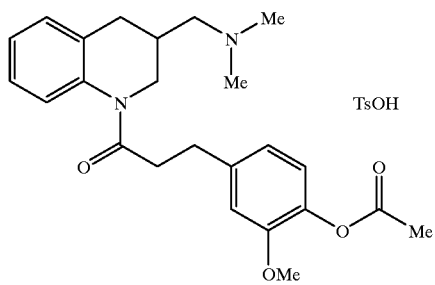

Eluent: hexane/ethyl acetate=3/1 to 1/1 m.p. 200–204° C. (Solvent for recrystallization: THF/diethyl ether)

EXAMPLE 15

3-(N,N-Dimethylamino)methyl-1-[(E)-3-(4-fluorophenyl)propenoyl]1,2,3,4-tetrahydroquinoline p-toluenesulfonate

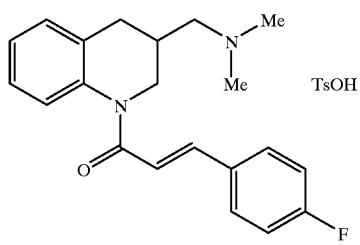

Eluent: hexane/ethyl acetate=5/1 to 3/1 m.p. 171–172° C. (Solvent for recrystallization: ethyl acetate/diethyl ether)

EXAMPLE 16

1-[(E)-3-(4-Chlorophenyl)propenoyl)-3-(N,N-dimethylamino)methyl-1,2,3,4-tetrahydroquinoline p-toluenesulfonate

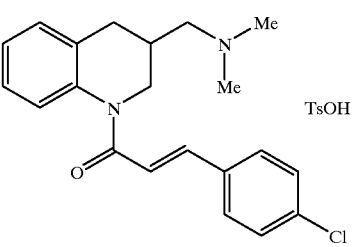

Eluent: hexanelethyl acetate=3/1 m.p. 165–166° C. (Solvent for recrystallization: THF/diethyl ether)

EXAMPLE 17

1-[3-[4-(4-Chlorophenoxy)phenyl]propanoyl]-3-(N,N-dimethylamino)methyl-1,2,3,4-tetrahydroquinoline p-toluenesulfonate

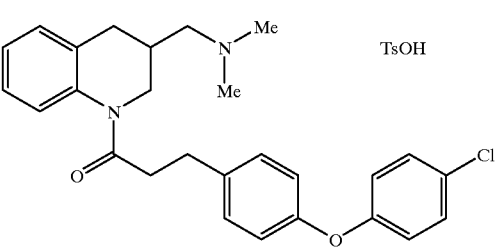

Eluent: hexane/ethyl acetate=3/1 m.p. 167–168° C. (Solvent for recrystallization: THF/diethyl ether)

EXAMPLE 18

3-(N,N-Dimethylamino)methyl-1-[(E)-3-(3,4-methylenedioxyphenyl)propenoyl]-1,2,3,4-tetrahydroquinoline oxalate

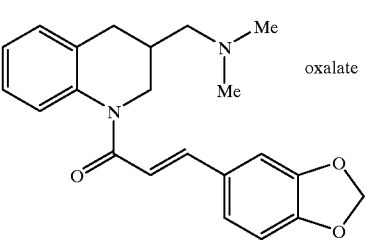

Eluent: hexane/ethyl acetate=3/1 m.p. 94–96° C. (Solvent for recrystallization: THF/diethyl ether)

EXAMPLE 19

3-(N,N-Dimethylamino)methyl-1-[3-(4-methyl-5-phenyloxazol-2-yl)propanoyl]-1,2,3,4-tetrahydroquinoline oxalate

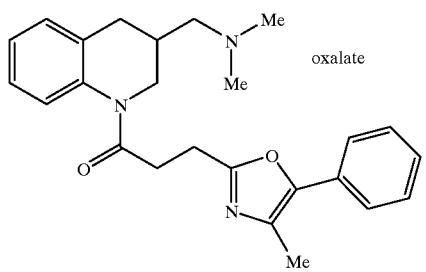

Eluent: hexane/ethyl acetate=3/1 to 2/1 m.p. 129–130° C. (Solvent for recrystallization: ethyl acetate/diethyl ether)

EXAMPLE 20

3-(N,N-Dimethylamino)methyl-1-(4-phenylbutanoyl)-1,2,3,4-tetrahydroquinoline oxalate

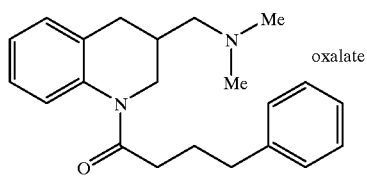

Eluent: hexane/ethyl acetate=3/1 m.p. 60–62° C. (Solvent for recrystallization: THF/diethyl ether)

EXAMPLE 21

1-[3-[3-(6-Methoxy-2-benzofuranyl)-1,2,4-oxadiazol-5-yl]propanoyl]3-(N,N-dimethylamino)methyl-1,2,3,4-tetrahydroquinoline p-toluenesulfonate

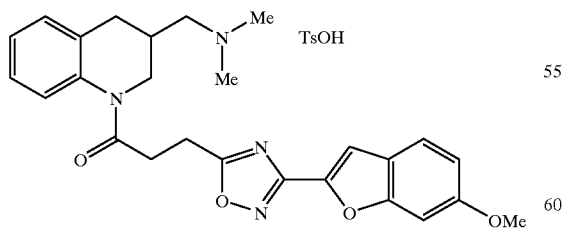

Eluent: hexane/ethyl acetate=1/1 m.p. 108–109° C. (Solvent for recrystallization: ethanol/ethyl acetate)

EXAMPLE 22

3-(N,N-Dimethylamino)methyl-1-[3-[4-(4-fluorophenyl)-2-methyloxazol-5-yl]propanoyl]-1,2,3,4-tetrahydroquinoline oxalate

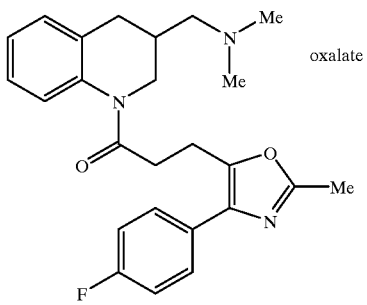

Eluent: hexane/ethyl acetate=3/1 to 2/1 m.p. 120–122° C. (Solvent for recrystallization: THF/diethyl ether)

EXAMPLE 23

1-[3-(4-Biphenylyl)propenoyl]-3-(N,N-dimethylamino)methyl-1,2,3,4-tetrahydroquinoline p-toluenesulfonate

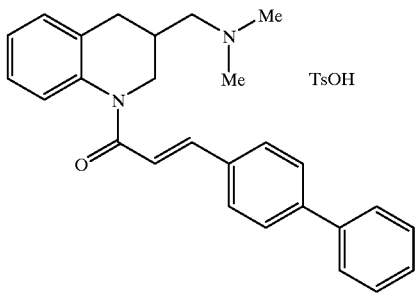

Eluent: hexane/ethyl acetate=1/1 m.p. 180–182° C. (Solvent for recrystallization: ethanol/ethyl acetate)

EXAMPLE 24

3-(N,N-Dimethylamino)methyl-1-[3-[3-(phenoxymethyl)-1,2,4-oxadiazol-5-yl]propanoyl]-1,2,3,4-tetrahydroquinoline p-toluenesulfonate

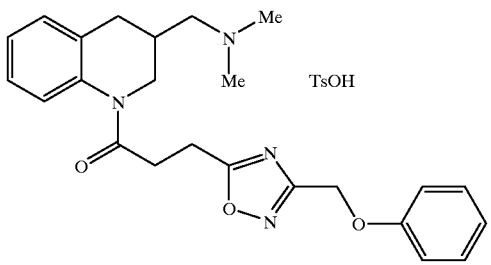

Eluent: hexane/ethyl acetate=2/1 m.p. 146–147° C. (Solvent for recrystallization: THF/diethyl ether)

EXAMPLE 25

3-(N,N-Dimethylamino)methyl-1-[3-[3-[(E)-2-(4-methylphenyl)ethenyl]-1,2,4-oxadiazol-5-yl)propanoyl]-1,2,3,4-tetrahydroquinoline p-toluenesulfonate

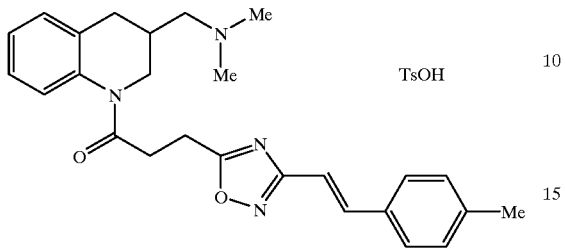

Eluent: hexane/ethyl acetate=4/1 to 3/1 m.p. 126–128° C. (Solvent for recrystallization: THF/diethyl ether)

EXAMPLE 26

1-[3-[3-(2-Benzofuranyl)-1,2,4-oxadiazol-5-yl]propanoyl]-3-(N,N-dimethylamino)methyl]-1,2,3,4-tetrahydroquinoline p-toluenesulfonate

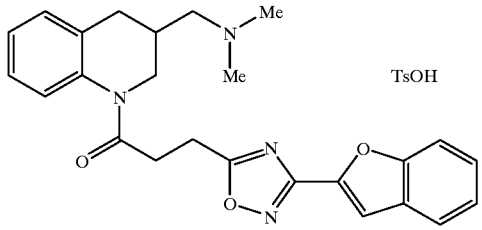

Eluent: hexanelethyl acetate=4/1 to 3/1 m.p. 108–110° C. (Solvent for recrystallization: THF/diethyl ether)

EXAMPLE 27

3-(N,N-Dimethylamino)methyl-1-[3-(E)-[4-(4-methoxyphenoxy)phenyl]propenoyl]-1,2,3,4-tetrahydroquinoline oxalate

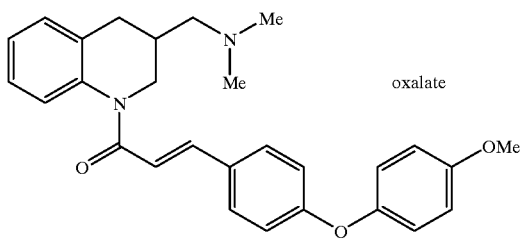

Eluent: hexane/ethyl acetate=3/1 to 2/1 m.p. 140–143° C. (Solvent for recrystallization: THF/diethyl ether)

Example 28

3-(N,N-Dimethylamino)methyl-1-(3-(1-methylindol-3-yl)propanoyl]-1,2,3,4-tetrahydroquinoline oxalate

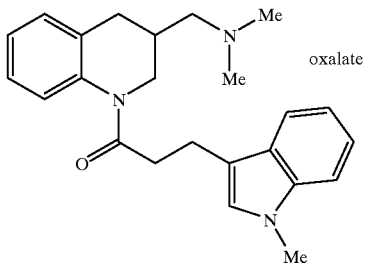

Eluent: hexane/ethyl acetate=3/1 to 2/1 m.p. 128–129° C. (Solvent for recrystallization: THF/ethyl acetate)

EXAMPLE 29

1-[3-(4-Biphenylyl)propanoyl)-3-(N,N-dimethylamino)methyl-1,2,3,4-tetrahydroquinoline p-toluenesulfonate

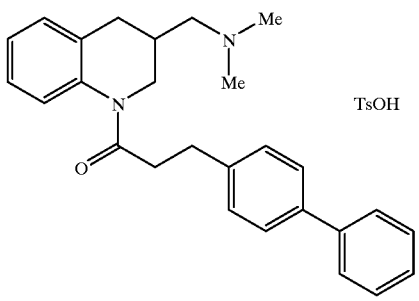

Eluent: hexane/ethyl acetate=5/1 to 4/1 m.p. 111–112° C. (Solvent for recrystallization: THF/dlethyl ether)

EXAMPLE 30

3-(N,N-Dimethylamino)methyl-1-[3-(2-methylindol-3-yl)propanoyl]-1,2,3,4-tetrahydroquinoline oxalate

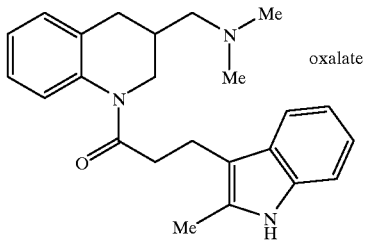

Eluent: hexane/ethyl acetate=3/1 to 2/1 m.p. 90–94° C. (Solvent for recrystallization: methanol/diethyl ether)

EXAMPLE 31

3-(N,N-Dimethylamino)methyl-1-[3-(2-ethoxycarbonyl-5-methoxyindol-3-yl)propanoyl]-1,2,3,4-tetrahydroquinoline oxalate

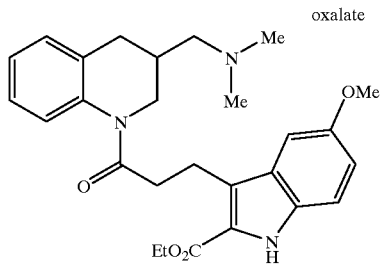

Eluent: hexane/ethyl acetate=2/1
m.p. 154–158° C. (Solvent for recrystallization: acetonitrile/THF/diethyl ether)

EXAMPLE 32

1-[3-[3-(2-Benzoxazolyl)-1,2,4-oxadiazol-5-yl]propanoyl]-3-(N,N-dimethylamino)methyl-1,2,3,4-tetrahydroquinoline p-toluenesulfonate

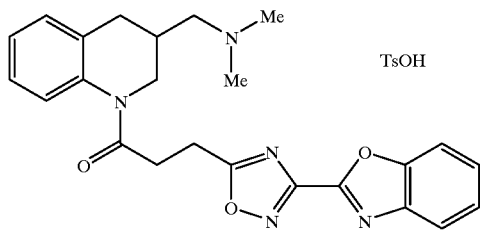

Eluent: hexane/ethyl acetate=4/1 to 3/1
m.p. 109–111° C. (Solvent for recrystallization: ethanol/THF/diethyl ether)

EXAMPLE 33

3-(N,N-Dimethylamino)methyl-1-[3-(E)-(3-quinolynyl)propenoyl]-1,2,3,4-tetrahydroquinoline dioxalate

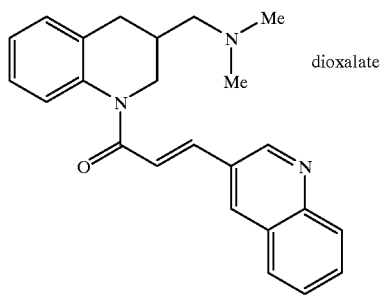

Eluent: hexane/ethyl acetate=4/1 to 3/1
Amorphous powder
IR(KBr): 1719, 1701, 1597, 1493, 1400, 1203, 1111, 966, 764, 721, 588cm$^{-1}$.

EXAMPLE 34

3-(N,N-Dimethylamino)methyl-1-[3-(3-quinolynyl)propanoyl]-1,2,3,4-tetrahydroquinoline dioxalate

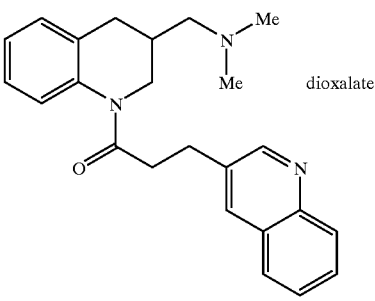

Eluent: hexane/ethyl acetate=4/1 to 3/1
m.p. 100–101° C. (Solvent for recrystallization: methanol/THF/diethyl ether)

EXAMPLE 35

3-(N,N-Dimethylamino)methyl-1-[3-[1-(4-methylsulfony)indol-3-yl3propanoyl]-1,2,3,4-tetrahydroquinoline oxalate

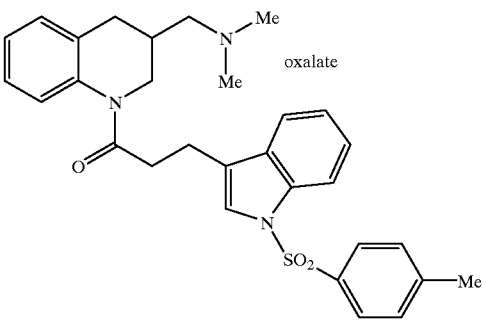

Eluent: hexane/ethyl acetate=4/1 to 2/1
Amorphous powder
IR(KBr): 1719, 1649, 1493, 1449, 1402, 1364, 1279, 1173, 1121, 1098, 974, 814, 762, 747, 721, 669, 596, 578, 538 cm$^{-1}$.

EXAMPLE 36

3-(N,N-Dimethylamino)methyl-1-[3-[3-(3-indolyl)-1,2,4-oxadiazol-5-yl]propanoyl]-1,2,3,4-tetrahydroquinoline

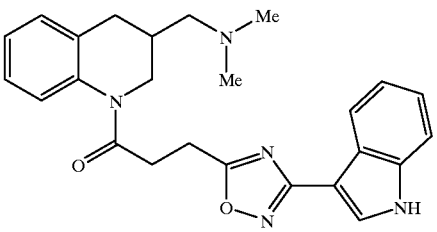

Eluent: hexane/ethyl acetate=1/1 to ethyl acetate/methanol=10/1

EXAMPLE 37

3-(N,N-Dimethylamino)methyl-1-[3-[3-(4-methoxyphenyl)methyl-1,2,4-oxadiazol-5-yl]propanoyl]-1,2,3,4-tetrahydroquinoline p-toluenesulfonate

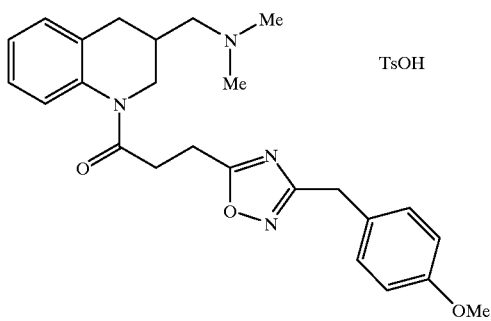

Eluent: hexane/ethyl acetate=2/1 to 1/1 m.p. 143–144° C. (Solvent for recrystallization: THF/diethyl ether)

EXAMPLE 38

3-(N,N-Dimethylamino)methyl-1-[3-(4-phenylthiazol-2-yl)propanoyl]-1,2,3,4-tetrahydroquinoline p-toluenesulfonate

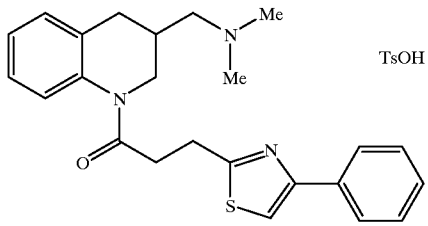

Eluent: hexane/ethyl acetate=5/1 to 3/1 m.p. 153–155° C. (Solvent for recrystallization: THF/diethyl ether).

EXAMPLE 39

1-[3-[4-(2-Benzofuranyl)thiazol-2-yl]propanoyl]-3-(N,N-dimethylamino)methyl-1,2,3,4-tetrahydroquinoline p-toluenesulfonate

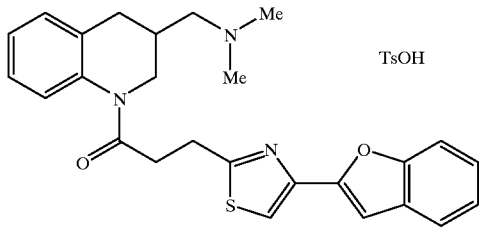

Eluent: hexane/ethyl acetate=5/1 to 4/1 m.p. 149–151° C. (Solvent for recrystallization: THF/diethyl ether)

m.p. 156–157° C. (Solvent for recrystallization: ethyl acetate/diethyl ether).

EXAMPLE 40

1-(4-Biphenylyloxy)acetyl-3-(N,N-dimethylamino)methyl-1,2,3,4-tetrahydroquinoline p-toluenesulfonate

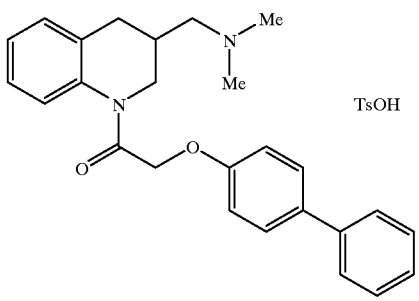

Eluent: hexane/ethyl acetate=3/1 m.p. 151–152° C. (Solvent for recrystallization: ethanol/diethyl ether)

EXAMPLE 41

3-(N,N-Dimethylamino)methyl-1-[3-[3-(2-naphthyl)-1,2,4-oxadiazol-5-yl]propanoyl]-1,2,3,4-tetrahydroquinoline

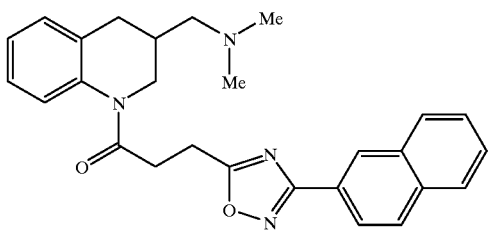

Eluent: hexane/ethyl acetate=3/1 m.p. 94–95° C. (Solvent for recrystallization: diethyl ether).

EXAMPLE 42

3-(N,N-Dimethylamino)methyl-1-[(E)-3-(3-pyridyl)propenoyl)-1,2,3,4-tetrahydroquinoline dioxalate

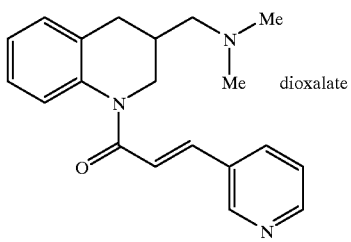

Eluent: hexane/ethyl acetate=1/1 m.p. 155–157° C. (Solvent for recrystallization: methanol/ethyl acetate/diethyl ether).

EXAMPLE 43

3-(N,N-Dimethylamino)methyl-1-[3-[N-(3-methoxyphenyl)-N-[(4-methylphenyl)sulfonyl]amino]propanoyl]-1,2,3,4-tetrahydroquinoline hydrochloride

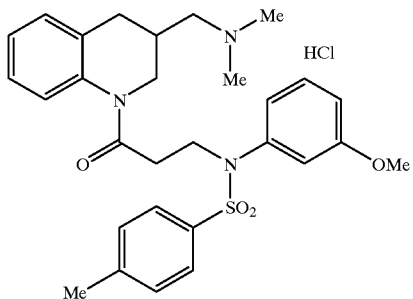

Eluent: hexane/ethyl acetate=3/1 to 1/1

Amorphous powder

IR(KBr): 1649, 1601, 1491, 1402, 1343, 1159, 1092, 1038, 947, 814, 766, 693, 656, 575, 548 cm$^{-1}$.

EXAMPLE 44

1-[3-[1-(2,4-Dichlorophenyl)methylindol-3-yl]propanoyl]-3-(N,N-dimethylamino)methyl-1,2,3,4-tetrahydroquinoline hydrochloride

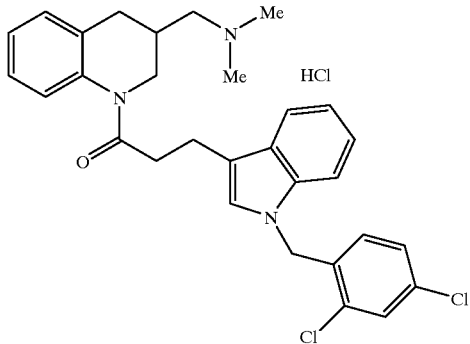

Eluent: hexane/ethyl acetate=4/1 to 3/1

Amorphous powder

IR(KBr): 1647, 1584, 1491, 1466, 1387, 1196, 1181, 1100, 1049, 1013, 959, 833, 743 cm$^-$.

EXAMPLE 45

1-[4-[3-(2-Benzofuranyl)-1,2,4-oxadiazol-5-yl]butanoyl]-3-(N,N-dimethylamino)methyl-1,2,3,4-tetrahydroquinoline p-toluenesulfonate

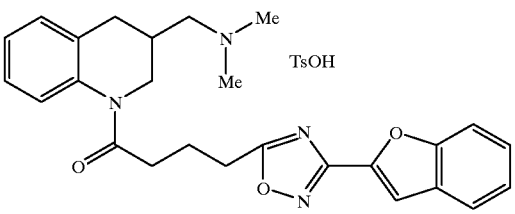

Eluent: hexane/ethyl acetate=3/1 m.p. 131–132° C. (Solvent for recrystallization: diethyl ether).

EXAMPLE 46

3-(N,N-Dimethylamino)methyl-1-[3-(3-indolyl)propanoyl]-1,2,3,4-tetrahydroquinoline hydrochloride

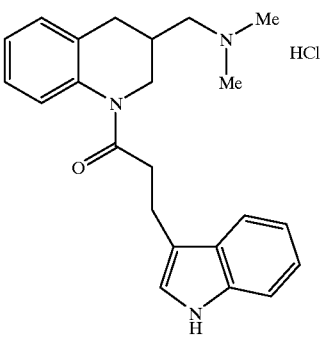

Eluent: hexane/ethyl acetate=4/1 to 2/1

Amorphous powder $^1$H-NMR δ: 1.94–2.32(3H, m), 2.19(6H, s), 2.60–3.34 (7H, m), 3.90–4.07(1H, m), 6.92–7.21(7H, m), 7.33(1H, d), 7.42–7.53(1H, m), 7.99(1H, br).

EXAMPLE 47

3-(N,N-Dimethylamino)methyl-1-[4-(3-indolyl)butanoyl]-1,2,3,4-tetrahydroquinoline hydrochloride

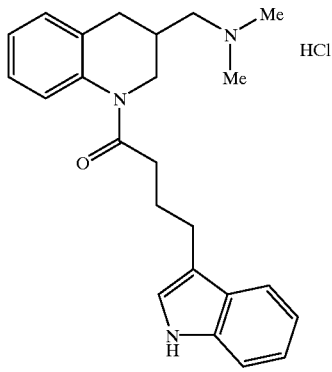

Eluent: hexane/ethyl acetate=4/1 to 2/1

Amorphous powder

IR(KBr): 3241, 2938, 2676, 1647, 1491, 1458, 1397, 747 cm$^{-1}$

EXAMPLE 48

1-(6-Cyano-6,6-diphenylhexanoyl)-3-(N,N-dimethylamino)methyl-1,2,3,4-tetrahydroquinoline oxalate

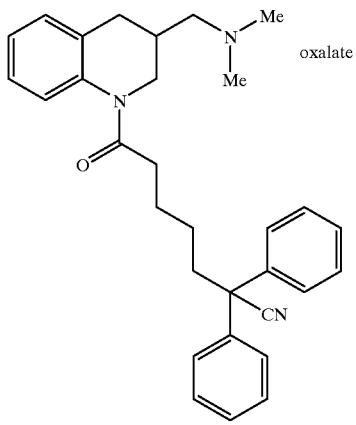

Eluent: hexane/ethyl acetate=4/1

Amorphous powder

IR(KBr): 3036, 2938, 2868, 1655, 1491, 1395, 1192, 1179, 758, 700 cm$^{-1}$.

EXAMPLE 49

4-(N,N-Dimethylamino)methyl-1-[3-(indol-3-yl)propanoyl]-8-methoxy-2,3,4,5-tetrahydro-1H-1-benzazepine

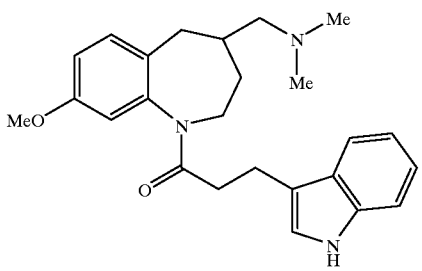

Eluent: hexane/ethyl acetate=3/1 to 1/1 m.p. 167–168° C. (Solvent for recrystallization: ethyl acetate/diethyl ether).

EXAMPLE 50

4-(N,N-Dimethylamino)methyl-8-methoxy-1-[3-[3-(phenoxymethyl)-1,2,4-oxadiazol-5-yl]propanoyl]-2,3,4,5-tetrahydro-1H-1-benzazepine

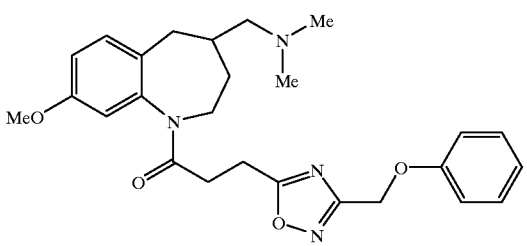

Eluent: hexane/ethyl acetate=3/1 to 1/1

Oily substance

IR(KBr): 1655, 1611, 1599, 1580, 1443, 1406, 1360, 1346, 1292, 1230, 1217, 1163, 1038, 858, 845, 826, 756, 693 cm$^{-1}$.

EXAMPLE 51

1-[3-[3-(2-Benzofuranyl)-1,2,4-oxadiazol-5-yl]propanoyl]-4-(N,N-dimethylamino)methyl-8-methoxy-2,3,4,5-tetrahydro-1H-1-benzazepine p-toluenesulfonate

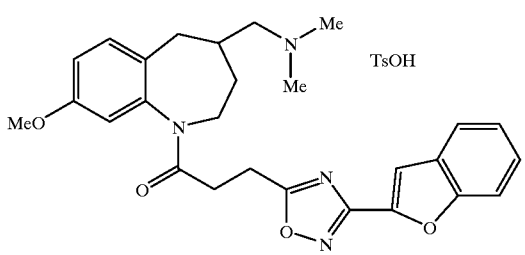

Eluent: hexane/ethyl acetate=3/1 to 1/1 m.p. 182–184° C. (Solvent for recrystallization: ethanol/THF/diethyl ether).

EXAMPLE 52

1-[3-[3-(2-Benzofuranyl)-1,2,4-oxadiazol-5-yl]propanoyl]-3-(N,N-diethylamino)methyl-1,2,3,4-tetrahydroquinoline

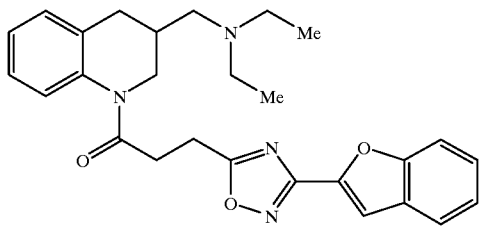

Eluent: hexane/ethyl acetate=5/1 to 4/1

Oily substance $^1$H-NMR δ: 0.97(6H, t), 2.1–2.6(8H, m), 2.92(1H, dd), 3.0–3.5(5H, m), 3.95–4.15(1H, m), 7.05–7.5(7H, m), 7.61(1H, d), 7.67(1H, d).

EXAMPLE 53

1-[3-(4-Biphenylyl)propanoyl]-3-(N,N-diethylamino)methyl-1,2,3,4-tetrahydroquinoline

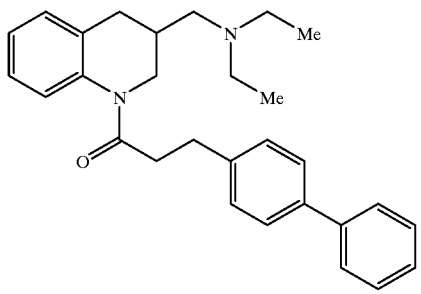

Eluent: hexane/ethyl acetate=6/1

Oily substance $^1$H-NMR δ: 0.97(6H, t), 2.1–2.6(8H, m), 2.47(4H, q), 2.92(1H, dd), 3.0–3.5(5H, m), 3.95–4.15(1H, m), 7.05–7.5(7H, m), 7.61(1H, d), 7.67(1H, d).

EXAMPLE 54

1-[3-[3-(2-Benzofuranyl)-1,2,4-oxadiazol-5-yl]propanoyl]-3-(4-phenylpiperazin-1-yl)methyl-1,2,3,4-tetrahydroquinoline di-p-toluenesulfonate

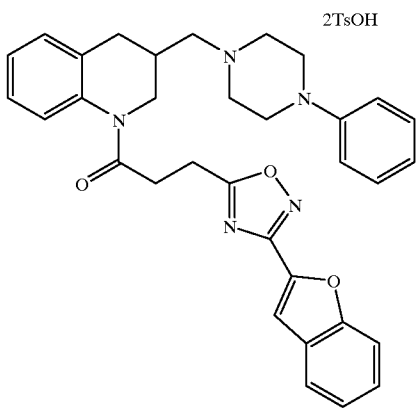

Eluent: hexane/ethyl acetate=5/1 to 4/1 m.p. 83–85° C. (Solvent for recrystallization: THF/diethyl ether).

EXAMPLE 55

1-[3-(4-Biphenylyl)propanoyl]-3-(4-phenylpiperazin-1-yl)methyl-1,2,3,4-tetrahydroquinoline dip-toluenesulfonate

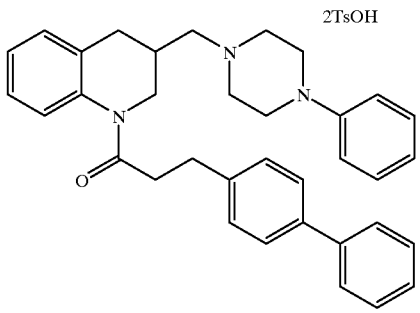

Eluent: hexane\ethyl acetate=6/1 to 5/1 m.p. 176–179° C. (Solvent for recrystallization: THF/diethyl ether)

EXAMPLE 56

1-[3-(3-(2-Benzofuranyl)-1,2,4-oxadiazol-5-yl] propanoyl]-3-(pirrolidin-1-yl)methyl-1,2,3,4-tetrahydroquinoline oxalate

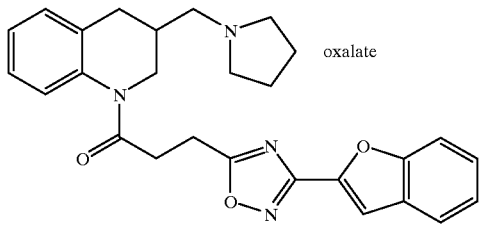

Starting compound: compound of Reference Example 10 and compound of Reference Example 47

Eluent: hexane/ethyl acetate=5/1 to 4/1 m.p. 190–192° C. (Solvent for recrystallization: THF/ethanol/diethyl ether).

EXAMPLE 57

1-[3-(4-Biphenylyl)propanoyl]-3-(pirrolidin-1-yl) methyl-1,2,3,4-tetrahydroquinoline oxalate

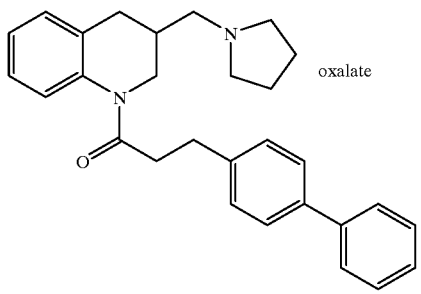

Eluent: hexane/ethyl acetate=6/1 m.p. 156–158° C. (Solvent for recrystallization: THF/diethyl ether)

EXAMPLE 58

1-[3-[3-(2-Benzofuranyl)-1,2,4-oxadiazol-5-yl] propanoyl]-3-[2-(N,N-dimethylamino)ethyl]-1,2,3,4-tetrahydroquinoline p-toluenesulfonate

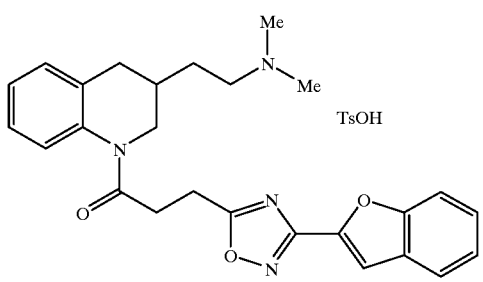

Eluent: hexane/ethyl acetate=1:1 m.p. 133–135° C. (Solvent for recrystallization: ethanol/IPE).

EXAMPLE 59

1-[3-(4-Biphenylyl)propanoyl]-3-piperidinomethyl-1,2,3,4-tetrahydroquinoline hydrochloride

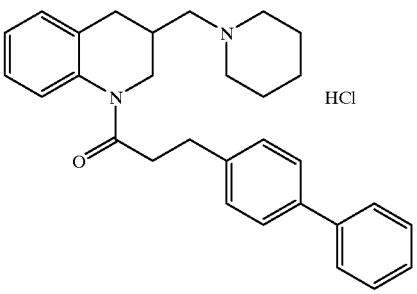

Eluent: hexane/ethyl acetate=1:1

Amorphous powder $^1$H-NMR δ: 1.1–1.8(6H, m), 1.9–2.5(7H, m), 2.6–3.0(6H, m), 3.1–3.4(1H, m), 3.8–4.0(1H, m), 7.05–7.6(13H, m).

EXAMPLE 60

1-[3-[3-(2-Benzofuranyl)-1,2,4-oxadiazol-5-yl] propanoyl]-1,2,3,4-tetrahydro-3-piperidinomethylquinoline

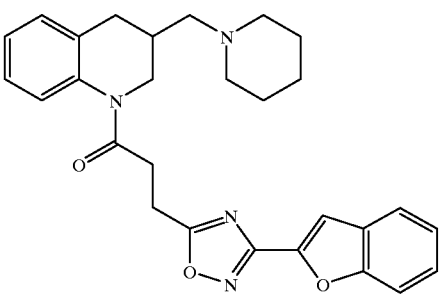

Eluent: hexane/ethyl acetate=2:1 m.p. 124–128° C. (Solvent for recrystallization: ethyl acetate/hexane).

EXAMPLE 61

1-[3-(4-Biphenylyl)propanoyl]-3-morpholinomethyl-1,2,3,4-tetrahydroquinoline hydrochloride

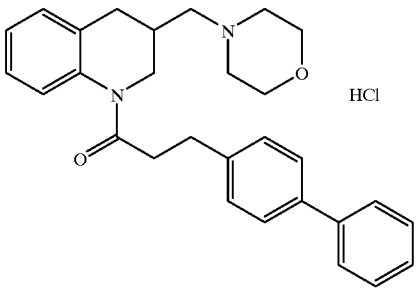

Eluent: hexane/ethyl acetate=1:1

Amorphous powder $^1$H-NMR δ: 2.1–2.5(8H, m), 2.6–3.4(5H, m), 3.2–3.6(1H, m), 3.5–3.9(4H, m), 3.8–4.1(1H, m), 7.05–7.6(13H, m).

EXAMPLE 62

1–13-[3-(2-Benzofuranyl)-1,2,4-oxadiazol-5-yl]
propanoyl]-3-morpholinomethyl-1,2,3,4-
tetrahydroquinoline p-toluenesulfonate

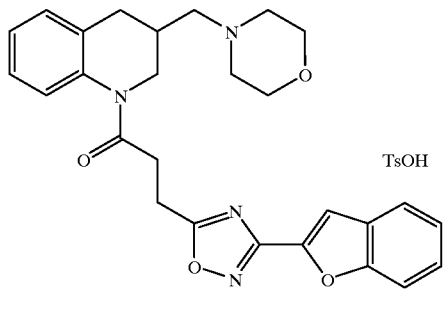

Eluent: hexane/ethyl acetate=1:1 m.p. 189–194° C. (Solvent for recrystallization: methanol).

EXAMPLE 63

1'-[3-(4-Biphenylyl)propanoyl]-1',2',3',4'-tetrahydro-
1-propylspiro[piperidin-3,3'-quinoline]oxalate

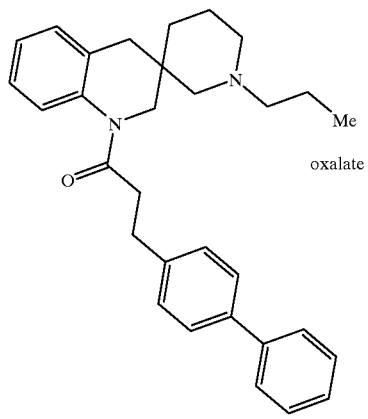

Eluent: hexane/ethyl acetate=4/1

Amorphous powder

IR(KBr): 3027, 2969, 2940, 2878, 1655, 1491, 1397, 762, 700 cm$^{-1}$.

EXAMPLE 64

1'-[3-8 3-(2-Benzofuranyl)-1,2,4-oxadiazol-5-yl]
propanoyl]-1',2',3',4'-tetrahydro-1-propylspiro
[piperidin-3,3'-quinoline]

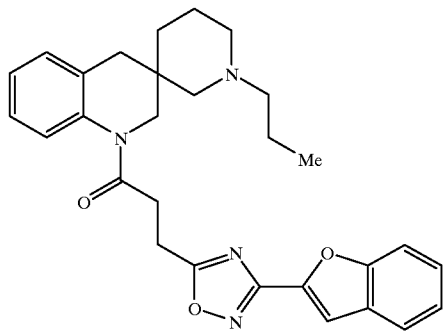

Eluent: hexane/ethyl acetate=2/1 m.p. 133–135° C. (Solvent for recrystallization: ethyl acetate/hexane).

EXAMPLE 65

3-(N-Benzyl-N-methylamino)methyl-1-[3-(4-
biphenylyl)propanoyl]-1,2,3,4-tetrahydroquinoline
oxalate

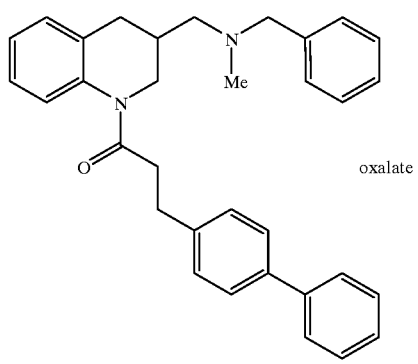

Eluent: hexane/ethyl acetate=4/1

Amorphous powder

IR(KBr): 3027, 1721, 1655, 1491, 1385, 1196, 924, 829, 760, 700 cm$^{-1}$.

EXAMPLE 66

7-(4-Biphenylyl)methoxy-3-(N,N-dimethylamino)
methyl-1-[3-(3-indolyl)propanoyl]-1,2,3,4-
tetrahydroquinoline hydrochloride

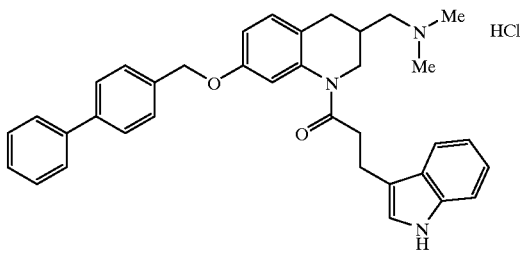

Amorphous powder
$^1$H-NMR δ: 1.85–2.20(4H, m), 2.17(6H, s), 2.50–2.95 (3H, m), 3.05–3.30(3H, m), 3.90–4.05(1H, m), 4.99(2H, s), 6.74(1H, dd), 6.84–7.18(5H, m), 7.22–7.64(11H, m), 8.16 (1H, br).

EXAMPLE 67

7-(4-Biphenylyl)methoxy-3-(N,N-dimethylamino)
methyl-1-[4-(3-indolyl)butyryl]-1,2,3,4-
tetrahydroquinoline hydrochloride

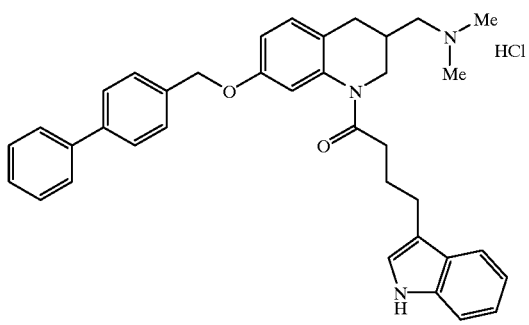

Amorphous powder
$^1$H-NMR δ: 1.80–2.20(6H, m), 2.15(6H, s), 2.50–2.95 (3H, m), 3.05–3.30(3H, m), 3.90–4.05(1H, m), 4.99(2H, s), 6.70–7.18(6H, m), 7.22–7.64(11H, m), 8.20(1H, br).

EXAMPLE 68

7-(4-Biphenylyl)methoxy-3-(N,N-dimethylamino)
methyl-1-[3-(5-methoxyindol-3-yl)propanoyl]-1,2,3,
4-tetrahydroquinoline hydrochloride

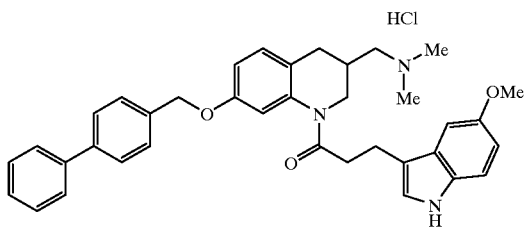

Amorphous powder
$^1$H-NMR δ: 1.80–2.20(4H, m), 2.16(6H, s), 2.50–2.95 (3H, m), 3.05–3.30(3H, m), 3.75(3H, s), 3.90–4.05(1H, m), 4.97(2H, s), 6.70–7.64(17H, m), 8.26(1H, br).

EXAMPLE 69

3-(N,N-Dimethylamino)methyl-1-[3-[1-(2,4,6-
triisopropylphenylsulfonyl)indol-3-yl]propanoyl]-1,
2,3,4-tetrahydroquinoline p-toluenesulfonate

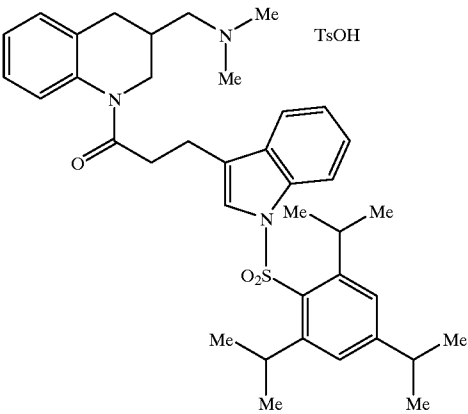

Chloroethylcarbonate (184.5 mg) was added dropwise to a THF (10 ml) solution of 3-[1-(2,4,6-triisopropylphenylsulfonyl)indol-3-yl]propionic acid (683.4mg) and triethylamine (0.32 ml) at 0° C. The reaction mixture was stirred at 0° C. for 30 minutes, to which was added dropwise a THF/acetonitrile (2 ml/20 ml) solution of N,N-dimethyl-N-[2-(1,2,3,4-tetrahydro-3-quinolinyl) methyl]amine (190.3 mg). The reaction mixture was stirred at 40° C. overnight, then concentrated. 5% Aqueous sodium hydrogencarbonate solution was added to the reaction mixture, which was extracted with ethyl acetate. The organic layer was washed with a saturated aqueous sodium chloride solution, then dried and concentrated. The residue was purified by alumina column chromatography (eluent: hexane/ethyl acetate=4/1 to 3/1), which was converted into its p-toluenesulfonate. The mixture was recrystallized from THF/diethyl ether to give the entitled compound (606.0 mg).
m.p. 122–125° C.

EXAMPLE 70

3-(N,N-Dimethylamino)methyl-1-[3-(5-
methoxyindol-3-yl)propanoyl]-1,2,3,4-
tetrahydroquinoline hydrochloride

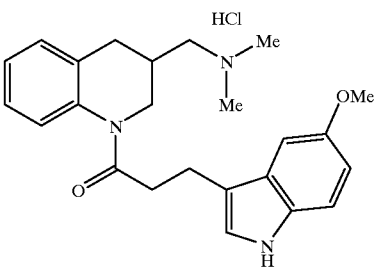

The entitled compound was obtained by the similar manner as in Example 67.
Eluent: hexane/ethyl acetate=4/1 to 1/2
Amorphous powder
IR(KBr): 1636, 1582, 1458, 1400, 1219, 1177, 1063, 1028, 802, 762 cm$^-$.

EXAMPLE 71

1-[3-(4-Bromophenyl)propanoyl]-3-(N,N-dimethylamino)methyl-1,2,3,4-tetrahydroquinoline p-toluenesulfonate

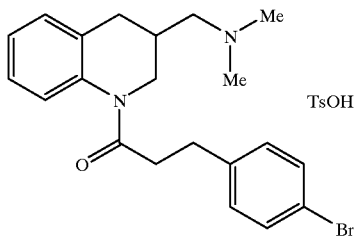

To a THF (20 ml) solution of 3-(4-bromophenyl) propionic acid (2.098 g), were added oxalyl chloride (0.92 ml) and DMF (2 drops) at 0° C. The reaction mixture was stirred at room temperature for 30 minutes, then concentrated. A THF (10 ml) solution of the residue was added dropwise to a THF (20 ml) solution of 3-(N,N-dimethylamino)methyl-1,2,3,4-tetrahydroquinoline (1.321 g) and triethylamine (1.5 ml) at 0° C. The reaction mixture was stirred at 0° C. for 30 minutes. Water was added to the reaction mixture, which was extracted with ethyl acetate. The organic layer was washed with a saturated aqueous sodium chloride solution, then dried and concentrated. The residue was purified by alumina column chromatography (eluent: ethyl acetate/hexane=1/4). An ethanol solution (10 ml) of p-toluenesulfonic acid monohydrate (1.263 g) was added to an ethanol (20 ml) solution of the residue, then concentrated. The obtained crude crystals were recrystallized from ethanol/ethyl acetate to give the entitled compound (3.130 g).

m.p. 182–187° C.

EXAMPLE 72

3-(N,N-Dimethylamino)methyl-1-[3-(4-methylphenyl]propanoyl]-1,2,3,4-tetrahydroquinoline p-toluenesulfonate

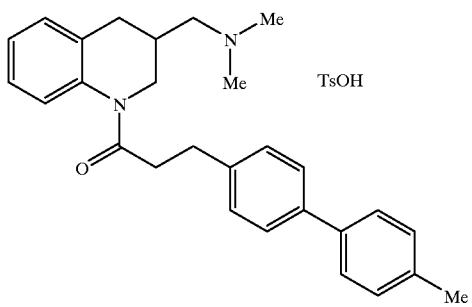

2M Aqueous sodium carbonate solution (1.25 ml) was added to a suspension of 1-[3-(4-bromophenyl)propanoyl]-3-(N,N-dimethylamino)methyl-1,2,3,4-tetrahydroquinoline p-toluenesulfonate (400 mg) in toluene (10 ml) and ethanol (1.25 ml), which was stirred at room temperature for 10 minutes. 4-Methylbenzene boronic acid (123 mg) and tetrakis(triphenylphosphine)palladium (24 mg) were added to the reaction mixture, which was heated under reflux under an argon atmosphere for 14 hours. Water was added to the reaction mixture, which was extracted with ethyl acetate. The organic layer was washed with a saturated aqueous sodium chloride solution, then dried and concentrated. The residue was purified by alumina column chromatography (eluent: hexane/ethyl acetate=10/1 to 2/1), which was converted into its p-toluenesulfonate. The mixture was recrystallized from ethyl acetate to give the entitled compound (296 mg).

m.p. 107–108° C.

Compounds of the following Examples 73 to 76 were synthesized by the similar manner as in Example 72 using the eluent described in the respective Example.

EXAMPLE 73

3-(N,N-Dimethylamino)methyl-1-[3-[4-(2-naphthyl)phenyl)propanoyl]-1,2,3,4-tetrahydroquinoline p-toluenesulfonate

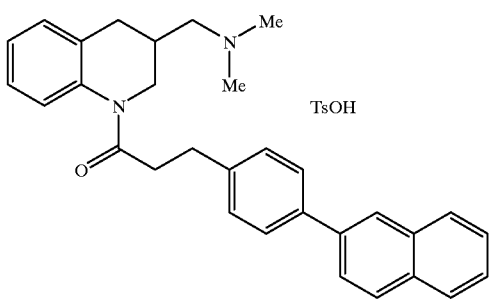

Eluent: hexane/ethyl acetate=10/1 to 2/1 m.p. 152–153° C. (Solvent for recrystallization: ethanol/ethyl acetate)

EXAMPLE 74

3-(N,N-Dimethylamino)methyl-1-[3-1(4-methoxyphenyl)phenyl]propanoyl]-1,2,3,4-tetrahydroquinoline p-toluenesulfonate

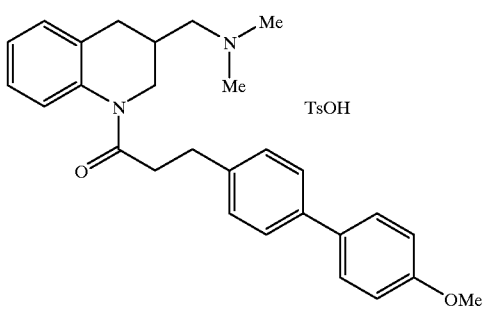

Eluent: hexane/ethyl acetate=10/1 to 2/1 m.p. 93–95° C. (Solvent for recrystallization: ethyl acetate).

EXAMPLE 75

1-[3-[4-(2-Chlorothiophen-5-yl)phenyl]propanoyl]-3-(N,N-dimethylamino)methyl-1,2,3,4-tetrahydroquinoline p-toluenesulfonate

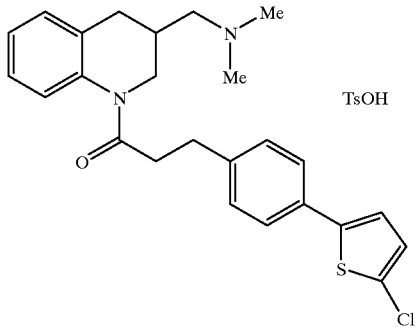

Eluent: hexane/ethyl acetate=7/1 to 5/1 m.p. 130.5–132.5° C. (Solvent for recrystallization: ethyl acetate).

EXAMPLE 76

3-(N,N-Dimethylamino)methyl-1-[3-4-(4-biphenylyl)phenyl]propanoyl]-1,2,3,4-tetrahydroquinoline p-toluenesulfonate

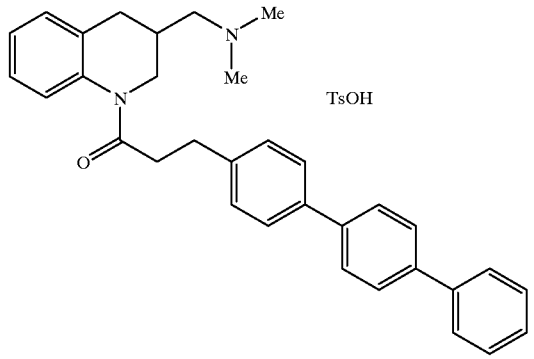

Eluent: hexane/ethyl acetate=10/1 to 2/1 m.p. 186–188° C. (Solvent for recrystallization: ethanol/ethyl acetate).

EXAMPLE 77

3-(N,N-Dimethylamino)methyl-1-[3-[4-(3-pyridyl)phenyl]propanoyl]-1,2,3,4-tetrahydroquinoline p-toluenesulfonate

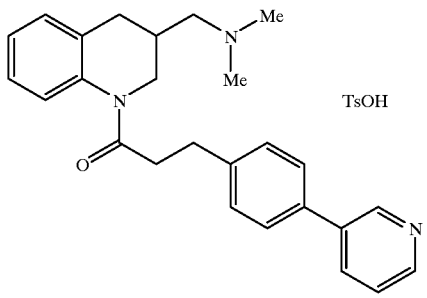

2M Aqueous sodium carbonate solution (1.25 ml) was added to a suspension of 1-[3-(4-bromophenyl)propanoyl]-3-(N,N-dimethylamino)methyl-1,2,3,4-tetrahydroquinoline p-toluenesulfonate (400 mg) in toluene (10 ml) and ethanol (1.25 ml), which was stirred at room temperature for 10 minutes. Diethyl(3-pyridyl)borane (154 mg) and tetrakis(triphenylphosphine)palladium (24 mg) were added to the reaction mixture, which was heated under reflux under an argon atmosphere for 14 hours. Water was added to the reaction mixture, which was extracted with ethyl acetate. The organic layer was washed with a saturated aqueous sodium chloride solution, then dried and concentrated. The residue was purified by alumina column chromatography (eluent: hexane/ethyl acetate=10/1 to 2/1), which was converted into its p-toluenesulfonate. The mixture was recrystallized from ethanol-IPE to give the entitled compound (250 mg).

m.p. 98–101° C.

EXAMPLE 78

3-(N-Benzyl-N-methylamino)methyl-1-[3-(4-biphenylyl)propyl]-1,2,3,4-tetrahydroquinoline oxalate

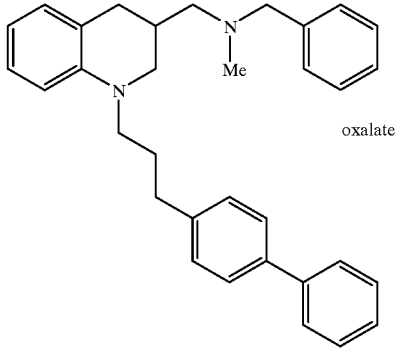

3-(N-Benzyl-N-methylamino)methyl-1-[3-(4-biphenylyl]propanoyl)-1,2,3,4-tetrahydroquinoline oxalate (0.800 g) was converted into a free form, which was dissolved in THF (5 ml). 1M Borane-THF complex (3 ml) was added to the reaction mixture, which was heated under reflux for 30 minutes, then left standing for cooling. Water (0.5 ml) and 6N hydrochloric acid (2 ml) were added to the reaction mixture, which was stirred at room temperature for 12 hours. The reaction mixture was made basic by adding 1N aqueous sodium hydroxide solution and extracted with ethyl acetate. The organic layer was washed with a saturated aqueous sodium chloride solution, then dried and concentrated. The residue was purified by alumina column chromatography (eluent: ethyl acetate/hexane=1/50). A methanol solution (3 ml) of oxalic acid dehydrate (149 mg) was added to a methanol solution (10 ml) of the residue, which was concentrated. Ethyl acetate was added to the residue, and the precipitates were collected by filtration to give the entitled compound (3.130 g) as an amorphous powder.

IR(KBr): 3029, 2938, 2907, 1725, 1603, 1508, 1466, 1260, 1221, 914, 760, 739, 698 cm$^{-1}$.

EXAMPLE 79

3-(N,N-Dimethylamino)methyl-1,2,3,4-tetrahydro-1-[3-(3-indolyl)propyl]quinoline hydrochloride

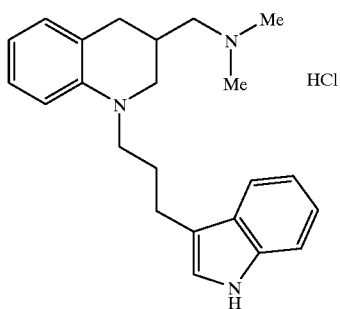

The entitled compound was obtained by the similar manner as in Example 78.

Eluent: hexane/ethyl acetate=4/1 m.p. 152–156° C. (Solvent for recrystallization: methanol/ethyl acetate).

EXAMPLE 80

3-(N,N-Dimethylamino)methyl-1,2,3,4-tetrahydro-1-[4-(3-indolyl)butyl]quinoline hydrochloride

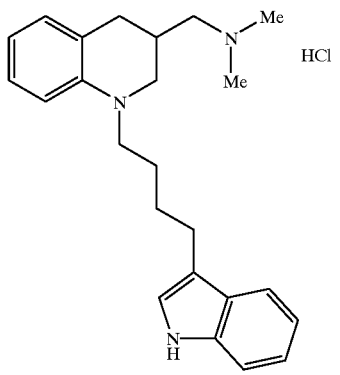

The entitled compound was obtained by the similar manner as in Example 78.

Eluent: hexane/ethyl acetate=4/1

$^1$H-NMR δ: 1.52–1.86(4H, m), 2.48–2.70(3H, m), 2.59 (6H, s), 2.72–2.86(3H, m), 2.88–3.18(2H, m), 3.28(2H, t), 3.45(1H, d), 6.46–6.68(2H, m), 6.90–7.24(5H, m), 7.36(1H, d), 7.61(1H, d), 7.94(1H, br).

EXAMPLE 81

1-[3-(4-Biphenylyl)propyl]-3-(N,N-dimethylamino)methyl-1,2,3,4-tetrahydro-guinoline oxalate

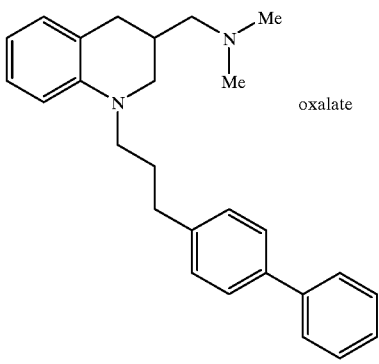

The entitled compound was obtained by the similar manner as in Example 78.

Eluent: ethyl acetate/hexane=1/10 m.p. 144° C. (Solvent for recrystallization: methanol/ethyl acetate).

EXAMPLE 82

1- [3-(4-Biphenylyl]propanoyl]-1,2,3,4-tetrahydro-3-(N-methylamino)methylquinoline oxalate

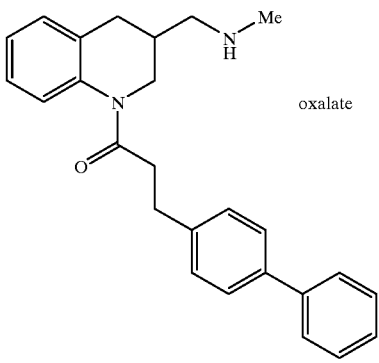

10% Palladium-carbon (64 mg) was added to a methanol (10 ml) solution of 3-(N-benzyl-N-methylamino)methyl-1-[3-(4-biphenylyl]propanoyl]-1,2,3,4-tetrahydroquinoline (0.302 g) and catalytic hydrogenation was conducted at room temperature under an atmospheric normal pressure for 3 hours. The catalyst was removed by filtration and the filtrate was concentrated. The residue was purified by alumina column chromatography (eluent: ethyl acetate to ethyl acetate/methanol=10/1). A methanol (2 ml) solution of oxalic acid dihydrate (42 mg) was added to a methanol (5 ml) solution of the residue, which was concentrated. Ethyl acetate was added to the residue, and the precipitates were collected by filtration to give the entitled compound (3.130 g) as an amorphous powder.

IR(KBr): 3058, 3029, 2840, 1655, 1489, 1379, 762, 696 cm$^{-1}$.

EXAMPLE 83

1-[3-(4-Biphenylyl)propyl]-1,2,3,4-tetrahydro-3-(N-methylamino)methylquinoline dihydrochloride

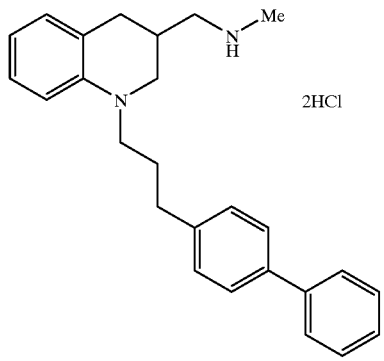

2HCl

The entitled compound was obtained by the similar manner as in Example 78.

Eluent: ethyl acetate/methanol=10/1

IR(KBr): 2949, 2735, 2118, 1732, 1485, 1468, 1252, 1044, 777, 743 cm$^{-1}$.

EXAMPLE 84

7-(4-Biphenylyl)methoxy-3-(N,N-dimethylamino)methyl-1-[3-(5-methoxyindol-3-yl)propyl]-1,2,3,4-tetrahydro-quinoline hydrochloride

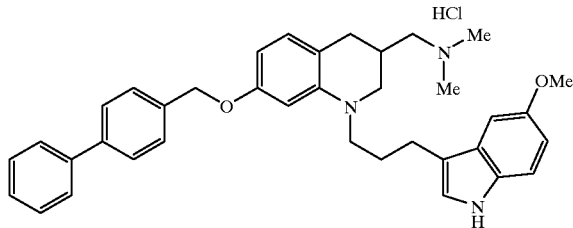

The entitled compound was obtained by the similar manner as in Example 78.

m.p. 202–203° C. (Solvent for recrystallization: methanol/IPE).

EXAMPLE 85

1-[2-(4-Biphenylyl)ethylsulfonyl]-3-(pyrrolidin-1-yl)methyl-1,2,3,4-tetrahydroquinoline oxalate

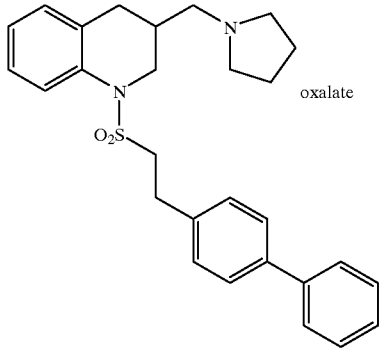

oxalate (1) 2-(4-Biphenylyl)-1-ethanesulfonyl chloride 2-(4-Biphenylyl)ethylthiocyanate (0.5 g) was suspended in water (15 ml) and acetic acid (15 ml). Chlorine gas was blown into the reaction mixture under ice-cooling. Ten minutes later, ethyl acetate (20 ml) was added to the reaction mixture. Chlorine gas was blown into the reaction mixture at room temperature for 50 minutes, and the organic layer was separated. The organic layer was washed twice with 10% aqueous potassium chloride solution, then dried and concentrated to give a crude product (0.7 g) of 2-(4-biphenylyl)-1-ethanesulfonyl chloride.

(2) 1-[2-(4-Biphenylyl)ethylsulfonyl]-3-(pyrrolidin-1-yl)methyl-1,2,3,4-tetrahydroquinoline oxalate An acetonitrile (20 ml) solution of 2-(4-biphenylyl)-1-ethanesulfonyl chloride (0.7 g) was added dropwise to an acetonitrile (20 ml) solution of 3-(pyrrolidin-1-yl)methyl-1,2,3,4-tetrahydroquinoline (450 mg) and triethylamine (0.44 ml) at 0° C. The reaction mixture was stirred at room temperature for 3 hours, then left standing for 2 days. 10% Aqueous potassium carbonate solution and water were added to the reaction mixture, which was extracted with ethyl acetate. The organic layer was washed with a saturated aqueous sodium chloride solution, then dried and concentrated. The residue was purified by alumina column chromatography (eluent: hexane/ethyl acetate=10/1), which was converted into its oxalate. The mixture was recrystallized from ethanol-diethyl ether to. give the entitled compound (267 mg).

m.p. 115–118° C.

EXAMPLE 86

3-(R,S)-(N,N-Dimethylamino)methyl-1-[2-(R)-(9-fluorenylmethoxy)carbonylamino-3-(indol-3-yl)propanoyl]-1,2,3,4-tetrahydroquinoline

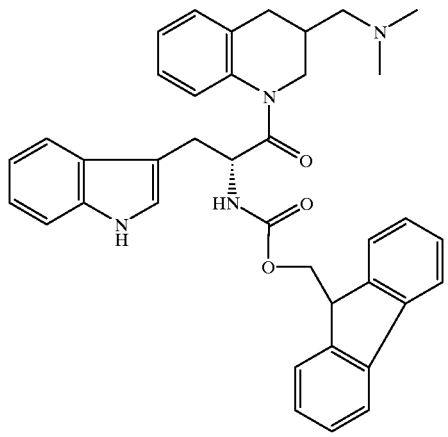

Oxalyl chloride (0.48 ml) was added dropwise to a THF (15 ml) solution of N-(9-fluorenylmethoxycarbonyl)-D-tryptophan (289 mg) and DMF (0.03 ml) at 0° C. The reaction mixture was stirred at room temperature for 30 minutes, then concentrated. The residue was dissolved in ethyl acetate (10 ml), which was added dropwise to the mixture of an ethyl acetate (15 ml) solution of 3-(N,N-dimethylamino)methyl-1,2,3,4-tetrahydroquinoline (298 mg) and a saturated aqueous sodium bicarbonate solution (10 ml) at 0° C. The reaction mixture was stirred at room temperature for one hour, and the organic layer was separated. The organic layer was washed with a saturated aqueous sodium chloride solution, then dried and concentrated. The residue was purified by silica gel column chromatography (eluent: ethyl acetate/methanol=10/1) to obtain the entitled compound (797 mg).

IR(KBr): 3295, 2971, 1707, 1647, 1491, 1233, 760, 741 cm$^{-1}$.

EXAMPLE 87

1-[2-(R)-Amino-3-(indol-3-yl)propanoyl]-3-(R,S)-(N,N-dimethylamino)methyl-1,2,3,4-tetrahydroquinoline

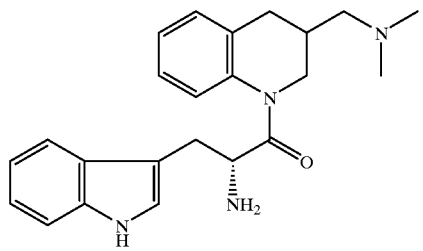

Piperidine (0.66 ml) was added to a methanol (10 ml) solution of 3-(R,S)-(N,N-dimethylamino)methyl-1-[2-(R)-(9-fluorenylmethoxy)carbonylamino-3-(indol-3-yl)propanoyl]-1,2,3,4-tetrahydroquinoline (0.797 g) at room temperature. The reaction mixture was stirred at room temperature for 18 hours, then concentrated. The residue was purified by alumina column chromatography (eluent: ethyl acetate/methanol=10/1) to obtain the entitled compound (0.382 g).

IR(KBr): 3281, 2938, 1647, 1582, 1493, 1458, 1240, 743 cm$^{-1}$.

EXAMPLE 88

3-(R,S)-(N,N-Dimethylamino)methyl-1-[3-(indol-3-yl)-2-[(R)-(4-phenylpiperazin-1-yl)]carbonylaminolpropanoyl]-1,2,3,4-tetrahydroquinoline

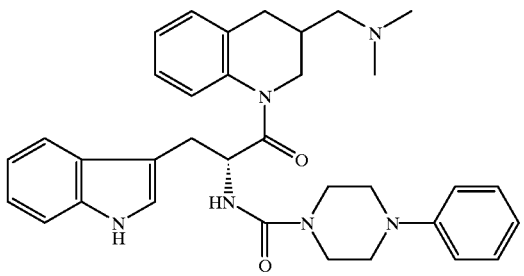

N,N'-Disuccinimidyl carbonate (45 mg) was added to a THF (5 ml) solution of 1-[2-(R)-amino-3-(indol-3-yl)propanoyl]-3-(R,S)-(N,N-dimethylamino)methyl-1,2,3,4-tetrahydroquinoline (99 mg) and N-ethyldiisopropylamine (0.1 ml). The reaction mixture was stirred at room temperature for 2 hours, to which were added a THF (3 ml) solution of I-phenylpiperazine (68 mg) and N-ethyldiisopropylamine (0.1 ml). The reaction mixture was stirred at room temperature for further 3 hours, then concentrated. The residue was purified by alumina column chromatography (eluent: ethyl acetate) to obtain the entitled compound (0.134 g) as an amorphous powder.

IR(KBr): 3297, 2820, 1630, 1493, 1233, 760, 743 cm$^{-1}$.

The following compounds of Examples 89 and 90 were produced by the similar manner as in Example 88.

EXAMPLE 89

3-(R,S)-(N,N-Dimethylamino)methyl-1-[3-(indol-3-yl)-2-[(R)-4-(2-oxo-2,3-dihydro-1H-benzimidazol-1-yl]piperidinocarbonylamino]propanoyl]-1,2,3,4-tetrahydroquinoline

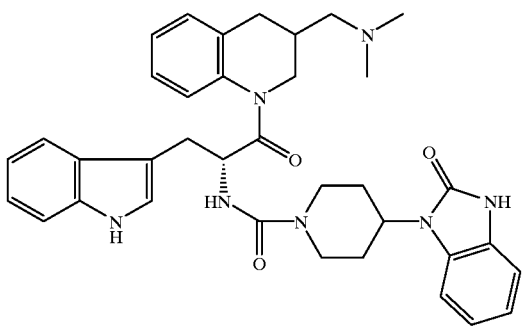

IR(KBr): 3258, 2940, 1692, 1630, 1487, 756, 741 cm$^{-1}$.

EXAMPLE 90

3-(R,S)-(N,N-Dimethylamino)methyl-1-[2-(R)-(1,2,3,4-tetrahydro-6,7-dimethoxyspiro[naphthalen-2,2'-piperidin]-1'-yl)carbonylamino-3-(indol-3-yl)propanoyl]-1,2,3,4-tetrahydroquinoline

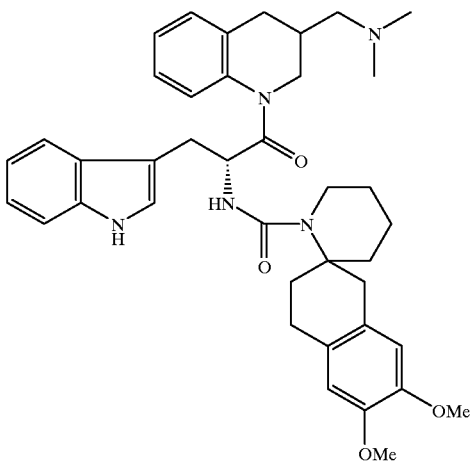

IR(KBr): 3299, 2934, 1638, 1514, 1256, 1115, 743 cm$^{-1}$.

EXAMPLE 91

1-[2-(R)-[4-(2-Chlorophenyl)piperazin-1-yl]carbonylamino-3-(R,S)-(N,N-dimethylamino)methyl-3-(indol-3-yl)propanoyl]-1,2,3,4-tetrahydroquinoline

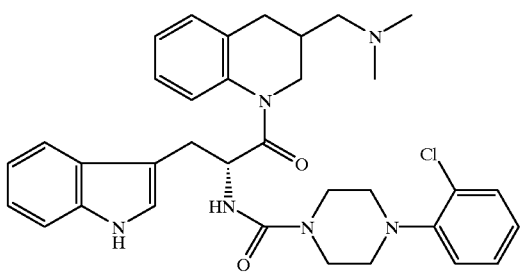

N,N'-Disuccinimidyl carbonate (102 mg) and N-ethyldiisopropylamine (0.14 ml) were added to an acetonitrile (5 ml) solution of 1-[2-(R)-amino-3-(indol-3-yl)propanoyl]-3-(R,S)-(N,N-dimethylamino)methyl-1,2,3,4-tetrahydroquinoline (150 mg). The reaction mixture was stirred at room temperature for 30 minutes, to which were added an acetonitrile (1 ml) solution of 1-(2-chlorophenyl)piperazine (78 mg) and N-ethyldiusopropylamine (0.07 ml). The reaction mixture was stirred at room temperature for 2 hours. A saturated aqueous sodium hydrogencarbonate solution was added to the reaction mixture, which was extracted with ethyl acetate. The organic layer was washed with a saturated aqueous sodium chloride solution, then dried and concentrated. The residue was purified by alumina column chromatography (eluent: ethyl acetate/hexane=1/1 to 3/1) to obtain the entitled compound (158 mg) as an amorphous powder.

IR(KBr): 3267, 1635, 1230, 760, 744 cm$^{-1}$.

The following compounds of Examples 92 to 97 were produced by the similar manner as in Example 91.

EXAMPLE 92

3-(R,S)-(N,N-Dimethylamino)methyl-1-[3-(indol-3-yl)-2-(R)-[4-(2-methoxy)phenylpiperazin-1-yl]carbonylaminopropanoyl]-1,2,3,4-tetrahydroquinoline

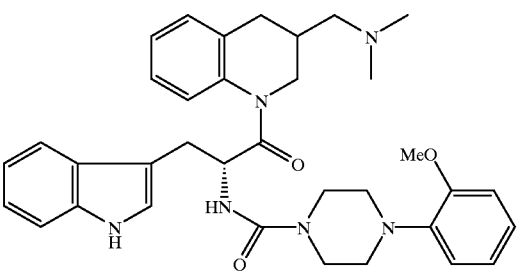

The similar procedure was conducted using 1-(2-methoxyphenyl)piperazine. The product was purified by aluminum column chromatography (eluent: ethyl acetate/hexane=1/1 to ethyl acetate) to obtain the entitled compound (165 mg) as an amorphous powder.

IR(KBr): 3265, 1635, 1498, 1240, 744 cm$^{-1}$.

EXAMPLE 93

3-(R,S)-(N,N-Dimethylamino)methyL-1-[3-(indol-3-yl)-2-[(R)-[4-(2-pyridyl)piperazin-1-yl)carbonylamino]propanoyl]-1,2,3,4-tetrahydroquinoline

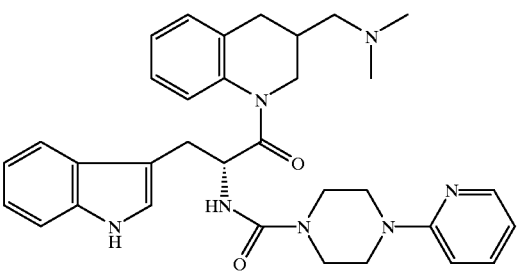

The similar procedure was conducted using 1-(2-pyridyl)piperazine. The product was purified by alumina column chromatography (eluent: ethyl acetate/hexane=1/1 to ethyl acetate/methanol=20/1) to obtain the entitled compound (190 mg) as an amorphous powder.

IR(KBr): 3265, 1635, 1491, 1437, 1240, 742cm$^{-1}$.

EXAMPLE 94

3-(R,S)-(N,N-Dimethylamino)methyl-1-[3-(indol-3-yl)-2-[(R)-4-[(2-pyrimidinyl)piperazin-1-yl]carbonylaminolpropanoyl]-1,2,3,4-tetrahydroquinoline

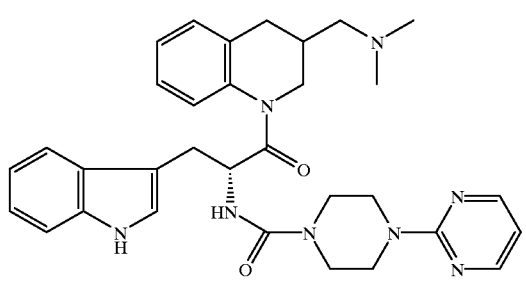

The similar procedure was conducted using 1-(2-pyrimidinyl)piperazine. The product was purified by alumina column chromatography (eluent: ethyl acetate/hexane=1/1 to ethyl acetate/methanol=20/1) to obtain the entitled compound (175 mg) as an amorphous powder.

IR(KBr): 3265, 1635, 1585, 1494, 1248, 983 cm$^{-1}$.

EXAMPLE 95

1-[2-(R)-(4-benzylpiperazin-1-yl)carbonylamino-3-(R,S)-(N,N-dimethylamino)methyl-3-(indol-3-yl)propanoyl]-1,2,3,4-tetrahydroquinoline

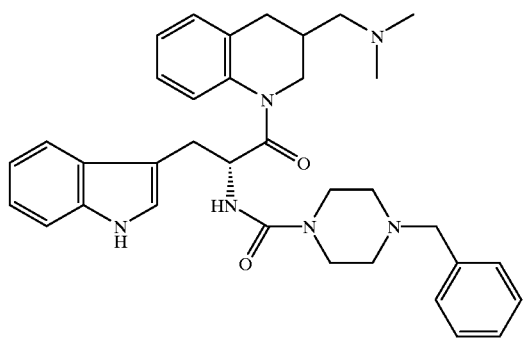

The similar procedure was conducted using 1-benzylpiperazine. The product was purified by aluminum column chromatography (eluent: ethyl acetate/hexane=1/1 to ethyl acetate) to obtain the entitled compound (115 mg) as an amorphous powder.

IR(KBr): 3263, 1635, 1491, 1234, 742 cm$^{-1}$.

EXAMPLE 96

3-(R,S)-(N,N-Dimethylamino)methyl-1-[3-(indol-3-yl)-2-(R)-[(4-phenylpiperidino)carbonylamino]propanoyl]-1,2,3,4-tetrahydroquinoline

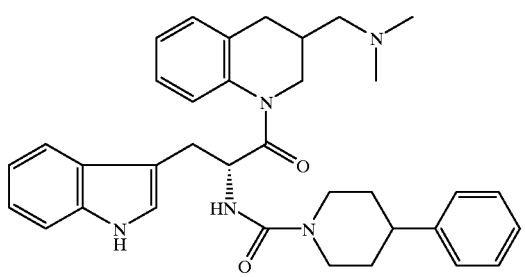

The similar procedure was conducted using 4-phenylpiperidine. The product was purified by alumina column chromatography (eluent: ethyl acetate /hexane=1/2 to 2/1) to obtain the entitled compound (120 mg) as an amorphous powder.

IR(KBr): 3265, 1635, 1491, 1230, 758, 742 cm$^{-1}$.

EXAMPLE 97

1-[2-(R)-[[4-(4-Chlorophenyl)-4-hydroxypiperidino)carbonyl]]amino-3-(indol-3-yl)propanoyl]-3-(R,S)-(N,N-dimethylamino)methyl-1,2,3,4-tetrahydroquinoline

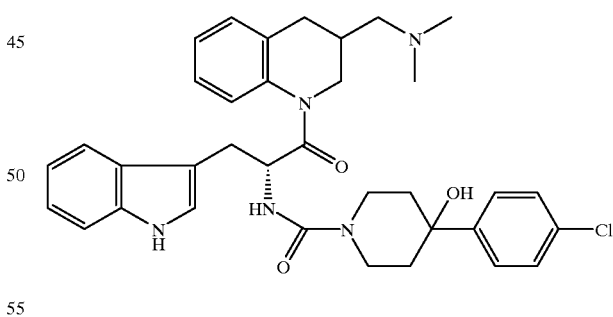

The similar procedure was conducted using 4-(4-chlorophenyl)-4-hydroxypiperidine. The product was purified by alumina column chromatography (eluent: ethyl acetate/hexane=1/1 to ethyl acetate/methanol=20/1) to obtain the entitled compound (200 mg) as an amorphous powder.

IR(KBr): 3298, 1624, 1491, 742 cm$^{-1}$.

EXAMPLE 98

4-Benzyl-2-(N,N-dimethylamino)methyl-1-formyl-1,2,3,4-tetrahydroquinoxaline

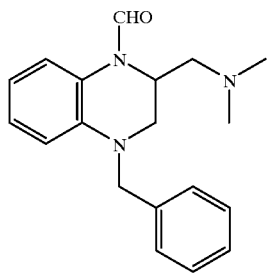

Borane-THF complex (1M THF solution; 21 ml) was added dropwise to a THF (30 ml) solution of 4-benzyl-N,N-dimethyl-3-oxo-1,2,3,4-tetrahydro-2-guinoxalinecarboxamide (1.33 g) under ice-cooling. The reaction mixture was stirred at room temperature for 30 minutes, which was heated under reflux for 2 hours. The reaction mixture was cooled to room temperature. Water (5 ml) was added to the reaction mixture, which was stirred for 10 minutes, then concentrated. The residue was dissolved in methanol (30 ml), which was heated under ref lux for an hour together with 6N hydrochloric acid (10 ml). 3N Aqueous sodium hydroxide solution (20 ml) was added to the reaction mixture under ice-cooling for neutralization, which was concentrated. 10% Aqueous potassium carbonate solution was added to the residue, which was extracted with ethyl acetate. The organic layer was washed with a saturated aqueous sodium chloride solution, then dried and concentrated to obtain a crude product of N-[(4-benzyl-1,2,3,4-tetrahydro-2-quinoxalinyl)methyl]-N,N-dimethylamine. (Trihydrochloride salt of this compound showed m.p. of 168 to 172° C.)

The crude product was dissolved in formic acid (12 ml), to which was added dropwise the mixture (prepared by mixing both and stirring for an hour at 50° C.) of formic acid (1.4 ml) and acetic acid anhydride (2.8 ml) under ice-cooling. The reaction mixture was stirred at room temperature for an hour, then concentrated. The residue was dissolved in ethyl acetate. The mixture was washed with 10% aqueous potassium carbonate solution and a saturated aqueous sodium chloride solution, then dried and concentrated. The residue was purified by alumina column chromatography (eluent: ethyl acetate/hexane=/1/1). The obtained crystals were washed with hexane to give the entitled compound (1.16 g).

m.p. 82–84° C.

EXAMPLE 99

4-[3-(4-Biphenylyl)propanoyl]-2-(N,N-dimethylamino)methyl-1-formyl-1,2,3,4-tetrahydroquinoxaline p-toluenesulfonate

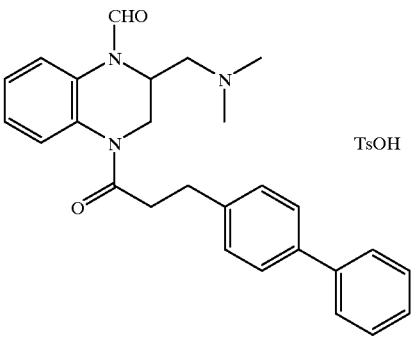

10% Pd-C (175 mg) and concentrated hydrochloric acid (0.3 ml) were added to a methanol (15 ml) solution of 4-benzyl-2-(N,N-dimethylamino)methyl-1-formyl-1,2,3,4-tetrahydroquinoxaline (350 mg). The reaction mixture was subjected to catalytic hydrogenation at room temperature under 4.5 atmospheric pressure for 2 hours. The catalyst was removed by filtration and the filtrate was concentrated. 10% Aqueous potassium carbonate solution was added to the residue, which was extracted with ethyl acetate. The organic layer was washed with a saturated aqueous sodium chloride solution, then dried and concentrated to give 2-(N,N-dimethylamino)methyl-1-formyl-1,2,3,4-tetrahydroquinoxaline (190 mg).

Oxalyl chloride (0.1 ml) was added to a THF (5 ml) solution of 3-(4-biphenylyl)propionic acid (210 mg) under ice-cooling, to which was further added DMF (one drop). The reaction mixture was stirred at room temperature for 30 minutes and concentrated. The residue was dissolved in THF and concentrated. The residue was dissolved in THF (5 ml), which was added dropwise to a THF (5 ml) solution of 2-(N,N-dimethylamino)methyl-1-formyl-1,2,3,4-tetrahydroquinoxaline (170 mg) and triethylamine (0.16 ml) under ice-cooling. The reaction mixture was stirred at the same temperature for an hour. Water was added to the reaction mixture, which was extracted with ethyl acetate. The organic layer was washed with a saturated aqueous sodium chloride solution, then dried and concentrated. The residue was purified by alumina column chromatography (eluent: hexane to hexane/ethyl acetate=4/1), which was converted into its p-toluenesulfonate. The mixture was washed with methanol-IPE to obtain the entitled compound (220 mg).

m.p. 195–197° C.

EXAMPLE 100

4-[3-(4-Biphenylyl)propanoyl]-2-(N,N-dimethylamino)methyl-1-ethyl-1,2,3,4-tetrahydroquinoxaline p-toluenesulfonate

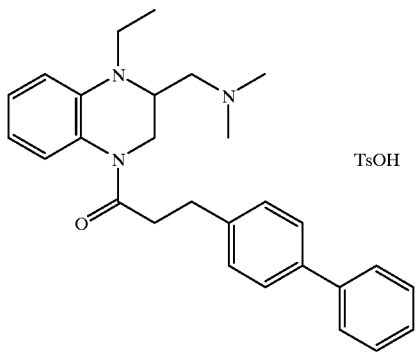

Oxalyl chloride (0.18 ml) was added to a THF (7 ml) solution of 3-(4-biphenylyl)propionic acid (370 mg) under ice-cooling, to which was added DMF (one drop). The reaction mixture was stirred at room temperature for 30 minutes and concentrated. The residue was again dissolved in THF, which was concentrated. The residue was dissolved in THF (7 ml), which was added dropwise to a THF (7 ml) solution of 2-(N,N-dimethylamino)methyl-1-ethyl-1,2,3,4-tetrahydroquindxallne (obtained by 10% neutralization of trihydrochloride(450 mg)) and triethylamine (0.29 ml) under ice-cooling. The reaction mixture was stirred at same temperature for an hour. Water was added to the reaction mixture, which was extracted with ethyl acetate. The organic layer was washed with a saturated aqueous sodium chloride solution, then dried and concentrated. The residue was purified by alumina column chromatography (eluent: hexane to hexane/ethyl acetate=5/1), which was converted into its p-toluenesulfonate. The mixture was washed with IPE to obtain the entitled compound (620 mg).

m.p. 169–172° C.

EXAMPLE 101

4-Benzyl-1-formyl-2-(pyrrolidin-1-yl)methyl-1,2,3,4-tetrahydroquinoxaline

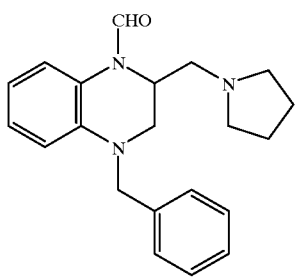

Borane-THF complex (1M THF solution; 17 ml) was added dropwise to a THF (20 ml) solution of 1-benzyl-3-(pyrrolidin-1-ylcarbonyl)-3,4-dihydro-2(1H)-quinoxaline (Reference Example 70; 1.05 g) under ice-cooling. The reaction mixture was stirred at room temperature for 30 minutes, which was heated under reflux for 2 hours. The reaction mixture was cooled to room temperature. Water (5 ml) was added to the reaction mixture, which was stirred for 10 minutes, then concentrated. The residue was dissolved in methanol (20 ml) and heated under reflux for an hour together with 6 N hydrochloric acid (6 ml). 3 N Aqueous sodium hydroxide solution (12 ml) was added to the reaction mixture under ice-cooling for neutralization, which was concentrated. 10% Aqueous potassium carbonate solution was added to the residue, which was extracted with ethyl acetate. The organic layer was washed with a saturated aqueous sodium chloride solution, then dried and concentrated to give a crude product of 1-benzyl-3-(pyrrolidin-1-yl)methyl-1,2,3,4-tetrahydroquinoxaline (Trihydrochloride salt of this compound showed m.p. of 207 to 212° C.).

The crude product was dissolved in formic acid (12 ml), to which was added dropwise the mixture (prepared by mixing both and stirring for an hour at 50° C.) of formic acid (1.4 ml) and acetic acid anhydride (2.8 ml) under ice-cooling. The reaction mixture was stirred at room temperature for one hour, then concentrated. The residue was dissolved in ethyl acetate. The mixture was washed with 10% aqueous potassium carbonate solution and a saturated aqueous sodium chloride solution, then dried and concentrated. The crystals were washed with hexane to give the entitled compound (800 mg).

m.p. 94–96° C.

EXAMPLE 102

4-(3-(4-Biphenylyl)propanoyl)-1-formyl-2-(pyrrolidin-1-yl)methyl-1,2,3,4-tetrahydroquinoxaline oxalate

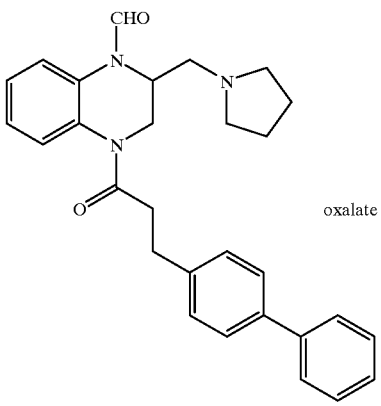

10% Pd-C (200 mg) and concentrated hydrochloric acid (0.3 ml) were added to a methanol (25 ml) solution of 4-benzyl-1-formyl-2-(pyrrolidin-1-yl)methyl-1,2,3,4-tetrahydroquinoxaline (500 mg). The reaction mixture was subjected to catalytic hydrogenation at room temperature under 4.5 atmospheric pressure for 2 hours. The catalyst was removed by filtration, and the filtrate was concentrated. 10% Aqueous potassium carbonate solution was added to the residue, which was extracted with ethyl acetate. The organic layer was washed with a saturated aqueous sodium chloride solution, then dried and concentrated to give 1-formyl-2-(pyrrolidin-1-yl)methyl-1,2,3,4-tetrahydroquinoxaline (360 mg). Oxalyl chloride (0.19 ml) was added to a THF (5 ml) solution of 3-(4-biphenylyl)propionic acid (410 mg) under ice-cooling, to which was added DMF (one drop). The reaction mixture was stirred at room temperature for 30 minutes, which was concentrated. The residue was again dissolved in THF, which was concentrated. The residue was dissolved in THF (7 ml), which was added dropwise to a THF (7 ml) solution of 1-formyl-2-(pyrrolidin-1-yl)methyl-1,2,3,4-tetrahydroquinoxaline (360 mg) and triethylamine (0.31 ml) underice-cooling. The reaction mixture was stirred

EXAMPLE 103

4-(3-(4-Biphenylyl)propanoyl)-2-(pyrrolidin-1-yl)methyl-1,2,3,4-tetrahydroquinoxaline oxalate

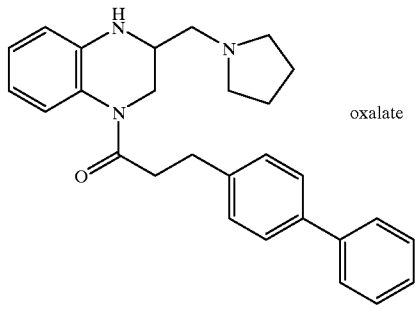

oxalate

4N Hydrochloric acid-ethyl acetate (2 ml) was added to a methanol (10 ml) solution of 4-(3-(4-biphenylyl)propanoyl)-1-formyl-2-(pyrrolidin-1-yl)methyl-1,2,3,4-tetrahydroquinoxaline (320 mg). The reaction mixture was stirred at 50° C. for one hour, then concentrated. 10% Aqueous potassium carbonate solution was added to the residue, which was extracted with ethyl acetate. The organic layer was washed with a saturated aqueous sodium chloride solution, then dried and concentrated. The residue was purified by alumina column chromatography (eluent: hexane to hexane/ethyl acetate=7/1), which was converted into its oxalate. The obtained crystals were washed with methanol-IPE to give the entitled compound (250 mg).

m.p. 196–198° C.

EXAMPLE 104

1-Acetyl-4-benzyl-2-(N,N-dimethylamino)methyl-1,2,3,4-tetrahydroquinoxaline

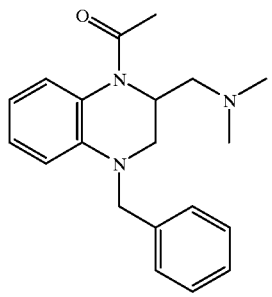

Borane-dimethylsulfide complex (10M-THF solution; 5 ml) was added to a THF (20 ml) solution of 4-benzyl-N,N-dimethyl-3-oxo-3,4-dihydro-2-quinoxalinecarboxamide (1.5 g). The reaction mixture was stirred at room temperature for one hour, further at 50° C. for 18 hours, then concentrated. The residue was dissolved in methanol (30 ml) and the mixture was stirred at 50° C. for 20 hours together with 6N hydrochloric acid (10 ml). The reaction mixture was concentrated, and the residue was dissolved in pyridine (10 ml). Acetic anhydride (0.5 ml) was added to the reaction mixture, which was stirred at room temperature for 5 hours. The reaction mixture was concentrated, and the residue was purified by alumina column chromatography (eluent: ethyl acetate/hexane=1/3) to obtain the entitled compound (0.6 g).

$^1$H-NMR δ: 2.2–2.4(11H, m), 3.4–3.6(2H, m), 4.4–4,6(2H, s), 5.2–5.3(1H, m), 6.5–6.7(2H, m), 6.9–7.1(1H, m), 7.2–7.4(7H, m).

EXAMPLE 105

1-[2-(4-Biphenylyl)ethyl]sulfonyl-3-(N,N-dimethylamino)methyl-1,2,3,4-tetrahydroquinoline

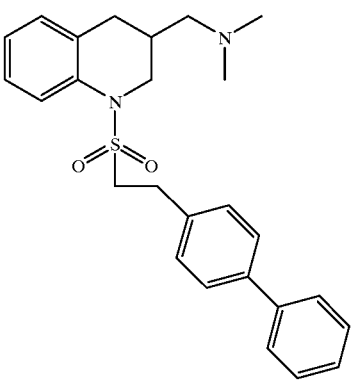

LDA (1.9 M/THF, 1.2 ml) was added dropwise to a THF solution of 3-(N,N-dimethylamino)methyl-1-methylsulfonyl-1,2,3,4-tetrahydroquinoline (0.24 g). The reaction mixture was stirred under ice-cooling for 30 minutes. A THF (1 ml) solution of 4-biphenylylmethyl bromide (0.16 g) was added to the reaction mixture, which was stirred at room temperature for 3 hours. Water was added to the reaction mixture, which was extracted with ethyl acetate. The organic layer was washed with water, LiI then dried and concentrated. The residue was purified by silica gel column chromatography (eluent: ethyl acetate), which was further recrystallized from hexane-ethyl acetate to give the entitled compound (30 mg).

m.p. 108–109° C.

EXAMPLE 106

1-[2-(4-Biphenylyl)ethylsulfonyl]-3-(pyrrolidin-1-yl)methyl-1,2,3,4-tetrahydroquinoline

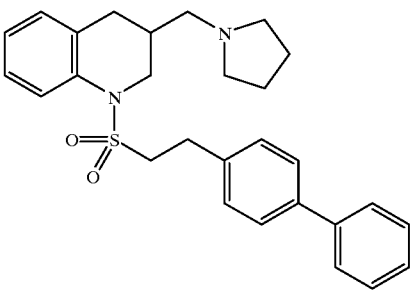

A THF (10 ml) solution of 1-(methylsulfonyl)-3-(pyrrolidin-1-yl)methyl-1,2,3,4-tetrahydroquinoline (0.6 g) was cooled to −15° C. under an argon flow. LDA (1.9 M heptane solution, 2.15 ml) was added dropwise to the reaction mixture. The reaction mixture was warmed to room temperature, which was stirred for 30 minutes, then cooled to −15° C. again. A THF (2 ml) solution of 4-biphenylymethyl bromide (0.4 g) was added dropwise to the reaction mixture. The reaction mixture was stirred at the same temperature for 30 minutes, which was warmed to 0° C. Water was added to the reaction mixture, which was extracted with ethyl acetate. The organic layer was washed with a saturated aqueous sodium chloride solution, then dried and concentrated. The residue was purified by alumina column chromatography (eluent: hexane to hexane/ethyl acetate=10/1) and silica gel column chromatography (eluent: ethyl acetate). The crystals were washed with IPE to give the entitled compound (28 mg).

m.p. 107–110° C.

EXAMPLE 107

1-N-(4-Biphenylyl)methylaminocarbonyl-3-(N,N-dimethylamino)methyl-1,2,3,4-tetrahydroquinoline p-toluenesulfonate

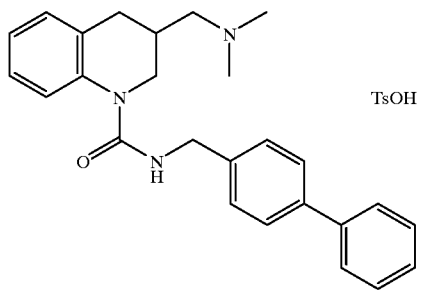

To a dichloromethane (4 ml) solution of triphosgene (156 mg) was added dropwise a dichloromethane (2 ml) solution of 3-(N,N-dimethylamino)methyl-1,2,3,4-tetrahydroquinoline (300 mg) and triethylamine (0.44 ml) under ice-cooling. The reaction mixture was stirred for 40 minutes, to which was added dropwise a dichloromethane (3 ml) solution of 4-biphenylymethylamine (290 mg) and triethylamine (0.44 ml) at the same temperature. The reaction mixture was stirred at room temperature for one hour, to which was added ethyl acetate. The insoluble substances were removed by filtration, then concentrated.

The residue was purified by alumina column chromatography (eluent: hexane to hexane/ethyl acetate=3/1), which was converted into its p-toluenesulfonate. The mixture was recrystallized from ethanol-IPE to give the entitled compound (310 mg).

m.p. 167–169° C.

EXAMPLE 108

1-[3-(4-Biphenylyl)propanoyl]-6-chloro-3-(N,N-dimethylamino)methyl-1,2,3,4-tetrahydroquinoline p-toluenesulfonate

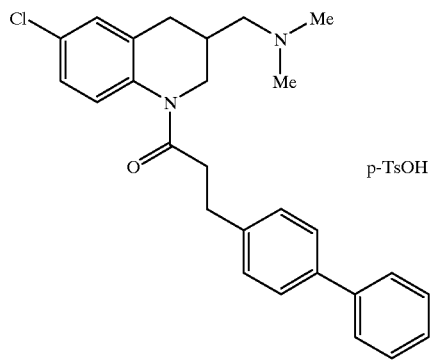

Oxalyl chloride (0.11 ml) and DMF (one drop) were added to a THF (5 ml) solution of 3-(4-biphenyly)propionic acid (249 mg) at 0° C. The reaction mixture was stirred at room temperature for one hour, then concentrated. The residue was dissolved in THF (5 ml), which was added dropwise to a THF (10 ml) solution of 6-chloro-3-(N,N-dimethylamino)methyl-1,2,3,4-tetrahydroquinoline (202 mg) and triethylamine (0.19 ml) at 0° C. The reaction mixture was stirred at room temperature for one hour. 10% Aqueous potassium carbonate solution was added to the reaction mixture, which was extracted with ethyl acetate. The organic layer was washed with a saturated aqueous sodium chloride solution, then dried and concentrated. The residue was purified by alumina column chromatography (eluent: hexane/ethyl acetate=4/1), which was converted into its p-toluenesulfonate. The mixture was recrystallized from ethanol-diethyl ether to give the entitled compound (466 mg).

m.p. 144–146° C.

EXAMPLE 109

1-[3-[3-(2-Benzofuranyl)-1,2,4-oxadiazol-5-yl] propanoyl,]-6-chloro-3-(N,N-dimethylamino) methyl-1,2,3,4-tetrahydroquinoline

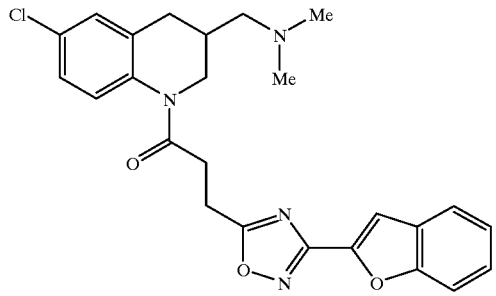

Synthesis was conducted by the similar manner as in Example 108.

m.p. 125–127° C. (Solvent for recrystallization: ethyl acetate/hexane).

EXAMPLE 110

1-[3-(4-Biphenylyl)propanoyl]-3-(N,N-dimethylamino)methyl-6-methoxy-1,2,3,4-tetrahydroquinoline

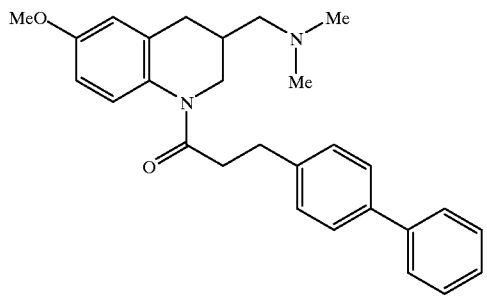

Synthesis was conducted by the similar manner as in Example 1.

m.p. 91–93° C. (Solvent for recrystallization: ethyl acetate/hexane).

EXAMPLE 111

1-[2-(R)-Amino-3-(indol-3-yl)propanoyl]-3-(R,S)-(pyrrolidin-1-yl)methyl-1,2,3,4-tetrahydroquinoline

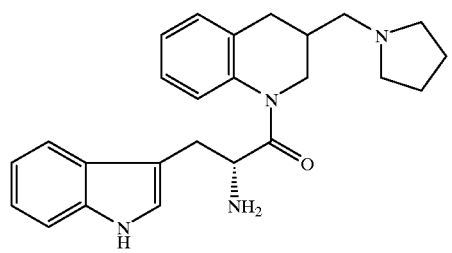

A THF (15 ml) solution of oxalyl chloride (1.16 ml) was added dropwise to a THF (45 ml) solution of N-(9-fluorenylmethoxycarbonyl)-D-tryptophan (4.73 g) and DMF (0.1 ml) at 0° C. The reaction mixture was stirred at room temperature for 30 minutes, then concentrated. The residue was dissolved in ethyl acetate (30 ml), which was added dropwise to the mixture of an ethyl acetate (40 ml) solution of 3-(R,S)-(pyrrolidin-1-yl)methyl-1,2,3,4-tetrahydroquinoline (800 mg) and 20% aqueous sodium carbonate solution (40 ml), at 0° C. The reaction mixture was stirred at room temperature for one hour, and the organic layer was separated. The organic layer was washed with a saturated aqueous sodium chloride solution, then dried and concentrated. The residue was purified by alumina column chromatography (eluent: ethyl acetate/hexane=1:2 to 1:1), then concentrated. The residue was dissolved In methanol (60 ml). Piperidine (2 ml) was added to the mixture, which was stirred at room temperature for 12 hours. The reaction mixture was concentrated, and purified by alumina column chromatography (eluent: ethyl acetate/hexane=1:2 to ethyl acetate/methanol=20:1) to obtain the entitled compound (1.1 g) as an amorphous powder.

IR(KBr): 3287, 2924, 1651, 1582, 1491, 1236, 741 cm$^{-1}$.

EXAMPLE 112

1-[2-(R)-Amino-3-(indol-3-yl)propanoyl]-3-(R)-(N,N-dimethylamino)methyl-1,2,3,4-tetrahydroquinoline

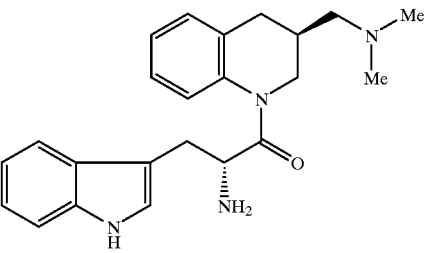

Synthesis was conducted by the similar manner as in Example 111.

IR(KBr): 3279, 2932, 1647, 1580, 1493, 1236, 741 cm$^{-1}$.
$[\alpha]_D^{20}$=−247° (C=0.347% in methanol).

EXAMPLE 113

1-[2-(R)-Amino-3-(indol-3-yl)propanoyl]-3-(S)-(N,N-dimethylamino)methyl-1,2,3,4-tetrahydroquinoline

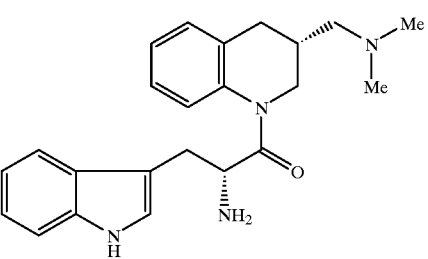

Synthesis was conducted by the similar manner as in Example 111.

IR(KBr): 3287, 2930, 1647, 1582, 1491, 1242, 743 cm$^{-1}$.
$[\alpha]_D^{20}$=−218° (C=0.345% in methanol).

EXAMPLE 114

1-[2-(R)-Amino-3-(indol-3-yl)propanoyl]-3-(R,S)-(N-benzyl-N-methylamino)methyl-1,2,3,4-tetrahydroquinoline

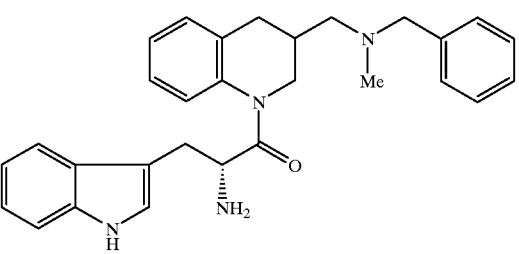

Synthesis was conducted by the similar manner as in Example 111.

IR(KBr): 3285, 2934, 2791, 1651, 1491, 743, 700 cm$^{-1}$.

EXAMPLE 115

1-[2-(R)-Amino-3-(indol-3-yl)propanoyl]-3-(R,S)-(N,N-dibenzylamino)methyl-1,2,3,4-tetrahydroquinoline

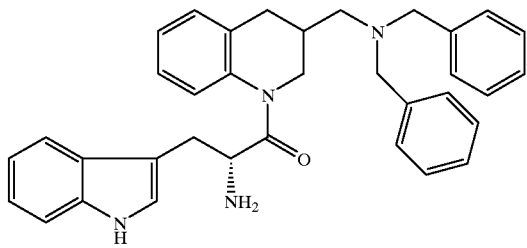

Synthesis was conducted by the similar manner as in Example 111.

IR(KBr): 3287, 2930, 2797, 1645, 1493, 743, 700 cm$^{-1}$.

EXAMPLE 116

1-[2-(R)-Amino-3-(indol-3-yl)propanoyl]-3-(R,S)-(N,N-dimethylamino)methyl-6-methoxy-1,2,3,4-tetrahydroquinoline

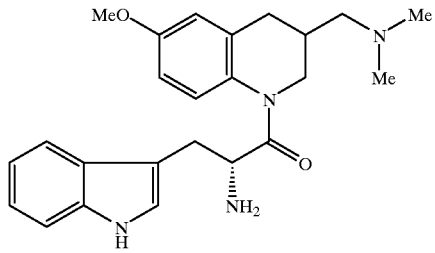

Synthesis was conducted by the similar manner as in Example 111.

IR(KBr): 3289, 2934, 1644, 1501, 1456, 1267, 741 cm$^{-1}$.

EXAMPLE 117

1-[2-(R)-Amino-3-(indol-3-yl)propanoyl]-6-chloro-3-(R,S)-(N,N-dimethylamino)methyl-1,2,3,4-tetrahydroquinoline

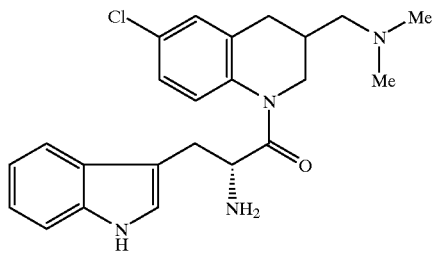

A THF (5 ml) solution of oxalyl chloride (1.5 ml) was added dropwise to a THF (30 ml) solution of N-(9-fluorenylmethoxycarbonyl)-D-tryptophan (5.887 g) and DMF (0.04 ml). The reaction mixture was stirred at 0° C. for one hour, then concentrated. The residue was dissolved in a mixed solution of ethyl acetate (15 ml) and THF (15 ml), which was added dropwise to the mixture of an ethyl acetate (30 ml) solution of 6-chloro-3-(N,N-dimethylamino)methyl-1,2,3,4-tetrahydroquinoline (1.030 g) and a saturated aqueous sodium bicarbonate solution (20 ml) at 0° C. The reaction mixture was stirred at room temperature for one hour, and the organic layer was separated. The organic layer was washed with a saturated aqueous sodium chloride solution, then dried and concentrated. The residue was purified by alumina column chromatography (eluent: hexane/ethyl acetate=1/1) and silica gel column chromatography (eluent: ethyl acetate/methanol=10/1) to obtain 6-chloro-3-(R,S)-(N,N-dimethylamino)methyl-1-[2-(R)-(9-fluorenylmethoxy)carbonylamino-3-(indol-3-yl)propanoyl]-1,2,3,4-tetrahydroquinoline (1.35 g). Piperidine (1.1 ml) was added to a methanol (15 ml) solution of this compound at room temperature. The reaction mixture was stirred at room temperature for 5 hours, then concentrated. The residue was purified by alumina column chromatography (eluent: ethyl acetate/methanol=10/1) to obtain the entitled compound (0.602 g).

IR(KBr): 2938, 1647, 1487, 1458, 1096, 743 cm$^{-1}$.

The following compounds of Examples 118 to 132 were synthesized by similar manner as in Example 91.

EXAMPLE 118

3-(R)-(N,N-Dimethylamino)methyl-1-[3-(indol-3-yl)-2-[(R)-(4-phenylpiperazin-1-yl)carbonylamino]propanoyl]-1,2,3,4-tetrahydroquinoline

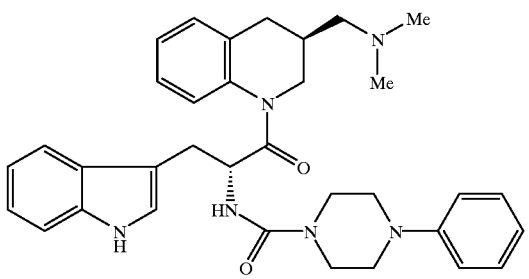

IR(KBr): 3266, 2820, 1634, 1493, 1233, 760, 743 cm$^{-1}$.

$[\alpha]_D^{20}$=−158° (C=0.475% in methanol).

EXAMPLE 119

3-(S)-(N,N-Dimethylamino)methyl-1-[3-(indol-3-yl)-2-[(R)-(4-phenylpiperazin-1-yl)carbonylamino]propanoyl]-1,2,3,4-tetrahydroquinoline

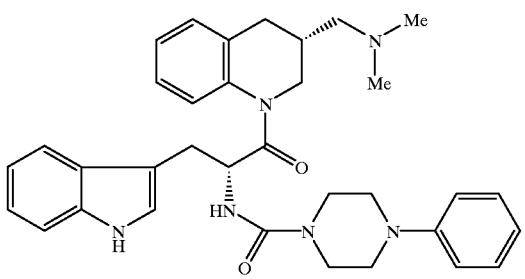

IR(KBr): 3266, 2820, 1634, 1493, 1233, 758, 743 cm$^{-1}$.

$[\alpha]_D^{20}$=−158° (C=0.432% in methanol).

EXAMPLE 120

3-(R)-(N,N-Dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline

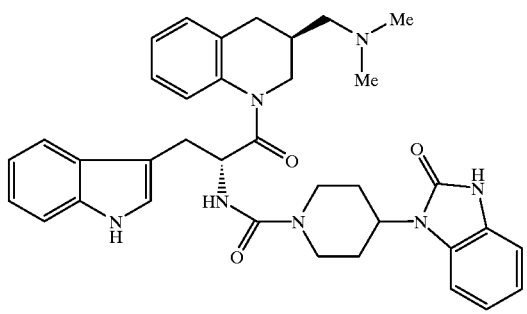

IR(KBr): 3252, 2968, 1698, 1634, 1489, 1235, 741 cm$^{-1}$.
$[\alpha]_D^{20}$=−128° (C=0.505% in methanol).

EXAMPLE 121

3-(S)-(N,N-Dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline

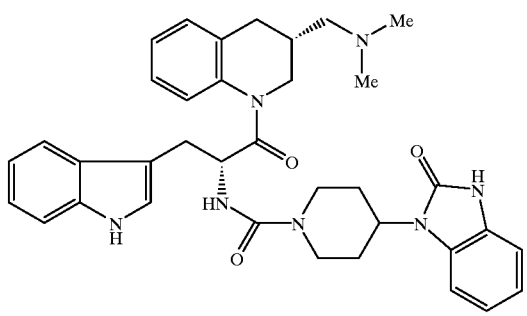

IR(KBr): 3196, 2968, 1698, 1634, 1489, 1236, 739 cm$^{-1}$.
$[\alpha]_D^{20}$=−131° (C=0.500% in methanol).

EXAMPLE 122

3-(R)-(N,N-Dimethylamino)methyl-1-[3-(indol-3-yl)-2-(R)-[4-(2-methyl)phenylpiperazin-1-yl]carbonylaminopropanoyl]-1,2,3,4-tetrahydroquinoline

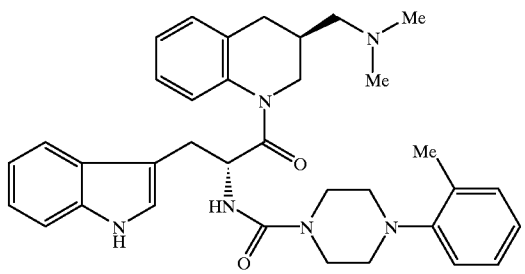

IR(KBr): 3247, 2818, 1634, 1493, 1227, 762, 741 cm$^{-1}$.
$[\alpha]_D^{20}$=−152° (C=0.504% in methanol).

EXAMPLE 123

3-(S)-(N,N-Dimethylamino)methyl-1-[3-(indol-3-yl)-2-(R)-[4-(2-methyl)phenylpiperazin-1-yl]carbonylaminopropanoyl]-1,2,3,4-tetrahydroquinoline

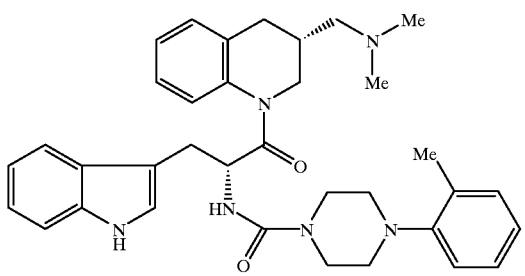

IR(KBr): 3247, 2818, 1634, 1491, 1227, 762, 743 cm$^{-1}$.
$[\alpha]_D^{20}$=−155° (C=0.498% in methanol).

EXAMPLE 124

3-(R,S)-(N-Benzyl-N-methylamino)methyl-1-[3-(indol-3-yl)-2-[(R)-(4-phenylpiperazin-1-yl)carbonylamino]propanoyl]-1,2,3,4-tetrahydroquinoline

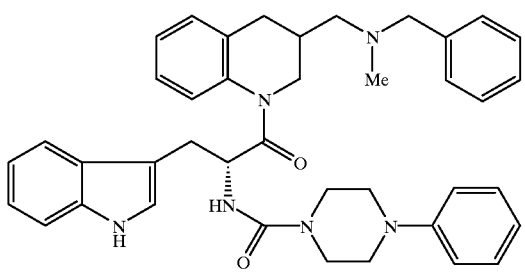

IR(KBr): 3260, 2922, 2849, 1632, 1493, 1233, 741 cm$^{-1}$.

EXAMPLE 125

3-(R,S)-(N,N-Dibenzylamino)methyl-1-[3-(indol-3-yl)-2-[(R)-(4-phenylpiperazin-1-yl)carbonylamino]propanoyl]-1,2,3,4-tetrahydroquinoline

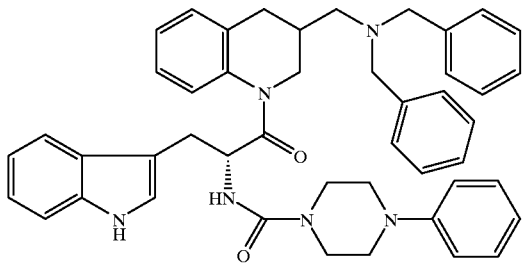

IR(KBr): 3281, 2922, 2813, 1636, 1493, 1233, 745 cm$^{-1}$.

EXAMPLE 126

3-(R,S)-(N,N-Dimethylamino)methyl-1-[2-[(R)-(4-benzotriazol-1-yl)piperidinocarbonylamino]-3-(indol-3-yl)propanoyl]-1,2,3,4-tetrahydroquinoline

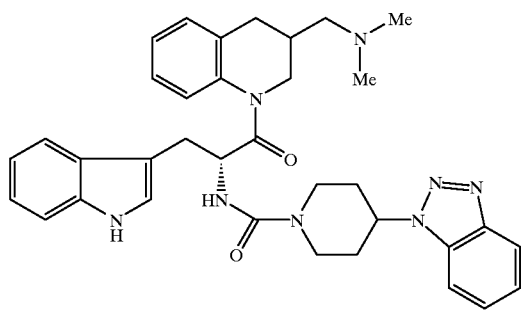

IR(KBr): 3260, 2936, 1634, 1491, 1456, 1233, 745 cm$^{-1}$.

EXAMPLE 127

3-(R,S)-(N,N-Dimethylamino)methyl-1-[3-(indol-3-yl)-2-[(R)-4-[5-(trifluoromethyl)benzotriazol-1-yl]piperidinocarbonylamino]propanoyl]-1,2,3,4-tetrahydroquinoline

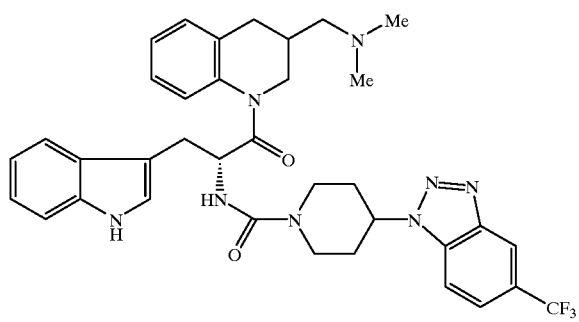

IR(KBr): 2934, 1632, 1493, 1333, 1235, 1163, 1125 cm$^{-1}$.

EXAMPLE 128

3-(R,S)-(N,N-Dimethylamino)methyl-1-2-[(R)-[4-(2,3-dimethyl)phenylpiperazin-1-yl]carbonylamino]-3-(indol-3-yl)propanoyl]-1,2,3,4-tetrahydroquinoline

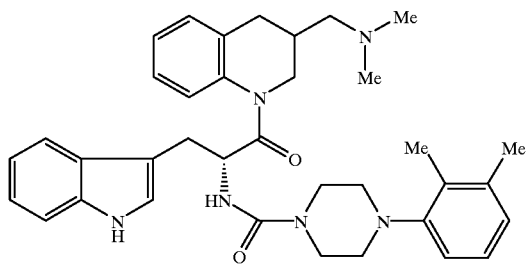

IR(KBr): 3263, 2971, 1632, 1491, 1456, 1235, 741 cm$^{-1}$.

EXAMPLE 129

3-(R,S)-(N,N-Dimethylamino)methyl-1-[2-[(R)-[4-(2,4-dimethyl)phenylpiperazin-1-yl]carbonylamino]-3-(indol-3-yl)propanoyl]-1,2,3,4-tetrahydroquinoline

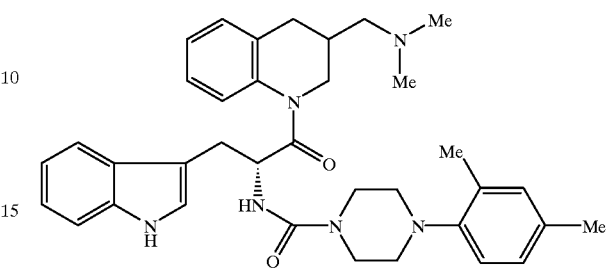

IR(KBr): 3254, 2942, 1632, 1493, 1416, 1225, 741 cm$^{-1}$.

EXAMPLE 130

3-(R,S)-(N,N-Dimethylamino)methyl-1-[2-[(R)-[4-(2,5-dimethyl)phenylpiperazin-1-yl]carbonylamino]-3-(indol-3-yl)propanoyl]-1,2,3,4-tetrahydroquinoline

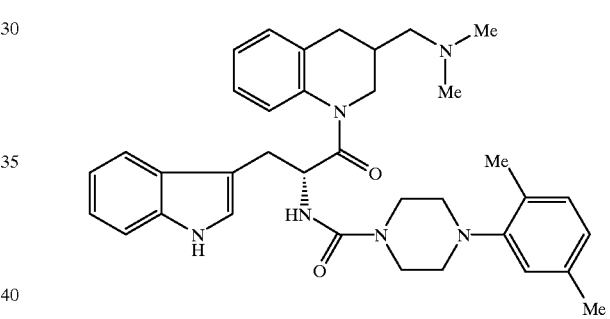

IR(KBr): 3264, 2969, 1632, 1493, 1416, 1242, 741 cm$^{-1}$.

EXAMPLE 131

3-(R,S)-(N,N-Dimethylamino)methyl-1-[3-(indol-3-yl)-2-[(R)-[4-(3-methoxy)phenylpiperazin-1-yl]carbonylamino]propanoyl]-1,2,3,4-tetrahydroquinoline

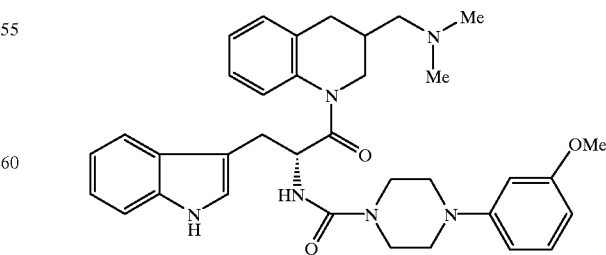

IR(KBr): 3227, 2938, 1632, 1493, 1456, 1250, 1202 cm$^{-1}$.

EXAMPLE 132

3-(R,S)-(N,N-Dimethylamino)methyl-1-[3-(indol-3-yl)-2-[(R)-[4-(tert-butoxycarbonyl)piperazin-1-yl]carbonylamino]propanoyl]-1,2,3,4-tetrahydroquinoline

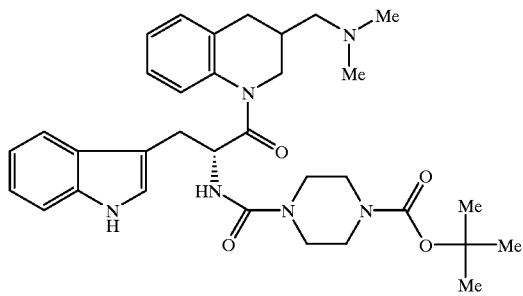

IR(KBr): 3316, 2975, 1698, 1634, 1416, 1238, 1169 cm$^{-1}$.

EXAMPLE 133

1-[3-(Indol-3-yl)-2-[(R)-(4-phenylpiperazin-1-yl)carbonylamino]propanoyl]-3-(R,S)-(N-methylamino)methyl-1,2,3,4-tetrahydroquinoline

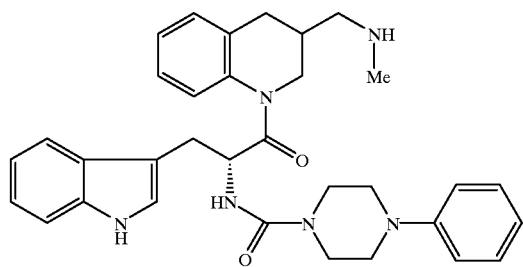

10% Palladium-carbon (50 mg) and concentrated hydrochloric acid (5 drops) were added to a methanol (10 ml) solution of 3-(R,S)-(N-benzyl-N-methylamino)methyl-1-[3-(indol-3-yl)-2-[(R)-(4-phenylpiperazin-1-yl)carbonylamino]propanoyl]-1,2,3,4-tetrahydroquinoline (400 mg), and catalytic hydrogenation was conducted at room temperature under 4 atmospheric pressure of hydrogen for 40 hours. The catalyst was removed by filtration and the filtrate was concentrated. 10% Aqueous potassium carbonate solution was added to the residue, which was extracted with ethyl acetate. The organic layer was washed with a saturated aqueous sodium chloride solution, then dried and concentrated. The residue was purified by alumina column chromatography (eluent: ethyl acetate/hexane=1:1 to ethyl acetate/methanol/triethylamine=5:1:0.1) to obtain the entitled compound (140 mg) as an amorphous powder.

IR(KBr): 3252, 2922, 1636, 1493, 1233, 760, 745 cm$^{-1}$.

EXAMPLE 134

3-(R,S)-(N-Benzylamino)methyl-1-[3-(indol-3-yl)-2-[(R)-(4-phenylpiperazin-1-yl)carbonylamino]propanoyl]-1,2,3,4-tetrahydroquinoline

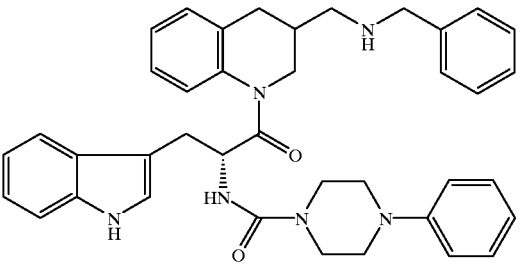

10% Palladium-carbon (50 mg) and concentrated hydrochloric acid (5 drops) were added to a methanol (10 ml) solution of 3-(R,S)-(N,N-dibenzylamino)methyl-1-[3-(indol-3-yl)-2-[(R)-(4-phenylpiperazin-1-yl)carbonylamino]propanoyl]-1,2,3,4-tetrahydroquinoline (400 mg), and catalytic hydrogenation was conducted at room temperature under 4 atmospheric pressure of hydrogen for 8 hours. The catalyst was removed by filtration, and the filtrate was concentrated. 10% Aqueous potassium carbonate solution was added to the residue, which was extracted with ethyl acetate. The organic layer was washed with a saturated aqueous sodium chloride solution, then dried and concentrated to obtain the entitled compound (300 mg) as an amorphous powder.

IR(KBr): 3271, 2921, 2840, 1634, 1495, 1233, 743 cm$^{-1}$.

The following compounds of Examples 135 to 138 were synthesized by similar manner as in Example 147.

EXAMPLE 135

3-(R,S)-(N,N-Dimethylamino)methyl-1-[3-(indol-3-yl)-2-[(R)-[4-(1-naphthyl)piperazin-1-yl]carbonylamino]propanoyl]-1,2,3,4-tetrahydroquinoline

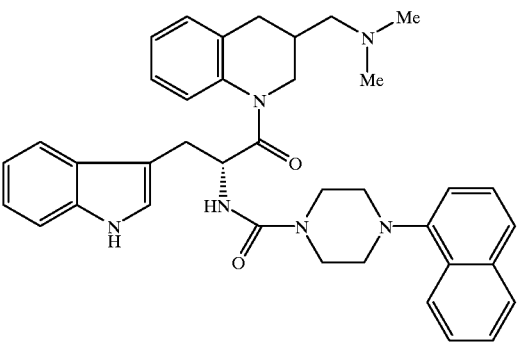

IR(KBr): 3291, 2940, 2820, 1636, 1508, 1491, 1399, 1254, 1011, 775, 743 cm$^{-1}$.

EXAMPLE 136

3-(R,S)-(N,N-Dimethylamino)methyl-1-[3-(indol-3-yl)-2-[(R)-(4-phenylpiperazin-1-yl)carbonylamino]propanoyl]-6-methoxy-1,2,3,4-tetrahydroquinoline

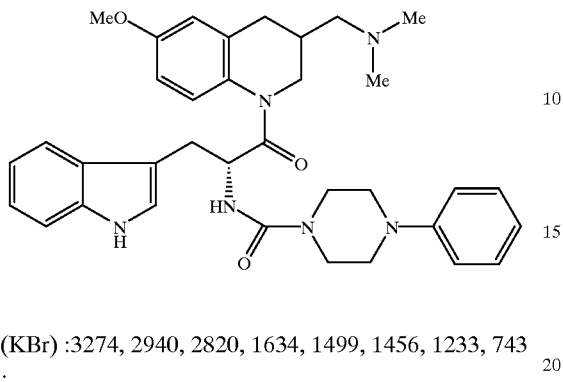

IR(KBr) :3274, 2940, 2820, 1634, 1499, 1456, 1233, 743 cm$^{-1}$.

EXAMPLE 137

3-(R,S)-(N,N-Dimethylamino)methyl-1-[3-(indol-3-yl)-2-[(R)-4-(2-oxo-2,3-dihydro-1H-benzimidazol-1-yl)piperidinocarbonylamino]propanoyl]-6-methoxy-1,2,3,4-tetrahydroquinoline

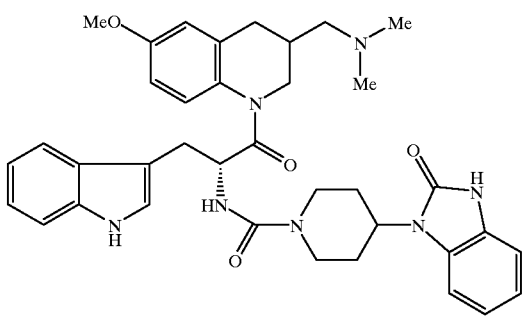

IR(KBr) : 3247, 2934, 1698, 1628, 1501, 1269, 1244, 741 cm$^{-1}$.

EXAMPLE 138

3-(R,S)-(N,N-Dimethylamino)methyl-1-[3-(indol-3-yl)-2-[(R)-1-(benzoylpiperidin-4-yl)carbonylamino]propanoyl]-6-methoxy-1,2,3,4-tetrahydroquinoline

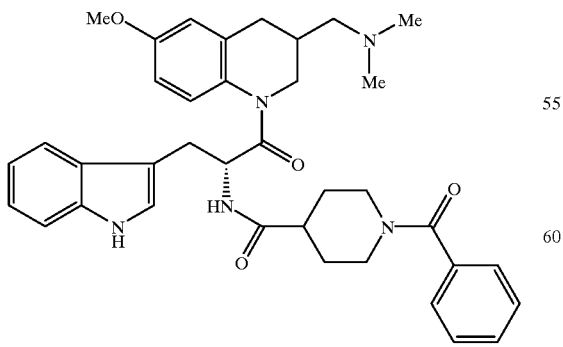

IR(KBr) :3293, 2940, 1628, 1501, 1448, 1279, 743 cm$^{-1}$.

EXAMPLE 139

6-Chloro-3-(R,S)-(N,N-dimethylamino)methyl-1-[3-(indol-3-yl)-2-[(R)-(4-phenylpiperazin-1-yl)carbonylamino]propanoyl]-1,2,3,4-tetrahydroquinoline

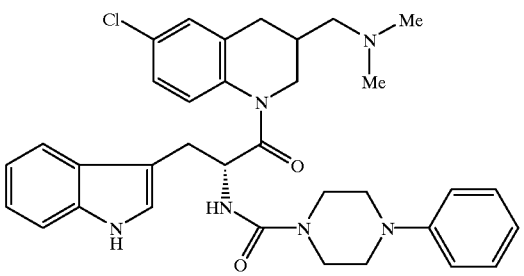

N,N'-Disuccinimidyl carbonate (42 mg) was added to an acetonitrile (5 ml) solution of 1–12-(R)-amino-3-(indol-3-yl)propanoyl]-6-chloro-3-(R,S)-(N,N-dimethylamino)methyl-1,2,3,4-tetrahydroquinoline (101 mg) and N-ethyldiisopropylamine (0.1 ml). The reaction mixture was stirred at room temperature for 30 minutes, to which was added a THF (3 ml) solution of 1-phenylpiperazine (63 mg) and N-ethyldiisopropylamine (0.1 ml). The reaction mixture was further stirred at room temperature for 3 hours, then concentrated. The residue was purified by alumina column chromatography (eluent: ethyl acetate/methanol=10/1) to obtain the entitled compound (55 mg) as an amorphous powder.

IR(KBr): 2820, 1632, 1489, 1233, 743 cm$^{-1}$.

The following compounds of Examples 140 and 141 were synthesized by similar manner as in Example 139.

EXAMPLE 140

6-Chloro-3-(R,S)-(N,N-dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline

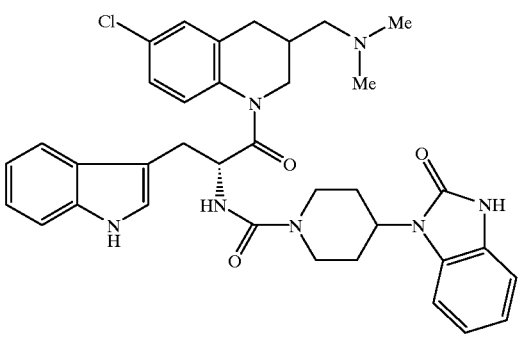

IR(KBr) 2969, 2938, 1698, 1632, 1485, 741 cm$^{-1}$.

EXAMPLE 141

1-Benzoyl-N-[(R)-2-[6-chloro-3-[(N,N-dimethylamino)methyl]-1,2,3,4-tetrahydroquinolin-1-yl]-1-[3-(indol-3-yl)propanoyl]-4-piperidinecarboxamide

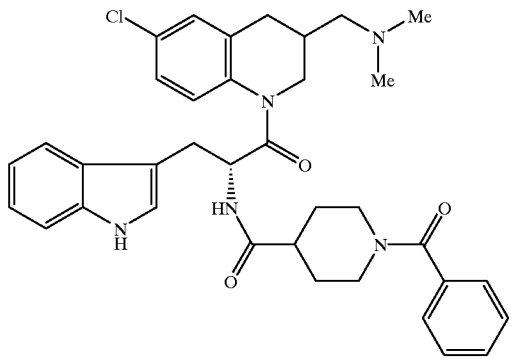

WSC (68 mg) was added to the mixture of 1-[2-(R)-amino-3-(indol-3-yl)propanoyl]-6-chloro-3-(R,S)-[(N,N-dimethylamino)methyl-1,2,3,4-tetrahydroquinoline (100 mg), 1-benzoyl-4-piperidinecarboxylic acid (60 mg) and HOBt (41 mg) in acetonitrile (5 ml). The reaction mixture was stirred at room temperature for 16 hours. 10% Aqueous potassium carbonate solution was added to the reaction mixture, which was extracted with ethyl acetate. The organic layer was washed with a saturated aqueous sodium chloride solution, then dried and concentrated. The residue was purified by alumina column chromatography (eluent: ethyl acetate/methanol=10/1) to obtain the entitled compound (151 mg) as an amorphous powder.

IR(KBr) 3281, 2942, 1634, 1487, 1447, 1281, 1231, 741, 710 cm$^{-1}$.

EXAMPLE 142

N-[2-(R)-[3-(R,S)-[(N,N-Dimethylamino)methyl]-1,2,3,4-tetrahydroquinolin-1-yl]-1-[3-(indol-3-yl)propanoyl]-3-phenylpropanamide

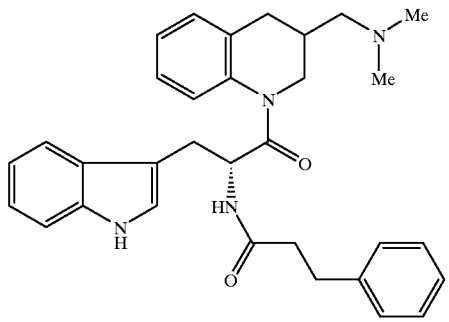

WSC (84 mg) was added to the mixture of 1-[2-(R)-amino-3-(indol-3-yl)propanoyl]-3-(R,S)-[(N,N-dimethylamino)methyl-1,2,3,4-tetrahydroquinoline (150 mg), 3-phenylpropionic acid (63 mg) and HOBt (66 mg) in acetonitrile (10 ml). The reaction mixture was stirred at room temperature for 16 hours. 10% Aqueous potassium carbonate solution was added to the reaction mixture, which was extracted with ethyl acetate. The organic layer was washed with a saturated aqueous sodium chloride solution, then dried and concentrated. The residue was purified by alumina column chromatography (eluent: ethyl acetate) to obtain the entitled compound (169 mg) as an amorphous powder.

IR(KBr): 3299, 2938, 1630, 1493, 743 cm$^{-1}$.

EXAMPLE 143

N-[2-(R)-[3-(R,S)-[(N,N-Dimethylamino)methyl]-1,2,3,4-tetrahydroquinolin-1-yl]-1-[3-(indol-3-yl)propanoyl]-4-phenylbutanamide

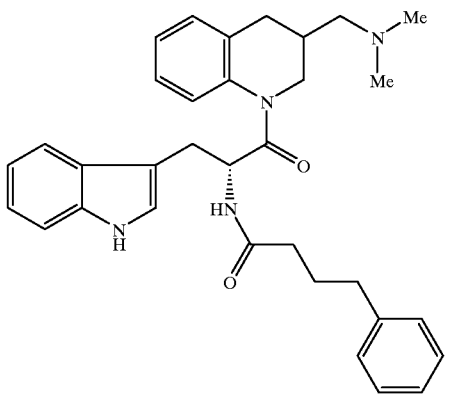

Synthesis was conducted by the similar method as in Example 142.

IR(KBr): 3299, 2938, 1632, 1493, 743 cm$^{-1}$.

EXAMPLE 144

1-[3-(4-Biphenylyl)propanoyl]-3-(R)-(N,N-dimethylamino)methyl-1,2,3,4-tetrahydroquinoline p-toluenesulfonate

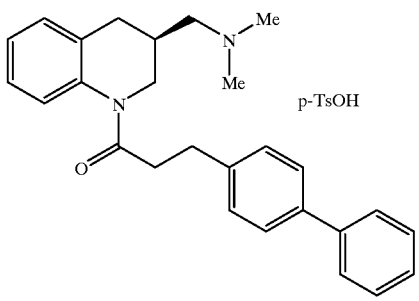

Synthesis was conducted by the similar method as in Example 1.

m.p. 130–130.5° C. (Solvent for recrystallization: ethanol/ethyl acetate).

$[\alpha]_D^{20}$=−14.2° (C=0.374% in methanol).

EXAMPLE 145

1-[3-(4-Biphenylyl)propanoyl]-3-(S)-(N,N-dimethylamino)methyl-1,2,3,4-tetrahydroquinoline p-toluenesulfonate

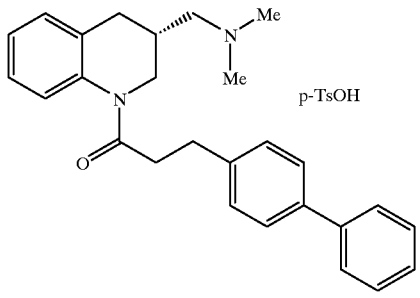

Synthesis was conducted by the similar method as in Example 1.

m.p. 130–130.5° C. (Solvent for recrystallization: ethanol/ethyl acetate).

$[\alpha]_D^{20}$=+12.8° (C=0.3825 in methanol).

EXAMPLE 146

1-[2-(R)-Amino-3-(indol-3-yl)propanoyl]-3-(R,S)-(N-benzyloxycarbonylamino)methyl-1,2,3,4-tetrahydroquinoline

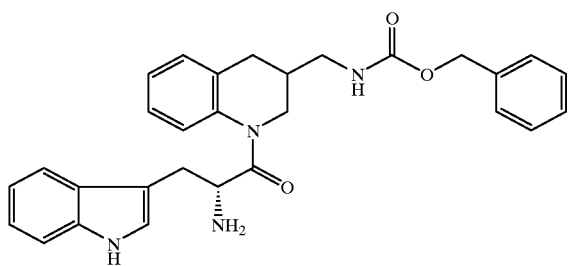

A THF (5 ml) solution of oxalyl chloride (0.45 ml) was added dropwise to a THF (20 ml) solution of N-(9-fluorenylmethoxycarbonyl)-D-tryptophan (1.83 g) and DMF (5 drops) at 0° C. The reaction mixture was stirred at room temperature for 30 minutes, then concentrated. The residue was dissolved in ethyl acetate (5 ml), which was added dropwise to the mixture of an ethyl acetate (20 ml) solution of 3-(N-benzyloxycarbonylamino)methyl-1,2,3,4-tetrahydroquinoline (425 mg) and 10% aqueous sodium carbonate solution (20 ml) at 0° C. The reaction mixture was stirred at room temperature for one hour, and the organic layer was separated. The organic layer was washed with a saturated aqueous sodium chloride solution, then dried and concentrated. The residue was purified by alumina column chromatography (eluent: ethyl acetate/hexane=1:1) and then silica gel column chromatography (eluent: ethyl acetate/hexane=1:1 to ethyl acetate). The obtained purified product was dissolved in methanol (20 ml). Piperidine (1 ml) was added to the reaction mixture, which was stirred at room temperature for 5 hours. The reaction mixture was concentrated, and the residue was purified by alumina column chromatography (eluent: ethyl acetate to ethyl acetate/methanol=10:1) to obtain the entitled compound (390 mg) as an amorphous powder.

IR(KBr): 3289, 2921, 1705, 1645, 1493, 1248, 745 cm$^{-1}$.

EXAMPLE 147

3-(R,S)-(N-Benzyloxycarbonylamino)methyl-1-[3-(indol-3-yl)-2-[(R)-(4-phenylpiperazin-1-yl)carbonylamino]propanoyl]-1,2,3,4-tetrahydroquinoline

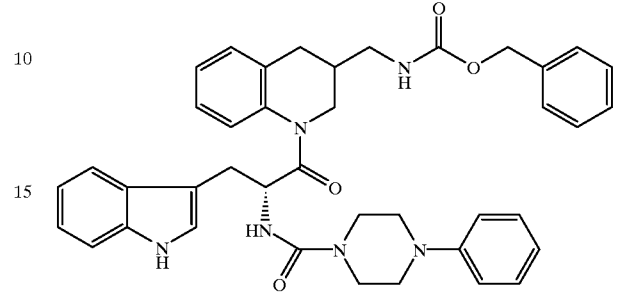

N,N'-Disuccinimidyl carbonate (160 mg) and N-ethyldiisopropylamine (0.21 ml) were added to an acetonitrile (9 ml) solution of 1-[2-(R)-amino-3-(indol-3-yl)propanoyl]-3-(N-benzyloxycarbonylamino)methyl-1,2,3,4-tetrahydroquinoline (300 mg). The reaction mixture was stirred at room temperature for 30 minutes, to which was added an acetonitrile (1.5 ml) solution of 1-phenylpiperazine (101 mg) and N-ethyldiisopropylamine (0.11 ml). The reaction mixture was further stirred at room temperature for one hour. A saturated aqueous sodium hydrogencarbonate solution was added to the reaction mixture, which was extracted with ethyl acetate. The organic layer was washed with a saturated aqueous sodium chloride solution, then dried and concentrated. The residue was purified by silica gel column chromatography (eluent: ethyl acetate/hexane=3:1) to obtain the entitled compound (390 mg) as an amorphous powder.

IR(KBr): 3295, 2921, 1705, 1634, 1495, 1235, 756 cm$^{-1}$.

EXAMPLE 148

3-(R,S)-Aminomethyl-1-[3-(indol-3-yl)-2-[(R)-(4-phenylpiperazin-1-yl)carbonylamino]propanoyl]-1,2,3,4-tetrahydroquinoline

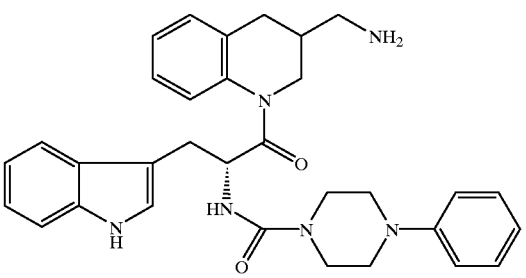

10% Palladium-carbon (25 mg) was added to a methanol (5 ml) solution of 3-(N-benzyloxycarbonylamino)methyl-1-[3-(indol-3-yl)-2-[(R)-(4-phenylpiperazin-1-yl)carbonylamino]propanoyl]-1,2,3,4-tetrahydroquinoline (250 mg), and catalytic hydrogenation was conducted at room temperature under an atmospheric pressure for 24 hours. The catalyst was removed by filtration, and the filtrate was concentrated to give the entitled compound (200 mg) as an amorphous powder.

IR(KBr):2915, 2855, 1634, 1599, 1493, 1233, 762 cm$^{-1}$.

EXAMPLE 149

1-[3-(4-Biphenylyl)propanoyl]-7-chloro-3-(N,N-dimethylamino)methyl-1,2,3,4-tetrahydroquinoline p-toluenesulfonate

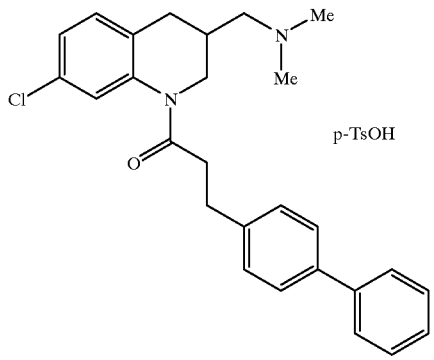

Oxalyl chloride (0.11 ml) and DMF (one drop) were added to a THF (10 ml) solution of 3-(4-biphenylyl) propionic acid (249 mg) at 0° C. The reaction mixture was stirred at room temperature for one hour. The residue was dissolved in THF (5 ml), which was added dropwise to a THF (10 ml) solution of 7-chloro-3-(N,N-dimethylamino) methyl-1,2,3,4-tetrahydroquinoline (220 mg) and triethylamine (0.17 ml) at 0° C. The reaction mixture was stirred at room temperature for one hour. 10% Aqueous potassium carbonate solution was added to the reaction mixture, which was extracted with ethyl acetate. The organic layer was washed with a saturated aqueous sodium chloride solution, then dried and concentrated. The residue was purified by silica gel column chromatography (eluent: hexanelethyl acetate=4/1), which was further converted into its p-toluenesulfonate. The mixture was recrystallized from ethanol-diethyl ether to give the entitled compound (528 mg).

m.p. 144–145° C.

EXAMPLE 150

1-[2-(R)-Amino-3-(indol-3-yl)propanoyl]-7-chloro-3-(R,S)-(N,N-dimethylamino)methyl-1,2,3,4-tetrahydroquinoline

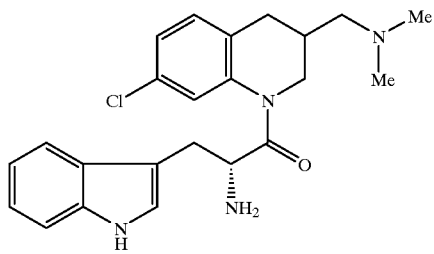

A THF (10 ml) solution of oxalyl chloride (1.6 ml) was added dropwise to a THF (50 ml) solution of N-(9-fluorenylmethoxycarbonyl)-D-tryptophan (6.444 g) and DMF (0.14 ml) at 0° C. The reaction mixture was stirred at 0° C. for one hour, then concentrated. An ethyl acetate (15 ml) solution of the residue was added dropwise to the mixture of an ethyl acetate (30 ml) solution of 7-chloro-3-(N, N-dimethylamino )methyl-1,2,3, 4-tetrahydroquinoline (1.128 g) and a saturated aqueous sodium bicarbonate solution (25 ml) at 0° C. The reaction mixture was stirred at room temperature f or one hour, and the organic layer was separated. The organic layer was washed with a saturated aqueous sodium chloride solution, then dried and concentrated. The residue was purified by alumina column chromatography (eluent: hexane/ethyl acetate=1/1) to obtain 7-chloro-3-(R,S)-(N,N-dimethylamino)methyl-1-[2-(R)-(9-fluorenylmethoxy)carbonylamino-3-(indol-3-yl) propanoyl]-1,2,3,4-tetrahydroquinoline (107.4 g). Piperidine (1.4 ml) was added to a methanol (30 ml) solution of this compound at room temperature. The reaction mixture was stirred at room temperature for 15 hours, then concentrated. The residue was purified by alumina column chromatography (eluent: ethyl acetate/methanol=10/1) to obtain the entitled compound (1.012 g).

IR(KBr): 3293, 2938, 1651, 1487, 1456, 1412, 1354, 1094, 743 cm$^{-1}$.

EXAMPLE 151

7-Chloro-3-(R,S)-(N,N-dimethylamino)methyl-1-[3-(indol-3-yl)-2-[(R)-(4-phenylpiperazin-1-yl) carbonylamino]propanoyl]-1,2,3,4-tetrahydroquinoline

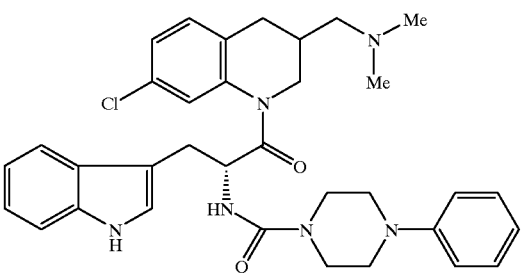

N,N'-Disuccinimidyl carbonate (96 mg) was added to an acetonitrile (5 ml) solution of 1-(2-(R)-amino-3-(indol-3-yl) propanoyl]-7-chloro-3-(R,S)-(N,N-dimethylamino)methyl-1,2,3,4-tetrahydroquinoline (153 mg) and N-ethyldiisopropylamine (0.13 ml). The reaction mixture was stirred at room temperature for 30 minutes, to which was added a THF (5 ml) solution of 1-phenylpiperazine (62 mg) and N-ethyldiisopropylamine (0.07 ml). The reaction mixture was further stirred at room temperature for 15 hours. 10% Aqueous potassium carbonate solution was added to the reaction mixture, which was extracted with ethyl acetate. The organic layer was washed with a saturated aqueous sodium chloride solution, then dried and concentrated. The residue was purified by alumina column chromatography (eluent: ethyl acetate/methanol=10/1) to obtain the entitled compound (148 mg) as an amorphous powder.

IR(KBr): 3262, 2971, 1636, 1599, 1489, 1233, 995, 758, 743, 694 cm$^{-1}$.

The following compounds of Examples 152 and 153 were synthesized by similar manner as in Example 151.

EXAMPLE 152

7-Chloro-3-(R,S)-(N,N-dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline

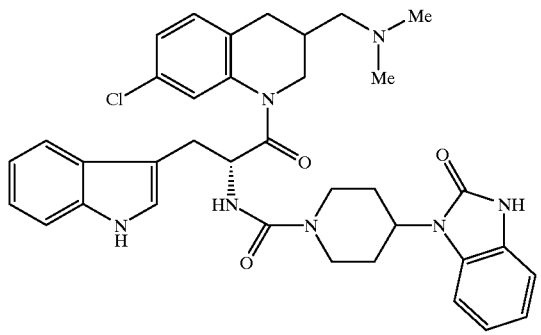

IR(KBr): 3225, 2971, 1694, 1485, 1246, 1235, 741, 696 cm$^{-1}$.

EXAMPLE 153

1-Benzoyl-N-[(R)-2-[7-chloro-3-[(dimethylamino)methyl]-1,2,3,4-tetrahydroquinolin-1-yl]-1-[3-(indol-3-yl)propanoyl]-4-piperidincarboxamide

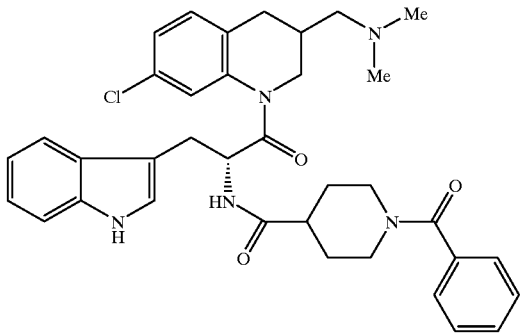

WSC (97 mg) was added to the mixture of 1-[2-(R)-amino-3-(indol-3-yl)propanoyl]-7-chloro-3-(R,S)-(N,N-dimethylamino)methyl-1,2,3,4-tetrahydroquinoline (159 mg), 1-benzoyl-4-piperidinecarboxylic acid (97 mg) and HOBt (66 mg) in acetonitrile (10 ml). The reaction mixture was stirred at room temperature for 16 hours. 10% Aqueous potassium carbonate solution was added to the reaction mixture, which was extracted with ethyl acetate. The organic layer was washed with a saturated aqueous sodium chloride solution, then dried and concentrated. The residue was purified by alumina column chromatography (eluent: ethyl acetate/methanol=10/1) to obtain the entitled compound (239 mg) as an amorphous powder.

IR(KBr): 3279, 2942, 1634, 1447, 1281, 741, 710 cm$^{-1}$.

EXAMPLE 154

7-Acetylamino-1-[3-(4-biphenylyl)propanoyl)]-3-(N,N-dimethylamino)methyl-1,2,3,4-tetrahydroquinoline p-toluenesulfonate

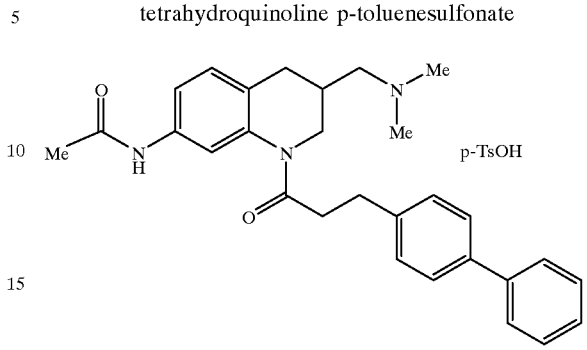

The entitled compound was synthesized by the similar manner as in Example 1.

m.p.: 234–236° C. (Solvent for recrystallization: ethanol).

EXAMPLE 155

1-[3-(4-Biphenylyl)propanoyl]-3-(N,N-dimethylamino)methyl-7-methoxy-1,2,3,4-tetrahydroquinoline

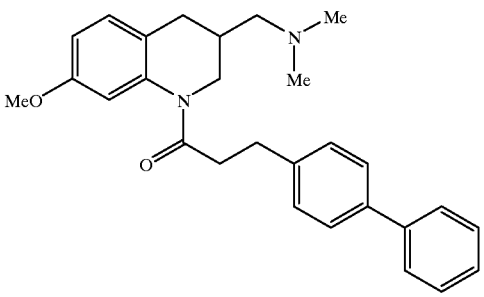

The entitled compound was synthesized by the similar manner as in Example 1.

Amorphous powder $^1$H-NMR(CDCl$_3$) d: 1.8–2.4(4H, m), 2.18(6H, s), 2.64–3.14(5H, m), 3.16–3.36(1H, m), 3.76(3H, s),3.92–4.10 (1H, m), 6.67(1H, dd), 7.04(1H, d), 7.14–7.62(1H, m).

Formulation Example 1

| | | |
|---|---|---|
| (1) Compound obtained in Example 56 | | 50.0 mg |
| (2) Lactose | | 34.0 mg |
| (3) Corn Starch | | 10.6 mg |
| (4) Corn Starch (pasty) | | 5.0 mg |
| (5) Magnesium Stearate | | 0.4 mg |
| (6) Carboxymethyl Cellulose Calcium | | 20.0 mg |
| Total | | 120.0 mg |

The above (1) to (6) were admixed in an ordinary manner, and tabletted using a tabletting machine, to obtain tablets.

Experimental Example 1

The followings are some examples of the pharmacological actions of the compounds of the present invention, which should not be construed as being limiting to them. The genetic operation using *E. coli* was conducted in accordance with the method described in the 1989 Edition of Molecular Cloning.

(1) Cloning of human somatostatin receptor protein subtype 4 (hSSTR4) DNA

DNA oligomers S4-1 and S4-2 were synthesized based on the known human SSTR4 DNA sequence (Rohrer etal., Proc. Natl, Acad. Sci., USA 90, 4196–4200, 1993). The sequence of S4-1 is 5'-GGCTCGAGTCACCATGAGCGCCCCTCG-3' (Sequence No.1) and that of S4-2 is 5'-GGGCTCGAGCTCCTCAGAAGGTGGTGG-3'. (Sequence No. 2). Human chromosome DNA (Clone Tech Inc. Catalog No. CL6550-1) was used as the template. To 0.5 ng of said DNA was added 25 pmol of each of the above mentioned DNA oligomers and the polymerase chain reaction was carried out using 2.5 units of PfuDNA polymerase (Strata gene). The composition of the reaction mixture was in accordance with the directions attached to said PfuDNA polymerase. The conditions of the reaction were as follows: One cycle consisting of the reactions at 94° C. for 1 minute, at 66° C. for 1 minute and at 75° C. for 2 minutes, and 35 cycles were repeated. The reaction mixture was subjected to electrophoresis on 1% agarose gel to find that the DNA fragments of the intended size (about 1.2 kb) was specifically amplified. Said DNA fragments were recovered from the agarose gel in the usual manner and connected to pUC118 cleaved at the Hinc II site to transform into the competent cells, *Escherichia coli* JM109. The transformant having plasmid containing said DNA fragments was selected out and the sequence of the intercalated DNA fragments was confirmed by the automatic sequence analyzer employing fluorochroming, ALF DNA Sequencer (Pharmacia). As the results, the amino acid sequence expected from the base sequence was completely in agreement with the sequence described in the above-mentioned reports by Rohrer et al.

(2) Organization of the expression plasmid of human somatostatin receptor protein subtype 4 (hSSTR4) DNA pAKKO-111 was used as the expression vector in CHO (Chinese Hamster Ovary) cells. pAKKO-111 was organized as follows: The 1.4 kb DNA fragment containing SRα promoter and poly A appositional signal was obtained from pTB1417 described in the official gazette JPA-H5(1993)-076385 by treatment with a restriction enzyme (Hind III) and a restriction enzyme (Cla I). On the other hand, the 4.5 kb DNA fragment containing dihydrofolic acid reductase gene (dhfr) was obtained from pTB348 [Naruo, K. et al., Biochem. Biophys. Res. Commun., 128, 256–264, 1985] by treatment with a restriction enzyme (Cal I) and a restriction enzyme (Sal I). These DNA fragments were treated with T4 polymerase to make the terminal blunt-ended and connected with T4 ligase to organize pAKKO-111 plasmid. Then, 5 μg of the plasmid having human SSTR4 DNA fragment was digested with a restriction enzyme (XhoI) and subjected to electrophoresis on 1% agarose gel to recover the 1.2 kb DNA fragment coded with human SSTR4. Next, 1 μg of the above-mentioned expression vector pAKKO-111 (5.5 kb) was digested with Sal I to prepare the cloning site for intercalation of human SSTR4 DNA fragment. Said expression vector fragment and the 1.2 kb DNA fragment were combined using T4DNA ligase. The reaction mixture was transduced into *E. coli* JM 109 by the calcium chloride method to obtain the expression plasmid pA1-11-SSTR4 in which human SSTR4 DNA fragment was intercalated from the transformants in regular sequence against the promoter. This transformant is expressed as *Escherichia coli* JM109/pA-1-11-hSSTR4.

(3) Transfection and expression of human somatostatin receptor protein subtype 4 (hSSTR4) DNA in CHO (dhfr) cells $1 \times 10^6$ CHO (dhfr) cells were cultured for 24 hours in HAM F12 medium containing 10% bovine fetal serum on a laboratory dish of 8 cm in diameter. To the cells was transfected 10 μg of the human SSTR4 DNA expression plasmid, pA-1-11-hSSTR4 obtained above by the calcium phosphate method (Cell Phect Transfection Kit; Pharmacia). The medium was switched to Dulbecco's Modified Eagle Medium (DMEM) containing 10% dialyzed bovine fetal serum 24 hours after the transfection to select the colony-forming cells (i.e. dhfr$^+$ cells) in this medium. Further, the selected cells were cloned from a single cell by the limiting dilution method and the somatostatin receptor protein expression activity of these cells was measured as follows: Human SSTR4 receptor expression cell strain was diluted with a buffer solution for assay [50 mM of tris hydrochloride, 1 mM of EDTA, 5 mM of magnesium chloride, 0.1%t of BSA, 0.2 mg/ml of bacitracin, 10 μg/ml of leupeptin, 1 μg/ml of pepstatin and 200 units/ml of aprotinin (pH 7.5)] to adjust the cell count to $2 \times 10^4 / 200$ μl. 200 μl of the dilution was placed in a tube and to this was added 2 μl of 5 nM[$^{125}$I]-somatostatin-14 (2000 Ci/mmol, Amersham). The mixture was incubated at 25° C. for 60 minutes. For measurement of non-specific binding (NSB), the tube to which 2 μl of somatostatin-14 ($10^{-4}$ M) was added was also incubated. To the tube was added 1.5 ml of a buffer solution for washing [50 mM of tris hydrochloride, 1 m of EDTA and 5 mM of magnesium chloride (pH 7.5)] and the mixture was filtered by GF/F glass fiber filter paper (Whatman) and washed further with 1.5 ml of the same buffer solution. [125I] of the filter was measured by a γ-counter. Thus, a highly somatostatin-binding cell strain, hSSTR4-1-2, was selected.

(4) Cloning of rat somatostatin receptor protein subtype 4 (rSSTR4) DNA

DNA oligomers S4-3 and S4-4 were synthesized based on the known rat SSTR4 DNA sequence (Bito.H etal., J. Biol. Chem., 269, 12722–12730, 1994). The sequence of S4-3 is 5'-AAGCATGAACACGCCTGCAACTC-3' (Sequence No. 3) and that of S4-4 is 5'-GGTTTTCAGAAAGTAGTGGTCTT-3'. (Sequence No. 4). As the template, a chromosome DNA prepared from Sprague-Dawley rats by using Easy-DNA™ KIT (Invitrogen) was used. To 0.5 ng of said DNA was added 25 pmol of each of the above mentioned DNA oligomers and the polymerase chain reaction was carried out using TaKaRa LAPCR KIT (TaKaRa). The conditions of the reaction were as follows: One cycle consisting of the reactions at 95° C. for 30 seconds, at 65° C. for 2 minutes and 30 seconds, and 30 cycles were repeated. The reaction mixture was subjected to electrophoresis on 1% agarose gel to find that the DNA fragments of the intended size (about 1.2 kb) was specifically amplified. Said DNA fragments were recovered from the agarose gel in the usual manner and connected to a vector (pCR™ 2.1 (Trade name)) of ORIGINALTA CLONINGKIT (Invitrogen) to transform into the competent cells, *Escherichia coli* JM109. The transformant having plasmid containing said DNA fragments was selected out and the sequence of the intercalated DNA fragments was confirmed by the automatic sequence analyzer employing fluorochroming, ALF DNA Sequencer (Pharmacia). As the results, the amino acid sequence expected from the base sequence was completely in agreement with the sequence described in the above-mentioned reports by Bito.H et al.

(5) Organization of the expression plasmid of rat somatostatin receptor protein subtype 4 (rSSTR4) DNA pAKKO-111 was used as the expression vector in CHO cells. 5 μg of the plasmid having rat SSTR4 DNA fragment obtained above was digested with a restriction enzyme (EcoRI), treated with T4DNApolymerase, and subjected to electrophoresis on 1% agarose gel to recover the 1.2 kb DNA fragment coded with rat SSTR4. Next, 1 μg of the above-mentioned expression vector pAKKO-111 (5.5 kb) was digested with a restriction enzyme (ClaI), treated with T4DNApolymerase and Alikaline Phosphatase, to prepare the cloning site for intercalation of rat SSTR4 DNA fragment. Said expression vector fragment and the 1.2 kb DNA fragment were combined using T4DNA ligase. The reaction mixture was transduced into *E. coli* JM 109 by the calcium chloride method to obtain the expression plasmid pA1-11-rSSTR4 in which rat SSTR4 DNA fragment was intercalated from the transformants in regular sequence against the promoter. This transformant is expressed as *Escherichia coli* JM109/pA-1-11-rSSTR4.

(6) Transfection and expression of rat somatostatin receptor protein subtype 4 (rSSTR4) DNA in CHO (dhfr⁻) cells $1 \times 10^6$ CHO (dhfr) cells were cultured for 24 hours in α-MEM medium (containing ribonucleoside and deoxynucleoside) containing 10% bovine fetal serum on a laboratory dish of 8 cm in diameter. To the cells was. transfected 10 μg of the rat SSTR4 DNA expression plasmid 1, pA-1-11-rSSTR4 obtained above by the calcium phosphate method (Cell Phect Transfection Kit; Pharmacia). The medium was switched to α-MEM medium (free of ribonucleoside and deoxynucleoside) containing 10% dialyzed bovine fetal serum 24 hours after the transfection to select the colony-forming cells (i.e. dhfr⁺ cells) in this medium. Further, the selected cells were cloned from a single cell by the limiting dilution method and the somatostatin receptor protein expression activity of these cells was measured by the binding method mentioned above. Thus, a highly somatostatin-binding cell strain, rSSTR4-20-25, was selected.

(7) Prepartion of CHO cell membrane fractions containing somatostatin receptor 4

Human and rat somatostatin receptor 4 expression CHO cell strain, hSSTR4-1-2 or rSSTR4-20-25 ($1 \times 10^9$) was floated on a phosphate buffered saline supplemented with 5 mM EDTA (PBS-EDTA) and centrifuged. To the cell pellets was added 10 ml of a homogenate buffer for cells (10 mMNaHCO₃, 5 mM EDTA, pH7.5), which was homogenated using a politron homogenizer. The supernatant obtained by centrifugation at 400×g for 15 minutes was further centrifuged at 10,000×g for 1 hour to give a precipitate of the membrane fraction. The precipitates were suspended in 2 ml of a buffer solution for assay [25 mM of Tris-HCl, 1 mM of EDTA (Ethylenediaminetetraacetic Acid), 0.1% of BSA (Bovine Serum Albumin), 0.25 mM of PMSF (Phenylmethylsulfonyl Fluoride), 1 μg/ml pepstatin, 20 μg/ml leupeptin, 10 μg/ml Phosphoramidone, pH7.5], which was centrifuged at 100,000×g for 1 hour. The membrane fraction recovered as precipitates was suspended again in 20 ml of the buffer solution for assay, which was placed in tubes and stored at −80° C. The suspension was thawed and used at every use.

Experimental Example 2

(1) Cloning of human somatostatin receptor protein subtype 1 (SSTR1) DNA

DNA oligomers S1-1 and S1-2 were synthesized based on the known human SSTR1c DNA sequence (Proc. Natl. Acad. Sci., USA 89, 251–255, 1992). The sequence of S1-1 is 5'-GGTCGACCTCAGCT AGGATGTTCCCCAATG-3' (Sequence No. 5) and that of S1-2 is 5'-GGTCGACCCGGGCTCAGAGCGTCGTGAT-3' (Sequence No. 6). Human chromosome DNA (Clone Tech Inc. Catalog No. CL 6550–1) was used as the template. To 0.5 ng of said DNA was added 25 pmol of each of the above mentioned DNA oligomers and the polymerase chain reaction was carried out using 2.5 units of PfuDNA polymerase (Stratagene). The composition of the reaction mixture was in accordance with the directions attached to said PfuDNA polymerase. The conditions of the reaction were as follows: One cycle consisting of the reactions at 94° C. for 1 minute, at 63° C. for 1 minute and at 75° C. for 2 minutes, and 35 cycles were repeated. The reaction mixture was subjected to electrophoresis on 1% agarose gel to find that the DNA fragments of the intended size (about 1.2 kb) was specifically amplified. Said DNA fragments were recovered from the agarose gel in the usual manner and connected to pUC118 cleaved at the Hinc II site to transform into the competent cells, *Escherichia coli* JM109. The transformant having plasmid containing said DNA fragments was selected out and the sequence of the intercalated DNA fragments was confirmed by the automatic sequence analyzer employing fluorochroming, ALF DNA Sequencer (Pharmacia). As the results, the amino acid sequence expected from the base sequence was completely in agreement with the sequence described in the above-mentioned literature.

(2) Organization of the expression plasmid of human somatostatin receptor protein subtype 1 (SSTR1) DNA pAKKO-111 was used as the expression vector in CHO (Chinese Hamster Ovary) cells. PAKKO-111 was organized as follows: The 1.4 kb DNA fragment containing SRα promoter and poly A appositional signal was obtained from pTB1417 described in the official gazette JPA-H5(1993)-076385 by treatment with Hind III and Cla I. On the other hand, the 4.5 kb DNA fragment containing dihydrofolic acid reductase (DHFR) gene was obtained from pTB348 [Biochem. Biophys. Res. Commun., 128, 256–264, 1985] by treatment with Cal I and Sal I. These DNA fragments were treated with T4 polymerase to make the terminal bluntended and connected with T4 ligase to organize pAKKO-111 plasmid. Then, 5 μg of the plasmid having human SSTR1 DNA fragment obtained under the above (1) was digested with the restriction enzyme Sal I and subjected to electrophoresis on 1% agarose gel to recover the 1.2 kb DNA fragment coded with human SSTR1. Next, 1 μg of the above-mentioned expression vector pAKKO-111 (5.5 kb) was digested with Sal I to prepare the cloning site for intercalation of human SSTR1 DNA fragment. Said expression vector fragment and the 1.2 kb DNA fragment were combined using T4DNA ligase. The reaction mixture was transduced into *E. coli* JM 109 by the calcium chloride method to obtain the expression plasmid pA1-11-SSTR1 in which human SSTR1 DNA fragment was intercalated from the transformants in regular sequence against the promoter. This transformant is expressed as *Escherichia coli* JM109/pA-1-11-SSTR1.

(3) Transfection and expression of human somatostatin receptor protein subtype 1 (SSTR1) DNA in CHO (dhfr⁻) cells $1 \times 10^6$ CHO (dhfr⁻) cells were cultured for 24 hours in HAM F12 medium containing 10% bovine fetal serum on a laboratory dish of 8 cm in diameter. To the cells was transfected 10 μg of the human SSTR1c DNA expression plasmid 1, pA-1-11-SSTR1, obtained under the above (2) by the calcium phosphate method (Cell Phect Transfection Kit: Pharmacia). The medium was switched to DMEM medium containing 10% dialyzed bovine fetal serum 24 hours after the transfection to select the colony-forming cells (i.e. DHFR+cells) in this medium. Further, the selected cells were cloned from a single cell by the limiting dilution method and the somatostatin protein activity was measured as follows: Human SSTRc DNA expression cell strain was diluted with a buffer solution for assay [50 mM of tris hydrochloride, 1 mM of EDTA, 5 mM of magnesium chloride, 0.1% of BSA, 0.2 mg/ml of bacitracin, 10 [g/ml of leupeptin, 1 µg/ml of pepstatin and 200 units/ml of aprotinin (pH 7.5)] to adjust the cell count to $2\times10^4/200$ µl. 200 µl of the dilution was placed in a tube and to this was added 2 µl of 5 nM[$^{125}$I]-somatostatin-14(2000 Ci/mmol,Amersham). The mixture was incubated at 25° C. for 60 minutes. For measurement of non-specific binding (NSB), the tube to which 2 µl of somatostatin-14 ($10^{-4}$ M) was added was also incubated. To the tube was added 1.5 ml of a buffer solution for washing [50 mM of tris hydrochloride, 1 mM of EDTA and 5 mM of magnesium chloride (pH 7.5)] and the mixture was filtered by GF/F glass fiber filter paper (Whatman) and washed further with 1.5 ml of the same buffer solution. [125I] of the filter was measured by a γ-counter. Thus, a highly somatostatin-binding cell strain, SSTR1-8-3, was selected.

(4) Cloning of human somatostatin receptor protein subtype 2 (SSTR2) DNA

DNA oligomers PT-1 and PT-2 were synthesized based on the known human SSTR2c DNA sequence (Proc. Natl. Acad. Sci., USA 89: 251–255, 1992). The sequence of PT-1 is 5'-GGTCGACACCATGGACATGGCGGATGAG-3' (Sequence No. 7) and that of PT-2 is 5'-GGTCGACAGTTCAGATACTGGTTTGG-3' (Sequence No. 8). Human pituitary gland cDNA (Clone Tech Inc. Catalog No. 7173-1) was used as the template. To 1 ng of said cDNA was added 25 pmol of each of the above mentioned DNA oligomers and the polymerase chain reaction was carried out using 2.5 units of TaqDNA polymerase (Takara Shuzo). The composition of the reaction mixture was in accordance with the directions attached to said TaqDNA polymerase. The conditions of the reaction were as follows: One cycle consisting of the reactions at 94° C. for 30 seconds, at 52° C. for 20 seconds and at 72° C. for 60 seconds, and 30 cycles were repeated. The reaction mixture was subjected to electrophoresis on 1% agarose gel to find that the DNA fragments of the intended size (about 1.1 kb) was specifically amplified. Said DNA fragments were recovered from the agarose gel in the usual manner and connected to pUC118 cleaved at the Hinc II site to transform into the competent cells, *Escherichia coli* JM109. Two strains (No. 5 and No. 7) of the transformant having plasmid containing said DNA fragments were selected out and the sequence of the intercalated DNA fragments was confirmed by the automatic sequence analyzer employing fluorochroming, 373A DNA Sequencer (Applied Biosystem). As the results, point mutation was confirmed at one site in the sequence of the 770 base fragment of No. 5 strain between Sal I and Bst PI, and point mutation was also confirmed at one site in the sequence of the 360 base fragment of No. 7 strain between Bst PI and Sal I. Therefore, the fragments remaining after removing the Bst PI-Sal I fragment of No. 5 strain and the Bst PI-Sal I fragment of No. 7 strain were purified by electrophoresis on agarose to organize a plasmid in which these fragments were bound by the ligation reaction. Confirmation of the insertion sequence of the DNA fragment of this plasmid revealed that it was completely in agreement with the sequence described in the above literature.

(5) Organization of the expression plasmid of human somatostatin receptor protein subtype 2 (SSTR2) DNA pAKKO-111 mentioned under the above (2) was used as the expression vector in CHO (Chinese Hamster Ovary) cells. 5 µg of the plasmid having human SSTR2 cDNA fragment obtained under the above (4) was digested with the restriction enzyme Sal I and subjected to electrophoresis on 1% agarose gel to recover the 1.1 kb DNA fragment coded with human SSTR2. Next, 1 µg of the above-mentioned expression vector pAKKO-111 (5.5 kb) was digested with Sal I to prepare the cloning site for intercalation of human SSTR2 DNA fragment. Said expression vector fragment and the 1.1 kb DNA fragment were combined using T4DNA ligase. The reaction mixture was transduced into *E. coli* JM 109 by the calcium chloride method to obtain the expression plasmid pAC01 in which human SSTR2 DNA fragment was intercalated from the transformants in regular sequence against the promoter. This transformant is expressed as *Escherichia coli* JM109/pAC-01.

(6) Transfection and expression of human somatostatin receptor protein subtype 2 (SSTR2) DNA in CHO (dhfr) cells $1\times10^6$ CHO (dhfr$^-$) cells were cultured for 24 hours in HAM F12 medium containing 10% bovine fetal serum on a laboratory dish of 8 cm in diameter. To the cells was transfected 10 µg of the human SSTR2 cDNA expression plasmid, pA-C01, obtained under the above (5) by the calcium phosphate method (Cell Phect Transfection Kit: Pharmacia). The medium was switched to DMEM medium containing 10% dialyzed bovine fetal serum 24 hours after the transfection to select the colony-forming cells (i.e. DHFR$^+$ cells) in this medium. Further, the selected cells were cloned from a single cell by the limiting dilution method and a cell strain which highly expresses human SSTR2, SSTR2-HS5-9, was selected.

(7) Cloning of human somatostatin receptor protein subtype 3 (SSTR3) DNA

DNA oligomers S3-1 and S3-2 were synthesized based on the known human SSTR3c DNA sequence (Mol. Endocrinol., 6: 2136–2142, 1992). The sequence of S3-1 is 5'-GGTCGACCTCAACCATGGACATGCTTCATC-3' (Sequence No. 9) and that of S3-2 is 5'-GGTCGACTTTCCCCAGGCCCCTACAGGTA-3' (Sequence No. 10). Human chromosome DNA (Clone Tech Inc. Catalog No. CL6550-1) was used as the template. To 0.5 ng of said DNA was added 25 pmol of each of the above mentioned DNA oligomers and the polymerase chain reaction was carried out using 2.5 units of PfuDNA polymerase (Stratagene). The composition of the reaction mixture was in accordance with the directions attached to said PfuDNA polymerase. The conditions of the reaction were as follows: One cycle consisting of the reactions at 94° C. for 1 minute, at 63° C. for 1 minute and at 75° C. for 2 minutes, and 35 cycles were repeated. The reaction mixture was subjected to electrophoresis on 1% agarose gel to find that the DNA fragments of the intended size (about 1.3 kb) was specifically amplified. As the results, the amino acid sequence expected from the base sequence was completely in agreement with the sequence described in the above-mentioned literature.

(8) Organization of the expression plasmid of human somatostatin receptor protein subtype 3 (SSTR3) DNA pAKKO-111 mentioned under the above (2) was used as the expression vector in CHO cells. 5 µg of the plasmid having human SSTR3 DNA fragment obtained under the above (7) was digested with the restriction enzyme Sal I and subjected to electrophoresis on 1% agarose gel to recover the 1.3 kb DNA fragment coded with human SSTR3. Next, 1 µg of the above-mentioned expression vector pAKKO-111

(5.5 kb) was digested with Sal I to prepare the cloning site for intercalation of human SSTR3 DNA fragment. Said expression vector and the 1.3 kb DNA fragment were combined using T4DNA ligase. The reaction mixture was transduced into *E. coli* JM 109 by the calcium chloride method to obtain the expression plasmid pA1-11-SSTR3 in which human SSTR3 DNA fragment was intercalated from the transformants in regular sequence against the promoter. This transformant is expressed as *Escherichia coli* JM109/pA-1-11-SSTR3.

(9) Transfection and expression of human somatostatin receptor protein subtype 3 (SSTR3) DNA in CHO (dhfr⁻) cells $1 \times 10^6$ CHO (dhfr⁻) cells were cultured for 24 hours in HAM F12 medium containing 10% bovine fetal serum on a laboratory dish of 8 cm in diameter. To the cells was transfected 10 $\mu$g of the human SSTR3 DNA expression plasmid, pA-1-11-SSTR3, obtained under the above (5) by the calcium phosphate method. The medium was switched to DMEM medium containing 10% dialyzed bovine fetal serum 24 hours after the transfection to select the colony-forming cells (i.e. DHFR⁺ cells) in this medium. Further, the selected cells were cloned from a single cell by the limiting dilution method and the somatostatin receptor protein expression activity of these cells was measured by the binding assay mentioned under the above (3). Thus, a highly somatostatin-binding cell strain, SSTR3-15-19, was selected.

(10) Cloning of human somatostatin receptor protein subtype (SSTR5) DNA

DNA oligomers S5-1 and S5-2 were synthesized based on the known human SSTR5c DNA sequence (Biochem Biophys. Res. Commun., 195, 844–852, 1993). The sequence of S5-1 is 5'-GGTCGACCACCATGGAGCCCCTGTTCCC-3' (Sequence No. 11) and that of S5-2 is 5'-CCGTCGACACTCTCACAGCTTGCTGG-3' (Sequence No. 12). Human chromosome DNA (Clone Tech Inc. Catalog No. CL6550-1) was used as the template. To 0.5 ng of said DNA was added 25 pmol of each of the above mentioned DNA oligomers and the polymerase chain reaction was carried out using 2.5 units of PfuDNA polymerase (Strata gene). The composition of the reaction mixture was in accordance with the directions attached to PfuDNA polymerase. The conditions of the reaction were as follows: One cycle consisting of the reactions at 94° C. for 1 minute, at 66° C. for 1 minute and at 75° C. for 2 minutes, and 35 cycles were repeated. The reaction mixture was subjected to electrophoresis on 1% agarose gel to find that the DNA fragments of the intended size (about 1.1 kb) were specifically amplified. Confirmation of the insertion sequence of said DNA fragment by the method mentioned under the above (1) revealed that the amino acid sequence expected from the base sequence was completely in agreement with the sequence described in the above-mentioned literature.

(11) Organization of the expression plasmid of human somatostatin receptor protein subtype 5 (SSTR5) DNA pAKKO-111 mentioned under the above (2) was used as the expression vector in CHO cells. 5 $\mu$g of the plasmid having human SSTR5 DNA fragment obtained under the above (10) was digested with the restriction enzyme Sal I and subjected to electrophoresis on 1% agarose gel to recover the 1.1 kb DNA fragment coded with human SSTR5. Next, 1 $\mu$g of the above-mentioned expression vector pAKKO-111 (5.5 kb) was digested with Sal I to prepare the cloning site for intercalation of human SSTR5 DNA fragment. Said expression vector fragment and the 1.1 kb DNA fragment were combined using T4DNA ligase. The reaction mixture was transduced into *E. coli* JM 109 by the calcium chloride method to obtain the expression plasmid pA1-11-SSTR5 in which human SSTR5 DNA fragment was intercalated from the transformants in regular sequence against the promoter. This transformant is expressed as *Escherichia coli* JM109/pA-1-11-SSTR5.

(12) Transfection and expression of human somatostatin receptor protein subtype 5 (SSTR5) DNA in CHO (dhfr⁻) cells $1 \times 10^6$ CHO (dhfr⁻) cells were cultured for 24 hours in HAM F12 medium containing 10% bovine fetal serum on a laboratory dish of 8 cm in diameter. To the cells was transfected 10 $\mu$g of the human SSTR5c DNA expression plasmid, pA-1-11-SSTR5, obtained under the above (11) by the calcium phosphate method. The medium was switched to DMEM medium containing 10% dialyzed bovine fetal serum 24 hours after the transfection to select the colony-forming cells (i.e. DHFR⁺ cells) in this medium. Further, the selected cells were cloned from a single cell by the limiting dilution method and the somatostatin receptor protein expression activity of these cells was measured by binding assay mentioned under the above (3). Thus, a highly somatostatin-biding cell strain, SSTR5-3-2-4, was selected.

Experimental Example 3

Measurement of the binding inhibition rate of $^{125}$I-Somatostatin

The receptor binding inhibition rate of the subject compound was calculated using each of the membrane fractions prepared in Experimental Examples 1 and 2. The membrane fraction was diluted with a buffer solution for assay to adjust the concentration to 3 $\mu$g/ml. The diluate was placed in tubes each in quantity of 173 $\mu$l. To this were simultaneously added 2 $\mu$l of a solution of a subject compound in DMSO and 25 $\mu$l of a 200 pM radioisotope-labeled somatostatin-14 ($^{125}$I-somatostatin-14: Amersham). For measurement of the maximum binding, a reaction mixture added with 2 $\mu$l of DMSO and 25 $\mu$l of a 200 pM $^{125}$I-somatostatin was prepared. For measurement of non-specific binding, a reaction mixture added with 2 $\mu$l of a 100 $\mu$M somatostatin solution in DMSO and 25 $\mu$l of a 200 pM $^{125}$I-somatostatin solution was prepared at the same time. The mixtures were allowed to react at 25° C. for 60 minutes. Then, the reaction mixture was filtered by aspiration using a Whatman glass filter(GF-B) treated with polyethylenimine. After filtration, the radioactivity of $^{125}$I-somatostatin-14 remaining on the filter paper was measured by a γ-counter.

The binding inhibition rate (%) of each subject compound was calculated by the following formula:

$$(TB-SB)/(TB-NSB) \times 100$$

SB: radioactivity when a compound was added
TB: maximum binding radioactivity
NSB: non-specific binding radioactivity
The binding rates were measured by changing the concentrations of the subject compound, and the 50% inhibiting concentration of the subject compound (IC$_{50}$ value) was calculated by the Hill plots.

Results

| Example No. | IC$_{50}$ ($\mu$M) | | |
|---|---|---|---|
| | SSTR2 | SSTR3 | SSTR4 |
| 56 | | | 0.007 |
| 88 | 0.009 | 0.0008 | |
| 89 | 0.003 | 0.002 | |

Further, the IC$_{50}$ value of the compound obtained in Example 56 for rat SSTR4 was 10 nM.

This shows that the compound (I) of the present invention have a binding inhibition effect on the human and rat somatostatin receptor.

Experimental Example 4

Inhibitory effect on forskolin-stimulated accumulation of cAMP in rat astrocyte For measurement of the accumulated intracellular adenosine 3',5'-monophosphate (cAMP), newborn rat astrocytes prepared in accordance with the method of Mc carthy, K. D. et al. [Cell Biology, 85, 890–920, 1980] were proliferated in 24-well plate until they were confluent. Said cells were washed twice with 1 ml of Medium A [Dulbecco's Modified Eagle Medium (DMEM), 20 mM 2-[4-(2-hydroxyethyl)-1-piperazinyl]ethanesulfonic acid (HEPES) (pH 7.5), 0.2% bovine serum albumin and 0.2 mM 3-isobutyl-1-methylxanthine (IBMX)]. The medium A was placed in wells each in a quantity of 400 $\mu$l and incubated at 37° C. for an hour. Both 50 $\mu$l of a somatostatin-14 solution (final concentration) or a subject compound in various concentrations and 50 $\mu$l of a forskolin solution (final concentration 100 $\mu$M) were placed in each well, which were incubated at 37° C. for an hour. The cells were washed twice with 1 ml of Medium A. 500 $\mu$l of Medium A and 100 $\mu$l of a 20% aqueous perchloric acid solution were placed in each well and left standing for 20 minutes at 4° C. to lyse the cells. The lyzate was placed in an Eppendorf's tube and centrifuged (15.000 rpm, 10 minutes). The supernatant was placed in another Eppendorf's tube in quantity of 500 $\mu$l and neutralized with 60 mM of a HEPES aqueous solution containing 1.5 M of potassium chloride. The content of cAMP in this extract was determined by the Amersham kit (cAMP EIA system).

Results

Somatostatin-14 (10 nM) and the compound obtained in Example 56 (10 nM) inhibit the intracellular accumulation of cAMP at the time of stimulation by forskolin (10 $\mu$M) by 83% and 43%, respectively.

This shows that the compound obtained in Example 56 has an agonistic effect on the rat somatostatin receptor.

Industrial Applicability

Compound (I) of the present invention has an excellent somatostatin receptor binding inhibition action with low toxicity.

Compound (I') of the present invention also has an excellent somatostatin receptor binding inhibition action with low toxicity.

Therefore, compounds (I) and (I') are useful for disorders of an intracellular signal transduction system (e.g., diseases accompanied by excess sthenia or suppression); diseases accompanied by disorders of regulating cell proliferation; diseases accompanied by disorders of production and(or) secretion of hormones, growth factors, or physiologically active substances; in a mammal.

What is claimed is:

1. A compound of the formula (I):

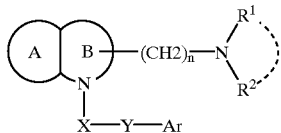

wherein Ar represents an aromatic group which may be substituted;
X represents methylene, S, SO, SO$_2$ or CO;
Y represents a spacer having a main chain of 2 to 5 atoms;
n represents an integer of 1 to 5;
i) R$^1$ and R$^2$ each represents a hydrogen atom or a lower alkyl which may be substituted;
ii) R$^1$ and R$^2$ form, taken together with the adjacent nitrogen atom, a nitrogen-containing heterocyclic ring which may be substituted;
Ring A represents a benzene ring which may be substituted;
Ring B represents a 6 membered nitrogen-containing non-aromatic ring with 5 carbon atoms and 1 nitrogen atom which may be further substituted by alkyl or acyl,
With a proviso that X represents S, SO, SO$_2$ or CO when Ring A has as a substituent a group represented by the formula:

—NHCOR$^{11}$ where R$^{11}$ represents alkyl, alkoxyalkyl, alkylthioalkyl, cycloalkyl, cycloalkylalkyl, aryl, arylalkyl or a group represented by the formula

—NHR$^{12}$ where R$^{12}$ represents alkyl, cycloalkyl, cycloalkylalkyl, aryl, or arylalkyl, or a salt thereof.

2. A compound of claim 1, wherein Ring B represents a 6-membered nitrogen-containing non-aromatic ring with 5 carbon atoms and 1 nitrogen atom which may be substituted by alkyl.

3. A compound of claim 1, wherein Ar represents an aromatic ring assembly group which may be substituted or a fused aromatic group which may be substituted.

4. A compound of claim 1, wherein X represents CO.

5. A compound of claim 1, wherein Y represents a C$_{2-5}$ alkenylene which may be substituted.

6. A compound of claim 5, wherein the substituent of the C$_{2-5}$ alkenylene represented by Y is acylamino.

7. A compound of claim 1, wherein n represents 1 or 2.

8. A compound of claim 1, wherein R$^1$ and R$^2$ each represents a hydrogen atom or a lower alkyl which may be substituted.

9. A compound of claim 1, wherein R$^1$ and R$^2$ form, taken together with the adjacent nitrogen atom, a nitrogen-containing heterocyclic ring which may be substituted.

10. A compound of claim 9, wherein the nitrogen-containing heterocyclic ring is pyrrolidine, piperidine, piperazine or morpholine.

11. A compound of claim 1, which is a compound of the formula:

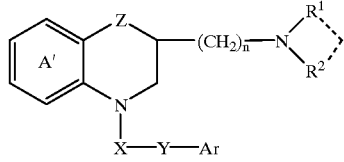

wherein Ring A' is a benzene ring which may be substituted,

Z represents methylene which may be substituted, the other symbols have the same meanings as in claim 1, or a salt thereof.

12. A compound of claim 1, wherein Ar represents (i) phenyl; 2-, 4- or 5-thiazolyl; 2-, 4- or 5-oxazolyl; 2-, 3- or 4-pyridyl; or 1,2,4- or 1,3,4-oxadiazlolyl;

(ii) 2-, 3- or 4-biphenylyl; 3-(1-naphthyl)-1,2,4-oxadiazlol-5-yl; 3-(2-naphthyl)-1,2,4-oxadiazol-5-yl; 3-(2-benzofuranyl)-1,2,4-oxadiazol-5-yl; 3-phenyl-1,2,4oxadiazol-5-yl; 3-(2-benzoxazolyl)-1,2,4-oxadiazol-5-yl; 3-(3-indolyl)-1,2,4-oxadiazol-5-yl; 3-(2-indolyl)-1,2,4-oxadiazol-5-yl; 4-phenylthiazol-2-yl; 4-(2-benzofuranyl)thiazol-2-yl; 4-phenyl-1,3-oxazol-5-yl; 5-phenyl-oxazol-2-yl; 4-(2-thienyl)phenyl; 4-(3-pyridyl)phenyl; 4-(2-naphthyl)phenyl; or 4,4'-terphenyl; or (iii) 2-, 3- or 4-quinolyl; or 1-, 2- or 3-indolyl;

each of which (i), (ii) and (iii) may be substituted by a group selected from the group consisting of halogen atom; $C_{1-3}$ alkylenedioxy; optionally halogenated $C_{1-6}$ alkyl; $C_{6-10}$ aryloxy-$C_{1-6}$ alkyl; $C_{1-6}$ alkyl-$C_{6-10}$ aryl-$C_{2-6}$ alkenyl; $C_{7-16}$ aralkyl optionally substituted by halogen atom or $C_{1-6}$ alkoxy; hydroxy; $C_{6-10}$ aryloxy optionally substituted by halogen atom or $C_{1-6}$ alkoxy; optionally halogenated $C_{1-6}$ alkyl-carbonyl; $C_{1-6}$ alkoxy-carbonyl; $C_{6-10}$ aryl-carbonyl and $C_{6-10}$ arylsulfonyl optionally substituted by $C_{1-6}$ alkyl;

X represents methylene, CO or $SO_2$;

Y represents (a) $C_{2-5}$ alkylene which may be substituted by (1) cyano, (2) $C_{6-10}$ aryl, (3) a group represented by the formula:

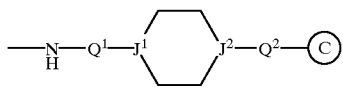

wherein $J^1$ and $J^2$ each represents CH, C(OH) or N; $Q^1$ and $Q^2$ each represents —$(CH_2)_p$— or —$(CH_2)_p$—CO—$(CH_2)_q$— where p and q each represents an integer of 0 to 3;

represents (i) a group represented by the formula:

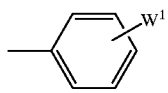

wherein $W^1$ represents halogen atom, cyano, optionally halogenated $C_{1-6}$ alkyl, optionally halogenated $C_{1-6}$ alkoxy, optionally halogenated $C_{1-6}$ alkyl-carbonyl, nitro or $C_{6-10}$ aryl;

(ii) pyridyl, or pyrimidinyl, or (iii) a group represented by the formula:

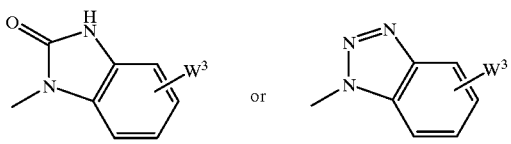

wherein $W^3$ represents hydrogen atom or optionally halogenated $C_{1-6}$ alkyl, (4) $C_{7-16}$ aralkyloxy-carboxamido, (5) amino, (6) $C_{7-16}$ aralkyl-carboxamido, (7) $C_{1-6}$ alkoxy-carbonyl-piperazinyl-carboxamido, or (8) a group represented by the formula:

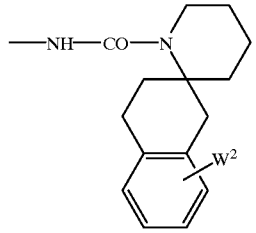

wherein $W^2$ represents optionally halogenated $C_{1-6}$ alkoxy;

(b) $C_{2-5}$ alkenylene, (c) —$(CH)_m$—$Y^{1a}$— wherein m represents an integer of 1 to 4, $Y^{1a}$ represents O or $NR^{8a}$ where $R^{8a}$ represents hydrogen atom or $C_{6-10}$ arylsulfonyl which may be substituted by $C_{1-6}$ alkyl, or (d) —NH—$(CH_2)_r$— wherein r represents an integer of 1 to 4;

n represents 1 or 2;

i) $R^1$ and $R^2$ each represents a hydrogen atom or $C_{1-6}$ alkyl which may be substituted by $C_{6-10}$ aryl, ii) $R^1$ and $R^2$ form, taken together with the adjacent nitrogen atom, morpholine, piperidine, piperazine or pirrolidine, each of which may be substituted by $C_{6-10}$ aryl, or iii) $R^1$ together with —$(CH_2)_n$—$N(R^2)$— forms, bonded to a component atom of Ring B, a 6-membered spiro-ring represented by the formula:

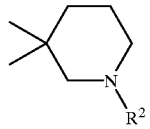

wherein $R^2$ represents $C_{1-6}$ alkyl;

Ring A represents benzene ring which may be substituted by $C_{1-6}$ alkoxy, $C_{6-10}$ aryl-$C_{7-16}$ aralkyloxy, halogen atom, or optionally halogenated $C_{1-6}$ alkyl-carboxamido; and Ring B represents

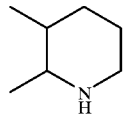

which may be substituted by $C_{1-6}$ alkyl, formyl or $C_{1-6}$ alkyl-carbonyl.

13. A compound of claim 12, wherein wherein Y represents (a) $C_{2-5}$ alkylene which may be substituted by ① cyano, ② $C_{6-10}$ aryl, ③ $C_{1-6}$ aralkyloxy-carboxamido, or ④ amino, (b) $C_{2-5}$ alkenylene, (c) —(CH)$_m$—Y$^{1a}$— wherein m represents an integer of 1 to 4, Y$^{1a}$ represents O or NR$^{8a}$ where R$^{8a}$ represents hydrogen atom or $C_{6-10}$ arylsulfonyl which may be substituted by $C_{1-6}$ alkyl, or (d) —NH—(CH$_2$)$_r$— wherein r represents an integer of 1 to 4.

14. A compound of claim 12, wherein X represents CO; Y represents (a) $C_{2-5}$ alkylene which may be substituted by ① a group represented by the formula:

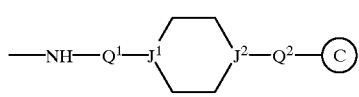

wherein J$^1$ and J$^2$ each represents CH, C(OH) or N; Q$^1$ and Q$^2$ each represents —(CH$_2$)$_p$— or —(CH$_2$)$_p$—CO—(CH$_2$)$_q$— where p and q each represents an integer of 0 to 3;

represents (i) a group represented by the formula:

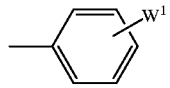

wherein W$^1$ represents halogen atom, cyano, optionally halogenated $C_{1-6}$ alkyl, optionally halogenated $C_{1-6}$ alkoxy, optionally halogenated $C_{1-6}$ alkyl-carbonyl, nitro, or $C_{6-10}$ aryl;

(ii) pyridyl, or pyrimidinyl, or (iii) a group represented by the formula:

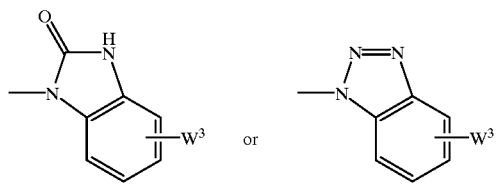

wherein W$^3$ represents hydrogen atom or optionally halogenated $C_{1-6}$ alkyl, ② $C_{7-16}$ aralkyloxy-carboxamido, ③ amino, ④ $C_{7-16}$ aralkyl-carboxamido, ⑤ $C_{1-6}$ alkoxy-carbonyl-piperazinyl-carboxamido, or ⑥ a group represented by the formula:

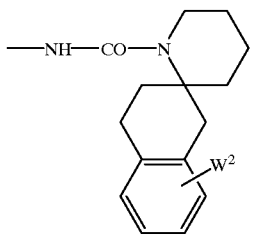

wherein W$^2$ represents optionally halogenated $C_{1-6}$ alkoxy;

(b) —(CH)$_m$—Y$^{1a}$— wherein m represents an integer of 1 to 4, Y$^{1a}$ represents O or NR$^{8a}$ where R$^{8a}$ represents hydrogen atom or $C_{6-10}$ arylsulfonyl which may be substituted by $C_{1-6}$ alkyl, or (c) —NH—(CH$_2$)$_r$— wherein r represents an integer of 1 to 4; n represents 1;

i) R$^1$ and R$^2$ each represents a hydrogen atom or $C_{1-6}$ alkyl;

Ring A represents benzene ring; and

Ring B represents

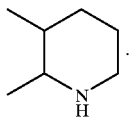

15. A compound of claim 14, wherein Ar is 3-indolyl.

16. A compound of claim 1, which is 3-(R)-(N,N-Dimethylamino)methyl-1-[3-(indol-3-yl)-2-[(R)-(4-phenylpiperazin-1-yl)carbonylamino]propanoyl]-1,2,3,4-tetrahydroquinoline or a salt thereof, 3-(S)-(N,N-Dimethylamino)methyl-1-[3-(indol-3-yl)-2-[(R)-(4-phenylpiperazin-1-yl)carbonylamino]propanoyl]-1,2,3,4-tetrahydroquinoline or a salt thereof, 3-(R)-(N,N-Dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline or a salt thereof, 3-(S)-(N,N-Dimethylamino)methyl-1-[3-(indol-3-yl)-2-[(R)-4-(2-oxo-2,3-dihydro-1H-benzimidazol-1-yl)piperidinocarbonylamino]propanoyl]-1,2,3,4-tetrahydroquinoline or a salt thereof, 3-(R)-(N,N-Dimethylamino)methyl-1-[3-(indol-3-yl)-2-(R)-[4-(2-methyl)phenylpiperazin-1-yl]carbonylaminopropanoyl]-1,2,3,4-tetrahydroquinoline or a salt thereof, 3-(S)-(N,N-Dimethylamino)methyl-1-[3-(indol-3-yl)-2-(R)-(4-(2-methyl)phenylpiperazin-1-yl]carbonylaminopropanoyl]-1,2,3,4-tetrahydroquinoline or a salt thereof, 3-(R,S)-(N,N-Dimethylamino)methyl-1-[3-(indol-3-yl)2-[(R)-1-(benzoylpiperidin-4-yl)carbonylamino]propanoyl]-6-methoxy-1,2,3,4-tetrahydroquinoline or a salt thereof, 6-Chloro-3-(R,S)-(N,N-dimethylamino)methyl-1-[3-(indol-3-yl)-2-[(R)-(4-phenylpiperazin-1 -yl)carbonylamino]propanoyl]-1,2,3,4-tetrahydroquinoline or a salt thereof, 6-Chloro-3-(R,S)-(N,N-dimethylamino)methyl-1-[3-(indol-3-yl)-2-((R)-4-(2-oxo-2,3-dihydro-1H-benzimidazol-1-yl)piperidinocarbonylamino]propanoyl]-1,2,3,4-tetrahydroquinoline or a salt thereof, 1-Benzoyl-N-[(R)-2-[6-chloro-3-[(N,N-dimethylamino)methyl]-1,2,3,4-tetrahydroquinolin-1-yl]-1-[3-(indol-3-yl)propanoyl]-4-piperidinecarboxamide or a salt thereof, 1-[3-(4-Biphenylyl)propanoyl]-3-(R)-(N,N-dimethylamino)methyl-1,2,3,4-tetrahydroquinoline or a salt thereof, or 1-[3-(4-Biphenylyl)propanoyl]-3-(S)-(N,N-dimethylamino)methyl-1,2,3,4-tetrahydroquinoline or a salt thereof.

17. A process for producing a compound of claim 1, which comprises;

reacting a compound of the formula:

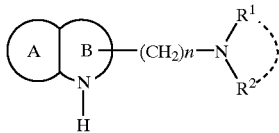

wherein each symbols has the same meanings as in claim 1, or a salt thereof, with a compound of the formula:

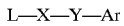

wherein L represents a leaving group, and the other symbols have the same meanings as in claim 1, or a salt thereof.

18. A pharmaceutical composition comprising a compound of claim 1 and a pharmaceutically acceptable carrier, diluent or excipient.

19. A somatostatin receptor binding inhibiting pharmaceutical composition of claim 18 comprising a somatostatin receptor binding inhibiting amount of a compound of claim 1.

20. A pharmaceutical composition of claim 19 wherein the somatostatin receptor binding inhibitor is a somatostatin receptor agonist.

21. A pharmaceutical composition of claim 19 wherein the somatostatin receptor binding inhibitor is a somatostatin receptor antagonist.

22. A prodrug of a compound of claim 1.

23. A pharmaceutical composition which comprises a prodrug of claim 22.

24. A method for inhibiting somatostatin receptor binding in a mammal in need thereof, which comprises administering to said mammal an effective amount of a compound of the formula (I'):

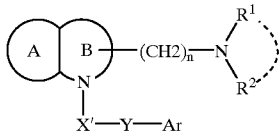

wherein Ar represents an aromatic group which may be substituted;

X' represents methylene, S, SO, $SO_2$ or CO;

Y represents a spacer having a main chain of 2 to 5 atoms;

n represents an integer of 1 to 5;

i) $R^1$ and $R^2$ each represents a hydrogen atom or a lower alkyl which may be substituted, ii) $R^1$ and $R^2$ form, taken together with the adjacent nitrogen atom, a nitrogen-containing heterocyclic ring which may be substituted;

Ring A represents a benzene ring which may be substituted;

Ring B represents a 6 membered nitrogen-containing non-aromatic ring with 5 carbon atoms and 1 nitrogen atom which may be further substituted by alkyl or acyl, or a salt thereof.

25. A method for treating glaucoma, acromegaly, diabetes, diabetic complication, depression or tumor in a mammal, comprising administering a pharmaceutical composition of claim 18 to a mammal in need thereof.

26. A method for treating a disease condition in a mammal with an analgesic treatment, said method comprising administering a pharmaceutical of claim 18 to a mammal in need thereof.

27. A method for preventing or treating glaucoma, acromegaly, diabetes, diabetic complication, depression or tumor in a mammal in need thereof, which comprises administering to said mammal an effective amount of a compound of the formula (I'):

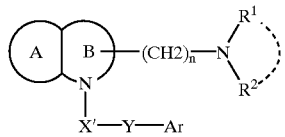

wherein Ar represents an aromatic group which may be substituted;

X' represents methylene, S, SO, $SO_2$ or CO;

Y represents a spacer having a main chain of 2 to 5 atoms;

n represents an integer of 1 to 5;

i) $R^1$ and $R^2$ each represents a hydrogen atom or a lower alkyl which may be substituted;

ii) $R^1$ and $^2$ form, taken together with the adjacent nitrogen atom, a nitrogen-containing heterocyclic ring which may be substituted;

Ring A represents a benzene ring which may be substituted;

Ring B represents a 6 membered nitrogen-containing non-aromatic ring with 5 carbon atoms and 1 nitrogen atom which may be further substituted by alkyl or acyl, or a pharmaceutically acceptable salt thereof with a pharmaceutically acceptable excipient, carrier or diluent.

28. A method for manufacturing a pharmaceutical composition for inhibiting somatostatin receptor binding, said method comprising combining a compound of claim 1 with a pharmaceutically acceptable carrier, diluent or excipient.

* * * * *

UNITED STATES PATENT AND TRADEMARK OFFICE
CERTIFICATE OF CORRECTION

PATENT NO. : 6,329,389 B1
DATED : December 11, 2001
INVENTOR(S) : Nobuhiro Suzuki, Kaneyoshi Kato, Shiro Takekawa, Jun Terauchi and Satoshi Endo It is certified that error appears in the above-identified patent and that said Letters Patent is hereby corrected as shown below:

Column 157,
Line 15, "4oxidiazol" should read -- 4-oxadiazol --;

Column 159,
Line 9, "$C_{1-6}$" should read -- $C_{7-6}$ --;

Signed and Sealed this

Twenty-first Day of May, 2002

Attest:

JAMES E. ROGAN
Director of the United States Patent and Trademark Office

Attesting Officer